(12) United States Patent
Murer et al.

(10) Patent No.: US 9,673,408 B2
(45) Date of Patent: Jun. 6, 2017

(54) LUMINESCENT DIAZABENZIMIDAZOLE CARBENE METAL COMPLEXES

(71) Applicant: UDC Ireland Limited, Ballycoolin (IE)

(72) Inventors: Peter Murer, Oberwil (CH); Glauco Battagliarin, Mannheim (DE); Korinna Dormann, Bad Dürkheim (DE); Stefan Metz, Mannheim (DE); Gerhard Wagenblast, Wachenheim (DE); Flavio Luiz Benedito, Ludwigshafen (DE); Soichi Watanabe, Seoul (KR); Christian Lennartz, Schifferstadt (DE); Thomas Geβner, Heidelberg (DE)

(73) Assignee: UDC Ireland Limited, Dublin (IE)

(*) Notice: Subject to any disclaimer, the term of this patent is extended or adjusted under 35 U.S.C. 154(b) by 0 days.

(21) Appl. No.: 14/908,606

(22) PCT Filed: Jul. 29, 2014

(86) PCT No.: PCT/EP2014/066272
§ 371 (c)(1),
(2) Date: Jan. 29, 2016

(87) PCT Pub. No.: WO2015/014835
PCT Pub. Date: Feb. 5, 2015

(65) Prior Publication Data
US 2016/0181549 A1    Jun. 23, 2016

(30) Foreign Application Priority Data

Jul. 31, 2013 (EP) ..................................... 13178675
Jul. 4, 2014 (EP) ..................................... 14175848

(51) Int. Cl.
| | | |
|---|---|---|
| C01G 55/00 | (2006.01) | |
| C07D 487/04 | (2006.01) | |
| H01L 51/00 | (2006.01) | |
| C07F 15/00 | (2006.01) | |
| H05B 33/14 | (2006.01) | |
| C09K 11/06 | (2006.01) | |
| C07F 5/02 | (2006.01) | |
| C09K 11/02 | (2006.01) | |
| H01L 51/50 | (2006.01) | |

(52) U.S. Cl.
CPC .......... *H01L 51/0085* (2013.01); *C07F 5/025* (2013.01); *C07F 15/0033* (2013.01); *C07F 15/0086* (2013.01); *C09K 11/025* (2013.01); *C09K 11/06* (2013.01); *H05B 33/14* (2013.01); *C09K 2211/1007* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/0072* (2013.01); *H01L 51/0073* (2013.01); *H01L 51/5012* (2013.01); *H01L 51/5016* (2013.01); *H01L 51/5096* (2013.01); *Y02E 10/549* (2013.01); *Y02P 70/521* (2015.11)

(58) Field of Classification Search
CPC .............................. C01G 55/00; C07D 487/04
USPC ............................................. 423/22; 544/350
See application file for complete search history.

(56) References Cited

U.S. PATENT DOCUMENTS

2013/0032766 A1    2/2013    Molt et al.

FOREIGN PATENT DOCUMENTS

EP                 1956008 A1      8/2008
WO       WO-2011/073149 A1      6/2011

OTHER PUBLICATIONS

International Search Report for PCT/EP2014/066272 mailed Sep. 26, 2014.

*Primary Examiner* — Douglas M Willis
(74) *Attorney, Agent, or Firm* — Riverside Law LLP

(57) ABSTRACT

The present invention relates to metal-carbene complexes of the general formula (I), where variable M is Ir or Pt and that are characterized by variable R being a group of formula (a). The complexes are used in organic electronic devices, especially OLEDs (Organic Light-Emitting Diodes), illuminating elements, stationary visual display units and in material layers as emitter, charge transport material and/or charge or exiton blocker.

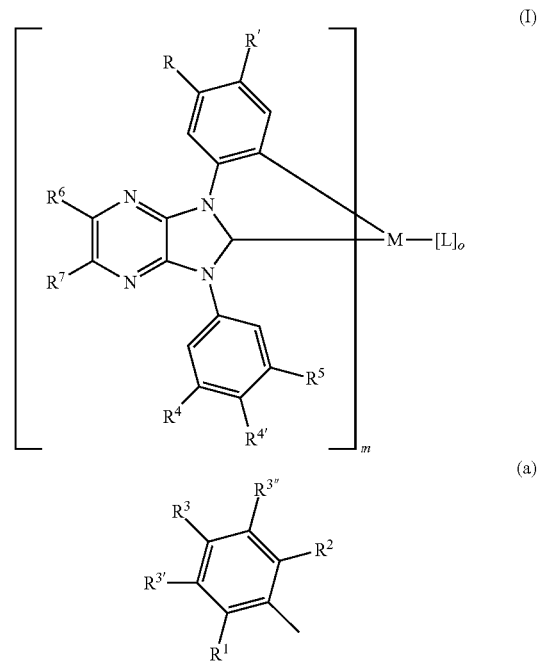

22 Claims, 1 Drawing Sheet

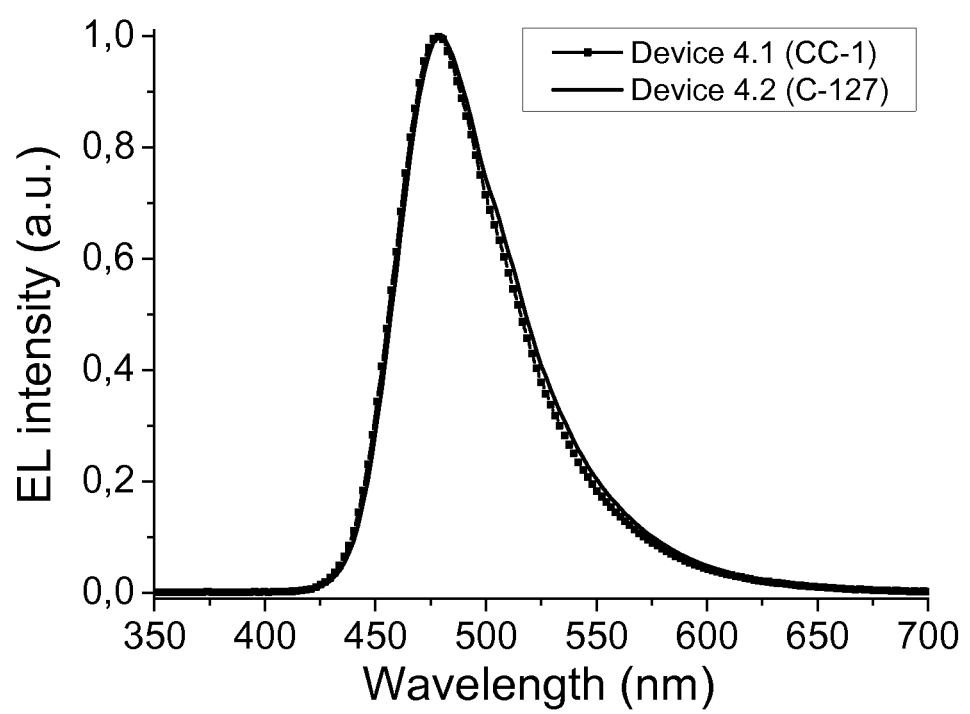

LUMINESCENT DIAZABENZIMIDAZOLE CARBENE METAL COMPLEXES

CROSS-REFERENCE TO RELATED APPLICATIONS

This application is a national stage application (under 35 U.S.C. §371) of PCT/EP2014/066272, filed Jul. 29, 2014, which claims benefit of European Application Nos. 13178675.8, filed Jul. 31, 2013, and 14175848.2, filed Jul. 4, 2014, all of which are incorporated herein by reference in their entirety.

The present invention relates to metal-carbene complexes of the general formula (I), to organic electronic devices, especially OLEDs (Organic Light-Emitting Diodes) which comprise such complexes, to an apparatus selected from the group consisting of illuminating elements, stationary visual display units and mobile visual display units comprising such an OLED, to the use of such a metal-carbene complex in OLEDs, for example as emitter, matrix material, charge transport material and/or charge or exciton blocker.

Organic light-emitting diodes (OLEDs) exploit the propensity of materials to emit light when they are excited by electrical current. OLEDs are of particular interest as an alternative to cathode ray tubes and liquid-crystal displays for production of flat visual display units. Owing to the very compact design and the intrinsically low power consumption, devices comprising OLEDs are suitable especially for mobile applications, for example for applications in cellphones, smartphones, digital cameras, mp3 players, laptops, etc. In addition, white OLEDs give great advantages over the illumination technologies known to date, especially a particularly high efficiency.

The prior art proposes numerous materials which emit light on excitation by electrical current.

EP1956008 relates to organic compounds represented by formula

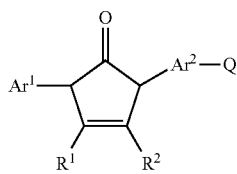

and charge-transporting materials composed of the compounds.

WO2005/019373 discloses transition metal complexes with carbene ligands as emitters for organic light emitting diodes (OLEDs). The ligands of these transition metal complexes are preferably attached via a metal-carbene bond and via a bond between the metal atom and an aromatic radical. Numerous heterocycles attached to the metal atom via a carbene bond are disclosed, but no complexes which have diazabenzimidazolocarbene ligands are disclosed.

WO2006/056418A2 discloses the use of transition metal-carbene complexes in organic light-emitting diodes. In the corresponding transition metal complexes, a metal atom is bonded to the ligands via at least one metal-carbene bond and via a bond between the metal atom and an aromatic radical. The metal-carbene bond is preferably bonded via an imidazole ring, to which, according to the document cited, aromatic cycles may also be fused. However, no complexes which have diazabenzimidazolocarbene ligands are disclosed.

WO2007/088093A1 and WO2007/185981A1 disclose transition metalcomplexes comprising ligands attached via metal-carbene bonds. Preferred carbene ligands mentioned are imidazole ligands. These may also have fused aromatic six-membered rings, where 1 to 4 of the carbon atoms present in the aromatic six-membered ring may be replaced by nitrogen. The documents cited do not disclose the positions of the nitrogens in the aromatic six-membered ring.

WO2007/1115970A1 likewise discloses transition metal-carbene complexes, preference being given to imidazole units as the carbene ligand. An aromatic six-membered ring may likewise be fused to this imidazole unit, wherein 1 to 4 carbon atoms may be replaced by nitrogen atoms. This document does not comprise any disclosure as to the position of the nitrogen atoms.

KR2012/0135837, KR2013/0043342, WO2012/170463 and WO12/172482 relate to metal-carbene complexes comprising a central atom selected from iridium and platinum, and specific azabenzimidazolocarbene ligands and to OLEDs, which comprise such complexes. US2012/0305894, WO2012/170461, WO2012/121936 and US2013/032766 (WO2011/073149) relate to metal-carbene complexes comprising a central atom selected from iridium and platinum, and diazabenzimidazolocarbene ligands, to organic light diodes which comprise such complexes and to light-emitting layers comprising at least one such metal-carbene complex. However, no complexes which have diazabenzimidazolocarbene ligands, wherein the phenyl group bonded to the Ir atom is substituted by a dialkylphenyl group, are disclosed by said documents.

It is an object of the present invention to provide organic electronic devices, preferably OLEDs, having—compared with the organic electronic devices known in the art—a high color purity in the blue region of the visible electromagnetic spectrum, a high efficiency, low voltage and/or improved lifetime/stability.

Surprisingly, it was found that substitution of the cyclometallating N-aryl group of the diazabenzimidazole carbene ligand by an optionally substituted aryl group R can result in a decrease of the lifetime of the luminescence ($\tau_v$) and increase of the radiative rate $k_{rad}$ of the respective Pt, or Ir carbene complexes, comprising at least one ligand of formula

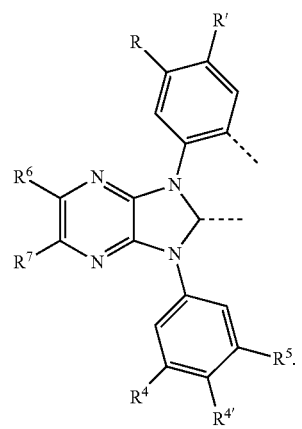

(D)

These metal-carbene complexes may spend less time in the excited state, thereby decreasing the possibility for photochemical reactions, or quenching to occur. Therefore, these compounds may provide devices with improved stability and/or also improved device efficiency. In addition, the inventive metal-carbene complexes may provide reduced color-shift of the emission with increasing doping concentration of the compounds in a host material.

The ligands of formula

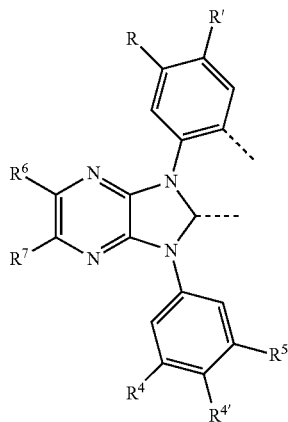

(D)

can be used for the production of metal carbene-complexes, especially Pt and Ir carbene complexes. The metal carbene-complexes may have reduced lifetime of luminescence.

It has been further found by the inventors of the present invention that OLEDs comprising the metal-carbene complexes of formula (I) according to the present invention in an organic electronic device, preferably in an OLED, especially as an emitter material in an OLED, show improved device performance such as high quantum efficiency, high luminous efficacy, low voltage, good stabilities and/or long lifetimes. The metal-carbene complexes of formula (I) are particularly suitable as emitter materials with an emission in the blue region with a CIE-y color coordinate below 0.42, especially below 0.38, which enables for example the production of white OLEDs, or full-color displays.

The objects of the present invention are achieved by metal-carbene complexes of the general formula

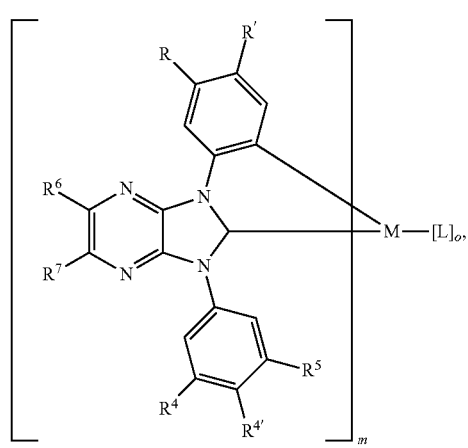

(I)

M is Pt, or Ir;
if M is Ir, m is 1, 2, or 3; o is 0, 1, or 2; and the sum of m+o is 3;
with the proviso that, if o=2, the ligands L may be the same or different;
if M is Pt, m is 1, or 2; o is 0, or 1; and the sum of m+o is 2;
L is a monoanionic bidentate ligand,
R is a group of formula

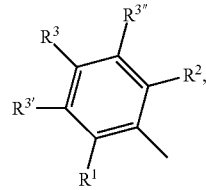

R' is H, $C_1$-$C_5$alkyl group, or a fluoro$C_1$-$C_4$alkyl group;
$R^1$ is H, a $C_1$-$C_5$alkyl group, a fluoro$C_1$-$C_4$alkyl group, or a $C_3$-$C_6$cycloalkyl group,
$R^2$ is H, a $C_1$-$C_5$alkyl group, a fluoro$C_1$-$C_4$alkyl group, or a $C_3$-$C_6$cycloalkyl group,
$R^3$, $R^{3'}$ and $R^{3''}$ are independently of each other hydrogen; a $C_1$-$C_{18}$alkyl group, which can optionally be substituted by E and/or interrupted by D; a $C_3$-$C_{12}$cycloalkyl group, which can optionally be substituted by G; a $C_3$-$C_{10}$heterocycloalkyl radical which is interrupted by at least one of O, S and $NR^{65}$ and/or substituted by E; a $C_6$-$C_{24}$aryl group, which can optionally be substituted by G; or a $C_2$-$C_{30}$heteroaryl group, which can optionally be substituted by G; a halogen atom, especially F or Cl; $CF_3$, CN, or $SiR^{80}R^{81}R^{82}$.

$R^3$ and $R^{3'}$, or $R^1$ and $R^3$ together form a group of formula

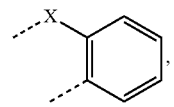

wherein X is O, S, $NR^{75}$ or $CR^{73}R^{74}$;
$R^4$, $R^{4'}$ and $R^5$ are independently of each other hydrogen; a $C_1$-$C_{18}$alkyl group, which can optionally be substituted by E and/or interrupted by D; a $C_3$-$C_{12}$cycloalkyl group, which can optionally be substituted by E; a $C_3$-$C_{10}$heterocycloalkyl radical which is interrupted by at least one of O, S and $NR^{65}$ and/or substituted by E; a $C_6$-$C_{14}$aryl group, which can optionally be substituted by G; or a $C_2$-$C_{10}$heteroaryl group, which can optionally be substituted by G; a halogen atom, especially F or Cl; $CF_3$, CN, or $SiR^{80}R^{81}R^{82}$; or
$R^4$ and $R^{4'}$ together form a group of formula

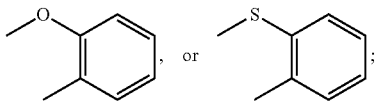

$R^6$ and $R^7$ are independently of each other hydrogen, a $C_1$-$C_8$alkyl group, optionally interrupted by at least one heteroatom selected from —O—, —S— and —$NR^{65}$—, optionally bearing at least one substituent, which is selected from the group consisting of $C_1$-$C_8$alkyl, $C_1$-$C_8$alkoxy, halogen, preferably F, and $C_1$-$C_8$haloalkyl, such as $CF_3$; a $C_3$-$C_6$cycloalkyl group, optionally bearing at least one substituent, which is selected from the group consisting of $C_1$-$C_8$alkyl, $C_1$-$C_8$alkoxy, halogen, preferably F, $C_1$-$C_8$haloalkyl, such as $CF_3$; a hetero$C_3$-$C_6$cyclo alkyl group, interrupted by at least one heteroatom selected from —O—, —S— and —NR$^{65}$—, optionally bearing at least one substituent, which is selected from $C_1$-$C_8$alkyl, $C_1$-$C_8$alkoxy, halogen, preferably F, $C_1$-$C_8$haloalkyl, such as CF$_3$; or a $C_6$-$C_{14}$aryl group, which can optionally be substituted by one, or two $C_1$-$C_8$alkyl groups; or R$^6$ and R$^7$ form together a ring

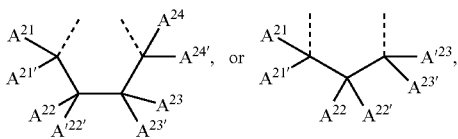

wherein A$^{21}$, A$^{21'}$, A$^{22}$, A$^{22'}$, A$^{23}$, A$^{23'}$, A$^{24'}$ and A$^{24}$ are independently of each other H, a $C_1$-$C_4$alkyl group, a $C_3$-$C_6$cycloalkyl group, a fluoro$C_1$-$C_4$alkyl group;

D is —CO—, —COO—, —S—, —SO—, —SO$_2$—, —O—, —NR$^{65}$—, —SiR$^{70}$R$^{71}$—, —POR$^{72}$—, —CR$^{63}$=CR$^{64}$—, or —C≡C—,

E is —OR$^{69}$, —SR$^{69}$, —NR$^{65}$R$^{66}$, —COR$^{68}$, —COOR$^{67}$, —CONR$^{65}$R$^{66}$, —CN, or F;

G is E, or a $C_1$-$C_{18}$alkyl group, a $C_6$-$C_{14}$aryl group, a $C_6$-$C_{14}$aryl group, which is substituted by F, $C_1$-$C_{18}$alkyl, or $C_1$-$C_{18}$alkyl, which is substituted by F and/or interrupted by O; a $C_2$-$C_{10}$heteroaryl group, or a $C_2$-$C_{10}$heteroaryl group, which is substituted by F, SiR$^{80}$R$^{81}$R$^{82}$, or $C_1$-$C_{18}$alkyl which is substituted by F and/or interrupted by O;

R$^{63}$ and R$^{64}$ are independently of each other H, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

R$^{65}$ and R$^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or R$^{65}$ and R$^{66}$ together form a five or six membered ring, R$^{67}$ is a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, R$^{68}$ is H; a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, R$^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, R$^{79}$ and R$^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and R$^{72}$ is a $C_1$-$C_{18}$alkyl group, a $C_6$-$C_{18}$aryl group, or a $C_6$-$C_{18}$aryl group, which is substituted by $C_1$-$C_{18}$alkyl, R$^{73}$ and R$^{74}$ are independently of each other H, $C_1$-$C_{25}$alkyl, $C_1$-$C_{25}$alkyl which is interrupted by O, $C_7$-$C_{25}$arylalkyl, $C_6$-$C_{24}$aryl, $C_6$-$C_{24}$aryl which is substituted by $C_1$-$C_{18}$alkyl, $C_2$-$C_{20}$heteroaryl, or $C_2$-$C_{20}$heteroaryl which is substituted by $C_1$-$C_{18}$alkyl;

R$^{73}$ and R$^{74}$ together form a group of formula =CR$^{76}$R$^{77}$, wherein R$^{76}$ and R$^{77}$ are independently of each other H, $C_1$-$C_{18}$alkyl which is interrupted by O, $C_6$-$C_{24}$aryl, $C_6$-$C_{24}$aryl which is substituted by $C_1$-$C_{18}$alkyl, or $C_2$-$C_{20}$heteroaryl, or $C_2$-$C_{20}$heteroaryl which is substituted by $C_1$-$C_{18}$alkyl, or R$^{73}$ and R$^{74}$ together form a five or six membered ring, which optionally can be substituted by $C_1$-$C_{18}$alkyl, $C_1$-$C_{18}$alkyl which is interrupted by O, and R$^{75}$ is a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, and R$^{80}$, R$^{81}$ and R$^{82}$ are independently of each other a $C_1$-$C_{25}$alkyl group, which can optionally be interrupted by O; a $C_6$-$C_{14}$aryl group, which can optionally be substituted by $C_1$-$C_{18}$alkyl; or a $C_2$-$C_{10}$heteroaryl group, which can optionally be substituted by $C_1$-$C_{18}$alkyl.

FIG. 1 provides a plot of the EL intensity of compounds CC-1 and C-127 as a function of wavelength.

R' is H, a $C_1$-$C_5$alkyl group, or a fluoro$C_1$-$C_4$alkyl group; preferably H, or a $C_1$-$C_5$alkyl group, more preferably H.

If R' is a a $C_1$-$C_5$alkyl group, or a fluoro$C_1$-$C_4$alkyl group the following preferences apply:

R' and R$^{4'}$ are the same.

R$^4$ and R$^5$ are H.

R$^1$ and R$^2$ are H, or—which case is more preferred—one of R$^1$ and R$^2$ is H and the other is different from H and is preferably a $C_1$-$C_5$alkyl group.

Examples of metal-carbene complexes of the general formula (I), wherein R' is a $C_1$-$C_5$alkyl group are shown below:

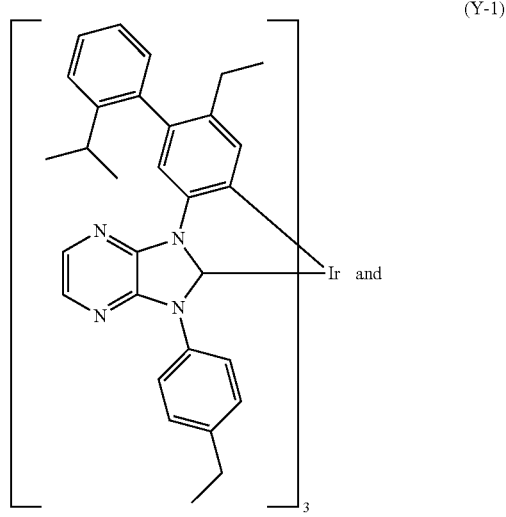

-continued (Y-2)

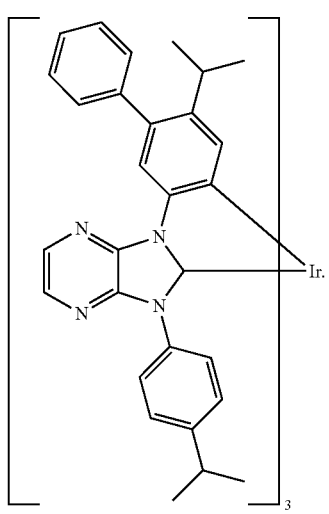

R is a group of formula

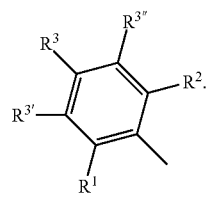

R¹ is H, a $C_1$-$C_5$alkyl group, a fluoro$C_1$-$C_4$alkyl group, or a $C_3$-$C_6$cycloalkyl group, especially H, a $C_1$-$C_5$alkyl group, a cyclopentyl, or cyclohexyl group; very especially a $C_1$-$C_5$alkyl group, a cyclopentyl or cyclohexyl group.

R² is H, a $C_1$-$C_5$alkyl group, a fluoro$C_1$-$C_4$alkyl group, or a $C_3$-$C_6$cycloalkyl group, especially H, a $C_1$-$C_5$alkyl group, a cyclopentyl, or cyclohexyl group; very especially a $C_1$-$C_5$alkyl group, a cyclopentyl or cyclohexyl group.

If R³ and R³' represent a halogen atom, they are preferably F or Cl, more preferably F.

If R³ and R³' represent a group of formula $SiR^{70}R^{71}R^{72}$ they are preferably $Si(CH_3)_3$, $Si(Ph)_3$, or $SiPh_2tBu$; with the proviso that only one of R³ and R³' is $SiR^{70}R^{71}R^{72}$, and the other is H.

The heteroaryl radical R³, R³' and R³'' is, for example, selected from the group consisting of pyridyl, methylpyridyl, pyrimidyl, pyrazinyl, carbazolyl, dibenzofuranyl, dibenzothiophenyl, indolyl, methylindolyl, benzofuranyl and benzothiophenyl, which can optionally be substituted by one, or more groups selected from a $C_1$-$C_4$alkyl group, a $C_3$-$C_6$cycloalkyl group and a $C_1$-$C_4$fluoroalkyl group; especially carbazolyl, dibenzofuranyl, dibenzothiophenyl, which can optionally be substituted by one, or more groups selected from a $C_1$-$C_4$alkyl group, a $C_3$-$C_6$cycloalkyl group and a $C_1$-$C_4$fluoroalkyl group; more especially dibenzofuranyl, dibenzothiophenyl, which can optionally be substituted by one, or more groups selected from a $C_1$-$C_4$alkyl group, and a $C_3$-$C_6$cycloalkyl group.

If R³, R³' and R³'' represent a $C_6$-$C_{14}$aryl group, they are, for example, a phenyl group, which can optionally be substituted by one, or more groups selected from a $C_1$-$C_4$alkyl group, a $C_3$-$C_6$cycloalkyl group and a fluoro$C_1$-$C_4$alkyl group.

R³ is preferably H, a $C_1$-$C_5$alkyl group, a cyclopentyl or cyclohexyl group, a group of formula

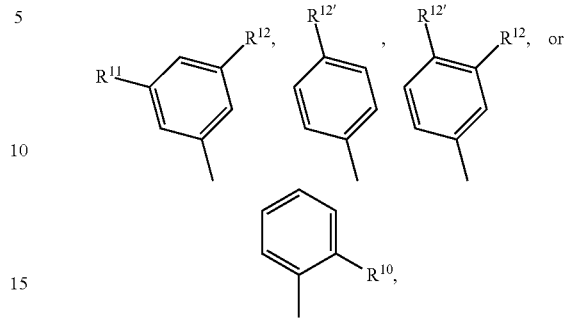

wherein
R¹⁰ is H, or a $C_1$-$C_5$alkyl group, R¹¹ is H, or a $C_1$-$C_5$alkyl group, R¹² is a $C_1$-$C_5$alkyl group, and R¹²' is a $C_1$-$C_5$alkyl group.

R³' is preferably H, a $C_1$-$C_5$alkyl group, a cyclopentyl or cyclohexyl group.

R³'' is preferably H, a $C_1$-$C_5$alkyl group, a cyclopentyl or cyclohexyl group.

R⁴, R⁴' and R⁵ are preferably independently of each other hydrogen, a $C_1$-$C_5$alkyl group, a $C_6$-$C_{14}$aryl group, which can optionally be substituted by one, or more groups selected from a $C_1$-$C_4$alkyl group and a fluoro$C_1$-$C_4$alkyl group; or a heteroaryl radical selected from the group consisting of pyridyl, methylpyridyl, pyrimidyl, pyrazinyl, carbazolyl, dibenzofuranyl, dibenzothiophenyl, indolyl, methylindolyl, benzofuranyl and benzothiophenyl, which can optionally be substituted by one, or more groups selected from a $C_1$-$C_4$alkyl group, a $C_3$-$C_6$cycloalkyl group and a $C_1$-$C_4$fluoroalkyl group; more preferably independently of each other hydrogen, a $C_1$-$C_5$alkyl group, a $C_6$-$C_{14}$aryl group, which can optionally be substituted by one, or more groups selected from a $C_1$-$C_4$alkyl group and a fluoro$C_1$-$C_4$alkyl group.

Preferably, R⁶ and R⁷ are independently of each other H, a $C_1$-$C_8$alkyl group, or a $C_3$-$C_6$cycloalkyl group, or a $C_6$-$C_{14}$aryl group, which can optionally be substituted by one, or two $C_1$-$C_8$alkyl groups, or R⁶ and R⁷ form together a ring

Examples of a $C_6$-$C_{14}$aryl group are a group of formula

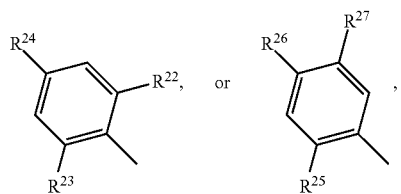

wherein
R²² and R²³ are independently of each other H, especially a $C_1$-$C_5$alkyl group, a cyclopentyl or cyclohexyl group;

$R^{24}$ is H, or a $C_1$-$C_5$alkyl group;

$R^{25}$ is H, especially a $C_1$-$C_5$alkyl group, a cyclopentyl or cyclohexyl group;

$R^{26}$ is H, a $C_1$-$C_5$alkyl group, a cyclopentyl or cyclohexyl group; and $R^{27}$ is H, a $C_1$-$C_5$alkyl group, a cyclopentyl or cyclohexyl group; with the proviso that in case one of $R^{26}$ and $R^{27}$ is a cyclopentyl or cyclohexyl group, the other is H. More preferably, $R^6$ is H, a $C_1$-$C_4$alkyl group, or a $C_3$-$C_6$cycloalkyl group and $R^7$ is H; or $R^6$ is H, and $R^7$ is a $C_1$-$C_4$alkyl group, or a $C_3$-$C_6$cycloalkyl group.

If two monoanionic bidentate ligands L are present, they can be different, but are preferably the same. The monoanionic bidentate ligand L in the metal-carbene complex has the following meaning:

a ligand of formula (A)

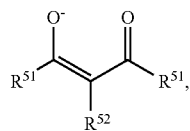

in which $R^{51}$ is in each case independently a linear or branched $C_1$-$C_8$alkyl group, preferably methyl, ethyl, isopropyl or tert-butyl; a substituted or unsubstituted $C_6$-$C_{18}$aryl radical, preferably an unsubstituted phenyl or 2,6-di$C_1$-$C_8$alkylphenyl; a substituted or unsubstituted $C_6$-$C_{12}$heteroaryl, $R^{52}$ is hydrogen; a linear or branched $C_1$-$C_6$alkyl group; a substituted or unsubstituted $C_6$-$C_{18}$aryl radical; preferably hydrogen or 2,6-dimethylphenyl; where the ligand of the formula (A) is preferably acetylacetonato (in case of ligand A, o is 1); or L is a carbene ligand of the general formula (B)

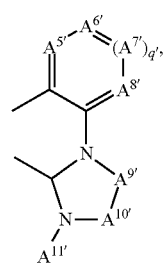

where $A^{9'}$ is $CR^{12'}$ or N;

$A^{10'}$ is $CR^{13'}$ or N;

$R^{11'}$ is a linear or branched, substituted or unsubstituted alkyl radical having 1 to 20 carbon atoms, optionally interrupted by at least one heteroatom, selected from O, S and N; a substituted or unsubstituted cycloalkyl radical having 3 to 18 carbon atoms; a substituted or unsubstituted heterocycloalkyl radical interrupted by at least one heteroatom, selected from O, S and N, and having 3 to 18 carbon atoms and/or heteroatoms; a substituted or unsubstituted aryl radical having 6 to 30 carbon atoms, a substituted or unsubstituted heteroaryl radical interrupted by at least one heteroatom, selected from O, S and N and having a total of 5 to 30 carbon atoms and/or heteroatoms;

$R^{12'}$ and $R^{13'}$ are each independently hydrogen; deuterium; a linear or branched, substituted or unsubstituted alkyl radical having 1 to 20 carbon atoms, optionally interrupted by at least one heteroatom, selected from O, S and N; a substituted or unsubstituted cycloalkyl radical having 3 to 18 carbon atoms; a substituted or unsubstituted heterocycloalkyl radical interrupted by at least one heteroatom, selected from O, S and N, and having 3 to 18 carbon atoms and/or heteroatoms; a substituted or unsubstituted aryl radical having 6 to 30 carbon atoms; a substituted or unsubstituted heteroaryl radical interrupted by at least one heteroatom, selected from O, S and N and having a total of 5 to 30 carbon atoms and/or heteroatoms; or a group with donor or acceptor action;

if $A^{9'}$ is $CR^{12'}$ and $A^{10'}$ is $CR^{13'}$, $CR^{12'}$ and $CR^{13'}$ together may form, a saturated or unsaturated or aromatic, optionally substituted ring, which is optionally interrupted by at least one heteroatom, selected from O, S and N, has a total of from 5 to 18 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 18 carbon atoms and/or heteroatoms;

$A^{5'}$ is $CR^{14'}$ or N;

$A^{6'}$ is $CR^{15'}$ or N;

$A^{7'}$ is $CR^{16'}$ or N;

$A^{8'}$ is $CR^{17'}$ or N;

$R^{14'}$, $R^{15'}$, $R^{16'}$ and $R^{17'}$ are each independently hydrogen; deuterium; a linear or branched, substituted or unsubstituted alkyl radical having 1 to 20 carbon atoms, optionally interrupted by at least one heteroatom, selected from O, S and N; a substituted or unsubstituted cycloalkyl radical having 3 to 18 carbon atoms; a substituted or unsubstituted heterocycloalkyl radical interrupted by at least one heteroatom, selected from O, S and N, and having 3 to 18 carbon atoms and/or heteroatoms; a substituted or unsubstituted aryl radical having 6 to 30 carbon atoms; a substituted or unsubstituted heteroaryl radical interrupted by at least one heteroatom, selected from O, S and N and having a total of 5 to 30 carbon atoms and/or heteroatoms; or a group with donor or acceptor action; or $R^{14'}$ and $R^{15'}$, $R^{15'}$ and $R^{16'}$ or $R^{16'}$ and $R^{17'}$ may form, together with the carbon atoms to which they are bonded, a saturated or unsaturated or aromatic, optionally substituted ring, which is optionally interrupted by at least one heteroatom, selected from O, S and N, has a total of from 5 to 18 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 18 carbon atoms and/or heteroatoms; or if $A^{9'}$ is $CR^{12'}$, $R^{12'}$ and $R^{17'}$ together may form a saturated or unsaturated, linear or branched bridge optionally comprising heteroatoms, selected from O, S and N, to which is optionally fused a substituted or unsubstituted, five- to eight-membered ring comprising carbon atoms and/or heteroatoms, and which are optionally substituted with aromatic units, heteroaromatic units or groups with donor or acceptor action (in case of ligand B, o is 2);

q' is 0 or 1; or

L is a ligand of the general formula (C)

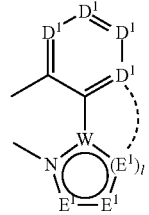
(C)

in which the symbols are each defined as follows:

$D^1$ are each independently $CR^{34'''}$ or N;

W is C or N;

$E^1$ are each independently $CR^{35'''}$, N, $NR^{36'''}$ or O;

l is 1 or 2;

$R^{34'''}$, $R^{35'''}$, $R^{36'''}$ are each independently hydrogen; substituted or unsubstituted or branched alkyl; substituted or unsubstituted aryl or substituted or unsubstituted heteroaryl; or in each case two $R^{34'''}$, $R^{35'''}$ or $R^{36'''}$ radicals together form a fused ring which may optionally comprise at least one heteroatom; or $R^{34'''}$, $R^{35'''}$, $R^{36'''}$ or $R^{37''''}$ is a radical having donor or acceptor action;

where the dotted line means an optional bridge between one of the D groups and one of the E groups; where the bridge may be defined as follows:

alkylene, arylene, heteroarylene, alkynylene, alkenylene, $NR^{38'''}$, O, S, $SiR^{41'''}R^{42'''}$, and $(CR^{43'''}R^{44'''})_v$, where one or more nonadjacent $(CR^{43'''}R^{44'''})$ groups may be replaced by $NR^{38'''}$, O, S, $SiR^{41'''}R^{42'''}$, where v is from 2 to 10; and $R^{38'''}$, $R^{41'''}$, $R^{42'''}$, $R^{43'''}$, $R^{44'''}$ are each H, alkyl, aryl or heteroaryl.

L is preferably a ligand of formula (B), or (C), more preferably a ligand of formula (B), if M is Ir.

L is preferably a group (X-1), (X-2), (X-3), (X-4), (X-5), (X-6), (X-7), (X-8), (X-9), (X-10), (X-11), (X-12), (X-13), (X-14), (X-15), (X-16), (X-17), (X-18), (X-19), (X-20), (X-21), (X-22), (X-23), (X-24), (X-25), (X-26), or (X-27) as defined in claim 10; more preferably a group (X-1), (X-2), (X-3), or (X-4). The synthesis and use of the ligands (X-1) to (X-27) for the preparation of metal complexes is, for example, described in WO2006121811, US20110057559, WO2011106344, WO2012048266, WO2007095118, WO2008156879, WO2010068876, WO2011157339, and WO2010086089.

In addition, In principal, the ligand L can also be a ligand

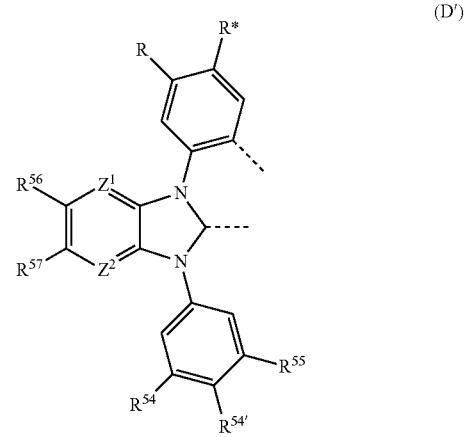
(D')

which is different from the ligand

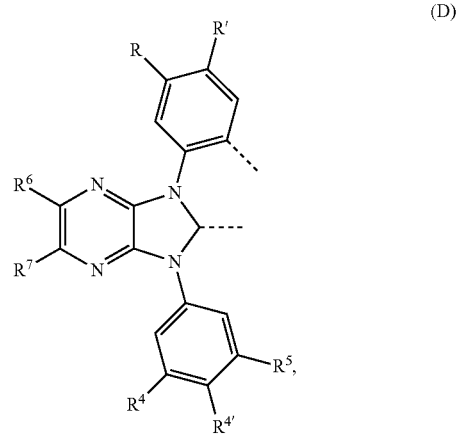
(D)

wherein $Z^1$ and $Z^2$ are N, or $Z^1$ and $Z^2$ are CH; R* has the meaning of R', $R^{54}$ has the meaning of $R^4$, $R^{54'}$ has the meaning of $R^{4'}$, $R^{55}$ has the meaning of $R^5$, $R^{56}$ has the meaning of $R^6$ and $R^{57}$ has the meaning of $R^7$ and each group R is the same within one metal-carbene complex. In said embodiment the present invention is directed to complexes of formula $D_2MD'(Va)$, or $D_2MD'(Vb)$. Complexes of formula $D_2MD'(Va)$ are preferred.

For R*, $R^{54}$, $R^{54'}$, $R^{55}$, $R^{56}$ and $R^{57}$ the same preferences apply as for R', $R^4$, $R^{4'}$, $R^5$, $R^6$ and $R^7$, respectively.

The metal-carbene complex is preferably a metal-carbene complex of formula

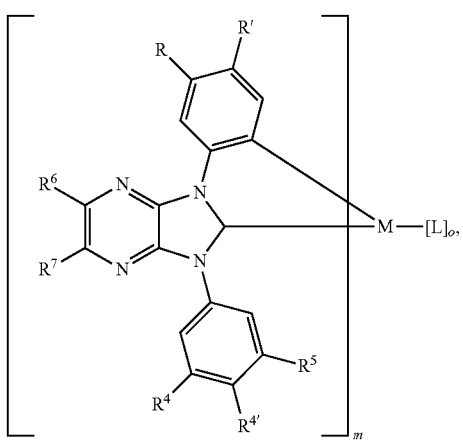
(II)

wherein
R is a group of formula

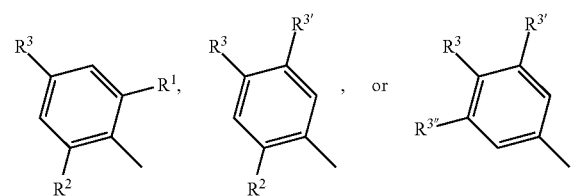

R' is H, or a $C_1$-$C_5$alkyl group, especially ethyl, isopropyl, or isobutyl; very especially H;

and

M, m, o, L, $R^1$, $R^2$, $R^3$, $R^{3'}$, $R^{3''}$, $R^4$, $R^{4'}$, $R^5$, $R^6$ and $R^7$ are as defined above.

Metal complexes of formula $D_2ML$ and $D_3M$ are more preferred than metal complexes of formula $DML_2$, such as, for example

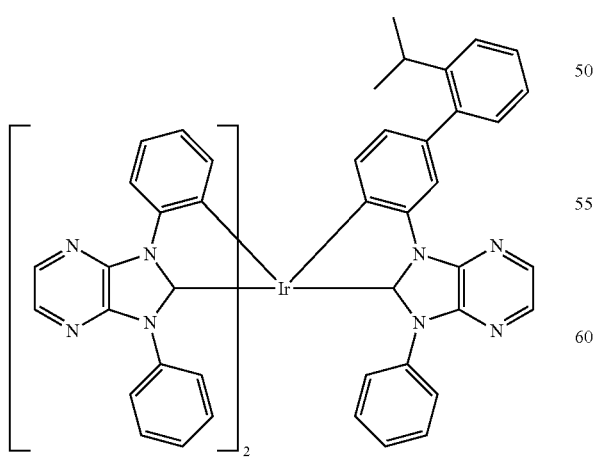
(X-1)

and

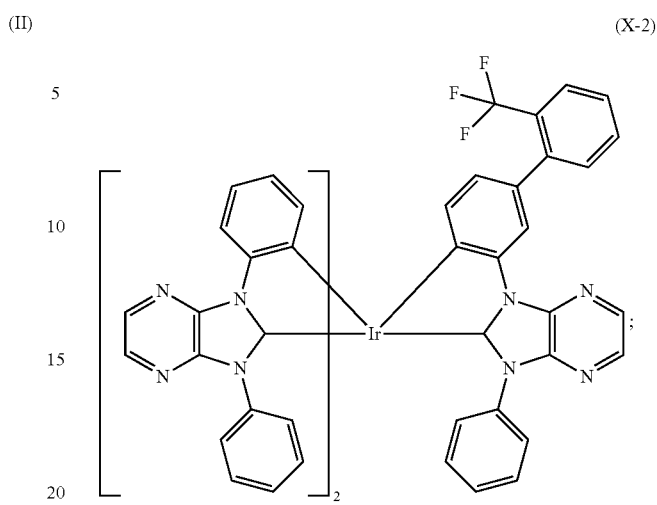
(X-2)

because, in general, the decrease of lifetime of luminescence in case of metal complexes of formula $D_2ML$ and $D_3M$ is more pronounced.

The metal-carbene complex is more preferably a metal-carbene complex of formula

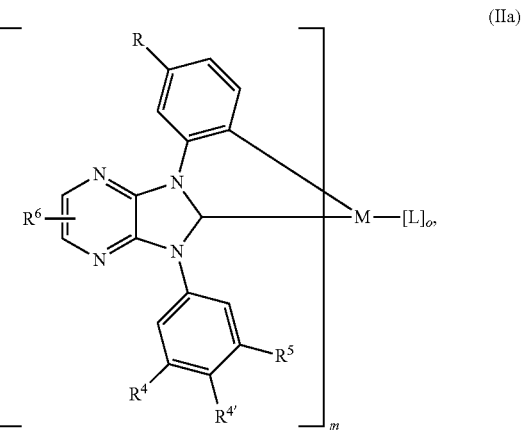
(IIa)

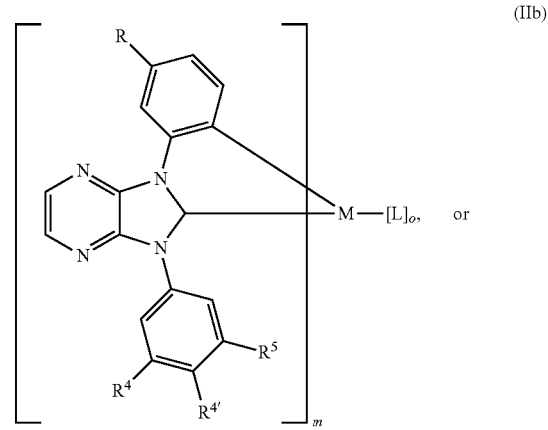
(IIb)

-continued

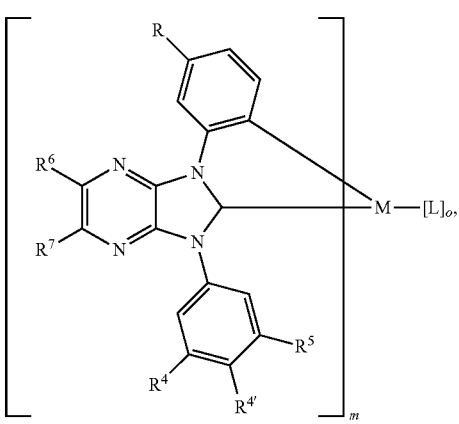

(IIc)

wherein
R is a group of formula

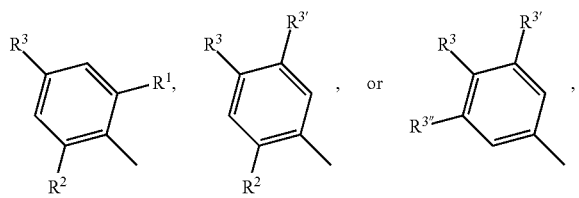

and $R^6$ in formula (IIa) is a $C_1$-$C_8$alkyl group, optionally interrupted by at least one heteroatom selected from —O—, —S— and —$NR^{65}$—, optionally bearing at least one substituent, which is selected from the group consisting of $C_1$-$C_8$alkyl, $C_1$-$C_8$alkoxy, halogen, preferably F, and $C_1$-$C_8$haloalkyl, such as $CF_3$; a $C_3$-$C_6$cycloalkyl group, optionally bearing at least one substituent, which is selected from the group consisting of $C_1$-$C_8$alkyl, $C_1$-$C_8$alkoxy, halogen, preferably F, $C_1$-$C_8$haloalkyl, such as $CF_3$; a hetero$C_3$-$C_6$cyclo alkyl group, interrupted by at least one heteroatom selected from —O—, —S— and —$NR^{65}$—, optionally bearing at least one substituent, which is selected from $C_1$-$C_8$alkyl, $C_1$-$C_8$alkoxy, halogen, preferably F, $C_1$-$C_8$haloalkyl, such as $CF_3$; or a group of formula

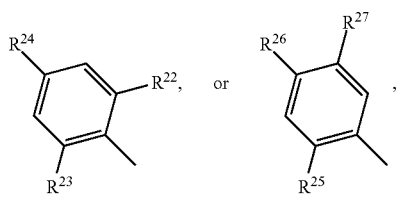

$R^{22}$ and $R^{23}$ are independently of each other H, especially a $C_1$-$C_5$alkyl group, a cyclopentyl or cyclohexyl group;
$R^{24}$ is H, or a $C_1$-$C_5$alkyl group;
$R^{25}$ is H, especially a $C_1$-$C_5$alkyl group, a cyclopentyl or cyclohexyl group;

$R^{26}$ is H, a $C_1$-$C_5$alkyl group, a cyclopentyl or cyclohexyl group; and $R^{27}$ is H, a $C_1$-$C_5$alkyl group, a cyclopentyl or cyclohexyl group; with the proviso that in case one of $R^{26}$ and $R^{27}$ is a cyclopentyl or cyclohexyl group, the other is H;

$R^6$ and $R^7$ in formula (IIc) form together a ring

M, m, L, o, $R^1$, $R^2$, $R^3$, $R^{3'}$, $R^{3''}$, $R^4$, $R^{4'}$, $R^5$ and $R^{65}$ are as defined above.

Preferably, $R^6$ is a $C_1$-$C_5$alkyl group, or a $C_3$-$C_6$cycloalkyl group.

Depending on its preparation the metal carbene complex of formula

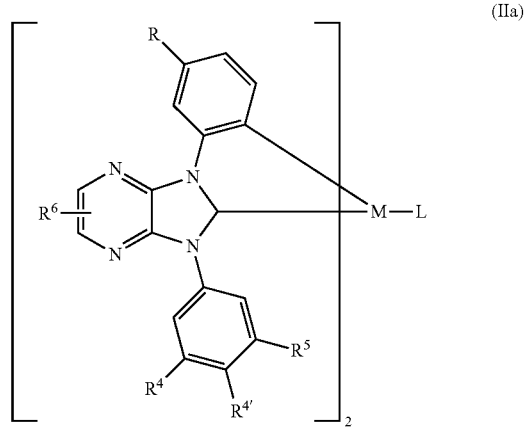

(IIa)

can be present as a mixture of different isomeric forms:

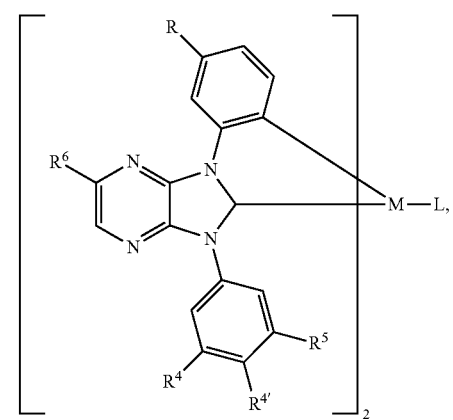

-continued

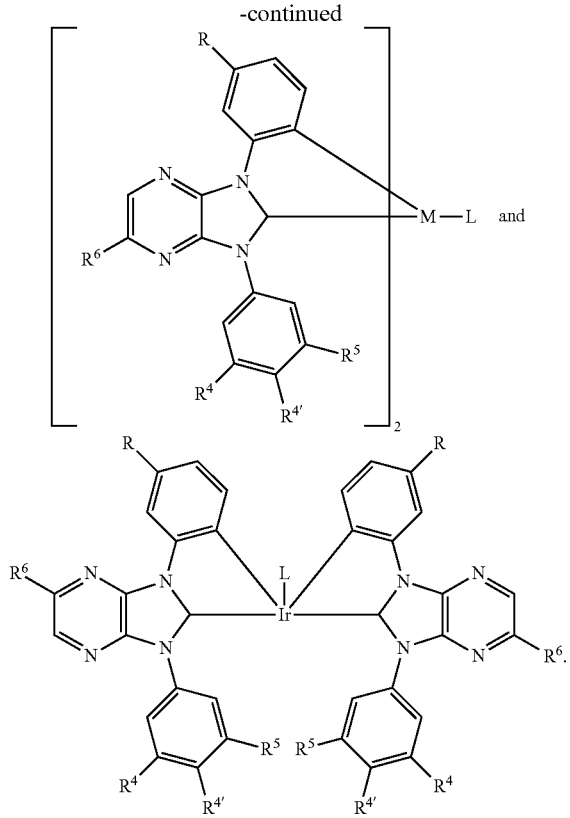

Formula (IIa) is an idealized or simplified manner of representation and shall comprise all isomeric forms.

In a preferred embodiment R is a group of formula

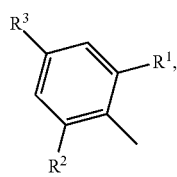

wherein
R[1] and R[2] are independently of each other a $C_1$-$C_5$alkyl group, a cyclopentyl or cyclohexyl group;
R[3] is H, a $C_1$-$C_4$alkyl group, a group of formula

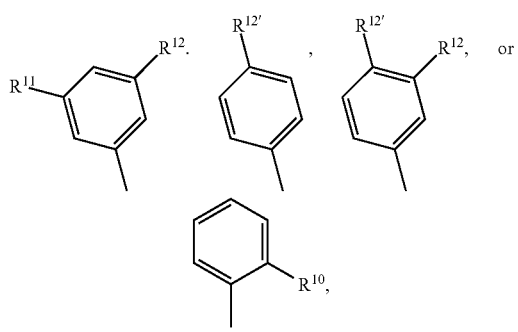

wherein
R[10] is H, or a $C_1$-$C_5$alkyl group,
R[11] is H, or a $C_1$-$C_5$alkyl group,
R[12] is a $C_1$-$C_5$alkyl group, and
R[12'] is a $C_1$-$C_5$alkyl group.

In another preferred embodiment R is a group of formula

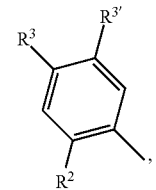

wherein
R[2] is $CF_3$, a $C_1$-$C_5$alkyl group, a cyclopentyl or cyclohexyl group;
R[3] is H, a $C_1$-$C_5$alkyl group, a cyclopentyl or cyclohexyl group; and
R[3'] is H, a $C_1$-$C_5$alkyl group, a cyclopentyl or cyclohexyl group, with the proviso that in case one of R[3] and R[3'] is a cyclopentyl or cyclohexyl group, the other is H.

In another preferred embodiment R is a group of formula

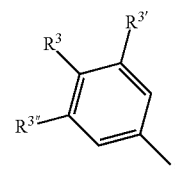

wherein
R[3] is H, or a $C_1$-$C_5$alkyl group, and
R[3'] is H, especially a $C_1$-$C_5$alkyl group, a cyclopentyl or cyclohexyl group, and
R[3''] is H, especially a $C_1$-$C_5$alkyl group, a cyclopentyl or cyclohexyl group, with the proviso that if R[3'] and R[3''] are different from H, then R[3] is H.

In another preferred embodiment R[4'] is H; R[4] is H, or a $C_1$-$C_5$alkyl group; and R[5] is H, or a $C_1$-$C_5$alkyl group.

In another preferred embodiment R[4] is H, or a $C_1$-$C_5$alkyl group, R[5] is H, or a $C_1$-$C_5$alkyl group, R[4'] is a group of formula

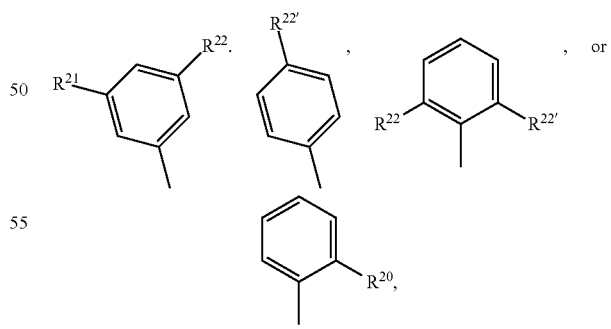

wherein
R[20] is H, or a $C_1$-$C_5$alkyl group,
R[21] is H, or a $C_1$-$C_5$alkyl group,
R[22] is a $C_1$-$C_5$alkyl group, and
R[22'] is a $C_1$-$C_5$alkyl group.

In another preferred embodiment R[4] is H; R[5] is H; and R[4'] is a group of formula

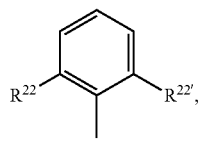

wherein R²² and R²²' are as defined above.

In another preferred embodiment R⁴ is H; R⁴' is H, or a C₁-C₅alkyl group; and R⁵ is C₁-C₅alkyl group.

In another preferred embodiment R⁴ and R⁴' are H; and R⁵ is a group of formula

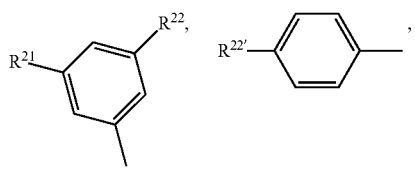

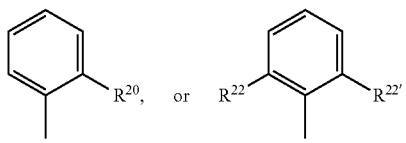

wherein $R^{20}$ is H, or a $C_1$-$C_5$alkyl group, $R^{21}$ is H, or a $C_1$-$C_5$alkyl group, $R^{22}$ is a $C_1$-$C_5$alkyl group, and $R^{22'}$ is a $C_1$-$C_5$alkyl group.

$R^6$ and $R^7$ are preferably independently of each other hydrogen, a $C_1$-$C_8$alkyl group, especially ethyl, isopropyl, isobutyl, or tert-butyl; a $C_3$-$C_6$cycloalkyl group, especially cyclopentyl, or cyclohexyl; or $R^6$ and $R^7$ form together a ring

with the proviso that if one of $R^6$ and $R^7$ is a $C_3$-$C_6$cycloalkyl group, the other is H.

L is preferably a group (X-1), (X-2), (X-3), (X-4), (X-5), (X-6), (X-7), (X-8), (X-9), (X-10), (X-11), (X-12), (X-13), (X-14), (X-15), (X-16), (X-17), (X-18), (X-19), (X-20), (X-21), (X-22), (X-23), (X-24), (X-25), (X-26), or (X-27); more preferably a group (X-1), (X-2), (X-3), or (X-4). In case M is Ir and L is a group (X-5) to (X-27), o is preferably 2 and m is preferably 1.

In a preferred embodiment the present invention is directed to metal-carbenes of formula

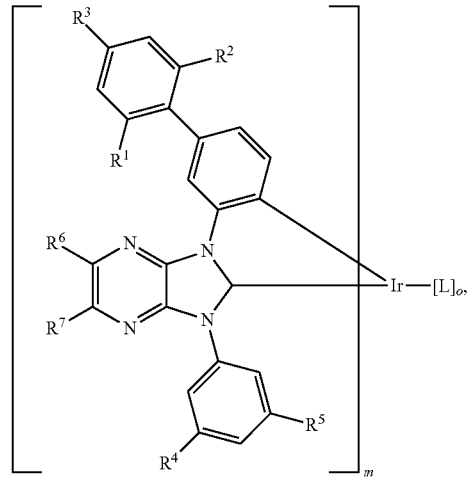

(IIIa)

wherein $R^1$ and $R^2$ are independently of each other a $C_1$-$C_5$alkyl group, especially methyl, ethyl, iso-propyl, isobutyl and neopentyl; a cyclopentyl or cyclohexyl group, $R^3$ is H, a $C_1$-$C_4$alkyl group, especially methyl, isopropyl, a group of formula

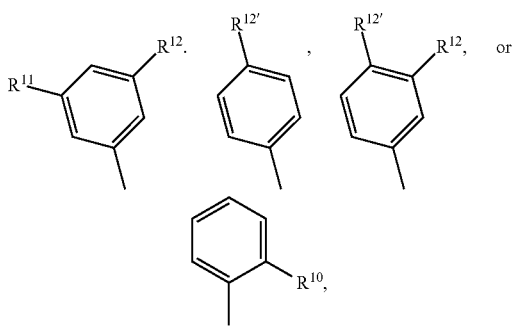

wherein $R^{10}$ is H, or a $C_1$-$C_5$alkyl group, $R^{11}$ is H, or a $C_1$-$C_5$alkyl group, especially methyl, or isopropyl;

$R^{12}$ is a $C_1$-$C_5$alkyl group, especially methyl, or isopropyl; and $R^{12'}$ is a $C_1$-$C_5$alkyl group, especially methyl, or isopropyl;

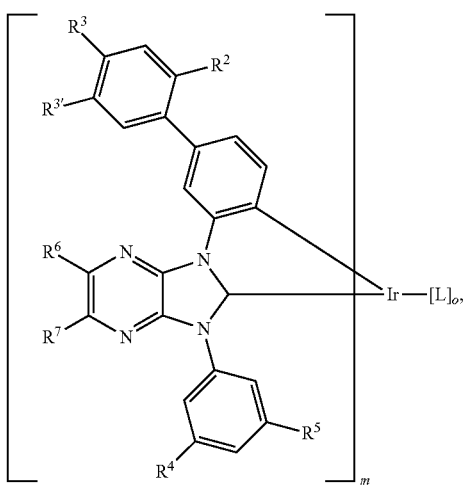

(IIIb)

wherein
$R^2$ is $CF_3$, a $C_1$-$C_5$alkyl group, a cyclopentyl or cyclohexyl group;
$R^3$ is H, a $C_1$-$C_5$alkyl group, a cyclopentyl or cyclohexyl group; and
$R^{3'}$ is H, a $C_1$-$C_5$alkyl group, a cyclopentyl or cyclohexyl group; with the proviso that in
case one of $R^3$ and $R^{3'}$ is a cyclopentyl or cyclohexyl group, the other is H; or

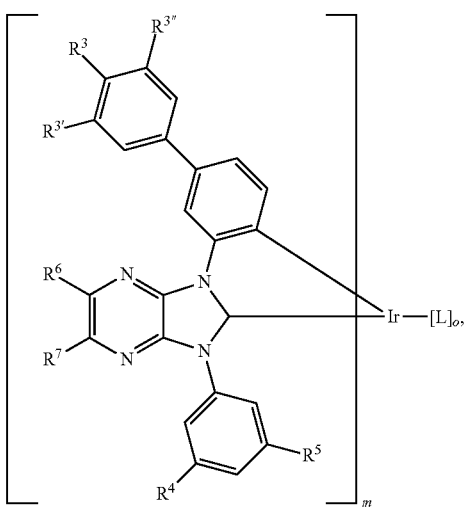

(IIIc)

wherein
$R^3$ is H, a $C_1$-$C_5$alkyl group, a cyclopentyl, or cyclohexyl group;
$R^{3'}$ is H, especially a $C_1$-$C_5$alkyl group, a cyclopentyl or cyclohexyl group, and
$R^{3''}$ is H, especially a $C_1$-$C_5$alkyl group, a cyclopentyl or cyclohexyl group;
with the proviso that in case one of $R^3$ and $R^{3'}$ is a cyclopentyl or cyclohexyl group, the other is H;
and with the further proviso that in case one of $R^{3''}$ and $R^3$ is a cyclopentyl or a cyclohexyl group, the other is H;
o is 1, or 2; m is 1, or 2; the sum of m+o is 3;
L is a group of formula (X-1), (X-2), (X-3), (X-4), (X-5), (X-6), (X-7), (X-8), (X-9), (X-10), (X-11), (X-12), (X-13), (X-14), (X-15), (X-16), (X-17), (X-18), (X-19), (X-20), (X-21), (X-22), (X-23), (X-24), (X-25), (X-26), or (X-27) as defined above, more preferably a group (X-1), (X-2), (X-3), or (X-4); $R^4$ and $R^5$ are independently of each other H, or a $C_1$-$C_5$alkyl group, especially methyl, ethyl, iso-propyl, or isobutyl, tert-butyl, or sec-butyl; a cyclopentyl or cyclohexyl group; and $R^6$ and $R^7$ are independently of each other hydrogen, a $C_1$-$C_8$alkyl group, a $C_3$-$C_6$cycloalkyl group; or
$R^6$ and $R^7$ form together a ring

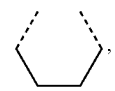

with the proviso that if one of $R^6$ and $R^7$ is a a $C_3$-$C_6$cycloalkyl group, the other is H.

In case M is Ir and L is a group (X-5) to (X-27), o is preferably 2 and m is preferably 1. In case M is Ir and L is a group (X-1) to (X-4), o is preferably 1 and m is preferably 2.

In said embodiment metal-carbene complexes of formula

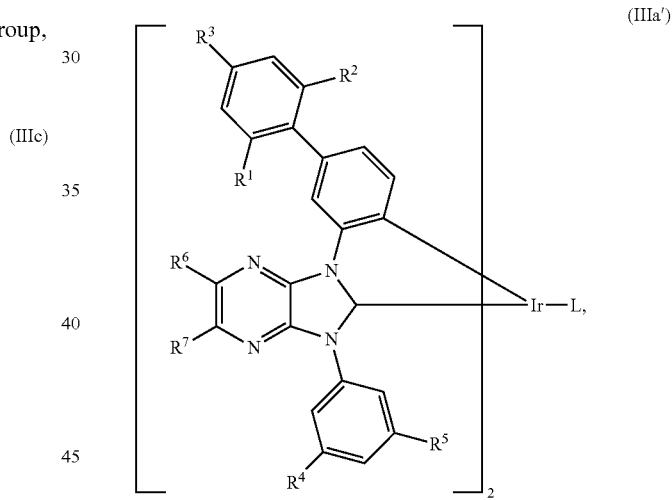

(IIIa')

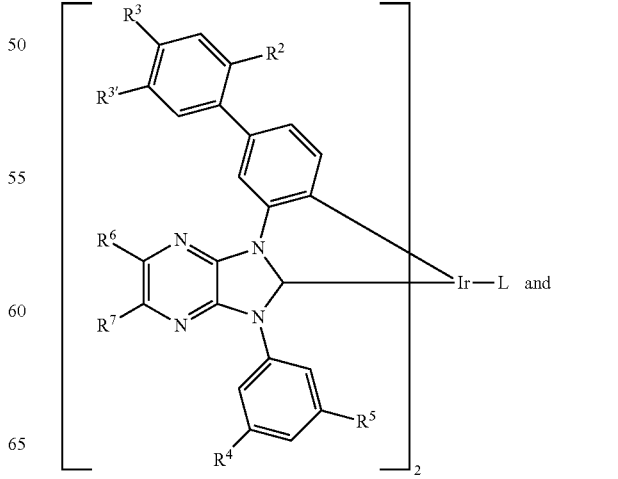

(IIIb')

and

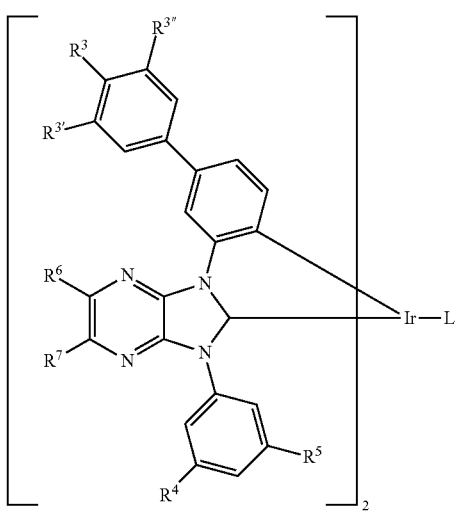

(IIIc′)

are preferred, wherein L is a group (X-1) to (X-4) and the other substituents are as defined above.

In another preferred embodiment the present invention is directed to metal-carbene complexes of formula

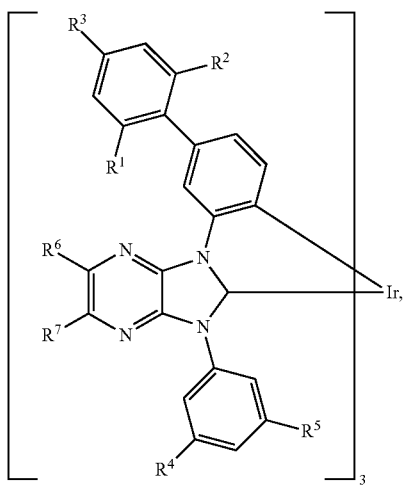

(IIId)

wherein
$R^1$ and $R^2$ are independently of each other a $C_1$-$C_5$alkyl group, especially methyl, ethyl, iso-propyl and isobutyl; a cyclopentyl or cyclohexyl group,
$R^3$ is H, a $C_1$-$C_4$alkyl group, especially methyl, isopropyl, a group of formula

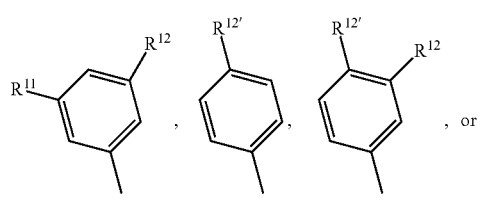

, or

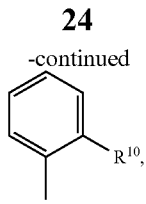

wherein
$R^{10}$ is H, or a $C_1$-$C_5$alkyl group, especially methyl, or isopropyl;
$R^{11}$ is a $C_1$-$C_5$alkyl group, especially methyl, or isopropyl;
$R^{12}$ is a $C_1$-$C_5$alkyl group, especially methyl, or isopropyl;
$R^{12'}$ is a $C_1$-$C_5$alkyl group, especially methyl, or isopropyl;

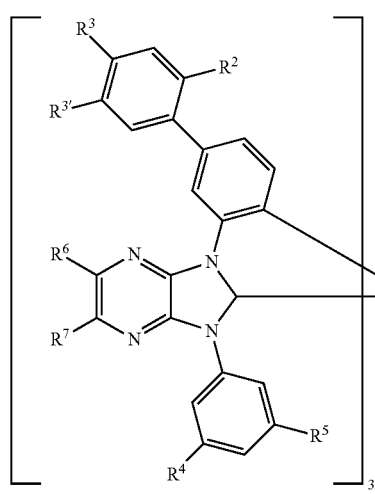

(IIIe)

wherein
$R^2$ is $CF_3$, a $C_1$-$C_5$alkyl group, a cyclopentyl or cyclohexyl group;
$R^3$ is H, a $C_1$-$C_5$alkyl group, a cyclopentyl or cyclohexyl group; and
$R^{3'}$ is H, a $C_1$-$C_5$alkyl group, a cyclopentyl or cyclohexyl group; with the proviso that in case one of $R^3$ and $R^{3'}$ is a cyclopentyl or cyclohexyl group, the other is H; or

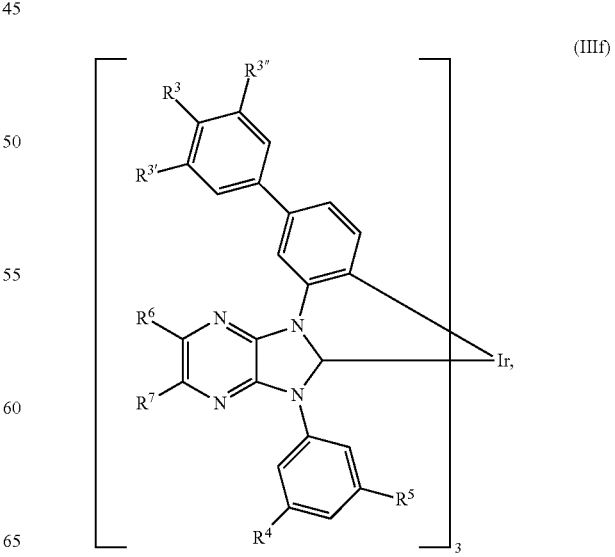

(IIIf)

wherein

R³ is H, or a C₁-C₅alkyl group, and

R³' is H, especially a C₁-C₅alkyl group, a cyclopentyl or cyclohexyl group, and

R³" is H, especially a C₁-C₅alkyl group, a cyclopentyl or cyclohexyl group; with the proviso that in case one of R³ and R³' is a cyclopentyl or cyclohexyl group, the other is H; and with the further proviso that in case one of R³" and R³ is a cyclopentyl or a cyclohexyl group, the other is H; and R⁴ and R⁵ are independently of each other H, or a C₁-C₅alkyl group, especially methyl, ethyl, iso-propyl, or isobutyl, tert-butyl, or sec-butyl; a cyclopentyl or cyclohexyl group; and R⁶ and R⁷ are independently of each other hydrogen, a C₁-C₈alkyl group, a C₃-C₆cycloalkyl group; or R⁶ and R⁷ form together a ring

, with the proviso that if one of R⁶ and R⁷ is a C₃-C₆cycloalkyl group, the other is H.

Compounds of formula (IIIa), (IIIb), (IIId) and (IIIe) are more preferred than compounds of formula (IIIc) and (IIIf). Compounds of formula (IIIa') and (IIIb') are more preferred than compounds of formula (IIIc').

In a particularly preferred embodiment the present invention is directed to metal-carbene complexes of formula especially

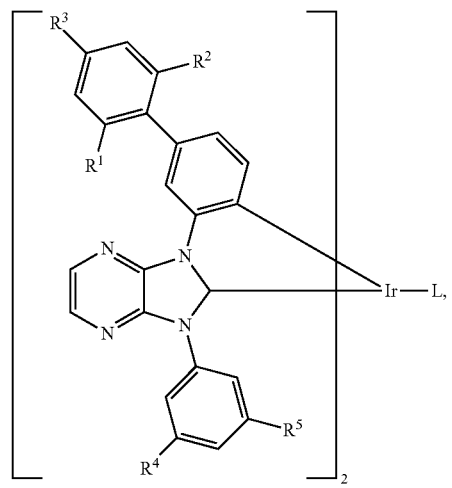

(IIIa-1)

wherein

R¹ and R² are independently of each other a C₁-C₅alkyl group, especially methyl, ethyl, iso-propyl, isobutyl and neopentyl; a cyclopentyl or cyclohexyl group, R³ is H, or a C₁-C₄alkyl group;

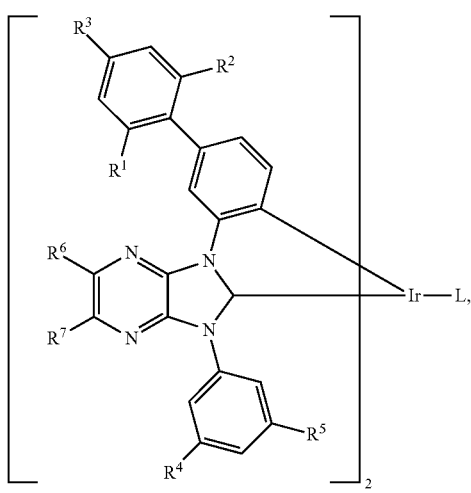

(IIIa)

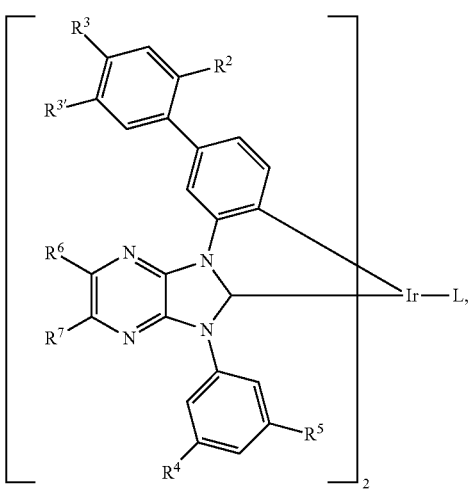

(IIIb)

especially

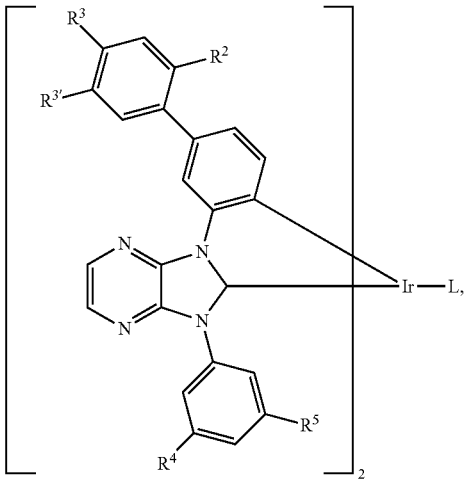

(IIIb-1)

wherein
- R² is CF₃, especially a $C_1$-$C_5$alkyl group, especially methyl, ethyl, iso-propyl and isobutyl; a cyclopentyl or cyclohexyl group;
- R³ is H, a $C_1$-$C_5$alkyl group, especially methyl, ethyl, iso-propyl and isobutyl; a cyclopentyl or cyclohexyl group; and
- R³' is H, a $C_1$-$C_5$alkyl group, especially methyl, ethyl, iso-propyl and isobutyl; a cyclopentyl or cyclohexyl group; with the proviso that in case one of R³ and R³' is a cyclopentyl or cyclohexyl group, the other is H; or

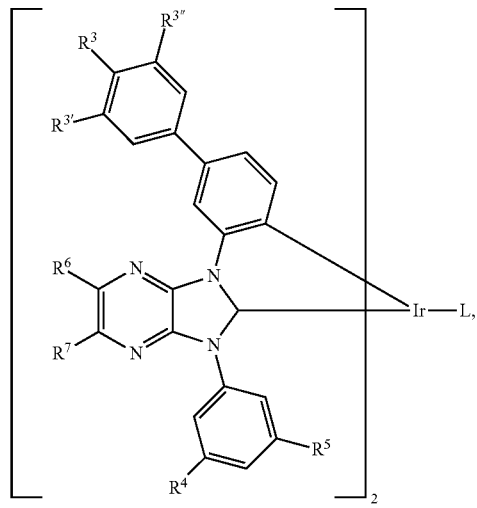

(IIIc)

especially

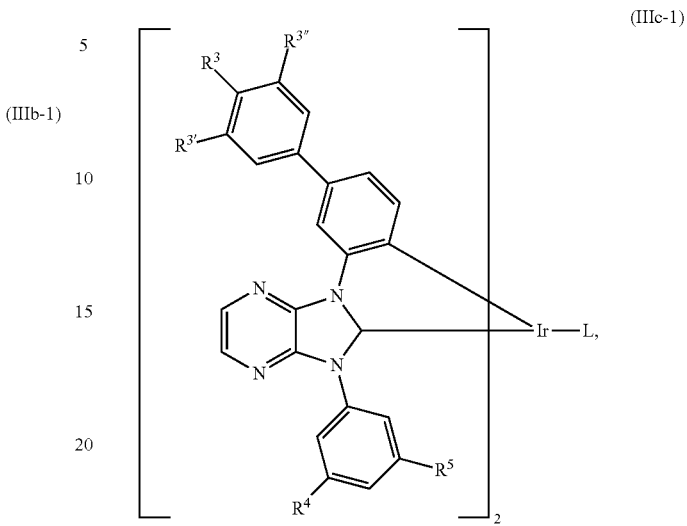

(IIIc-1)

wherein
- R³ is H, or a $C_1$-$C_5$alkyl group, especially methyl, ethyl, iso-propyl and isobutyl;
- R³' is H, or a $C_1$-$C_5$alkyl group, especially methyl, ethyl, iso-propyl and isobutyl; and
- R³" is H, or a $C_1$-$C_5$alkyl group, especially methyl, ethyl, iso-propyl and isobutyl; with the proviso that if R³' and R³" are different from H, then R³ is H;

L is a group (X-1), (X-2), (X-3), (X-4), (X-5), (X-6), (X-7), (X-8), (X-9), (X-10), (X-11), (X-12), (X-13), (X-14), (X-15), (X-16), (X-17), (X-18), (X-19), (X-20), (X-21), (X-22), (X-23), (X-24), (X-25), (X-26), or (X-27), especially (X-1), (X-2), (X-3), or (X-4), very especially (X-4); and R⁴ and R⁵ are independently of each other H, or a $C_1$-$C_5$alkyl group, especially methyl, ethyl, iso-propyl, or isobutyl, and R⁶ and W are independently of each other hydrogen, a $C_1$-$C_8$alkyl group, a $C_3$-$C_6$cycloalkyl group; or R⁶ and R⁷ form together a ring

with the proviso that if one of R⁶ and R⁷ is a a $C_1$-$C_8$alkyl group, or $C_3$-$C_6$cycloalkyl group, the other is H.

In another particularly preferred embodiment the present invention is directed to metal-carbene complexes of formula

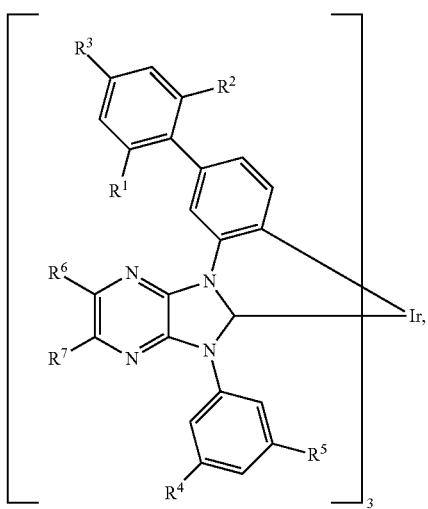

(IIId)

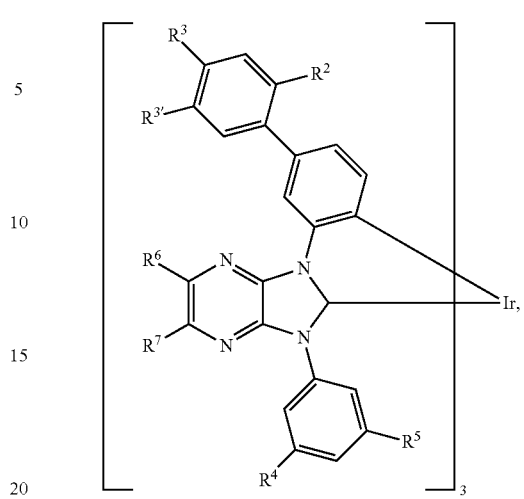

(IIIe)

especially

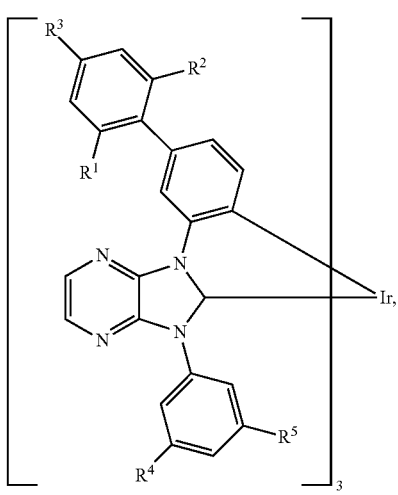

(IIId-1)

especially

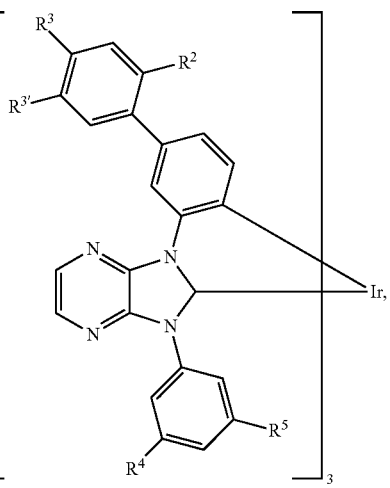

(IIIe-1)

wherein
$R^1$ and $R^2$ are independently of each other a $C_1$-$C_5$alkyl group, especially methyl, ethyl, iso-propyl, isobutyl and neopentyl; a cyclopentyl or cyclohexyl group,
$R^3$ is H, or a $C_1$-$C_4$alkyl group;

wherein
$R^2$ is $CF_3$, especially a $C_1$-$C_5$alkyl group, especially methyl, ethyl, iso-propyl and isobutyl; a cyclopentyl or cyclohexyl group;
$R^3$ is H, a $C_1$-$C_5$alkyl group, especially methyl, ethyl, iso-propyl and isobutyl; a cyclopentyl or cyclohexyl group; and
$R^{3'}$ is H, a $C_1$-$C_5$alkyl group, especially methyl, ethyl, iso-propyl and isobutyl; a cyclopentyl or cyclohexyl group; with the proviso that in case one of $R^3$ and $R^{3'}$ is a cyclopentyl or cyclohexyl group, the other is H; or (IIIf)

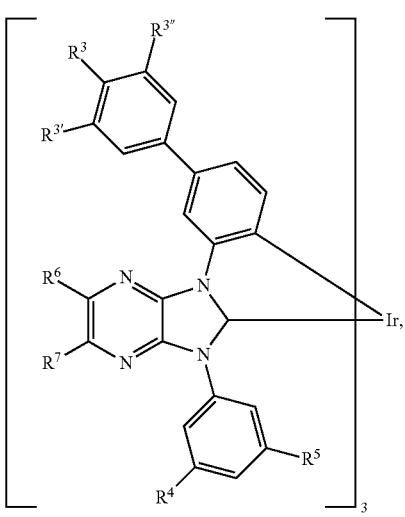

especially (IIIf-1)

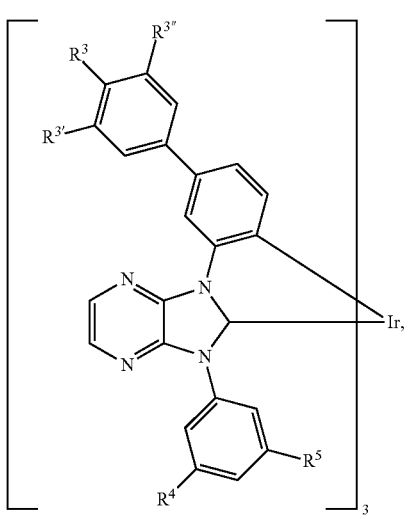

wherein
- $R^3$ is H, or a $C_1$-$C_5$alkyl group, especially methyl, ethyl, iso-propyl and isobutyl;
- $R^{3'}$ is H, or a $C_1$-$C_5$alkyl group, especially methyl, ethyl, iso-propyl and isobutyl; and
- $R^{3''}$ is H, or a $C_1$-$C_5$alkyl group, especially methyl, ethyl, iso-propyl and isobutyl; with the proviso that if $R^3$ and $R^{3'}$ are different from H, then $R^3$ is H; and
- $R^4$ and $R^5$ are independently of each other H, or a $C_1$-$C_5$alkyl group, especially methyl, ethyl, iso-propyl, or isobutyl, and
- $R^6$ and $R^7$ are independently of each other hydrogen, a $C_1$-$C_8$alkyl group, a $C_3$-$C_6$cycloalkyl group; or
- $R^6$ and $R^7$ form together a ring

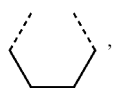, with the proviso that if one of $R^6$ and $R^7$ is a $C_1$-$C_8$alkyl group, or a $C_3$-$C_6$cycloalkyl group, the other is H. $R^4$ and $R^5$ are preferably H.

Metal-carbene complexes of formula (IIId-1) and (IIIe-1) are more preferred than metal-carbene complexes of formula (IIId-2)

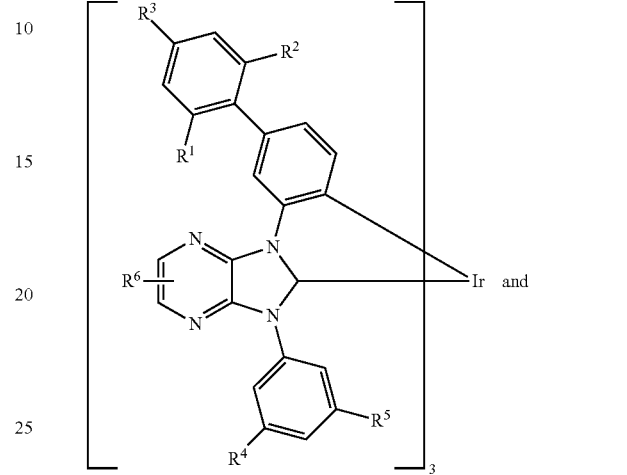

and (IIIe-2)

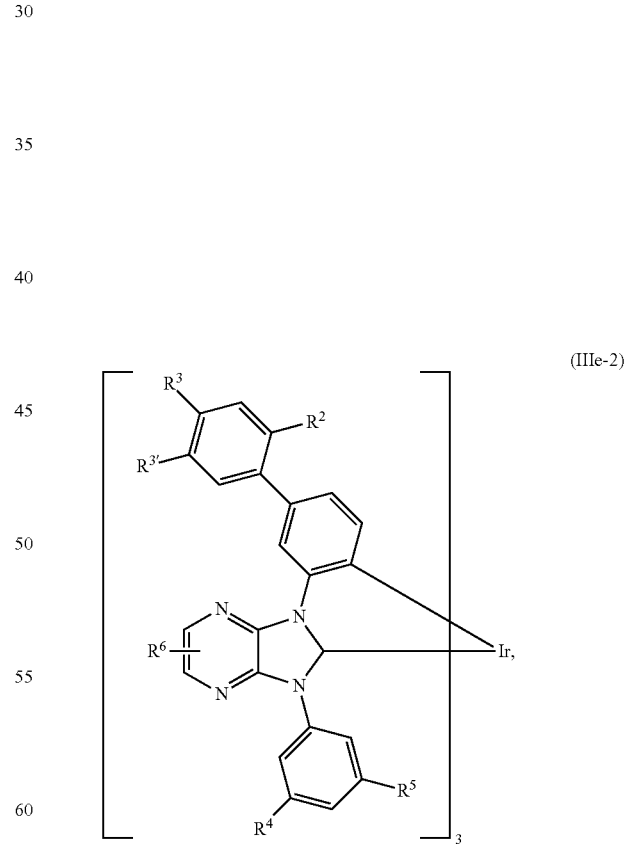

respectively. $R^6$ is in the metal-carbene complexes of formula (IIId-2) and (IIIe-2) a $C_1$-$C_8$alkyl group, or a $C_3$-$C_6$cycloalkyl group, especially a $C_1$-$C_8$alkyl group. $R^1$, $R^2$, $R^3$, $R^{3'}$, $R^4$ and $R^6$ are as defined above.

For example, the metal-carbene complex of formula
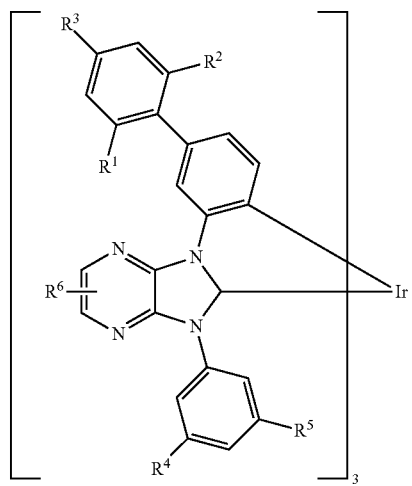
(IIId-2)
Isomer 1
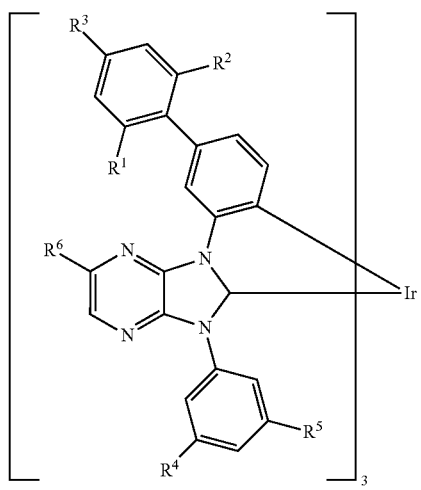
Isomer 2
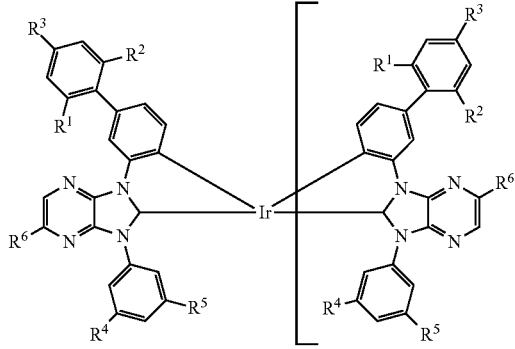
Isomer 3
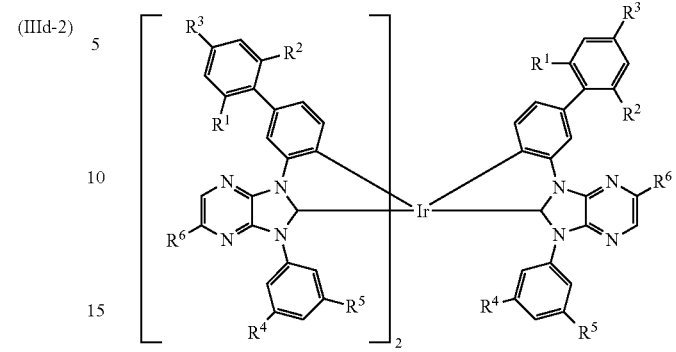
Isomer 4
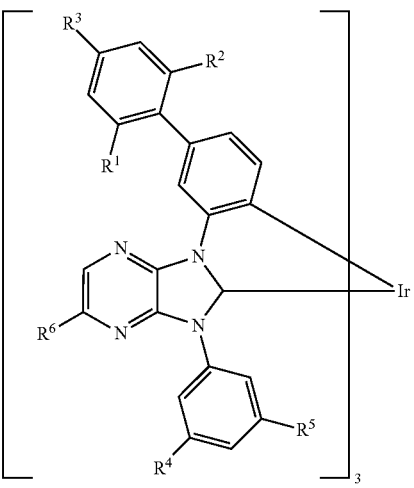
can be present as a mixture of different isomeric forms:
Formula (IIId-2) is an idealized or simplified manner of representation and shall comprise all isomeric forms. $R^4$ and $R^5$ are preferably H.
Examples of metal carbene-complexes are shown below:
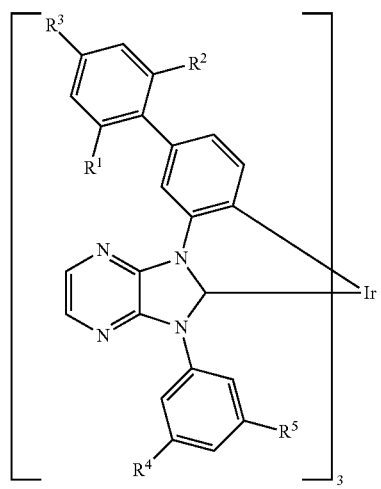

| Cpd. | R¹ | R² | R³ | R⁴ = R⁵ |
|---|---|---|---|---|
| A-1 | —CH₃ | —CH₃ | H | H |
| A-2 | —CH₂CH₃ | —CH₂CH₃ | H | H |
| A-3 | iso-propyl | iso-propyl | H | H |
| A-4 | iso-butyl | iso-butyl | H | H |
| A-5 | neopentyl | neopentyl | H | H |
| A-6 | —CH₃ | —CH₂CH₃ | H | H |
| A-7 | cyclopentyl | cyclopentyl | H | H |
| A-8 | cyclohexyl | cyclohexyl | H | H |
| A-9 | —CH₃ | —CH₃ | —CH₃ | H |
| A-10 | ethyl | ethyl | —CH₃ | H |
| A-11 | iso-propyl | iso-propyl | —CH₃ | H |
| A-12 | —CH₃ | —CH₃ | iso-propyl | H |
| A-13 | ethyl | ethyl | iso-propyl | H |
| A-14 | iso-propyl | iso-propyl | iso-propyl | H |
| A-15 | —CH₃ | —CH₃ | H | —CH₃ |
| A-16 | —CH₂CH₃ | —CH₂CH₃ | H | —CH₃ |
| A-17 | iso-propyl | iso-propyl | H | —CH₃ |
| A-18 | iso-butyl | iso-butyl | H | —CH₃ |
| A-19 | neopentyl | neopentyl | H | —CH₃ |
| A-20 | —CH₃ | —CH₂CH₃ | H | —CH₃ |
| A-21 | cyclopentyl | cyclopentyl | H | —CH₃ |
| A-22 | cyclohexyl | cyclohexyl | H | —CH₃ |
| A-23 | —CH₃ | —CH₃ | —CH₃ | —CH₃ |
| A-24 | ethyl | ethyl | —CH₃ | —CH₃ |
| A-25 | iso-propyl | iso-propyl | —CH₃ | —CH₃ |
| A-26 | —CH₃ | —CH₃ | iso-propyl | —CH₃ |
| A-27 | ethyl | ethyl | iso-propyl | —CH₃ |
| A-28 | iso-propyl | iso-propyl | iso-propyl | —CH₃ |
| A-29 | —CH₃ | —CH₃ | H | —CH₂CH₃ |
| A-30 | —CH₂CH₃ | —CH₂CH₃ | H | —CH₂CH₃ |
| A-31 | iso-propyl | iso-propyl | H | —CH₂CH₃ |
| A-32 | iso-butyl | iso-butyl | H | —CH₂CH₃ |
| A-33 | —CH₃ | —CH₂CH₃ | H | —CH₂CH₃ |
| A-34 | neopentyl | neopentyl | H | —CH₂CH₃ |
| A-35 | cyclopentyl | cyclopentyl | H | —CH₂CH₃ |
| A-36 | cyclohexyl | cyclohexyl | H | —CH₂CH₃ |
| A-37 | —CH₃ | —CH₃ | —CH₃ | —CH₂CH₃ |
| A-38 | ethyl | ethyl | —CH₃ | —CH₂CH₃ |
| A-39 | iso-propyl | iso-propyl | —CH₃ | —CH₂CH₃ |
| A-40 | —CH₃ | —CH₃ | iso-propyl | —CH₂CH₃ |
| A-41 | ethyl | ethyl | iso-propyl | —CH₂CH₃ |
| A-42 | iso-propyl | iso-propyl | iso-propyl | —CH₂CH₃ |
| A-43 | —CH₃ | —CH₃ | H | iso-propyl |
| A-44 | —CH₂CH₃ | —CH₂CH₃ | H | iso-propyl |
| A-45 | iso-propyl | iso-propyl | H | iso-propyl |
| A-46 | iso-butyl | iso-butyl | H | iso-propyl |
| A-47 | neopentyl | neopentyl | H | iso-propyl |
| A-48 | —CH₃ | —CH₂CH₃ | H | iso-propyl |
| A-49 | cyclopentyl | cyclopentyl | H | iso-propyl |
| A-50 | cyclohexyl | cyclohexyl | H | iso-propyl |
| A-51 | —CH₃ | —CH₃ | —CH₃ | iso-propyl |
| A-52 | ethyl | ethyl | —CH₃ | iso-propyl |
| A-53 | iso-propyl | iso-propyl | —CH₃ | iso-propyl |
| A-54 | —CH₃ | —CH₃ | iso-propyl | iso-propyl |
| A-55 | ethyl | ethyl | iso-propyl | iso-propyl |
| A-56 | iso-propyl | iso-propyl | iso-propyl | iso-propyl |
| A-57 | —CH₃ | —CH₃ | H | iso-butyl |
| A-58 | —CH₂CH₃ | —CH₂CH₃ | H | iso-butyl |
| A-59 | iso-propyl | iso-propyl | H | iso-butyl |
| A-60 | iso-butyl | iso-butyl | H | iso-butyl |
| A-61 | neopentyl | neopentyl | H | iso-butyl |
| A-62 | —CH₃ | —CH₂CH₃ | H | iso-butyl |
| A-63 | cyclopentyl | cyclopentyl | H | iso-butyl |
| A-64 | cyclohexyl | cyclohexyl | H | iso-butyl |
| A-65 | —CH₃ | —CH₃ | —CH₃ | iso-butyl |
| A-66 | ethyl | ethyl | —CH₃ | iso-butyl |
| A-67 | iso-propyl | iso-propyl | —CH₃ | iso-butyl |
| A-68 | —CH₃ | —CH₃ | iso-propyl | iso-butyl |
| A-69 | ethyl | ethyl | iso-propyl | iso-butyl |
| A-70 | iso-propyl | iso-propyl | iso-propyl | iso-butyl |
| A-71 | —CH₃ | —CH₃ | H | tert-butyl |
| A-72 | —CH₂CH₃ | —CH₂CH₃ | H | tert-butyl |
| A-73 | iso-propyl | iso-propyl | H | tert-butyl |
| A-74 | iso-butyl | iso-butyl | H | tert-butyl |
| A-75 | neopentyl | neopentyl | H | tert-butyl |
| A-76 | —CH₃ | —CH₂CH₃ | H | tert-butyl |
| A-77 | cyclopentyl | cyclopentyl | H | tert-butyl |
| A-78 | cyclohexyl | cyclohexyl | H | tert-butyl |
| A-79 | —CH₃ | —CH₃ | —CH₃ | tert-butyl |
| A-80 | ethyl | ethyl | —CH₃ | tert-butyl |
| A-81 | iso-propyl | iso-propyl | —CH₃ | tert-butyl |
| A-82 | —CH₃ | —CH₃ | iso-propyl | tert-butyl |
| A-83 | ethyl | ethyl | iso-propyl | tert-butyl |
| A-84 | iso-propyl | iso-propyl | iso-propyl | tert-butyl |

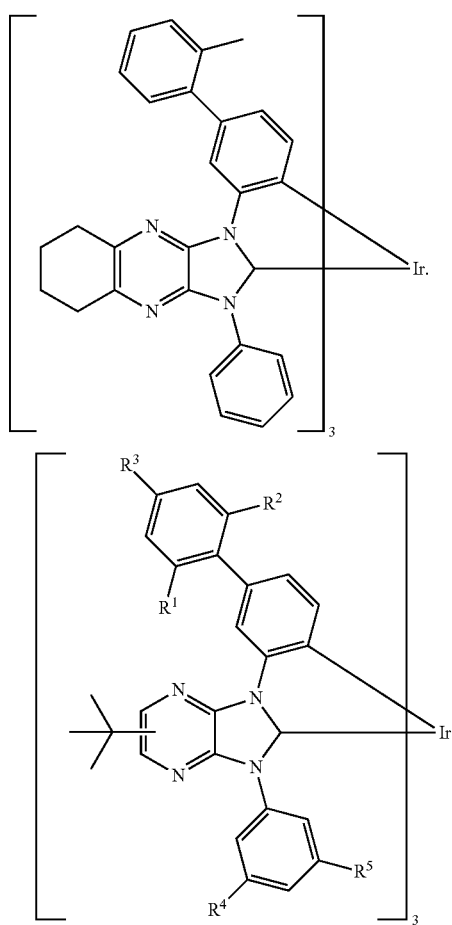

(A-85)

-continued

| Cpd. | R¹ | R² | R³ | R⁴ = R⁵ |
|---|---|---|---|---|
| A'-21 | cyclopentyl | cyclopentyl | H | —CH₃ |
| A'-22 | cyclohexyl | cyclohexyl | H | —CH₃ |
| A'-23 | —CH₃ | —CH₃ | —CH₃ | —CH₃ |
| A'-24 | ethyl | ethyl | —CH₃ | —CH₃ |
| A'-25 | iso-propyl | iso-propyl | —CH₃ | —CH₃ |
| A'-26 | —CH₃ | —CH₃ | iso-propyl | —CH₃ |
| A'-27 | ethyl | ethyl | iso-propyl | —CH₃ |
| A'-28 | iso-propyl | iso-propyl | iso-propyl | —CH₃ |
| A'-29 | —CH₃ | —CH₃ | H | —CH₂CH₃ |
| A'-30 | —CH₂CH₃ | —CH₂CH₃ | H | —CH₂CH₃ |
| A'-31 | iso-propyl | iso-propyl | H | —CH₂CH₃ |
| A'-32 | iso-butyl | iso-butyl | H | —CH₂CH₃ |
| A'-33 | —CH₃ | —CH₂CH₃ | H | —CH₂CH₃ |
| A'-34 | neopentyl | neopentyl | H | —CH₂CH₃ |
| A'-35 | cyclopentyl | cyclopentyl | H | —CH₂CH₃ |
| A'-36 | cyclohexyl | cyclohexyl | H | —CH₂CH₃ |
| A'-37 | —CH₃ | —CH₃ | —CH₃ | —CH₂CH₃ |
| A'-38 | ethyl | ethyl | —CH₃ | —CH₂CH₃ |
| A'-39 | iso-propyl | iso-propyl | —CH₃ | —CH₂CH₃ |
| A'-40 | —CH₃ | —CH₃ | iso-propyl | —CH₂CH₃ |
| A'-41 | ethyl | ethyl | iso-propyl | —CH₂CH₃ |
| A'-42 | iso-propyl | iso-propyl | iso-propyl | —CH₂CH₃ |
| A'-43 | —CH₃ | —CH₃ | H | iso-propyl |
| A'-44 | —CH₂CH₃ | —CH₂CH₃ | H | iso-propyl |
| A'-45 | iso-propyl | iso-propyl | H | iso-propyl |
| A'-46 | iso-butyl | iso-butyl | H | iso-propyl |
| A'-47 | neopentyl | neopentyl | H | iso-propyl |
| A'-48 | —CH₃ | —CH₂CH₃ | H | iso-propyl |
| A'-49 | cyclopentyl | cyclopentyl | H | iso-propyl |
| A'-50 | cyclohexyl | cyclohexyl | H | iso-propyl |
| A'-51 | —CH₃ | —CH₃ | —CH₃ | iso-propyl |
| A'-52 | ethyl | ethyl | —CH₃ | iso-propyl |
| A'-53 | iso-propyl | iso-propyl | —CH₃ | iso-propyl |
| A'-54 | —CH₃ | —CH₃ | iso-propyl | iso-propyl |
| A'-55 | ethyl | ethyl | iso-propyl | iso-propyl |
| A'-56 | iso-propyl | iso-propyl | iso-propyl | iso-propyl |
| A'-57 | —CH₃ | —CH₃ | H | iso-butyl |
| A'-58 | —CH₂CH₃ | —CH₂CH₃ | H | iso-butyl |
| A'-59 | iso-propyl | iso-propyl | H | iso-butyl |
| A'-60 | iso-butyl | iso-butyl | H | iso-butyl |
| A'-61 | neopentyl | neopentyl | H | iso-butyl |
| A'-62 | —CH₃ | —CH₂CH₃ | H | iso-butyl |
| A'-63 | cyclopentyl | cyclopentyl | H | iso-butyl |
| A'-64 | cyclohexyl | cyclohexyl | H | iso-butyl |

| Cpd. | R¹ | R² | R³ | R⁴ = R⁵ |
|---|---|---|---|---|
| A'-1 | —CH₃ | —CH₃ | H | H |
| A'-2 | —CH₂CH₃ | —CH₂CH₃ | H | H |
| A'-3 | iso-propyl | iso-propyl | H | H |
| A'-4 | iso-butyl | iso-butyl | H | H |
| A'-5 | neopentyl | neopentyl | H | H |
| A'-6 | —CH₃ | —CH₂CH₃ | H | H |
| A'-7 | cyclopentyl | cyclopentyl | H | H |
| A'-8 | cyclohexyl | cyclohexyl | H | H |
| A'-9 | —CH₃ | —CH₃ | —CH₃ | H |
| A'-10 | ethyl | ethyl | —CH₃ | H |
| A'-11 | iso-propyl | iso-propyl | —CH₃ | H |
| A'-12 | —CH₃ | —CH₃ | iso-propyl | H |
| A'-13 | ethyl | ethyl | iso-propyl | H |
| A'-14 | iso-propyl | iso-propyl | iso-propyl | H |
| A'-15 | —CH₃ | —CH₃ | H | —CH₃ |
| A'-16 | —CH₂CH₃ | —CH₂CH₃ | H | —CH₃ |
| A'-17 | iso-propyl | iso-propyl | H | —CH₃ |
| A'-18 | iso-butyl | iso-butyl | H | —CH₃ |
| A'-19 | neopentyl | neopentyl | H | —CH₃ |
| A'-20 | —CH₃ | —CH₂CH₃ | H | —CH₃ |

-continued

| Cpd. | R¹ | R² | R³ | R⁴ = R⁵ |
|---|---|---|---|---|
| A'-65 | —CH₃ | —CH₃ | —CH₃ | iso-butyl |
| A'-66 | ethyl | ethyl | —CH₃ | iso-butyl |
| A'-67 | iso-propyl | iso-propyl | —CH₃ | iso-butyl |
| A'-68 | —CH₃ | —CH₃ | iso-propyl | iso-butyl |
| A'-69 | ethyl | ethyl | iso-propyl | iso-butyl |
| A'-70 | iso-propyl | iso-propyl | iso-propyl | iso-butyl |

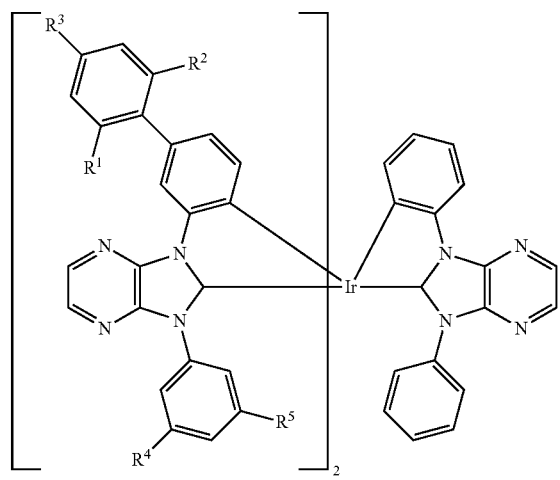

| Cpd. | R¹ | R² | R³ | R⁴ = R⁵ |
|---|---|---|---|---|
| B-1 | —CH₃ | —CH₃ | H | H |
| B-2 | —CH₂CH₃ | —CH₂CH₃ | H | H |
| B-3 | iso-propyl | iso-propyl | H | H |
| B-4 | iso-butyl | iso-butyl | H | H |
| B-5 | neopentyl | neopentyl | H | H |
| B-6 | —CH₃ | —CH₂CH₃ | H | H |
| B-7 | cyclopentyl | cyclopentyl | H | H |
| B-8 | cyclohexyl | cyclohexyl | H | H |
| B-9 | —CH₃ | —CH₃ | —CH₃ | H |
| B-10 | ethyl | ethyl | —CH₃ | H |
| B-11 | iso-propyl | iso-propyl | —CH₃ | H |
| B-12 | —CH₃ | —CH₃ | iso-propyl | H |
| B-13 | ethyl | ethyl | iso-propyl | H |
| B-14 | iso-propyl | iso-propyl | iso-propyl | H |
| B-15 | —CH₃ | —CH₃ | H | —CH₃ |
| B-16 | —CH₂CH₃ | —CH₂CH₃ | H | —CH₃ |
| B-17 | iso-propyl | iso-propyl | H | —CH₃ |
| B-18 | iso-butyl | iso-butyl | H | —CH₃ |
| B-19 | neopentyl | neopentyl | H | —CH₃ |
| B-20 | —CH₃ | —CH₂CH₃ | H | —CH₃ |
| B-21 | cyclopentyl | cyclopentyl | H | —CH₃ |
| B-22 | cyclohexyl | cyclohexyl | H | —CH₃ |
| B-23 | —CH₃ | —CH₃ | —CH₃ | —CH₃ |
| B-24 | ethyl | ethyl | —CH₃ | —CH₃ |
| B-25 | iso-propyl | iso-propyl | —CH₃ | —CH₃ |
| B-26 | —CH₃ | —CH₃ | iso-propyl | —CH₃ |
| B-27 | ethyl | ethyl | iso-propyl | —CH₃ |
| B-28 | iso-propyl | iso-propyl | iso-propyl | —CH₃ |
| B-29 | —CH₃ | —CH₃ | H | —CH₂CH₃ |
| B-30 | —CH₂CH₃ | —CH₂CH₃ | H | —CH₂CH₃ |
| B-31 | iso-propyl | iso-propyl | H | —CH₂CH₃ |
| B-32 | iso-butyl | iso-butyl | H | —CH₂CH₃ |
| B-33 | —CH₃ | —CH₂CH₃ | H | —CH₂CH₃ |
| B-34 | neopentyl | neopentyl | H | —CH₂CH₃ |
| B-35 | cyclopentyl | cyclopentyl | H | —CH₂CH₃ |
| B-36 | cyclohexyl | cyclohexyl | H | —CH₂CH₃ |
| B-37 | —CH₃ | —CH₃ | —CH₃ | —CH₂CH₃ |
| B-38 | ethyl | ethyl | —CH₃ | —CH₂CH₃ |
| B-39 | iso-propyl | iso-propyl | —CH₃ | —CH₂CH₃ |
| B-40 | —CH₃ | —CH₃ | iso-propyl | —CH₂CH₃ |
| B-41 | ethyl | ethyl | iso-propyl | —CH₂CH₃ |
| B-42 | iso-propyl | iso-propyl | iso-propyl | —CH₂CH₃ |
| B-43 | —CH₃ | —CH₃ | H | iso-propyl |
| B-44 | —CH₂CH₃ | —CH₂CH₃ | H | iso-propyl |
| B-45 | iso-propyl | iso-propyl | H | iso-propyl |
| B-46 | iso-butyl | iso-butyl | H | iso-propyl |
| B-47 | neopentyl | neopentyl | H | iso-propyl |
| B-48 | —CH₃ | —CH₂CH₃ | H | iso-propyl |
| B-49 | cyclopentyl | cyclopentyl | H | iso-propyl |
| B-50 | cyclohexyl | cyclohexyl | H | iso-propyl |
| B-51 | —CH₃ | —CH₃ | —CH₃ | iso-propyl |
| B-52 | ethyl | ethyl | —CH₃ | iso-propyl |
| B-53 | iso-propyl | iso-propyl | —CH₃ | iso-propyl |
| B-54 | —CH₃ | —CH₃ | iso-propyl | iso-propyl |
| B-55 | ethyl | ethyl | iso-propyl | iso-propyl |
| B-56 | iso-propyl | iso-propyl | iso-propyl | iso-propyl |
| B-57 | —CH₃ | —CH₃ | H | iso-butyl |
| B-58 | —CH₂CH₃ | —CH₂CH₃ | H | iso-butyl |
| B-59 | iso-propyl | iso-propyl | H | iso-butyl |
| B-60 | iso-butyl | iso-butyl | H | iso-butyl |
| B-61 | neopentyl | neopentyl | H | iso-butyl |
| B-62 | —CH₃ | —CH₂CH₃ | H | iso-butyl |
| B-63 | cyclopentyl | cyclopentyl | H | iso-butyl |
| B-64 | cyclohexyl | cyclohexyl | H | iso-butyl |
| B-65 | —CH₃ | —CH₃ | —CH₃ | iso-butyl |
| B-66 | ethyl | ethyl | —CH₃ | iso-butyl |
| B-67 | iso-propyl | iso-propyl | —CH₃ | iso-butyl |
| B-68 | —CH₃ | —CH₃ | iso-propyl | iso-butyl |
| B-69 | ethyl | ethyl | iso-propyl | iso-butyl |
| B-70 | iso-propyl | iso-propyl | iso-propyl | iso-butyl |
| B-71 | —CH₃ | —CH₃ | H | tert-butyl |
| B-72 | —CH₂CH₃ | —CH₂CH₃ | H | tert-butyl |
| B-73 | iso-propyl | iso-propyl | H | tert-butyl |
| B-74 | iso-butyl | iso-butyl | H | tert-butyl |

-continued

| Cpd. | R¹ | R² | R³ | R⁴ = R⁵ |
|---|---|---|---|---|
| B-75 | neopentyl | neopentyl | H | tert-butyl |
| B-76 | —CH₃ | —CH₂CH₃ | H | tert-butyl |
| B-77 | cyclopentyl | cyclopentyl | H | tert-butyl |
| B-78 | cyclohexyl | cyclohexyl | H | tert-butyl |
| B-79 | —CH₃ | —CH₃ | —CH₃ | tert-butyl |
| B-80 | ethyl | ethyl | —CH₃ | tert-butyl |
| B-81 | iso-propyl | iso-propyl | —CH₃ | tert-butyl |
| B-82 | —CH₃ | —CH₃ | iso-propyl | tert-butyl |
| B-83 | ethyl | ethyl | iso-propyl | tert-butyl |
| B-84 | iso-propyl | iso-propyl | iso-propyl | tert-butyl |

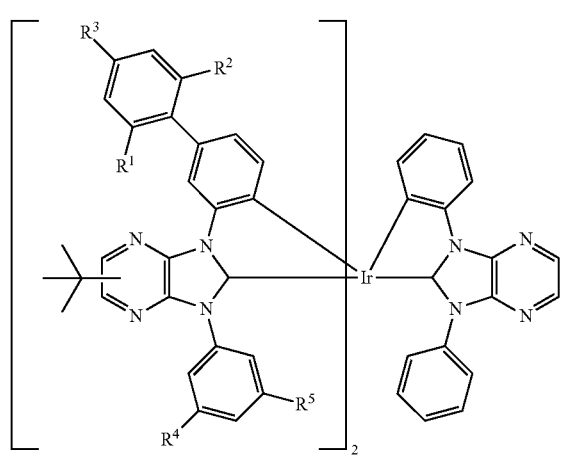

| Cpd. | R¹ | R² | R³ | R⁴ = R⁵ |
|---|---|---|---|---|
| B'-1 | —CH₃ | —CH₃ | H | H |
| B'-2 | —CH₂CH₃ | —CH₂CH₃ | H | H |
| B'-3 | iso-propyl | iso-propyl | H | H |
| B'-4 | iso-butyl | iso-butyl | H | H |
| B'-5 | neopentyl | neopentyl | H | H |
| B'-6 | —CH₃ | —CH₂CH₃ | H | H |
| B'-7 | cyclopentyl | cyclopentyl | H | H |
| B'-8 | cyclohexyl | cyclohexyl | H | H |
| B'-9 | —CH₃ | —CH₃ | —CH₃ | H |
| B'-10 | ethyl | ethyl | —CH₃ | H |
| B'-11 | iso-propyl | iso-propyl | —CH₃ | H |
| B'-12 | —CH₃ | —CH₃ | iso-propyl | H |
| B'-13 | ethyl | ethyl | iso-propyl | H |
| B'-14 | iso-propyl | iso-propyl | iso-propyl | H |
| B'-15 | —CH₃ | —CH₃ | H | —CH₃ |
| B'-16 | —CH₂CH₃ | —CH₂CH₃ | H | —CH₃ |
| B'-17 | iso-propyl | iso-propyl | H | —CH₃ |
| B'-18 | iso-butyl | iso-butyl | H | —CH₃ |
| B'-19 | neopentyl | neopentyl | H | —CH₃ |
| B'-20 | —CH₃ | —CH₂CH₃ | H | —CH₃ |
| B'-21 | cyclopentyl | cyclopentyl | H | —CH₃ |
| B'-22 | cyclohexyl | cyclohexyl | H | —CH₃ |
| B'-23 | —CH₃ | —CH₃ | —CH₃ | —CH₃ |
| B'-24 | ethyl | ethyl | —CH₃ | —CH₃ |
| B'-25 | iso-propyl | iso-propyl | —CH₃ | —CH₃ |
| B'-26 | —CH₃ | —CH₃ | iso-propyl | —CH₃ |
| B'-27 | ethyl | ethyl | iso-propyl | —CH₃ |
| B'-28 | iso-propyl | iso-propyl | iso-propyl | —CH₃ |
| B'-29 | —CH₃ | —CH₃ | H | —CH₂CH₃ |
| B'-30 | —CH₂CH₃ | —CH₂CH₃ | H | —CH₂CH₃ |
| B'-31 | iso-propyl | iso-propyl | H | —CH₂CH₃ |
| B'-32 | iso-butyl | iso-butyl | H | —CH₂CH₃ |
| B'-33 | —CH₃ | —CH₂CH₃ | H | —CH₂CH₃ |
| B'-34 | neopentyl | neopentyl | H | —CH₂CH₃ |
| B'-35 | cyclopentyl | cyclopentyl | H | —CH₂CH₃ |
| B'-36 | cyclohexyl | cyclohexyl | H | —CH₂CH₃ |
| B'-37 | —CH₃ | —CH₃ | —CH₃ | —CH₂CH₃ |
| B'-38 | ethyl | ethyl | —CH₃ | —CH₂CH₃ |
| B'-39 | iso-propyl | iso-propyl | —CH₃ | —CH₂CH₃ |
| B'-40 | —CH₃ | —CH₃ | iso-propyl | —CH₂CH₃ |
| B'-41 | ethyl | ethyl | iso-propyl | —CH₂CH₃ |
| B'-42 | iso-propyl | iso-propyl | iso-propyl | —CH₂CH₃ |
| B'-43 | —CH₃ | —CH₃ | H | iso-propyl |
| B'-44 | —CH₂CH₃ | —CH₂CH₃ | H | iso-propyl |
| B'-45 | iso-propyl | iso-propyl | H | iso-propyl |
| B'-46 | iso-butyl | iso-butyl | H | iso-propyl |
| B'-47 | neopentyl | neopentyl | H | iso-propyl |
| B'-48 | —CH₃ | —CH₂CH₃ | H | iso-propyl |
| B'-49 | cyclopentyl | cyclopentyl | H | iso-propyl |
| B'-50 | cyclohexyl | cyclohexyl | H | iso-propyl |
| B'-51 | —CH₃ | —CH₃ | —CH₃ | iso-propyl |
| B'-52 | ethyl | ethyl | —CH₃ | iso-propyl |
| B'-53 | iso-propyl | iso-propyl | —CH₃ | iso-propyl |
| B'-54 | —CH₃ | —CH₃ | iso-propyl | iso-propyl |
| B'-55 | ethyl | ethyl | iso-propyl | iso-propyl |
| B'-56 | iso-propyl | iso-propyl | iso-propyl | iso-propyl |
| B'-57 | —CH₃ | —CH₃ | H | iso-butyl |
| B'-58 | —CH₂CH₃ | —CH₂CH₃ | H | iso-butyl |
| B'-59 | iso-propyl | iso-propyl | H | iso-butyl |
| B'-60 | iso-butyl | iso-butyl | H | iso-butyl |
| B'-61 | neopentyl | neopentyl | H | iso-butyl |
| B'-62 | —CH₃ | —CH₂CH₃ | H | iso-butyl |
| B'-63 | cyclopentyl | cyclopentyl | H | iso-butyl |

-continued

| Cpd. | R¹ | R² | R³ | R⁴ = R⁵ |
|---|---|---|---|---|
| B'-64 | cyclohexyl | cyclohexyl | H | iso-butyl |
| B'-65 | —CH₃ | —CH₃ | —CH₃ | iso-butyl |
| B'-66 | ethyl | ethyl | —CH₃ | iso-butyl |
| B'-67 | iso-propyl | iso-propyl | —CH₃ | iso-butyl |
| B'-68 | —CH₃ | —CH₃ | iso-propyl | iso-butyl |
| B'-69 | ethyl | ethyl | iso-propyl | iso-butyl |
| B'-70 | iso-propyl | iso-propyl | iso-propyl | iso-butyl |

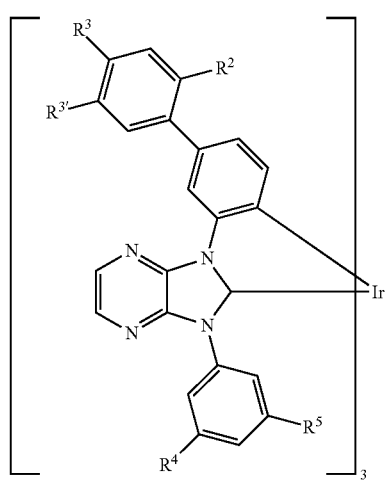

| Cpd. | R² | R³' | R³ | R⁴ = R⁵ |
|---|---|---|---|---|
| C-1 | —CH₃ | —CH₃ | H | H |
| C-2 | —CH₂CH₃ | —CH₂CH₃ | H | H |
| C-3 | iso-propyl | iso-propyl | H | H |
| C-4 | iso-butyl | iso-butyl | H | H |
| C-5 | cyclopentyl | cyclopentyl | H | H |
| C-6 | dicyclohexyl | | H | H |
| C-7 | —CH₂CH₃ | —CH₃ | H | H |
| C-8 | —CH₃ | —CH₂CH₃ | H | H |
| C-9 | —CH₃ | H | —CH₃ | H |
| C-10 | —CH₂CH₃ | H | —CH₂CH₃ | H |
| C-11 | iso-propyl | H | iso-propyl | H |
| C-12 | iso-butyl | H | iso-butyl | H |
| C-13 | cyclopentyl | H | cyclopentyl | H |
| C-14 | cyclohexyl | H | cyclohexyl | H |
| C-15 | —CH₂CH₃ | H | —CH₃ | H |
| C-16 | —CH₃ | H | —CH₂CH₃ | H |
| C-17 | —CH₃ | —CH₃ | —CH₃ | H |
| C-18 | —CH₂CH₃ | —CH₃ | —CH₃ | H |
| C-19 | iso-propyl | —CH₃ | —CH₃ | H |
| C-20 | iso-butyl | —CH₃ | —CH₃ | H |
| C-21 | cyclopentyl | —CH₃ | —CH₃ | H |
| C-22 | cyclohexyl | —CH₃ | —CH₃ | H |
| C-23 | —CH₃ | —CH₃ | H | —CH₃ |
| C-24 | —CH₂CH₃ | —CH₂CH₃ | H | —CH₃ |
| C-25 | iso-propyl | iso-propyl | H | —CH₃ |
| C-26 | iso-butyl | iso-butyl | H | —CH₃ |
| C-27 | cyclopentyl | cyclopentyl | H | —CH₃ |
| C-28 | dicyclohexyl | | H | —CH₃ |
| C-29 | —CH₂CH₃ | —CH₃ | H | —CH₃ |
| C-30 | —CH₃ | —CH₂CH₃ | H | —CH₃ |
| C-31 | —CH₃ | H | —CH₃ | —CH₃ |
| C-32 | —CH₂CH₃ | H | —CH₂CH₃ | —CH₃ |
| C-33 | iso-propyl | H | iso-propyl | —CH₃ |
| C-34 | iso-butyl | H | iso-butyl | —CH₃ |
| C-35 | cyclopentyl | H | cyclopentyl | —CH₃ |
| C-36 | cyclohexyl | H | cyclohexyl | —CH₃ |
| C-37 | —CH₂CH₃ | H | —CH₃ | —CH₃ |
| C-38 | —CH₃ | H | —CH₂CH₃ | —CH₃ |
| C-39 | —CH₃ | —CH₃ | —CH₃ | —CH₃ |
| C-40 | —CH₂CH₃ | —CH₃ | —CH₃ | —CH₃ |
| C-41 | iso-propyl | —CH₃ | —CH₃ | —CH₃ |
| C-42 | iso-butyl | —CH₃ | —CH₃ | —CH₃ |
| C-43 | cyclopentyl | —CH₃ | —CH₃ | —CH₃ |
| C-44 | cyclohexyl | —CH₃ | —CH₃ | —CH₃ |
| C-45 | —CH₃ | —CH₃ | H | —CH₂CH₃ |
| C-46 | —CH₂CH₃ | —CH₂CH₃ | H | —CH₂CH₃ |
| C-47 | iso-propyl | iso-propyl | H | —CH₂CH₃ |
| C-48 | iso-butyl | iso-butyl | H | —CH₂CH₃ |
| C-49 | cyclopentyl | cyclopentyl | H | —CH₂CH₃ |
| C-50 | dicyclohexyl | | H | —CH₂CH₃ |
| C-51 | —CH₂CH₃ | —CH₃ | H | —CH₂CH₃ |

| Cpd. | R² | R³' | R³ | R⁴ = R⁵ |
|---|---|---|---|---|
| C-52 | —CH₃ | —CH₂CH₃ | H | —CH₂CH₃ |
| C-53 | —CH₃ | H | —CH₃ | —CH₂CH₃ |
| C-54 | —CH₂CH₃ | H | —CH₂CH₃ | —CH₂CH₃ |
| C-55 | iso-propyl | H | iso-propyl | —CH₂CH₃ |
| C-56 | iso-butyl | H | iso-butyl | —CH₂CH₃ |
| C-57 | cyclopentyl | H | cyclopentyl | —CH₂CH₃ |
| C-58 | cyclohexyl | H | cyclohexyl | —CH₂CH₃ |
| C-59 | —CH₂CH₃ | H | —CH₃ | —CH₂CH₃ |
| C-60 | —CH₃ | H | —CH₂CH₃ | —CH₂CH₃ |
| C-61 | —CH₃ | —CH₃ | —CH₃ | —CH₂CH₃ |
| C-62 | —CH₂CH₃ | —CH₃ | —CH₃ | —CH₂CH₃ |
| C-63 | iso-propyl | —CH₃ | —CH₃ | —CH₂CH₃ |
| C-64 | iso-butyl | —CH₃ | —CH₃ | —CH₂CH₃ |
| C-65 | cyclopentyl | —CH₃ | —CH₃ | —CH₂CH₃ |
| C-66 | cyclohexyl | —CH₃ | —CH₃ | —CH₂CH₃ |
| C-67 | —CH₃ | —CH₃ | H | iso-propyl |
| C-68 | —CH₂CH₃ | —CH₂CH₃ | H | iso-propyl |
| C-69 | iso-propyl | iso-propyl | H | iso-propyl |
| C-70 | iso-butyl | iso-butyl | H | iso-propyl |
| C-71 | cyclopentyl | cyclopentyl | H | iso-propyl |
| C-72 | bicyclohexyl | | H | iso-propyl |
| C-73 | —CH₂CH₃ | —CH₃ | H | iso-propyl |
| C-74 | —CH₃ | —CH₂CH₃ | H | iso-propyl |
| C-75 | —CH₃ | H | —CH₃ | iso-propyl |
| C-76 | —CH₂CH₃ | H | —CH₂CH₃ | iso-propyl |
| C-77 | iso-propyl | H | iso-propyl | iso-propyl |
| C-78 | iso-butyl | H | iso-butyl | iso-propyl |
| C-79 | cyclopentyl | H | cyclopentyl | iso-propyl |
| C-80 | cyclohexyl | H | cyclohexyl | iso-propyl |
| C-81 | —CH₂CH₃ | H | —CH₃ | iso-propyl |
| C-82 | —CH₃ | H | —CH₂CH₃ | iso-propyl |
| C-83 | —CH₃ | —CH₃ | —CH₃ | iso-propyl |
| C-84 | —CH₂CH₃ | —CH₃ | —CH₃ | iso-propyl |
| C-85 | iso-propyl | —CH₃ | —CH₃ | iso-propyl |
| C-86 | iso-butyl | —CH₃ | —CH₃ | iso-propyl |
| C-87 | cyclopentyl | —CH₃ | —CH₃ | iso-propyl |
| C-88 | cyclohexyl | —CH₃ | —CH₃ | iso-propyl |
| C-89 | —CH₃ | —CH₃ | H | iso-butyl |
| C-90 | —CH₂CH₃ | —CH₂CH₃ | H | iso-butyl |
| C-91 | iso-propyl | iso-propyl | H | iso-butyl |
| C-92 | iso-butyl | iso-butyl | H | iso-butyl |
| C-93 | cyclopentyl | cyclopentyl | H | iso-butyl |
| C-94 | bicyclohexyl | | H | iso-butyl |
| C-95 | —CH₂CH₃ | —CH₃ | H | iso-butyl |
| C-96 | —CH₃ | —CH₂CH₃ | H | iso-butyl |
| C-97 | —CH₃ | H | —CH₃ | iso-butyl |
| C-98 | —CH₂CH₃ | H | —CH₂CH₃ | iso-butyl |
| C-99 | iso-propyl | H | iso-propyl | iso-butyl |
| C-100 | iso-butyl | H | iso-butyl | iso-butyl |
| C-101 | cyclopentyl | H | cyclopentyl | iso-butyl |
| C-102 | cyclohexyl | H | cyclohexyl | iso-butyl |
| C-103 | —CH₂CH₃ | H | —CH₃ | iso-butyl |
| C-104 | —CH₃ | H | —CH₂CH₃ | iso-butyl |
| C-105 | —CH₃ | —CH₃ | —CH₃ | iso-butyl |
| C-106 | —CH₂CH₃ | —CH₃ | —CH₃ | iso-butyl |
| C-107 | iso-propyl | —CH₃ | —CH₃ | iso-butyl |
| C-108 | iso-butyl | —CH₃ | —CH₃ | iso-butyl |
| C-109 | cyclopentyl | —CH₃ | —CH₃ | iso-butyl |
| C-110 | cyclohexyl | —CH₃ | —CH₃ | iso-butyl |
| C-111 | —CH₃ | —CH₃ | H | tert-butyl |
| C-112 | —CH₂CH₃ | —CH₂CH₃ | H | tert-butyl |
| C-113 | iso-propyl | iso-propyl | H | tert-butyl |
| C-114 | iso-butyl | iso-butyl | H | tert-butyl |
| C-115 | ethyl | methyl | H | tert-butyl |
| C-116 | —CH₃ | —CH₂CH₃ | H | tert-butyl |
| C-117 | cyclopentyl | cyclopentyl | H | tert-butyl |
| C-118 | bicyclohexyl | | H | tert-butyl |
| C-119 | —CH₃ | —CH₃ | —CH₃ | tert-butyl |
| C-120 | ethyl | ethyl | —CH₃ | tert-butyl |
| C-121 | iso-propyl | iso-propyl | —CH₃ | tert-butyl |
| C-122 | —CH₃ | —CH₃ | iso-propyl | tert-butyl |
| C-123 | ethyl | ethyl | iso-propyl | tert-butyl |
| C-124 | iso-propyl | iso-propyl | iso-propyl | tert-butyl |
| C-125 | —CH₃ | H | H | H |
| C-126 | —CH₂CH₃ | H | H | H |

-continued

| Cpd. | R² | R³' | R³ | R⁴ = R⁵ |
|---|---|---|---|---|
| C-127 | iso-propyl | H | H | H |
| C-128 | iso-butyl | H | H | H |
| C-129 | cyclopentyl | H | H | H |
| C-130 | cyclohexyl | H | H | H |
| C-131 | —CH₃ | H | H | —CH₃ |
| C-132 | —CH₂CH₃ | H | H | —CH₃ |
| C-133 | iso-propyl | H | H | —CH₃ |
| C-134 | iso-butyl | H | H | —CH₃ |
| C-135 | cyclopentyl | H | H | —CH₃ |
| C-136 | cyclohexyl | H | H | —CH₃ |
| C-137 | —CH₃ | H | H | —CH₂CH₃ |
| C-138 | —CH₂CH₃ | H | H | —CH₂CH₃ |
| C-139 | iso-propyl | H | H | —CH₂CH₃ |
| C-140 | iso-butyl | H | H | —CH₂CH₃ |
| C-141 | cyclopentyl | H | H | —CH₂CH₃ |
| C-142 | cyclohexyl | H | H | —CH₂CH₃ |
| C-143 | —CH₃ | H | H | iso-propyl |
| C-144 | —CH₂CH₃ | H | H | iso-propyl |
| C-145 | iso-propyl | H | H | iso-propyl |
| C-146 | iso-butyl | H | H | iso-propyl |
| C-147 | cyclopentyl | H | H | iso-propyl |
| C-148 | cyclohexyl | H | H | iso-propyl |
| C-149 | —CH₃ | H | H | iso-butyl |
| C-150 | —CH₂CH₃ | H | H | iso-butyl |
| C-151 | iso-propyl | H | H | iso-butyl |
| C-152 | iso-butyl | H | H | iso-butyl |
| C-153 | cyclopentyl | H | H | iso-butyl |
| C-154 | cyclohexyl | H | H | iso-butyl |
| C-155 | —CH₃ | H | H | tert-butyl |
| C-156 | —CH₂CH₃ | H | H | tert-butyl |
| C-157 | iso-propyl | H | H | tert-butyl |
| C-158 | iso-butyl | H | H | tert-butyl |
| C-159 | cyclopentyl | H | H | tert-butyl |
| C-160 | cyclohexyl | H | H | tert-butyl |
| C-161 | tert-butyl | H | H | H |
| C-162 | 2,2-dimethyl-butanyl | H | H | H |
| C-163 | 3,3-dimethyl-pentanyl | H | H | H |

| Cpd. | R² | R³' | R³ | R⁴ = R⁵ |
|---|---|---|---|---|
| C'-1 | —CH₃ | —CH₃ | H | H |
| C'-2 | —CH₂CH₃ | —CH₂CH₃ | H | H |
| C'-3 | iso-propyl | iso-propyl | H | H |
| C'-4 | iso-butyl | iso-butyl | H | H |
| C'-5 | cyclopentyl | cyclopentyl | H | H |
| C'-6 | cyclohexyl | cyclohexyl | H | H |
| C'-7 | —CH₂CH₃ | —CH₃ | H | H |
| C'-8 | —CH₃ | —CH₂CH₃ | H | H |
| C'-9 | —CH₃ | H | —CH₃ | H |
| C'-10 | —CH₂CH₃ | H | —CH₂CH₃ | H |
| C'-11 | iso-propyl | H | iso-propyl | H |
| C'-12 | iso-butyl | H | iso-butyl | H |
| C'-13 | cyclopentyl | H | cyclopentyl | H |
| C'-14 | cyclohexyl | H | cyclohexyl | H |

| Cpd. | R² | R³' | R³ | R⁴ = R⁵ |
|---|---|---|---|---|
| C'-15 | —CH₂CH₃ | H | —CH₃ | H |
| C'-16 | —CH₃ | H | —CH₂CH₃ | H |
| C'-17 | —CH₃ | —CH₃ | —CH₃ | H |
| C'-18 | —CH₂CH₃ | —CH₃ | —CH₃ | H |
| C'-19 | iso-propyl | —CH₃ | —CH₃ | H |
| C'-20 | iso-butyl | —CH₃ | —CH₃ | H |
| C'-21 | cyclopentyl | —CH₃ | —CH₃ | H |
| C'-22 | cyclohexyl | —CH₃ | —CH₃ | H |
| C'-23 | —CH₃ | —CH₃ | H | —CH₃ |
| C'-24 | —CH₂CH₃ | —CH₂CH₃ | H | —CH₃ |
| C'-25 | iso-propyl | iso-propyl | H | —CH₃ |
| C'-26 | iso-butyl | iso-butyl | H | —CH₃ |
| C'-27 | cyclopentyl | cyclopentyl | H | —CH₃ |
| C'-28 | bicyclohexyl | | H | —CH₃ |
| C'-29 | —CH₂CH₃ | —CH₃ | H | —CH₃ |
| C'-30 | —CH₃ | —CH₂CH₃ | H | —CH₃ |
| C'-31 | —CH₃ | H | —CH₃ | —CH₃ |
| C'-32 | —CH₂CH₃ | H | —CH₂CH₃ | —CH₃ |
| C'-33 | iso-propyl | H | iso-propyl | —CH₃ |
| C'-34 | iso-butyl | H | iso-butyl | —CH₃ |
| C'-35 | cyclopentyl | H | cyclopentyl | —CH₃ |
| C'-36 | cyclohexyl | H | cyclohexyl | —CH₃ |
| C'-37 | —CH₂CH₃ | H | —CH₃ | —CH₃ |
| C'-38 | —CH₃ | H | —CH₂CH₃ | —CH₃ |
| C'-39 | —CH₃ | —CH₃ | —CH₃ | —CH₃ |
| C'-40 | —CH₂CH₃ | —CH₃ | —CH₃ | —CH₃ |
| C'-41 | iso-propyl | —CH₃ | —CH₃ | —CH₃ |
| C'-42 | iso-butyl | —CH₃ | —CH₃ | —CH₃ |
| C'-43 | cyclopentyl | —CH₃ | —CH₃ | —CH₃ |
| C'-44 | cyclohexyl | —CH₃ | —CH₃ | —CH₃ |
| C'-45 | —CH₃ | —CH₃ | H | —CH₂CH₃ |
| C'-46 | —CH₂CH₃ | —CH₂CH₃ | H | —CH₂CH₃ |
| C'-47 | iso-propyl | iso-propyl | H | —CH₂CH₃ |
| C'-48 | iso-butyl | iso-butyl | H | —CH₂CH₃ |
| C'-49 | cyclopentyl | cyclopentyl | H | —CH₂CH₃ |
| C'-50 | bicyclohexyl | | H | —CH₂CH₃ |
| C'-51 | —CH₂CH₃ | —CH₃ | H | —CH₂CH₃ |
| C'-52 | —CH₃ | —CH₂CH₃ | H | —CH₂CH₃ |
| C'-53 | —CH₃ | H | —CH₃ | —CH₂CH₃ |
| C'-54 | —CH₂CH₃ | H | —CH₂CH₃ | —CH₂CH₃ |
| C'-55 | iso-propyl | H | iso-propyl | —CH₂CH₃ |
| C'-56 | iso-butyl | H | iso-butyl | —CH₂CH₃ |
| C'-57 | cyclopentyl | H | cyclopentyl | —CH₂CH₃ |
| C'-58 | cyclohexyl | H | cyclohexyl | —CH₂CH₃ |
| C'-59 | —CH₂CH₃ | H | —CH₃ | —CH₂CH₃ |
| C'-60 | —CH₃ | H | —CH₂CH₃ | —CH₂CH₃ |
| C'-61 | —CH₃ | —CH₃ | —CH₃ | —CH₂CH₃ |
| C'-62 | —CH₂CH₃ | —CH₃ | —CH₃ | —CH₂CH₃ |
| C'-63 | iso-propyl | —CH₃ | —CH₃ | —CH₂CH₃ |
| C'-64 | iso-butyl | —CH₃ | —CH₃ | —CH₂CH₃ |
| C'-65 | cyclopentyl | —CH₃ | —CH₃ | —CH₂CH₃ |
| C'-66 | cyclohexyl | —CH₃ | —CH₃ | —CH₂CH₃ |
| C'-67 | —CH₃ | —CH₃ | H | iso-propyl |
| C'-68 | —CH₂CH₃ | —CH₂CH₃ | H | iso-propyl |
| C'-69 | iso-propyl | iso-propyl | H | iso-propyl |
| C'-70 | iso-butyl | iso-butyl | H | iso-propyl |
| C'-71 | cyclopentyl | cyclopentyl | H | iso-propyl |
| C'-72 | bicyclohexyl | | H | iso-propyl |
| C'-73 | —CH₂CH₃ | —CH₃ | H | iso-propyl |
| C'-74 | —CH₃ | —CH₂CH₃ | H | iso-propyl |
| C'-75 | —CH₃ | H | —CH₃ | iso-propyl |
| C'-76 | —CH₂CH₃ | H | —CH₂CH₃ | iso-propyl |
| C'-77 | iso-propyl | H | iso-propyl | iso-propyl |
| C'-78 | iso-butyl | H | iso-butyl | iso-propyl |
| C'-79 | cyclopentyl | H | cyclopentyl | iso-propyl |
| C'-80 | cyclohexyl | H | cyclohexyl | iso-propyl |
| C'-81 | —CH₂CH₃ | H | —CH₃ | iso-propyl |
| C'-82 | —CH₃ | H | —CH₂CH₃ | iso-propyl |
| C'-83 | —CH₃ | —CH₃ | —CH₃ | iso-propyl |
| C'-84 | —CH₂CH₃ | —CH₃ | —CH₃ | iso-propyl |
| C'-85 | iso-propyl | —CH₃ | —CH₃ | iso-propyl |
| C'-86 | iso-butyl | —CH₃ | —CH₃ | iso-propyl |

-continued

| Cpd. | R² | R³' | R³ | R⁴ = R⁵ |
|---|---|---|---|---|
| C'-87 | cyclopentyl | —CH₃ | —CH₃ | iso-propyl |
| C'-88 | cyclohexyl | —CH₃ | —CH₃ | iso-propyl |
| C'-89 | —CH₃ | —CH₃ | H | iso-butyl |
| C'-90 | —CH₂CH₃ | —CH₂CH₃ | H | iso-butyl |
| C'-91 | iso-propyl | iso-propyl | H | iso-butyl |
| C'-92 | iso-butyl | iso-butyl | H | iso-butyl |
| C'-93 | cyclopentyl | cyclopentyl | H | iso-butyl |
| C'-94 | cyclohexyl | cyclohexyl | H | iso-butyl |
| C'-95 | —CH₂CH₃ | —CH₃ | H | iso-butyl |
| C'-96 | —CH₃ | —CH₂CH₃ | H | iso-butyl |
| C'-97 | —CH₃ | H | —CH₃ | iso-butyl |
| C'-98 | —CH₂CH₃ | H | —CH₂CH₃ | iso-butyl |
| C'-99 | iso-propyl | H | iso-propyl | iso-butyl |
| C'-100 | iso-butyl | H | iso-butyl | iso-butyl |
| C'-101 | cyclopentyl | H | cyclopentyl | iso-butyl |
| C'-102 | cyclohexyl | H | cyclohexyl | iso-butyl |
| C'-103 | —CH₂CH₃ | H | —CH₃ | iso-butyl |
| C'-104 | —CH₃ | H | —CH₂CH₃ | iso-butyl |
| C'-105 | —CH₃ | —CH₃ | —CH₃ | iso-butyl |
| C'-106 | —CH₂CH₃ | —CH₃ | —CH₃ | iso-butyl |
| C'-107 | iso-propyl | —CH₃ | —CH₃ | iso-butyl |
| C'-108 | iso-butyl | —CH₃ | —CH₃ | iso-butyl |
| C'-109 | cyclopentyl | —CH₃ | —CH₃ | iso-butyl |
| C'-110 | cyclohexyl | —CH₃ | —CH₃ | iso-butyl |
| C'-111 | —CH₃ | H | H | H |
| C'-112 | —CH₂CH₃ | H | H | H |
| C'-113 | iso-propyl | H | H | H |
| C'-114 | iso-butyl | H | H | H |
| C'-115 | cyclopentyl | H | H | H |
| C'-116 | cyclohexyl | H | H | H |
| C'-117 | —CH₃ | H | H | —CH₃ |
| C'-118 | —CH₂CH₃ | H | H | —CH₃ |
| C'-119 | iso-propyl | H | H | —CH₃ |
| C'-120 | iso-butyl | H | H | —CH₃ |
| C'-121 | cyclopentyl | H | H | —CH₃ |
| C'-122 | cyclohexyl | H | H | —CH₃ |
| C'-123 | —CH₃ | H | H | —CH₂CH₃ |
| C'-124 | —CH₂CH₃ | H | H | —CH₂CH₃ |
| C'-125 | iso-propyl | H | H | —CH₂CH₃ |
| C'-126 | iso-butyl | H | H | —CH₂CH₃ |
| C'-127 | cyclopentyl | H | H | —CH₂CH₃ |
| C'-128 | cyclohexyl | H | H | —CH₂CH₃ |
| C'-129 | —CH₃ | H | H | iso-propyl |
| C'-130 | —CH₂CH₃ | H | H | iso-propyl |
| C'-131 | iso-propyl | H | H | iso-propyl |
| C'-132 | iso-butyl | H | H | iso-propyl |
| C'-133 | cyclopentyl | H | H | iso-propyl |
| C'-134 | cyclohexyl | H | H | iso-propyl |
| C'-135 | —CH₃ | H | H | iso-butyl |
| C'-136 | —CH₂CH₃ | H | H | iso-butyl |
| C'-137 | iso-propyl | H | H | iso-butyl |
| C'-138 | iso-butyl | H | H | iso-butyl |
| C'-139 | cyclopentyl | H | H | iso-butyl |
| C'-140 | cyclohexyl | H | H | iso-butyl |

-continued

| Cpd. | R² | R³' | R³ | R⁴ = R⁵ |
|---|---|---|---|---|
| C'-141 | tert-butyl | H | H | H |
| C'-142 | 2,2-dimethyl butanyl | H | H | H |
| C'-143 | 3,3-dimethyl pentanyl | H | H | H |

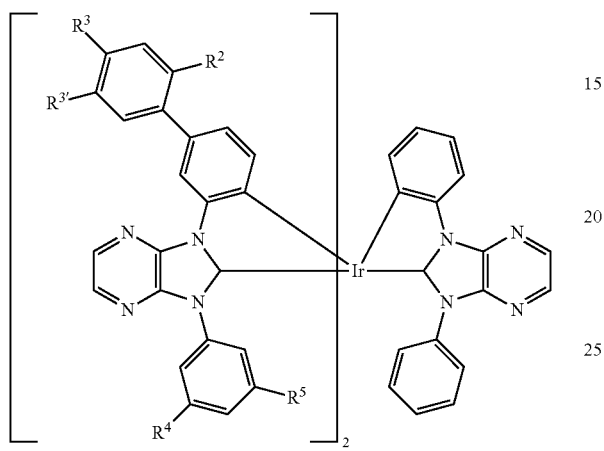

| Cpd. | R² | R³' | R³ | R⁴ = R⁵ |
|---|---|---|---|---|
| D-1 | —CH₃ | —CH₃ | H | H |
| D-2 | —CH₂CH₃ | —CH₂CH₃ | H | H |
| D-3 | iso-propyl | iso-propyl | H | H |
| D-4 | iso-butyl | iso-butyl | H | H |
| D-5 | cyclopentyl | cyclopentyl | H | H |
| D-6 | cyclohexyl | cyclohexyl | H | H |
| D-7 | —CH₂CH₃ | —CH₃ | H | H |
| D-8 | —CH₃ | —CH₂CH₃ | H | H |
| D-9 | —CH₃ | H | —CH₃ | H |
| D-10 | —CH₂CH₃ | H | —CH₂CH₃ | H |
| D-11 | iso-propyl | H | iso-propyl | H |
| D-12 | iso-butyl | H | iso-butyl | H |
| D-13 | cyclopentyl | H | cyclopentyl | H |
| D-14 | cyclohexyl | H | cyclohexyl | H |
| D-15 | —CH₂CH₃ | H | —CH₃ | H |
| D-16 | —CH₃ | H | —CH₂CH₃ | H |
| D-17 | —CH₃ | —CH₃ | —CH₃ | H |
| D-18 | —CH₂CH₃ | —CH₃ | —CH₃ | H |
| D-19 | iso-propyl | —CH₃ | —CH₃ | H |
| D-20 | iso-butyl | —CH₃ | —CH₃ | H |

-continued

| Cpd. | R² | R³' | R³ | R⁴ = R⁵ |
|---|---|---|---|---|
| D-21 | cyclopentyl | —CH₃ | —CH₃ | H |
| D-22 | cyclohexyl | —CH₃ | —CH₃ | H |
| D-23 | —CH₃ | —CH₃ | H | —CH₃ |
| D-24 | —CH₂CH₃ | —CH₂CH₃ | H | —CH₃ |
| D-25 | iso-propyl | iso-propyl | H | —CH₃ |
| D-26 | iso-butyl | iso-butyl | H | —CH₃ |
| D-27 | cyclopentyl | cyclopentyl | H | —CH₃ |
| D-28 | cyclohexyl | cyclohexyl | H | —CH₃ |
| D-29 | —CH₂CH₃ | —CH₃ | H | —CH₃ |
| D-30 | —CH₃ | —CH₂CH₃ | H | —CH₃ |
| D-31 | —CH₃ | H | —CH₃ | —CH₃ |
| D-32 | —CH₂CH₃ | H | —CH₂CH₃ | —CH₃ |
| D-33 | iso-propyl | H | iso-propyl | —CH₃ |
| D-34 | iso-butyl | H | iso-butyl | —CH₃ |
| D-35 | cyclopentyl | H | cyclopentyl | —CH₃ |
| D-36 | cyclohexyl | H | cyclohexyl | —CH₃ |
| D-37 | —CH₂CH₃ | H | —CH₃ | —CH₃ |
| D-38 | —CH₃ | H | —CH₂CH₃ | —CH₃ |
| D-39 | —CH₃ | —CH₃ | —CH₃ | —CH₃ |
| D-40 | —CH₂CH₃ | —CH₃ | —CH₃ | —CH₃ |
| D-41 | iso-propyl | —CH₃ | —CH₃ | —CH₃ |
| D-42 | iso-butyl | —CH₃ | —CH₃ | —CH₃ |
| D-43 | cyclopentyl | —CH₃ | —CH₃ | —CH₃ |
| D-44 | cyclohexyl | —CH₃ | —CH₃ | —CH₃ |
| D-45 | —CH₃ | —CH₃ | H | —CH₂CH₃ |
| D-46 | —CH₂CH₃ | —CH₂CH₃ | H | —CH₂CH₃ |
| D-47 | iso-propyl | iso-propyl | H | —CH₂CH₃ |
| D-48 | iso-butyl | iso-butyl | H | —CH₂CH₃ |
| D-49 | cyclopentyl | cyclopentyl | H | —CH₂CH₃ |
| D-50 | cyclohexyl | cyclohexyl | H | —CH₂CH₃ |
| D-51 | —CH₂CH₃ | —CH₃ | H | —CH₂CH₃ |
| D-52 | —CH₃ | —CH₂CH₃ | H | —CH₂CH₃ |
| D-53 | —CH₃ | H | —CH₃ | —CH₂CH₃ |
| D-54 | —CH₂CH₃ | H | —CH₂CH₃ | —CH₂CH₃ |
| D-55 | iso-propyl | H | iso-propyl | —CH₂CH₃ |

-continued

| Cpd. | R² | R³' | R³ | R⁴ = R⁵ |
|---|---|---|---|---|
| D-56 | iso-butyl | H | iso-butyl | —CH₂CH₃ |
| D-57 | 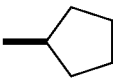 | H | 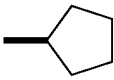 | —CH₂CH₃ |
| D-58 | 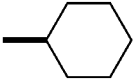 | H | 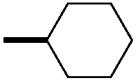 | —CH₂CH₃ |
| D-59 | —CH₂CH₃ | H | —CH₃ | —CH₂CH₃ |
| D-60 | —CH₃ | H | —CH₂CH₃ | —CH₂CH₃ |
| D-61 | —CH₃ | —CH₃ | —CH₃ | —CH₂CH₃ |
| D-62 | —CH₂CH₃ | —CH₃ | —CH₃ | —CH₂CH₃ |
| D-63 | iso-propyl | —CH₃ | —CH₃ | —CH₂CH₃ |
| D-64 | iso-butyl | —CH₃ | —CH₃ | —CH₂CH₃ |
| D-65 | 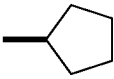 | —CH₃ | —CH₃ | —CH₂CH₃ |
| D-66 | 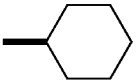 | —CH₃ | —CH₃ | —CH₂CH₃ |
| D-67 | —CH₃ | —CH₃ | H | iso-propyl |
| D-68 | —CH₂CH₃ | —CH₂CH₃ | H | iso-propyl |
| D-69 | iso-propyl | iso-propyl | H | iso-propyl |
| D-70 | iso-butyl | iso-butyl | H | iso-propyl |
| D-71 | 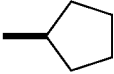 | 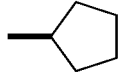 | H | iso-propyl |
| D-72 | 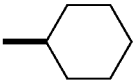 | 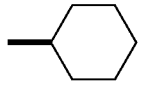 | H | iso-propyl |
| D-73 | —CH₂CH₃ | —CH₃ | H | iso-propyl |
| D-74 | —CH₃ | —CH₂CH₃ | H | iso-propyl |
| D-75 | —CH₃ | H | —CH₃ | iso-propyl |
| D-76 | —CH₂CH₃ | H | —CH₂CH₃ | iso-propyl |
| D-77 | iso-propyl | H | iso-propyl | iso-propyl |
| D-78 | iso-butyl | H | iso-butyl | iso-propyl |
| D-79 | 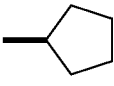 | H | 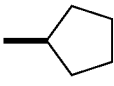 | iso-propyl |
| D-80 | 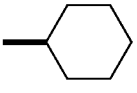 | H | 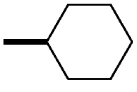 | iso-propyl |
| D-81 | —CH₂CH₃ | H | —CH₃ | iso-propyl |
| D-82 | —CH₃ | H | —CH₂CH₃ | iso-propyl |
| D-83 | —CH₃ | —CH₃ | —CH₃ | iso-propyl |
| D-84 | —CH₂CH₃ | —CH₃ | —CH₃ | iso-propyl |
| D-85 | iso-propyl | —CH₃ | —CH₃ | iso-propyl |
| D-86 | iso-butyl | —CH₃ | —CH₃ | iso-propyl |
| D-87 | 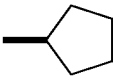 | —CH₃ | —CH₃ | iso-propyl |
| D-88 | 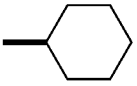 | —CH₃ | —CH₃ | iso-propyl |
| D-89 | —CH₃ | —CH₃ | H | iso-butyl |

-continued

| Cpd. | R² | R³' | R³ | R⁴ = R⁵ |
|---|---|---|---|---|
| D-90 | —CH₂CH₃ | —CH₂CH₃ | H | iso-butyl |
| D-91 | iso-propyl | iso-propyl | H | iso-butyl |
| D-92 | iso-butyl | iso-butyl | H | iso-butyl |
| D-93 | cyclopentyl | cyclopentyl | H | iso-butyl |
| D-94 | cyclohexyl | cyclohexyl | H | iso-butyl |
| D-95 | —CH₂CH₃ | —CH₃ | H | iso-butyl |
| D-96 | —CH₃ | —CH₂CH₃ | H | iso-butyl |
| D-97 | —CH₃ | H | —CH₃ | iso-butyl |
| D-98 | —CH₂CH₃ | H | —CH₂CH₃ | iso-butyl |
| D-99 | iso-propyl | H | iso-propyl | iso-butyl |
| D-100 | iso-butyl | H | iso-butyl | iso-butyl |
| D-101 | cyclopentyl | H | cyclopentyl | iso-butyl |
| D-102 | cyclohexyl | H | cyclohexyl | iso-butyl |
| D-103 | —CH₂CH₃ | H | —CH₃ | iso-butyl |
| D-104 | —CH₃ | H | —CH₂CH₃ | iso-butyl |
| D-105 | —CH₃ | —CH₃ | —CH₃ | iso-butyl |
| D-106 | —CH₂CH₃ | —CH₃ | —CH₃ | iso-butyl |
| D-107 | iso-propyl | —CH₃ | —CH₃ | iso-butyl |
| D-108 | iso-butyl | —CH₃ | —CH₃ | iso-butyl |
| D-109 | cyclopentyl | —CH₃ | —CH₃ | iso-butyl |
| D-110 | cyclohexyl | —CH₃ | —CH₃ | iso-butyl |
| D-111 | —CH₃ | —CH₃ | H | tert-butyl |
| D-112 | —CH₂CH₃ | —CH₂CH₃ | H | tert-butyl |
| D-113 | iso-propyl | iso-propyl | H | tert-butyl |
| D-114 | iso-butyl | iso-butyl | H | tert-butyl |
| D-115 | ethyl | methyl | H | tert-butyl |
| D-116 | —CH₃ | —CH₂CH₃ | H | tert-butyl |
| D-117 | cyclopentyl | cyclopentyl | H | tert-butyl |
| D-118 | cyclohexyl | cyclohexyl | H | tert-butyl |
| D-119 | —CH₃ | —CH₃ | —CH₃ | tert-butyl |
| D-120 | ethyl | ethyl | —CH₃ | tert-butyl |
| D-121 | iso-propyl | iso-propyl | —CH₃ | tert-butyl |
| D-122 | —CH₃ | —CH₃ | iso-propyl | tert-butyl |
| D-123 | ethyl | ethyl | iso-propyl | tert-butyl |
| D-124 | iso-propyl | iso-propyl | iso-propyl | tert-butyl |
| D-125 | —CH₃ | H | H | H |
| D-126 | —CH₂CH₃ | H | H | H |
| D-127 | iso-propyl | H | H | H |
| D-128 | iso-butyl | H | H | H |

-continued

| Cpd. | R² | R³' | R³ | R⁴ = R⁵ |
|---|---|---|---|---|
| D-129 | cyclopentyl | H | H | H |
| D-130 | cyclohexyl | H | H | H |
| D-131 | —CH₃ | H | H | —CH₃ |
| D-132 | —CH₂CH₃ | H | H | —CH₃ |
| D-133 | iso-propyl | H | H | —CH₃ |
| D-134 | iso-butyl | H | H | —CH₃ |
| D-135 | cyclopentyl | H | H | —CH₃ |
| D-136 | cyclohexyl | H | H | —CH₃ |
| D-137 | —CH₃ | H | H | —CH₂CH₃ |
| D-138 | —CH₂CH₃ | H | H | —CH₂CH₃ |
| D-139 | iso-propyl | H | H | —CH₂CH₃ |
| D-140 | iso-butyl | H | H | —CH₂CH₃ |
| D-141 | cyclopentyl | H | H | —CH₂CH₃ |
| D-142 | cyclohexyl | H | H | —CH₂CH₃ |
| D-143 | —CH₃ | H | H | iso-propyl |
| D-144 | —CH₂CH₃ | H | H | iso-propyl |
| D-145 | iso-propyl | H | H | iso-propyl |
| D-146 | iso-butyl | H | H | iso-propyl |
| D-147 | cyclopentyl | H | H | iso-propyl |
| D-148 | cyclohexyl | H | H | iso-propyl |
| D-149 | —CH₃ | H | H | iso-butyl |
| D-150 | —CH₂CH₃ | H | H | iso-butyl |
| D-151 | iso-propyl | H | H | iso-butyl |
| D-152 | iso-butyl | H | H | iso-butyl |
| D-153 | cyclopentyl | H | H | iso-butyl |
| D-154 | cyclohexyl | H | H | iso-butyl |
| D-155 | —CH₃ | H | H | tert-butyl |
| D-156 | —CH₂CH₃ | H | H | tert-butyl |
| D-157 | iso-propyl | H | H | tert-butyl |
| D-158 | iso-butyl | H | H | tert-butyl |
| D-159 | cyclopentyl | H | H | tert-butyl |

-continued

| Cpd. | R² | R³' | R³ | R⁴ = R⁵ |
|---|---|---|---|---|
| D-160 | cyclohexyl | H | H | tert-butyl |
| D-161 | tert-butyl | H | H | H |
| D-162 | 2,2-dimethyl-butanyl | H | H | H |
| D-163 | 3,3-dimethyl-pentanyl | H | H | H |

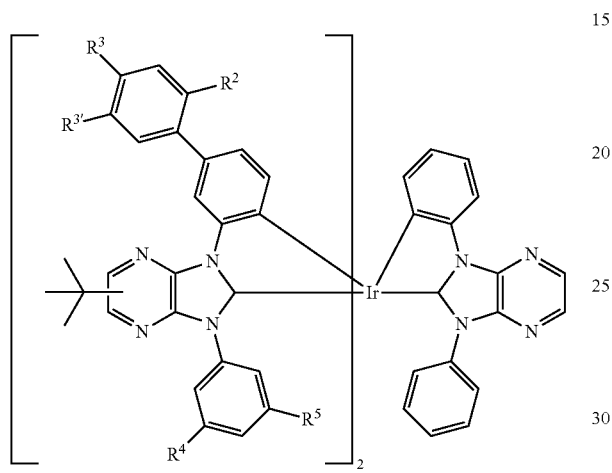

| Cpd. | R² | R³' | R³ | R⁴ = R⁵ |
|---|---|---|---|---|
| D'-1 | —CH₃ | —CH₃ | H | H |
| D'-2 | —CH₂CH₃ | —CH₂CH₃ | H | H |
| D'-3 | iso-propyl | iso-propyl | H | H |
| D'-4 | iso-butyl | iso-butyl | H | H |
| D'-5 | cyclopentyl | cyclopentyl | H | H |
| D'-6 | cyclohexyl | cyclohexyl | H | H |
| D'-7 | —CH₂CH₃ | —CH₃ | H | H |
| D'-8 | —CH₃ | —CH₂CH₃ | H | H |
| D'-9 | —CH₃ | H | —CH₃ | H |
| D'-10 | —CH₂CH₃ | H | —CH₂CH₃ | H |
| D'-11 | iso-propyl | H | iso-propyl | H |
| D'-12 | iso-butyl | H | iso-butyl | H |
| D'-13 | cyclopentyl | H | cyclopentyl | H |
| D'-14 | cyclohexyl | H | cyclohexyl | H |
| D'-15 | —CH₂CH₃ | H | —CH₃ | H |
| D'-16 | —CH₃ | H | —CH₂CH₃ | H |
| D'-17 | —CH₃ | —CH₃ | —CH₃ | H |
| D'-18 | —CH₂CH₃ | —CH₃ | —CH₃ | H |
| D'-19 | iso-propyl | —CH₃ | —CH₃ | H |

-continued

| Cpd. | R² | R³' | R³ | R⁴ = R⁵ |
|---|---|---|---|---|
| D'-20 | iso-butyl | —CH₃ | —CH₃ | H |
| D'-21 | cyclopentyl | —CH₃ | —CH₃ | H |
| D'-22 | cyclohexyl | —CH₃ | —CH₃ | H |
| D'-23 | —CH₃ | —CH₃ | H | —CH₃ |
| D'-24 | —CH₂CH₃ | —CH₂CH₃ | H | —CH₃ |
| D'-25 | iso-propyl | iso-propyl | H | —CH₃ |
| D'-26 | iso-butyl | iso-butyl | H | —CH₃ |
| D'-27 | cyclopentyl | cyclopentyl | H | —CH₃ |
| D'-28 | cyclohexyl | cyclohexyl | H | —CH₃ |
| D'-29 | —CH₂CH₃ | —CH₃ | H | —CH₃ |
| D'-30 | —CH₃ | —CH₂CH₃ | H | —CH₃ |
| D'-31 | —CH₃ | H | —CH₃ | —CH₃ |
| D'-32 | —CH₂CH₃ | H | —CH₂CH₃ | —CH₃ |
| D'-33 | iso-propyl | H | iso-propyl | —CH₃ |
| D'-34 | iso-butyl | H | iso-butyl | —CH₃ |
| D'-35 | cyclopentyl | H | cyclopentyl | —CH₃ |
| D'-36 | cyclohexyl | H | cyclohexyl | —CH₃ |
| D'-37 | —CH₂CH₃ | H | —CH₃ | —CH₃ |
| D'-38 | —CH₃ | H | —CH₂CH₃ | —CH₃ |
| D'-39 | —CH₃ | —CH₃ | —CH₃ | —CH₃ |
| D'-40 | —CH₂CH₃ | —CH₃ | —CH₃ | —CH₃ |
| D'-41 | iso-propyl | —CH₃ | —CH₃ | —CH₃ |
| D'-42 | iso-butyl | —CH₃ | —CH₃ | —CH₃ |
| D'-43 | cyclopentyl | —CH₃ | —CH₃ | —CH₃ |
| D'-44 | cyclohexyl | —CH₃ | —CH₃ | —CH₃ |
| D'-45 | —CH₃ | —CH₃ | H | —CH₂CH₃ |
| D'-46 | —CH₂CH₃ | —CH₂CH₃ | H | —CH₂CH₃ |
| D'-47 | iso-propyl | iso-propyl | H | —CH₂CH₃ |
| D'-48 | iso-butyl | iso-butyl | H | —CH₂CH₃ |
| D'-49 | cyclopentyl | cyclopentyl | H | —CH₂CH₃ |
| D'-50 | cyclohexyl | cyclohexyl | H | —CH₂CH₃ |
| D'-51 | —CH₂CH₃ | —CH₃ | H | —CH₂CH₃ |
| D'-52 | —CH₃ | —CH₂CH₃ | H | —CH₂CH₃ |
| D'-53 | —CH₃ | H | —CH₃ | —CH₂CH₃ |

-continued

| Cpd. | $R^2$ | $R^{3'}$ | $R^3$ | $R^4 = R^5$ |
|---|---|---|---|---|
| D'-54 | —CH$_2$CH$_3$ | H | —CH$_2$CH$_3$ | —CH$_2$CH$_3$ |
| D'-55 | iso-propyl | H | iso-propyl | —CH$_2$CH$_3$ |
| D'-56 | iso-butyl | H | iso-butyl | —CH$_2$CH$_3$ |
| D'-57 | cyclopentyl | H | cyclopentyl | —CH$_2$CH$_3$ |
| D'-58 | cyclohexyl | H | cyclohexyl | —CH$_2$CH$_3$ |
| D'-59 | —CH$_2$CH$_3$ | H | —CH$_3$ | —CH$_2$CH$_3$ |
| D'-60 | —CH$_3$ | H | —CH$_2$CH$_3$ | —CH$_2$CH$_3$ |
| D'-61 | —CH$_3$ | —CH$_3$ | —CH$_3$ | —CH$_2$CH$_3$ |
| D'-62 | —CH$_2$CH$_3$ | —CH$_3$ | —CH$_3$ | —CH$_2$CH$_3$ |
| D'-63 | iso-propyl | —CH$_3$ | —CH$_3$ | —CH$_2$CH$_3$ |
| D'-64 | iso-butyl | —CH$_3$ | —CH$_3$ | —CH$_2$CH$_3$ |
| D'-65 | cyclopentyl | —CH$_3$ | —CH$_3$ | —CH$_2$CH$_3$ |
| D'-66 | cyclohexyl | —CH$_3$ | —CH$_3$ | —CH$_2$CH$_3$ |
| D'-67 | —CH$_3$ | —CH$_3$ | H | iso-propyl |
| D'-68 | —CH$_2$CH$_3$ | —CH$_2$CH$_3$ | H | iso-propyl |
| D'-69 | iso-propyl | iso-propyl | H | iso-propyl |
| D'-70 | iso-butyl | iso-butyl | H | iso-propyl |
| D'-71 | cyclopentyl | cyclopentyl | H | iso-propyl |
| D'-72 | cyclohexyl | cyclohexyl | H | iso-propyl |
| D'-73 | —CH$_2$CH$_3$ | —CH$_3$ | H | iso-propyl |
| D'-74 | —CH$_3$ | —CH$_2$CH$_3$ | H | iso-propyl |
| D'-75 | —CH$_3$ | H | —CH$_3$ | iso-propyl |
| D'-76 | —CH$_2$CH$_3$ | H | —CH$_2$CH$_3$ | iso-propyl |
| D'-77 | iso-propyl | H | iso-propyl | iso-propyl |
| D'-78 | iso-butyl | H | iso-butyl | iso-propyl |
| D'-79 | cyclopentyl | H | cyclopentyl | iso-propyl |
| D'-80 | cyclohexyl | H | cyclohexyl | iso-propyl |
| D'-81 | —CH$_2$CH$_3$ | H | —CH$_3$ | iso-propyl |
| D'-82 | —CH$_3$ | H | —CH$_2$CH$_3$ | iso-propyl |
| D'-83 | —CH$_3$ | —CH$_3$ | —CH$_3$ | iso-propyl |
| D'-84 | —CH$_2$CH$_3$ | —CH$_3$ | —CH$_3$ | iso-propyl |
| D'-85 | iso-propyl | —CH$_3$ | —CH$_3$ | iso-propyl |
| D'-86 | iso-butyl | —CH$_3$ | —CH$_3$ | iso-propyl |
| D'-87 | cyclopentyl | —CH$_3$ | —CH$_3$ | iso-propyl |
| D'-88 | cyclohexyl | —CH$_3$ | —CH$_3$ | iso-propyl |

-continued

| Cpd. | R² | R³' | R³ | R⁴ = R⁵ |
|---|---|---|---|---|
| D'-89 | —CH₃ | —CH₃ | H | iso-butyl |
| D'-90 | —CH₂CH₃ | —CH₂CH₃ | H | iso-butyl |
| D'-91 | iso-propyl | iso-propyl | H | iso-butyl |
| D'-92 | iso-butyl | iso-butyl | H | iso-butyl |
| D'-93 | cyclopentyl | cyclopentyl | H | iso-butyl |
| D'-94 | cyclohexyl | cyclohexyl | H | iso-butyl |
| D'-95 | —CH₂CH₃ | —CH₃ | H | iso-butyl |
| D'-96 | —CH₃ | —CH₂CH₃ | H | iso-butyl |
| D'-97 | —CH₃ | H | —CH₃ | iso-butyl |
| D'-98 | —CH₂CH₃ | H | —CH₂CH₃ | iso-butyl |
| D'-99 | iso-propyl | H | iso-propyl | iso-butyl |
| D'-100 | iso-butyl | H | iso-butyl | iso-butyl |
| D'-101 | cyclopentyl | H | cyclopentyl | iso-butyl |
| D'-102 | cyclohexyl | H | cyclohexyl | iso-butyl |
| D'-103 | —CH₂CH₃ | H | —CH₃ | iso-butyl |
| D'-104 | —CH₃ | H | —CH₂CH₃ | iso-butyl |
| D'-105 | —CH₃ | —CH₃ | —CH₃ | iso-butyl |
| D'-106 | —CH₂CH₃ | —CH₃ | —CH₃ | iso-butyl |
| D'-107 | iso-propyl | —CH₃ | —CH₃ | iso-butyl |
| D'-108 | iso-butyl | —CH₃ | —CH₃ | iso-butyl |
| D'-109 | cyclopentyl | —CH₃ | —CH₃ | iso-butyl |
| D'-110 | cyclohexyl | —CH₃ | —CH₃ | iso-butyl |
| D'-111 | —CH₃ | H | H | H |
| D'-112 | —CH₂CH₃ | H | H | H |
| D'-113 | iso-propyl | H | H | H |
| D'-114 | iso-butyl | H | H | H |
| D'-115 | cyclopentyl | H | H | H |
| D'-116 | cyclohexyl | H | H | H |
| D'-117 | —CH₃ | H | H | —CH₃ |
| D'-118 | —CH₂CH₃ | H | H | —CH₃ |
| D'-119 | iso-propyl | H | H | —CH₃ |
| D'-120 | iso-butyl | H | H | —CH₃ |
| D'-121 | cyclopentyl | H | H | —CH₃ |
| D'-122 | cyclohexyl | H | H | —CH₃ |
| D'-123 | —CH₃ | H | H | —CH₂CH₃ |
| D'-124 | —CH₂CH₃ | H | H | —CH₂CH₃ |

-continued

| Cpd. | R² | R³' | R³ | R⁴ = R⁵ |
|---|---|---|---|---|
| D'-125 | iso-propyl | H | H | —CH₂CH₃ |
| D'-126 | iso-butyl | H | H | —CH₂CH₃ |
| D'-127 | cyclopentyl | H | H | —CH₂CH₃ |
| D'-128 | cyclohexyl | H | H | —CH₂CH₃ |
| D'-129 | —CH₃ | H | H | iso-propyl |
| D'-130 | —CH₂CH₃ | H | H | iso-propyl |
| D'-131 | iso-propyl | H | H | iso-propyl |
| D'-132 | iso-butyl | H | H | iso-propyl |
| D'-133 | cyclopentyl | H | H | iso-propyl |
| D'-134 | cyclohexyl | H | H | iso-propyl |
| D'-135 | —CH₃ | H | H | iso-butyl |
| D'-136 | —CH₂CH₃ | H | H | iso-butyl |
| D'-137 | iso-propyl | H | H | iso-butyl |
| D'-138 | iso-butyl | H | H | iso-butyl |
| D'-139 | cyclopentyl | H | H | iso-butyl |
| D'-140 | cyclohexyl | H | H | iso-butyl |
| D'-141 | tert-butyl | H | H | H |
| D'-142 | 2,2-dimethyl-butanyl | H | H | H |
| D'-143 | 3,3-dimethyl-pentanyl | H | H | H |

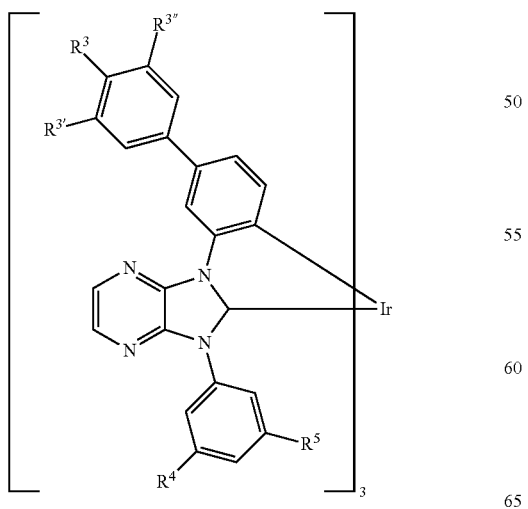

| Cpd. | R³' | R³ | R³" | R⁴ = R⁵ |
|---|---|---|---|---|
| E-1 | —CH₃ | H | —CH₃ | H |
| E-2 | —CH₂CH₃ | H | —CH₂CH₃ | H |
| E-3 | iso-propyl | H | iso-propyl | H |
| E-4 | iso-butyl | H | iso-butyl | H |
| E-5 | cyclopentyl | H | cyclopentyl | H |
| E-6 | cyclohexyl | H | cyclohexyl | H |
| E-7 | —CH₂CH₃ | H | —CH₃ | H |
| E-8 | —CH₃ | H | —CH₂CH₃ | H |
| E-9 | —CH₃ | —CH₃ | H | H |
| E-10 | —CH₂CH₃ | —CH₂CH₃ | H | H |
| E-11 | iso-butyl | iso-butyl | H | H |
| E-12 | —CH₂CH₃ | —CH₃ | H | H |
| E-13 | —CH₃ | —CH₂CH₃ | H | H |
| E-14 | —CH₃ | H | —CH₃ | —CH₂CH₃ |
| E-15 | —CH₂CH₃ | H | —CH₂CH₃ | —CH₂CH₃ |
| E-16 | iso-propyl | H | iso-propyl | —CH₂CH₃ |
| E-17 | iso-butyl | H | iso-butyl | —CH₂CH₃ |
| E-18 | cyclopentyl | H | cyclopentyl | —CH₂CH₃ |
| E-19 | cyclohexyl | H | cyclohexyl | —CH₂CH₃ |
| E-20 | —CH₂CH₃ | H | —CH₃ | —CH₂CH₃ |
| E-21 | —CH₃ | H | —CH₂CH₃ | —CH₂CH₃ |
| E-22 | —CH₃ | —CH₃ | H | —CH₂CH₃ |
| E-23 | —CH₂CH₃ | —CH₂CH₃ | H | —CH₂CH₃ |
| E-24 | iso-butyl | iso-butyl | H | —CH₂CH₃ |
| E-25 | —CH₂CH₃ | —CH₃ | H | —CH₂CH₃ |
| E-26 | —CH₃ | —CH₂CH₃ | H | —CH₂CH₃ |
| E-27 | —CH₃ | H | —CH₃ | iso-propyl |
| E-28 | —CH₂CH₃ | H | —CH₂CH₃ | iso-propyl |
| E-29 | iso-propyl | H | iso-propyl | iso-propyl |
| E-30 | iso-butyl | H | iso-butyl | iso-propyl |
| E-31 | cyclopentyl | H | cyclopentyl | iso-propyl |
| E-32 | cyclohexyl | H | cyclohexyl | iso-propyl |
| E-33 | —CH₂CH₃ | H | —CH₃ | iso-propyl |
| E-34 | —CH₃ | H | —CH₂CH₃ | iso-propyl |
| E-35 | —CH₃ | —CH₃ | H | iso-propyl |
| E-36 | —CH₂CH₃ | —CH₂CH₃ | H | iso-propyl |
| E-37 | iso-butyl | iso-butyl | H | iso-propyl |
| E-38 | —CH₂CH₃ | —CH₃ | H | iso-propyl |
| E-39 | —CH₃ | —CH₂CH₃ | H | iso-propyl |
| E-40 | —CH₃ | H | —CH₃ | iso-butyl |
| E-41 | —CH₂CH₃ | H | —CH₂CH₃ | iso-butyl |
| E-42 | iso-propyl | H | iso-propyl | iso-butyl |
| E-43 | iso-butyl | H | iso-butyl | iso-butyl |
| E-44 | cyclopentyl | H | cyclopentyl | iso-butyl |
| E-45 | cyclohexyl | H | cyclohexyl | iso-butyl |

-continued

| Cpd. | R$^{3'}$ | R$^3$ | R$^{3''}$ | R$^4$ = R$^5$ |
|---|---|---|---|---|
| E-46 | —CH$_2$CH$_3$ | H | —CH$_3$ | iso-butyl |
| E-47 | —CH$_3$ | H | —CH$_2$CH$_3$ | iso-butyl |
| E-48 | —CH$_3$ | —CH$_3$ | H | iso-butyl |
| E-49 | —CH$_2$CH$_3$ | —CH$_2$CH$_3$ | H | iso-butyl |
| E-50 | iso-butyl | iso-butyl | H | iso-butyl |
| E-51 | —CH$_2$CH$_3$ | —CH$_3$ | H | iso-butyl |
| E-52 | —CH$_3$ | —CH$_2$CH$_3$ | H | iso-butyl |
| E-53 | —CH$_3$ | —CH$_3$ | H | tert-butyl |
| E-54 | —CH$_2$CH$_3$ | —CH$_2$CH$_3$ | H | tert-butyl |
| E-55 | iso-propyl | iso-propyl | H | tert-butyl |
| E-56 | iso-butyl | iso-butyl | H | tert-butyl |
| E-57 | neopentyl | neopentyl | H | tert-butyl |
| E-58 | —CH$_3$ | —CH$_2$CH$_3$ | H | tert-butyl |
| E-59 | cyclopentyl | cyclopentyl | H | tert-butyl |
| E-60 | cyclohexyl | cyclohexyl | H | tert-butyl |
| E-61 | —CH$_3$ | —CH$_3$ | —CH$_3$ | tert-butyl |
| E-62 | ethyl | ethyl | —CH$_3$ | tert-butyl |
| E-63 | iso-propyl | iso-propyl | —CH$_3$ | tert-butyl |
| E-64 | —CH$_3$ | —CH$_3$ | iso-propyl | tert-butyl |
| E-65 | ethyl | ethyl | iso-propyl | tert-butyl |
| E-66 | iso-propyl | iso-propyl | iso-propyl | tert-butyl |
| E-67 | —CH$_3$ | —CH$_3$ | H | tert-butyl |
| E-68 | H | H | —CH$_3$ | H |
| E-69 | H | H | —CH$_2$CH$_3$ | H |
| E-70 | H | H | iso-propyl | H |
| E-71 | H | H | iso-butyl | H |
| E-72 | H | H | cyclopentyl | H |
| E-73 | H | H | cyclohexyl | H |
| E-74 | H | —CH$_3$ | H | H |
| E-75 | H | —CH$_3$ | H | H |
| E-76 | H | —CH$_2$CH$_3$ | H | H |
| E-77 | H | iso-propyl | H | H |
| E-78 | H | iso-butyl | H | H |
| E-79 | H | cyclopentyl | H | H |
| E-80 | H | cyclohexyl | H | H |
| E-81 | —CH$_3$ | H | —CH$_3$ | —CH$_3$ |
| E-82 | —CH$_2$CH$_3$ | H | —CH$_2$CH$_3$ | —CH$_3$ |
| E-83 | iso-propyl | H | iso-propyl | —CH$_3$ |
| E-84 | iso-butyl | H | iso-butyl | —CH$_3$ |
| E-85 | cyclopentyl | H | cyclopentyl | —CH$_3$ |
| E-86 | cyclohexyl | H | cyclohexyl | —CH$_3$ |
| E-87 | —CH$_2$CH$_3$ | H | —CH$_3$ | —CH$_3$ |
| E-88 | —CH$_3$ | H | —CH$_2$CH$_3$ | —CH$_3$ |

-continued

| Cpd. | R³' | R³ | R³" | R⁴ = R⁵ |
|---|---|---|---|---|
| E-89 | —CH₃ | —CH₃ | H | —CH₃ |
| E-90 | —CH₂CH₃ | —CH₂CH₃ | H | —CH₃ |
| E-91 | iso-butyl | iso-butyl | H | —CH₃ |
| E-92 | —CH₂CH₃ | —CH₃ | H | —CH₃ |
| E-93 | —CH₃ | —CH₂CH₃ | H | —CH₃ |

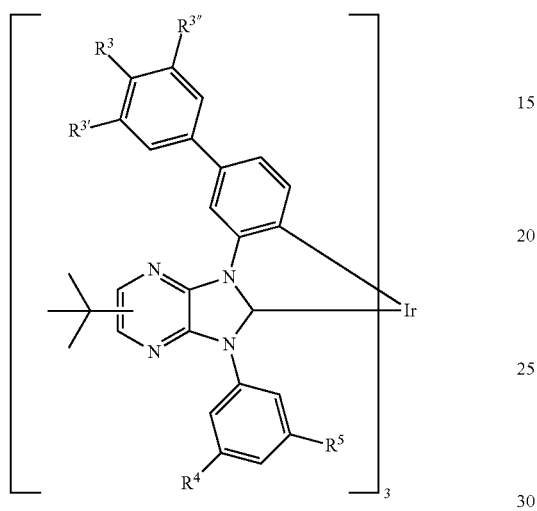

| Cpd. | R³' | R³ | R³" | R⁴ = R⁵ |
|---|---|---|---|---|
| E'-1 | —CH₃ | H | —CH₃ | H |
| E'-2 | —CH₂CH₃ | H | —CH₂CH₃ | H |
| E'-3 | iso-propyl | H | iso-propyl | H |
| E'-4 | iso-butyl | H | iso-butyl | H |
| E'-5 | cyclopentyl | H | cyclopentyl | H |
| E'-6 | cyclohexyl | H | cyclohexyl | H |
| E'-7 | —CH₂CH₃ | H | —CH₃ | H |
| E'-8 | —CH₃ | H | —CH₂CH₃ | H |
| E'-9 | —CH₃ | —CH₃ | H | H |
| E'-10 | —CH₂CH₃ | —CH₂CH₃ | H | H |
| E'-11 | iso-butyl | iso-butyl | H | H |
| E'-12 | —CH₂CH₃ | —CH₃ | H | H |
| E'-13 | —CH₃ | —CH₂CH₃ | H | H |
| E'-14 | —CH₃ | H | —CH₃ | —CH₂CH₃ |
| E'-15 | —CH₂CH₃ | H | —CH₂CH₃ | —CH₂CH₃ |
| E'-16 | iso-propyl | H | iso-propyl | —CH₂CH₃ |
| E'-17 | iso-butyl | H | iso-butyl | —CH₂CH₃ |
| E'-18 | cyclopentyl | H | cyclopentyl | —CH₂CH₃ |
| E'-19 | cyclohexyl | H | cyclohexyl | —CH₂CH₃ |
| E'-20 | —CH₂CH₃ | H | —CH₃ | —CH₂CH₃ |
| E'-21 | —CH₃ | H | —CH₂CH₃ | —CH₂CH₃ |
| E'-22 | —CH₃ | —CH₃ | H | —CH₂CH₃ |

-continued

| Cpd. | R³' | R³ | R³" | R⁴ = R⁵ |
|---|---|---|---|---|
| E'-23 | —CH₂CH₃ | —CH₂CH₃ | H | —CH₂CH₃ |
| E'-24 | iso-butyl | iso-butyl | H | —CH₂CH₃ |
| E'-25 | —CH₂CH₃ | —CH₃ | H | —CH₂CH₃ |
| E'-26 | —CH₃ | —CH₂CH₃ | H | —CH₂CH₃ |
| E'-27 | —CH₃ | H | —CH₃ | iso-propyl |
| E'-28 | —CH₂CH₃ | H | —CH₂CH₃ | iso-propyl |
| E'-29 | iso-propyl | H | iso-propyl | iso-propyl |
| E'-30 | iso-butyl | H | iso-butyl | iso-propyl |
| E'-31 | cyclopentyl | H | cyclopentyl | iso-propyl |
| E'-32 | cyclohexyl | H | cyclohexyl | iso-propyl |
| E'-33 | —CH₂CH₃ | H | —CH₃ | iso-propyl |
| E'-34 | —CH₃ | H | —CH₂CH₃ | iso-propyl |
| E'-35 | —CH₃ | —CH₃ | H | iso-propyl |
| E'-36 | —CH₂CH₃ | —CH₂CH₃ | H | iso-propyl |
| E'-37 | iso-butyl | iso-butyl | H | iso-propyl |
| E'-38 | —CH₂CH₃ | —CH₃ | H | iso-propyl |
| E'-39 | —CH₃ | —CH₂CH₃ | H | iso-propyl |
| E'-40 | —CH₃ | H | —CH₃ | iso-butyl |
| E'-41 | —CH₂CH₃ | H | —CH₂CH₃ | iso-butyl |
| E'-42 | iso-propyl | H | iso-propyl | iso-butyl |
| E'-43 | iso-butyl | H | iso-butyl | iso-butyl |
| E'-44 | cyclopentyl | H | cyclopentyl | iso-butyl |
| E'-45 | cyclohexyl | H | cyclohexyl | iso-butyl |
| E'-46 | —CH₂CH₃ | H | —CH₃ | iso-butyl |
| E'-47 | —CH₃ | H | —CH₂CH₃ | iso-butyl |
| E'-48 | —CH₃ | —CH₃ | H | iso-butyl |
| E'-49 | —CH₂CH₃ | —CH₂CH₃ | H | iso-butyl |
| E'-50 | iso-butyl | iso-butyl | H | iso-butyl |
| E'-51 | —CH₂CH₃ | —CH₃ | H | iso-butyl |
| E'-52 | —CH₃ | —CH₂CH₃ | H | iso-butyl |
| E'-53 | H | H | —CH₃ | H |
| E'-54 | H | H | —CH₂CH₃ | H |
| E'-55 | H | H | iso-propyl | H |
| E'-56 | H | H | iso-butyl | H |
| E'-57 | H | H | cyclopentyl | H |
| E'-58 | H | H | cyclohexyl | H |
| E'-59 | H | —CH₃ | H | H |
| E'-60 | H | —CH₃ | H | H |
| E'-61 | H | —CH₂CH₃ | H | H |
| E'-62 | H | iso-propyl | H | H |
| E'-63 | H | iso-butyl | H | H |
| E'-64 | H | cyclopentyl | H | H |
| E'-65 | H | cyclohexyl | H | H |

-continued

| Cpd. | R³' | R³ | R³" | R⁴ = R⁵ |
|---|---|---|---|---|
| E'-66 | —CH₃ | H | —CH₃ | —CH₃ |
| E'-67 | —CH₂CH₃ | H | —CH₂CH₃ | —CH₃ |
| E'-68 | iso-propyl | H | iso-propyl | —CH₃ |
| E'-69 | iso-butyl | H | iso-butyl | —CH₃ |
| E'-70 | cyclopentyl | H | cyclopentyl | —CH₃ |
| E'-71 | cyclohexyl | H | cyclohexyl | —CH₃ |
| E'-72 | —CH₂CH₃ | H | —CH₃ | —CH₃ |
| E'-73 | —CH₃ | H | —CH₂CH₃ | —CH₃ |
| E'-74 | —CH₃ | —CH₃ | H | —CH₃ |
| E'-75 | —CH₂CH₃ | —CH₂CH₃ | H | —CH₃ |
| E'-76 | iso-butyl | iso-butyl | H | —CH₃ |
| E'-77 | —CH₂CH₃ | —CH₃ | H | —CH₃ |
| E'-78 | —CH₃ | —CH₂CH₃ | H | —CH₃ |

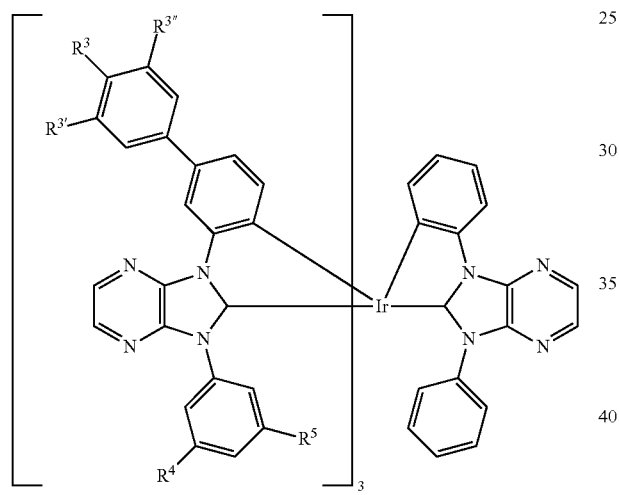

| Cpd. | R³' | R³ | R³" | R⁴ = R⁵ |
|---|---|---|---|---|
| F-1 | —CH₃ | H | —CH₃ | H |
| F-2 | —CH₂CH₃ | H | —CH₂CH₃ | H |
| F-3 | iso-propyl | H | iso-propyl | H |
| F-4 | iso-butyl | H | iso-butyl | H |
| F-5 | cyclopentyl | H | cyclopentyl | H |
| F-6 | cyclohexyl | H | cyclohexyl | H |
| F-7 | —CH₂CH₃ | H | —CH₃ | H |
| F-8 | —CH₃ | H | —CH₂CH₃ | H |
| F-9 | —CH₃ | —CH₃ | H | H |
| F-10 | —CH₂CH₃ | —CH₂CH₃ | H | H |
| F-11 | iso-butyl | iso-butyl | H | H |
| F-12 | —CH₂CH₃ | —CH₃ | H | H |
| F-13 | —CH₃ | —CH₂CH₃ | H | H |
| F-14 | —CH₃ | H | —CH₃ | —CH₂CH₃ |

-continued

| Cpd. | R³' | R³ | R³" | R⁴ = R⁵ |
|---|---|---|---|---|
| F-15 | —CH₂CH₃ | H | —CH₂CH₃ | —CH₂CH₃ |
| F-16 | iso-propyl | H | iso-propyl | —CH₂CH₃ |
| F-17 | iso-butyl | H | iso-butyl | —CH₂CH₃ |
| F-18 | cyclopentyl | H | cyclopentyl | —CH₂CH₃ |
| F-19 | cyclohexyl | H | cyclohexyl | —CH₂CH₃ |
| F-20 | —CH₂CH₃ | H | —CH₃ | —CH₂CH₃ |
| F-21 | —CH₃ | H | —CH₂CH₃ | —CH₂CH₃ |
| F-22 | —CH₃ | —CH₃ | H | —CH₂CH₃ |
| F-23 | —CH₂CH₃ | —CH₂CH₃ | H | —CH₂CH₃ |
| F-24 | iso-butyl | iso-butyl | H | —CH₂CH₃ |
| F-25 | —CH₂CH₃ | —CH₃ | H | —CH₂CH₃ |
| F-26 | —CH₃ | —CH₂CH₃ | H | —CH₂CH₃ |
| F-27 | —CH₃ | H | —CH₃ | iso-propyl |
| F-28 | —CH₂CH₃ | H | —CH₂CH₃ | iso-propyl |
| F-29 | iso-propyl | H | iso-propyl | iso-propyl |
| F-30 | iso-butyl | H | iso-butyl | iso-propyl |
| F-31 | cyclopentyl | H | cyclopentyl | iso-propyl |
| F-32 | cyclohexyl | H | cyclohexyl | iso-propyl |
| F-33 | —CH₂CH₃ | H | —CH₃ | iso-propyl |
| F-34 | —CH₃ | H | —CH₂CH₃ | iso-propyl |
| F-35 | —CH₃ | —CH₃ | H | iso-propyl |
| F-36 | —CH₂CH₃ | —CH₂CH₃ | H | iso-propyl |
| F-37 | iso-butyl | iso-butyl | H | iso-propyl |
| F-38 | —CH₂CH₃ | —CH₃ | H | iso-propyl |
| F-39 | —CH₃ | —CH₂CH₃ | H | iso-propyl |
| F-40 | —CH₃ | H | —CH₃ | iso-butyl |
| F-41 | —CH₂CH₃ | H | —CH₂CH₃ | iso-butyl |
| F-42 | iso-propyl | H | iso-propyl | iso-butyl |
| F-43 | iso-butyl | H | iso-butyl | iso-butyl |
| F-44 | cyclopentyl | H | | iso-butyl |
| F-45 | cyclohexyl | H | cyclohexyl | iso-butyl |
| F-46 | —CH₂CH₃ | H | —CH₃ | iso-butyl |
| F-47 | —CH₃ | H | —CH₂CH₃ | iso-butyl |
| F-48 | —CH₃ | —CH₃ | H | iso-butyl |
| F-49 | —CH₂CH₃ | —CH₂CH₃ | H | iso-butyl |
| F-50 | iso-butyl | iso-butyl | H | iso-butyl |
| F-51 | —CH₂CH₃ | —CH₃ | H | iso-butyl |
| F-52 | —CH₃ | —CH₂CH₃ | H | iso-butyl |
| F-53 | —CH₃ | —CH₃ | H | tert-butyl |
| F-54 | —CH₂CH₃ | —CH₂CH₃ | H | tert-butyl |
| F-55 | iso-propyl | iso-propyl | H | tert-butyl |
| F-56 | iso-butyl | iso-butyl | H | tert-butyl |
| F-57 | neopentyl | neopentyl | H | tert-butyl |
| F-58 | —CH₃ | —CH₂CH₃ | H | tert-butyl |
| F-59 | cyclopentyl | cyclopentyl | H | tert-butyl |

-continued

| Cpd. | R³' | R³ | R³" | R⁴ = R⁵ |
|---|---|---|---|---|
| F-60 | cyclohexyl | cyclohexyl | H | tert-butyl |
| F-61 | —CH₃ | —CH₃ | —CH₃ | tert-butyl |
| F-62 | ethyl | ethyl | —CH₃ | tert-butyl |
| F-63 | iso-propyl | iso-propyl | —CH₃ | tert-butyl |
| F-64 | —CH₃ | —CH₃ | iso-propyl | tert-butyl |
| F-65 | ethyl | ethyl | iso-propyl | tert-butyl |
| E-66 | iso-propyl | iso-propyl | iso-propyl | tert-butyl |
| F-67 | —CH₃ | —CH₃ | H | tert-butyl |
| F-68 | H | H | —CH₃ | H |
| F-69 | H | H | —CH₂CH₃ | H |
| F-70 | H | H | iso-propyl | H |
| F-71 | H | H | iso-butyl | H |
| F-72 | H | H | cyclopentyl | H |
| F-73 | H | H | cyclohexyl | H |
| F-74 | H | —CH₃ | H | H |
| F-75 | H | —CH₃ | H | H |
| F-76 | H | —CH₂CH₃ | H | H |
| F-77 | H | iso-propyl | H | H |
| F-78 | H | iso-butyl | H | H |
| F-79 | H | cyclopentyl | H | H |
| F-80 | H | cyclohexyl | H | H |
| F-81 | —CH₃ | H | —CH₃ | —CH₃ |
| F-82 | —CH₂CH₃ | H | —CH₂CH₃ | —CH₃ |
| F-83 | iso-propyl | H | iso-propyl | —CH₃ |
| F-84 | iso-butyl | H | iso-butyl | —CH₃ |
| F-85 | cyclopentyl | H | cyclopentyl | —CH₃ |
| F-86 | cyclohexyl | H | cyclohexyl | —CH₃ |
| F-87 | —CH₂CH₃ | H | —CH₃ | —CH₃ |
| F-88 | —CH₃ | H | —CH₂CH₃ | —CH₃ |
| F-89 | —CH₃ | —CH₃ | H | —CH₃ |
| F-90 | —CH₂CH₃ | —CH₂CH₃ | H | —CH₃ |
| F-91 | iso-butyl | iso-butyl | H | —CH₃ |
| F-92 | —CH₂CH₃ | —CH₃ | H | —CH₃ |
| F-93 | —CH₃ | —CH₂CH₃ | H | —CH₃ |

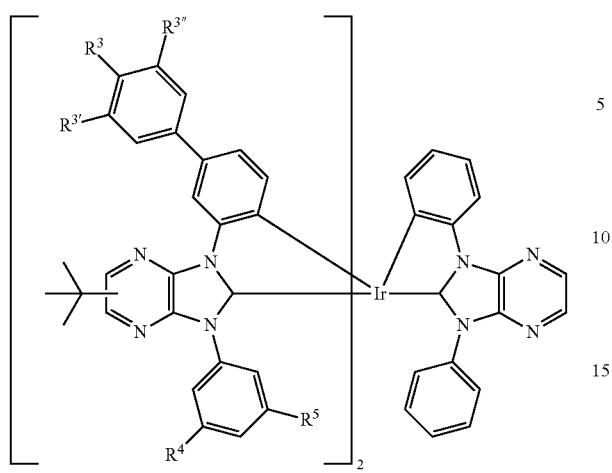

| Cpd.  | R³'      | R³       | R³"      | R⁴ = R⁵   |
|-------|----------|----------|----------|-----------|
| F'-1  | —CH₃     | H        | —CH₃     | H         |
| F'-2  | —CH₂CH₃  | H        | —CH₂CH₃  | H         |
| F'-3  | iso-propyl | H      | iso-propyl | H       |
| F'-4  | iso-butyl | H       | iso-butyl | H        |
| F'-5  | cyclopentyl | H     | cyclopentyl | H      |
| F'-6  | cyclohexyl | H      | cyclohexyl | H       |
| F'-7  | —CH₂CH₃  | H        | —CH₃     | H         |
| F'-8  | —CH₃     | H        | —CH₂CH₃  | H         |
| F'-9  | —CH₃     | —CH₃     | H        | H         |
| F'-10 | —CH₂CH₃  | —CH₂CH₃  | H        | H         |
| F'-11 | iso-butyl | iso-butyl | H      | H         |
| F'-12 | —CH₂CH₃  | —CH₃     | H        | H         |
| F'-13 | —CH₃     | —CH₂CH₃  | H        | H         |
| F'-14 | —CH₃     | H        | —CH₃     | —CH₂CH₃   |
| F'-15 | —CH₂CH₃  | H        | —CH₂CH₃  | —CH₂CH₃   |
| F'-16 | iso-propyl | H      | iso-propyl | —CH₂CH₃ |
| F'-17 | iso-butyl | H       | iso-butyl | —CH₂CH₃  |
| F'-18 | cyclopentyl | H     | cyclopentyl | —CH₂CH₃ |
| F'-19 | cyclohexyl | H      | cyclohexyl | —CH₂CH₃ |
| F'-20 | —CH₂CH₃  | H        | —CH₃     | —CH₂CH₃   |
| F'-21 | —CH₃     | H        | —CH₂CH₃  | —CH₂CH₃   |
| F'-22 | —CH₃     | —CH₃     | H        | —CH₂CH₃   |
| F'-23 | —CH₂CH₃  | —CH₂CH₃  | H        | —CH₂CH₃   |
| F'-24 | iso-butyl | iso-butyl | H     | —CH₂CH₃   |
| F'-25 | —CH₂CH₃  | —CH₃     | H        | —CH₂CH₃   |
| F'-26 | —CH₃     | —CH₂CH₃  | H        | —CH₂CH₃   |
| F'-27 | —CH₃     | H        | —CH₃     | iso-propyl |
| F'-28 | —CH₂CH₃  | H        | —CH₂CH₃  | iso-propyl |
| F'-29 | iso-propyl | H      | iso-propyl | iso-propyl |
| F'-30 | iso-butyl | H       | iso-butyl | iso-propyl |
| F'-31 | cyclopentyl | H     | cyclopentyl | iso-propyl |

-continued

| Cpd. | R³' | R³ | R³" | R⁴ = R⁵ |
|---|---|---|---|---|
| F'-32 | cyclohexyl | H | cyclohexyl | iso-propyl |
| F'-33 | —CH₂CH₃ | H | —CH₃ | iso-propyl |
| F'-34 | —CH₃ | H | —CH₂CH₃ | iso-propyl |
| F'-35 | —CH₃ | —CH₃ | H | iso-propyl |
| F'-36 | —CH₂CH₃ | —CH₂CH₃ | H | iso-propyl |
| F'-37 | iso-butyl | iso-butyl | H | iso-propyl |
| F'-38 | —CH₂CH₃ | —CH₃ | H | iso-propyl |
| F'-39 | —CH₃ | —CH₂CH₃ | H | iso-propyl |
| F'-40 | —CH₃ | H | —CH₃ | iso-butyl |
| F'-41 | —CH₂CH₃ | H | —CH₂CH₃ | iso-butyl |
| F'-42 | iso-propyl | H | iso-propyl | iso-butyl |
| F'-43 | iso-butyl | H | iso-butyl | iso-butyl |
| F'-44 | cyclopentyl | H | cyclopentyl | iso-butyl |
| F'-45 | cyclohexyl | H | cyclohexyl | iso-butyl |
| F'-46 | —CH₂CH₃ | H | —CH₃ | iso-butyl |
| F'-47 | —CH₃ | H | —CH₂CH₃ | iso-butyl |
| F'-48 | —CH₃ | —CH₃ | H | iso-butyl |
| F'-49 | —CH₂CH₃ | —CH₂CH₃ | H | iso-butyl |
| F'-50 | iso-butyl | iso-butyl | H | iso-butyl |
| F'-51 | —CH₂CH₃ | —CH₃ | H | iso-butyl |
| F'-52 | —CH₃ | —CH₂CH₃ | H | iso-butyl |
| F'-53 | H | H | —CH₃ | H |
| F'-54 | H | H | —CH₂CH₃ | H |
| F'-55 | H | H | iso-propyl | H |
| F'-56 | H | H | iso-butyl | H |
| F'-57 | H | H | cyclopentyl | H |
| F'-58 | H | H | cyclohexyl | H |
| F'-59 | H | —CH₃ | H | H |
| F'-60 | H | —CH₃ | H | H |
| F'-61 | H | —CH₂CH₃ | H | H |
| F'-62 | H | iso-propyl | H | H |
| F'-63 | H | iso-butyl | H | H |
| F'-64 | H | cyclopentyl | H | H |
| F'-65 | H | cyclohexyl | H | H |
| F'-66 | —CH₃ | H | —CH₃ | —CH₃ |
| F'-67 | —CH₂CH₃ | H | —CH₂CH₃ | —CH₃ |
| F'-68 | iso-propyl | H | iso-propyl | —CH₃ |
| F'-69 | iso-butyl | H | iso-butyl | —CH₃ |
| F'-70 | cyclopentyl | H | cyclopentyl | —CH₃ |
| F'-71 | cyclohexyl | H | cyclohexyl | —CH₃ |

-continued

| Cpd. | R³' | R³ | R³" | R⁴ = R⁵ |
|---|---|---|---|---|
| F'-72 | —CH₂CH₃ | H | —CH₃ | —CH₃ |
| F'-73 | —CH₃ | H | —CH₂CH₃ | —CH₃ |
| F'-74 | —CH₃ | —CH₃ | H | —CH₃ |
| F'-75 | —CH₂CH₃ | —CH₂CH₃ | H | —CH₃ |
| F'-76 | iso-butyl | iso-butyl | H | —CH₃ |
| F'-77 | —CH₂CH₃ | —CH₃ | H | —CH₃ |
| F'-78 | —CH₃ | —CH₂CH₃ | H | —CH₃ |

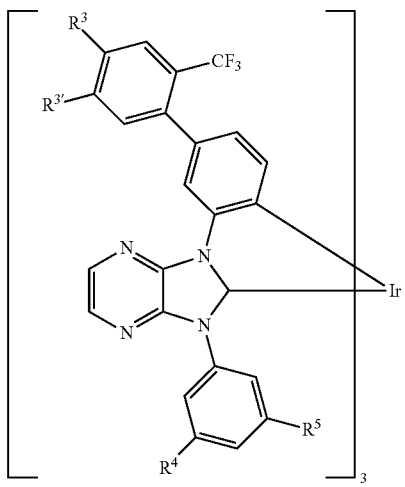

| Cpd. | R³' | R³ | R⁴ = R⁵ |
|---|---|---|---|
| G-1 | H | H | H |
| G-2 | —CH₃ | H | H |
| G-3 | —CH₂CH₃ | H | H |
| G-4 | iso-propyl | H | H |
| G-5 | iso-butyl | H | H |
| G-6 | cyclopentyl | H | H |
| G-7 | cyclohexyl | H | H |
| G-8 | H | H | H |
| G-9 | H | —CH₃ | H |
| G-10 | H | —CH₂CH₃ | H |
| G-11 | H | iso-propyl | H |
| G-12 | H | iso-butyl | H |
| G-13 | H | cyclopentyl | H |
| G-14 | H | cyclohexyl | H |
| G-15 | —CH₃ | —CH₃ | H |
| G-16 | —CH₂CH₃ | —CH₂CH₃ | H |
| G-17 | iso-propyl | iso-propyl | H |
| G-18 | iso-butyl | iso-butyl | H |
| G-19 | —CH₃ | —CH₂CH₃ | H |
| G-20 | —CH₂CH₃ | —CH₃ | H |
| G-21 | H | H | —CH₂CH₃ |
| G-22 | —CH₃ | H | —CH₂CH₃ |
| G-23 | —CH₂CH₃ | H | —CH₂CH₃ |
| G-24 | iso-propyl | H | —CH₂CH₃ |
| G-25 | iso-butyl | H | —CH₂CH₃ |
| G-26 | cyclopentyl | H | —CH₂CH₃ |
| G-27 | cyclohexyl | H | —CH₂CH₃ |
| G-28 | H | H | —CH₂CH₃ |
| G-29 | H | —CH₃ | —CH₂CH₃ |
| G-30 | H | —CH₂CH₃ | —CH₂CH₃ |
| G-31 | H | iso-propyl | —CH₂CH₃ |
| G-32 | H | iso-butyl | —CH₂CH₃ |
| G-33 | H | cyclopentyl | —CH₂CH₃ |
| G-34 | H | cyclohexyl | —CH₂CH₃ |
| G-35 | —CH₃ | —CH₃ | —CH₂CH₃ |
| G-36 | —CH₂CH₃ | —CH₂CH₃ | —CH₂CH₃ |
| G-37 | iso-propyl | iso-propyl | —CH₂CH₃ |
| G-38 | iso-butyl | iso-butyl | —CH₂CH₃ |
| G-39 | —CH₃ | —CH₂CH₃ | —CH₂CH₃ |
| G-40 | —CH₂CH₃ | —CH₃ | —CH₂CH₃ |
| G-41 | H | H | iso-propyl |
| G-42 | —CH₃ | H | iso-propyl |
| G-43 | —CH₂CH₃ | H | iso-propyl |
| G-44 | iso-propyl | H | iso-propyl |
| G-45 | iso-butyl | H | iso-propyl |
| G-46 | cyclopentyl | H | iso-propyl |
| G-47 | cyclohexyl | H | iso-propyl |
| G-48 | H | H | iso-propyl |
| G-49 | H | —CH₃ | iso-propyl |
| G-50 | H | —CH₂CH₃ | iso-propyl |

-continued

| Cpd. | R³' | R³ | R⁴ = R⁵ |
|---|---|---|---|
| G-51 | H | iso-propyl | iso-propyl |
| G-52 | H | iso-butyl | iso-propyl |
| G-53 | H | cyclopentyl | iso-propyl |
| G-54 | H | cyclohexyl | iso-propyl |
| G-55 | —CH₃ | —CH₃ | iso-propyl |
| G-56 | —CH₂CH₃ | —CH₂CH₃ | iso-propyl |
| G-57 | iso-propyl | iso-propyl | iso-propyl |
| G-58 | iso-butyl | iso-butyl | iso-propyl |
| G-59 | —CH₃ | —CH₂CH₃ | iso-propyl |
| G-60 | —CH₂CH₃ | —CH₃ | iso-propyl |
| G-61 | H | H | iso-butyl |
| G-62 | —CH₃ | H | iso-butyl |
| G-63 | —CH₂CH₃ | H | iso-butyl |
| G-64 | iso-propyl | H | iso-butyl |
| G-65 | iso-butyl | H | iso-butyl |
| G-66 | cyclopentyl | H | iso-butyl |
| G-67 | cyclohexyl | H | iso-butyl |
| G-68 | H | H | iso-butyl |
| G-69 | H | —CH₃ | iso-butyl |
| G-70 | H | —CH₂CH₃ | iso-butyl |
| G-71 | H | iso-propyl | iso-butyl |
| G-72 | H | iso-butyl | iso-butyl |
| G-73 | H | cyclopentyl | iso-butyl |
| G-74 | H | cyclohexyl | iso-butyl |
| G-75 | —CH₃ | —CH₃ | iso-butyl |
| G-76 | —CH₂CH₃ | —CH₂CH₃ | iso-butyl |
| G-77 | iso-propyl | iso-propyl | iso-butyl |
| G-78 | iso-butyl | iso-butyl | iso-butyl |
| G-79 | —CH₃ | —CH₂CH₃ | iso-butyl |
| G-80 | —CH₂CH₃ | —CH₃ | iso-butyl |
| G-81 | H | H | CH₃ |
| G-82 | —CH₃ | H | CH₃ |
| G-83 | —CH₂CH₃ | H | CH₃ |
| G-84 | iso-propyl | H | CH₃ |
| G-85 | iso-butyl | H | CH₃ |
| G-86 | cyclopentyl | H | CH₃ |
| G-87 | cyclopentyl | H | CH₃ |
| G-88 | H | H | CH₃ |
| G-89 | H | —CH₃ | CH₃ |
| G-90 | H | —CH₂CH₃ | CH₃ |
| G-91 | H | iso-propyl | CH₃ |
| G-92 | H | iso-butyl | CH₃ |
| G-93 | H | cyclopentyl | CH₃ |
| G-94 | H | cyclohexyl | CH₃ |
| G-95 | —CH₃ | —CH₃ | CH₃ |
| G-96 | —CH₂CH₃ | —CH₂CH₃ | CH₃ |
| G-97 | iso-propyl | iso-propyl | CH₃ |
| G-98 | iso-butyl | iso-butyl | CH₃ |
| G-99 | —CH₃ | —CH₂CH₃ | CH₃ |
| G-100 | —CH₂CH₃ | —CH₃ | CH₃ |

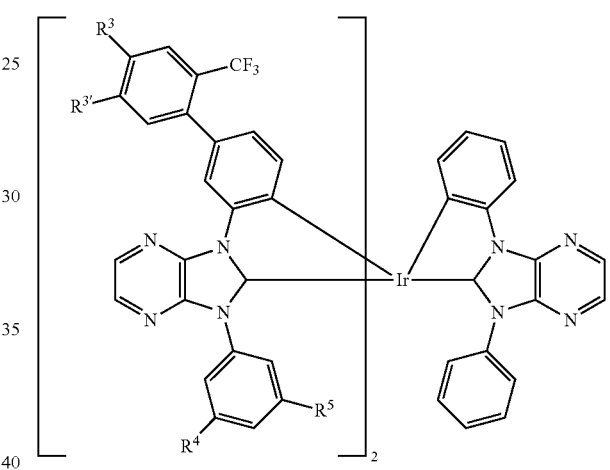

| Cpd. | R³' | R³ | R⁴ = R⁵ |
|---|---|---|---|
| H-1 | H | H | H |
| H-2 | —CH₃ | H | H |
| H-3 | —CH₂CH₃ | H | H |
| H-4 | iso-propyl | H | H |
| H-5 | iso-butyl | H | H |
| H-6 | cyclopentyl | H | H |
| H-7 | cyclohexyl | H | H |
| H-8 | H | H | H |
| H-9 | H | —CH₃ | H |
| H-10 | H | —CH₂CH₃ | H |
| H-11 | H | iso-propyl | H |
| H-12 | H | iso-butyl | H |
| H-13 | H | cyclopentyl | H |

| Cpd. | R³' | R³ | R⁴ = R⁵ |
|---|---|---|---|
| H-14 | H | cyclohexyl | H |
| H-15 | —CH₃ | —CH₃ | H |
| H-16 | —CH₂CH₃ | —CH₂CH₃ | H |
| H-17 | iso-propyl | iso-propl | H |
| H-18 | iso-butyl | iso-butyl | H |
| H-19 | —CH₃ | —CH₂CH₃ | H |
| H-20 | —CH₂CH₃ | —CH₃ | H |
| H-21 | H | H | —CH₂CH₃ |
| H-22 | —CH₃ | H | —CH₂CH₃ |
| H-23 | —CH₂CH₃ | H | —CH₂CH₃ |
| H-24 | iso-propyl | H | —CH₂CH₃ |
| H-25 | iso-butyl | H | —CH₂CH₃ |
| H-26 | cyclopentyl | H | —CH₂CH₃ |
| H-27 | cyclohexyl | H | —CH₂CH₃ |
| H-28 | H | H | —CH₂CH₃ |
| H-29 | H | —CH₃ | —CH₂CH₃ |
| H-30 | H | —CH₂CH₃ | —CH₂CH₃ |
| H-31 | H | iso-propyl | —CH₂CH₃ |
| H-32 | H | iso-butyl | —CH₂CH₃ |
| H-33 | H | cyclopentyl | —CH₂CH₃ |
| H-34 | H | cyclohexyl | —CH₂CH₃ |
| H-35 | —CH₃ | —CH₃ | —CH₂CH₃ |
| H-36 | —CH₂CH₃ | —CH₂CH₃ | —CH₂CH₃ |
| H-37 | iso-propyl | ios-propyl | —CH₂CH₃ |
| H-38 | iso-butyl | iso-butyl | —CH₂CH₃ |
| H-39 | —CH₃ | —CH₂CH₃ | —CH₂CH₃ |
| H-40 | —CH₂CH₃ | —CH₃ | —CH₂CH₃ |
| H-41 | H | H | iso-propyl |
| H-42 | —CH₃ | H | iso-propyl |
| H-43 | —CH₂CH₃ | H | iso-propyl |
| H-44 | iso-propyl | H | iso-propyl |
| H-45 | iso-butyl | H | iso-propyl |
| H-46 | cyclopentyl | H | iso-propyl |
| H-47 | cyclohexyl | H | iso-propyl |
| H-48 | H | H | iso-propyl |
| H-49 | H | —CH₃ | iso-propyl |
| H-50 | H | —CH₂CH₃ | iso-propyl |
| H-51 | H | iso-propyl | iso-propyl |
| H-52 | H | iso-butyl | iso-propyl |
| H-53 | H | cyclopentyl | iso-propyl |
| H-54 | H | cyclohexyl | iso-propyl |
| H-55 | —CH₃ | —CH₃ | iso-propyl |
| H-56 | —CH₂CH₃ | —CH₂CH₃ | iso-propyl |
| H-57 | iso-propyl | iso-propyl | iso-propyl |
| H-58 | iso-butyl | iso-butyl | iso-propyl |
| H-59 | —CH₃ | —CH₂CH₃ | iso-propyl |
| H-60 | —CH₂CH₃ | —CH₃ | iso-propyl |
| H-61 | H | H | iso-butyl |
| H-62 | —CH₃ | H | iso-butyl |
| H-63 | —CH₂CH₃ | H | iso-butyl |
| H-64 | iso-propyl | H | iso-butyl |
| H-65 | iso-butyl | H | iso-butyl |
| H-66 | cyclopentyl | H | iso-butyl |
| H-67 | cyclohexyl | H | iso-butyl |
| H-68 | H | H | iso-butyl |
| H-69 | H | —CH₃ | iso-butyl |
| H-70 | H | —CH₂CH₃ | iso-butyl |
| H-71 | H | iso-propyl | iso-butyl |
| H-72 | H | iso-butyl | iso-butyl |
| H-73 | H | cyclopentyl | iso-butyl |
| H-74 | H | cyclohexyl | iso-butyl |
| H-75 | —CH₃ | —CH₃ | iso-butyl |
| H-76 | —CH₂CH₃ | —CH₂CH₃ | iso-butyl |
| H-77 | iso-propyl | iso-propyl | iso-butyl |
| H-78 | iso-butyl | iso-butyl | iso-butyl |
| H-79 | —CH₃ | —CH₂CH₃ | iso-butyl |
| H-80 | —CH₂CH₃ | —CH₃ | iso-butyl |
| H-81 | H | H | CH₃ |
| H-82 | —CH₃ | H | CH₃ |
| H-83 | —CH₂CH₃ | H | CH₃ |
| H-84 | iso-propyl | H | CH₃ |
| H-85 | iso-butyl | H | CH₃ |
| H-86 | cyclopentyl | H | CH |
| H-87 | cyclohexyl | H | CH₃ |
| H-88 | H | H | CH₃ |
| H-89 | H | —CH₃ | CH₃ |
| H-90 | H | —CH₂CH₃ | CH₃ |
| H-91 | H | iso-propyl | CH₃ |
| H-92 | H | iso-butyl | CH₃ |

-continued

| Cpd. | R³' | R³ | R⁴ = R⁵ |
|---|---|---|---|
| H-93 | H | cyclopentyl | CH₃ |
| H-94 | H | cyclohexyl | CH₃ |
| H-95 | —CH₃ | —CH₃ | CH₃ |
| H-96 | —CH₂CH₃ | —CH₂CH₃ | CH₃ |
| H-97 | iso-propyl | iso-propyl | CH₃ |
| H-98 | iso-butyl | iso-butyl | CH₃ |
| H-99 | —CH₃ | —CH₂CH₃ | CH₃ |
| H-100 | —CH₂CH₃ | —CH₃ | CH₃ |

Among the above metal carbene-complexes A-1 to A-84, A'-1 to A'-70, B-1 to B-84, B'-1 to B'-70, C-1 to C-163, C'-1 to C'-143, D-1 to D-163, D'-1 to D'-143, E-1 to E-93, E'-1 to E'-78, F-1 to F-93, F'-1 to F'-78, G-1 to G-100, H-1 to H-100 the metal carbene-complexes A-1 to A-70, A'-1 to A'-70, B-1 to B-70, B'-1 to B'-70, C-1 to C-110, C-125 to C-154, C-161 to C-163, C'-1 to C'-116, C'-141 to C'-143, D-1 to D-110, D-125 to D-154, D-161 to D-163, D'-1 to D'-116, D'-141 to D'-143 are preferred. Among these metal carbene-complexes metal carbene-complexes are more preferred, wherein R⁴ and R⁵ are H.

Metal carbene-complexes A-1 to A-70, A'-1 to A'-70, C-1 to C-110, C-125 to C-154, C-161 to C-163, C'-1 to C'-116, C'-141 to C'-143 are more preferred. Metal carbene-complexes A-1 to A-70, C-1 to C-110, C-125 to C-154, C-161 to C-163 are even more preferred. Among these metal carbene-complexes metal carbene-complexes are more preferred, wherein R⁴ and R⁵ are H.

Metal carbene-complexes A-2, A-3, A-4, A-6, A-14, C-126, C-127 and C-128 are most preferred.

In another preferred embodiment the present invention is directed to metal complexes of formula (IIa), (IIb), or (IIc), wherein L is a ligand

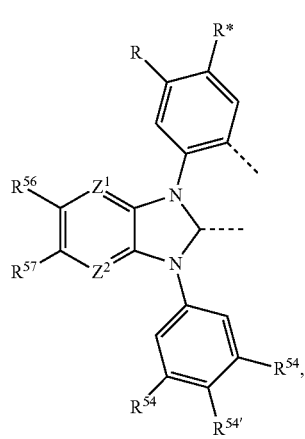

(D')

wherein wherein $Z^1$ and $Z^2$ are N, or $Z^1$ and $Z^2$ are CH; R* has the meaning of R', $R^{54}$ has the meaning of $R^4$, $R^{54'}$ has the meaning of $R^{4'}$, $R^{55}$ has the meaning of $R^5$, $R^{56}$ has the meaning of $R^6$ and $R^{57}$ has the meaning of $R^7$ and each group R is the same within one metal-carbene complex and is, for example, a group of formula

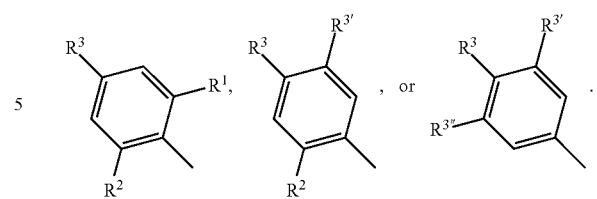

In said embodiment, the metal-carbene complex is preferably a metal-carbene complex of formula (IIa), (IIb), or (IIc), more preferably a metal-carbene complex of formula (IIIa), (IIIb), or (IIIc), most preferred a metal-carbene complex of formula (IIIa'), (IIIb'), or (IIIc').

For R*, $R^{54}$, $R^{54'}$, $R^{55}$, $R^{56}$ and $R^{57}$ the same preferences apply as for R', $R^4$, $R^{4'}$, $R^5$, $R^6$ and $R^7$, respectively.

Preferably, $Z^1$ is CH, $Z^2$ is CH, R* and R' are H, $R^{54}$ is the same as $R^4$, $R^{54'}$ is the same as $R^{4'}$, $R^{55}$ is the same as $R^5$, $R^{56}$ is the same as $R^6$ and $R^{57}$ is the same as $R^7$.

In said embodiment the metal-carbene complex is preferably a metal-carbene complex of formula

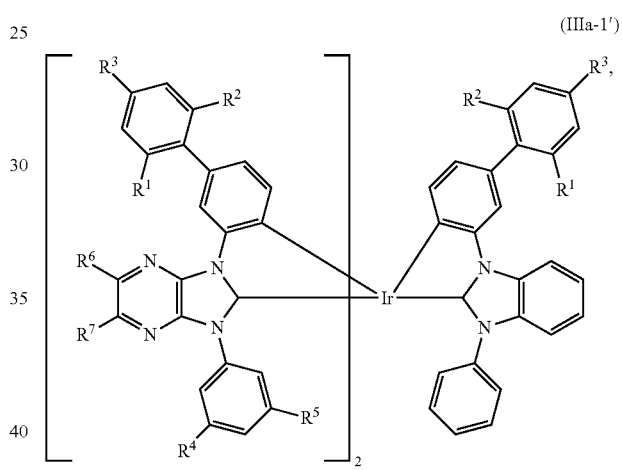

(IIIa-1')

wherein $R^1$ and $R^2$ are independently of each other a $C_1$-$C_5$alkyl group, especially methyl, ethyl, iso-propyl, isobutyl and neopentyl; a cyclopentyl or cyclohexyl group, $R^3$ is H, or a $C_1$-$C_4$alkyl group; or

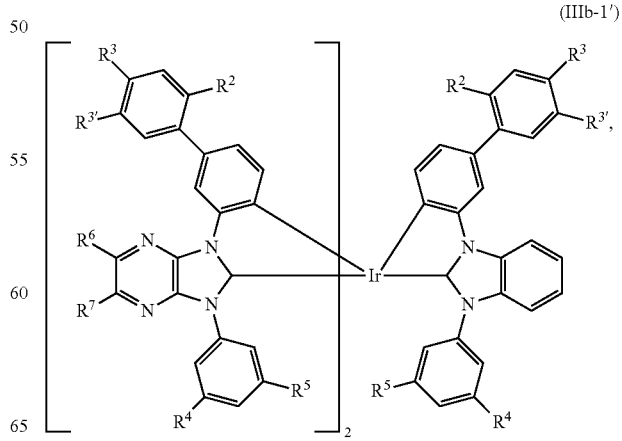

(IIIb-1')

wherein R² is CF₃, especially a $C_1$-$C_5$alkyl group, especially methyl, ethyl, iso-propyl and isobutyl; a cyclopentyl or cyclohexyl group;

R³ is H, a $C_1$-$C_5$alkyl group, especially methyl, ethyl, iso-propyl and isobutyl; a cyclopentyl or cyclohexyl group; and R³' is H, a $C_1$-$C_5$alkyl group, especially methyl, ethyl, iso-propyl and isobutyl; a cyclopentyl or cyclohexyl group; with the proviso that in case one of R³ and R³' is a cyclopentyl or cyclohexyl group, the other is H. R⁶ and R⁷ are independently of each other hydrogen, a $C_1$-$C_8$alkyl group, a $C_3$-$C_6$cycloalkyl group; or R⁶ and R⁷ form together a ring

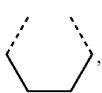

with the proviso that if one of R⁶ and R⁷ is a $C_1$-$C_8$alkyl group, or a $C_3$-$C_6$cycloalkyl group, the other is H. R⁶ and R⁷ are preferably H. R⁴ and R⁵ are preferably H. Examples of metal carbene complexes are shown below:

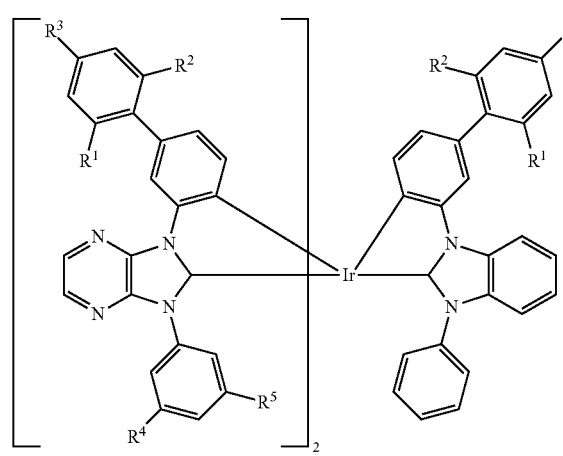

| Cpd. | R¹ | R² | R³ | R⁴ = R⁵ |
|---|---|---|---|---|
| I-1 | —CH₃ | —CH₃ | H | H |
| I-2 | —CH₂CH₃ | —CH₂CH₃ | H | H |
| I-3 | iso-propyl | iso-propyl | H | H |
| I-4 | iso-butyl | iso-butyl | H | H |
| I-5 | neopentyl | neopentyl | H | H |
| I-6 | —CH₃ | —CH₂CH₃ | H | H |
| I-7 | 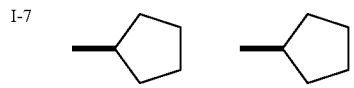 | | H | H |
| I-8 | 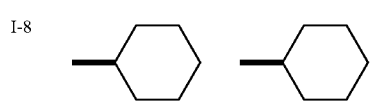 | | H | H |
| I-9 | —CH₃ | —CH₃ | —CH₃ | H |
| I-10 | ethyl | ethyl | —CH₃ | H |
| I-11 | iso-propyl | iso-propyl | —CH₃ | H |
| I-12 | —CH₃ | —CH₃ | iso-propyl | H |
| I-13 | ethyl | ethyl | iso-propyl | H |
| I-14 | iso-propyl | iso-propyl | iso-propyl | H |

-continued

| Cpd. | R¹ | R² | R³ | R⁴ = R⁵ |
|---|---|---|---|---|
| I-15 | —CH₃ | —CH₃ | H | —CH₃ |
| I-16 | —CH₂CH₃ | —CH₂CH₃ | H | —CH₃ |
| I-17 | iso-propyl | iso-propyl | H | —CH₃ |
| I-18 | iso-butyl | iso-butyl | H | —CH₃ |
| I-19 | neopentyl | neopentyl | H | —CH₃ |
| I-20 | —CH₃ | —CH₂CH₃ | H | —CH₃ |
| I-21 | 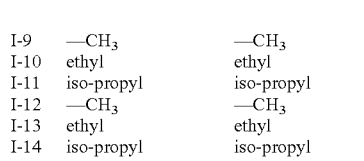 | | H | —CH₃ |
| I-22 | | | H | —CH₃ |
| I-23 | —CH₃ | —CH₃ | —CH₃ | —CH₃ |
| I-24 | ethyl | ethyl | —CH₃ | —CH₃ |
| I-25 | iso-propyl | iso-propyl | —CH₃ | —CH₃ |
| I-26 | —CH₃ | —CH₃ | iso-propyl | —CH₃ |
| I-27 | ethyl | ethyl | iso-propyl | —CH₃ |
| I-28 | iso-propyl | iso-propyl | iso-propyl | —CH₃ |
| I-29 | —CH₃ | —CH₃ | H | —CH₂CH₃ |
| I-30 | —CH₂CH₃ | —CH₂CH₃ | H | —CH₂CH₃ |
| I-31 | iso-propyl | iso-propyl | H | —CH₂CH₃ |
| I-32 | iso-butyl | iso-butyl | H | —CH₂CH₃ |
| I-33 | —CH₃ | —CH₂CH₃ | H | —CH₂CH₃ |
| I-34 | neopentyl | neopentyl | H | —CH₂CH₃ |
| I-35 | | | H | —CH₂CH₃ |
| I-36 | | | H | —CH₂CH₃ |
| I-37 | —CH₃ | —CH₃ | —CH₃ | —CH₂CH₃ |
| I-38 | ethyl | ethyl | —CH₃ | —CH₂CH₃ |
| I-39 | iso-propyl | iso-propyl | —CH₃ | —CH₂CH₃ |
| I-40 | —CH₃ | —CH₃ | iso-propyl | —CH₂CH₃ |
| I-41 | ethyl | ethyl | iso-propyl | —CH₂CH₃ |
| I-42 | iso-propyl | iso-propyl | iso-propyl | —CH₂CH₃ |
| I-43 | —CH₃ | —CH₃ | H | iso-propyl |
| I-44 | —CH₂CH₃ | —CH₂CH₃ | H | iso-propyl |
| I-45 | iso-propyl | iso-propyl | H | iso-propyl |
| I-46 | iso-butyl | iso-butyl | H | iso-propyl |
| I-47 | neopentyl | neopentyl | H | iso-propyl |
| I-48 | —CH₃ | —CH₂CH₃ | H | iso-propyl |
| I-49 | | | H | iso-propyl |
| I-50 | | | H | iso-propyl |
| I-51 | —CH₃ | —CH₃ | —CH₃ | iso-propyl |
| I-52 | ethyl | ethyl | —CH₃ | iso-propyl |
| I-53 | iso-propyl | iso-propyl | —CH₃ | iso-propyl |
| I-54 | —CH₃ | —CH₃ | iso-propyl | iso-propyl |
| I-55 | ethyl | ethyl | iso-propyl | iso-propyl |
| I-56 | iso-propyl | iso-propyl | iso-propyl | iso-propyl |
| I-57 | —CH₃ | —CH₃ | H | iso-butyl |
| I-58 | —CH₂CH₃ | —CH₂CH₃ | H | iso-butyl |
| I-59 | iso-propyl | iso-propyl | H | iso-butyl |
| I-60 | iso-butyl | iso-butyl | H | iso-butyl |
| I-61 | neopentyl | neopentyl | H | iso-butyl |
| I-62 | —CH₃ | —CH₂CH₃ | H | iso-butyl |

-continued

| Cpd. | R¹ | R² | R³ | R⁴ = R⁵ |
|---|---|---|---|---|
| I-63 |  |  | H | iso-butyl |
| I-64 |  |  | H | iso-butyl |
| I-65 | —CH₃ | —CH₃ | —CH₃ | iso-butyl |
| I-66 | ethyl | ethyl | —CH₃ | iso-butyl |
| I-67 | iso-propyl | iso-propyl | —CH₃ | iso-butyl |
| I-68 | —CH₃ | —CH₃ | iso-propyl | iso-butyl |
| I-69 | ethyl | ethyl | iso-propyl | iso-butyl |
| I-70 | iso-propyl | iso-propyl | iso-propyl | iso-butyl |

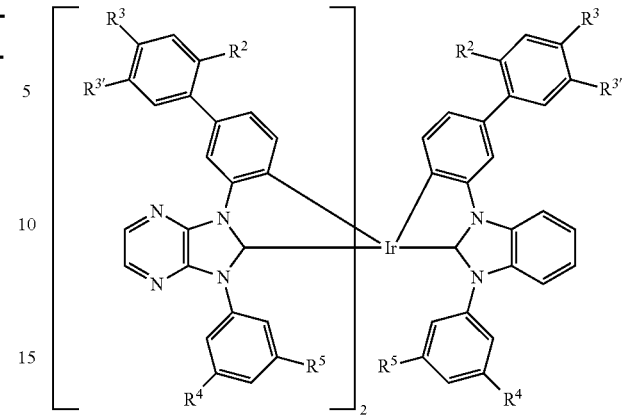

| Cpd. | R² | R³' | R³ | R⁴ = R⁵ |
|---|---|---|---|---|
| J-1 | —CH₃ | —CH₃ | H | H |
| J-2 | —CH₂CH₃ | —CH₂CH₃ | H | H |
| J-3 | iso-propyl | iso-propyl | H | H |
| J-4 | iso-butyl | iso-butyl | H | H |
| J-5 |  |  | H | H |
| J-6 |  |  | H | H |
| J-7 | —CH₂CH₃ | —CH₃ | H | H |
| J-8 | —CH₃ | —CH₂CH₃ | H | H |
| J-9 | —CH₃ | H | —CH₃ | H |
| J-10 | —CH₂CH₃ | H | —CH₂CH₃ | H |
| J-11 | iso-propyl | H | iso-propyl | H |
| J-12 | iso-butyl | H | iso-butyl | H |
| J-13 |  | H |  | H |
| J-14 |  | H |  | H |
| J-15 | —CH₂CH₃ | H | —CH₃ | H |
| J-16 | —CH₃ | H | —CH₂CH₃ | H |
| J-17 | —CH₃ | —CH₃ | —CH₃ | H |
| J-18 | —CH₂CH₃ | —CH₃ | —CH₃ | H |
| J-19 | iso-propyl | —CH₃ | —CH₃ | H |
| J-20 | iso-butyl | —CH₃ | —CH₃ | H |
| J-21 |  | —CH₃ | —CH₃ | H |
| J-22 |  | —CH₃ | —CH₃ | H |
| J-23 | —CH₃ | —CH₃ | H | —CH₃ |
| J-24 | —CH₂CH₃ | —CH₂CH₃ | H | —CH₃ |
| J-25 | iso-propyl | iso-propyl | H | —CH₃ |
| J-26 | iso-butyl | iso-butyl | H | —CH₃ |

-continued

| Cpd. | R² | R³' | R³ | R⁴ = R⁵ |
|---|---|---|---|---|
| J-27 | cyclopentyl | cyclopentyl | H | —CH₃ |
| J-28 | cyclohexyl | cyclohexyl | H | —CH₃ |
| J-29 | —CH₂CH₃ | —CH₃ | H | —CH₃ |
| J-30 | —CH₃ | —CH₂CH₃ | H | —CH₃ |
| J-31 | —CH₃ | H | —CH₃ | —CH₃ |
| J-32 | —CH₂CH₃ | H | —CH₂CH₃ | —CH₃ |
| J-33 | iso-propyl | H | iso-propyl | —CH₃ |
| J-34 | iso-butyl | H | iso-butyl | —CH₃ |
| J-35 | cyclopentyl | H | cyclopentyl | —CH₃ |
| J-36 | cyclohexyl | H | cyclohexyl | —CH₃ |
| J-37 | —CH₂CH₃ | H | —CH₃ | —CH₃ |
| J-38 | —CH₃ | H | —CH₂CH₃ | —CH₃ |
| J-39 | —CH₃ | —CH₃ | —CH₃ | —CH₃ |
| J-40 | —CH₂CH₃ | —CH₃ | —CH₃ | —CH₃ |
| J-41 | iso-propyl | —CH₃ | —CH₃ | —CH₃ |
| J-42 | iso-butyl | —CH₃ | —CH₃ | —CH₃ |
| J-43 | cyclopentyl | —CH₃ | —CH₃ | —CH₃ |
| J-44 | cyclohexyl | —CH₃ | —CH₃ | —CH₃ |
| J-45 | —CH₃ | —CH₃ | H | —CH₂CH₃ |
| J-46 | —CH₂CH₃ | —CH₂CH₃ | H | —CH₂CH₃ |
| J-47 | iso-propyl | iso-propyl | H | —CH₂CH₃ |
| J-48 | iso-butyl | iso-butyl | H | —CH₂CH₃ |
| J-49 | cyclopentyl | cyclopentyl | H | —CH₂CH₃ |
| J-50 | cyclohexyl | cyclohexyl | H | —CH₂CH₃ |
| J-51 | —CH₂CH₃ | —CH₃ | H | —CH₂CH₃ |
| J-52 | —CH₃ | —CH₂CH₃ | H | —CH₂CH₃ |
| J-53 | —CH₃ | H | —CH₃ | —CH₂CH₃ |
| J-54 | —CH₂CH₃ | H | —CH₂CH₃ | —CH₂CH₃ |
| J-55 | iso-propyl | H | iso-propyl | —CH₂CH₃ |
| J-56 | iso-butyl | H | iso-butyl | —CH₂CH₃ |
| J-57 | cyclopentyl | H | cyclopentyl | —CH₂CH₃ |

-continued

| Cpd. | R² | R³' | R³ | R⁴ = R⁵ |
|---|---|---|---|---|
| J-58 | cyclohexyl | H | cyclohexyl | —CH₂CH₃ |
| J-59 | —CH₂CH₃ | H | —CH₃ | —CH₂CH₃ |
| J-60 | —CH₃ | H | —CH₂CH₃ | —CH₂CH₃ |
| J-61 | —CH₃ | —CH₃ | —CH₃ | —CH₂CH₃ |
| J-62 | —CH₂CH₃ | —CH₃ | —CH₃ | —CH₂CH₃ |
| J-63 | iso-propyl | —CH₃ | —CH₃ | —CH₂CH₃ |
| J-64 | iso-butyl | —CH₃ | —CH₃ | —CH₂CH₃ |
| J-65 | cyclopentyl | —CH₃ | —CH₃ | —CH₂CH₃ |
| J-66 | cyclohexyl | —CH₃ | —CH₃ | —CH₂CH₃/ |
| J-67 | —CH₃ | —CH₃ | H | iso-propyl |
| J-68 | —CH₂CH₃ | —CH₂CH₃ | H | iso-propyl |
| J-69 | iso-propyl | iso-propyl | H | iso-propyl |
| J-70 | iso-butyl | iso-butyl | H | iso-propyl |
| J-71 | cyclopentyl | cyclopentyl | H | iso-propyl |
| J-72 | cyclohexyl | cyclohexyl | H | iso-propyl |
| J-73 | —CH₂CH₃ | —CH₃ | H | iso-propyl |
| J-74 | —CH₃ | —CH₂CH₃ | H | iso-propyl |
| J-75 | —CH₃ | H | —CH₃ | iso-propyl |
| J-76 | —CH₂CH₃ | H | —CH₂CH₃ | iso-propyl |
| J-77 | iso-propyl | H | iso-propyl | iso-propyl |
| J-78 | iso-butyl | H | iso-butyl | iso-propyl |
| J-79 | cyclopentyl | H | cyclopentyl | iso-propyl |
| J-80 | cyclohexyl | H | cyclohexyl | iso-propyl |
| J-81 | —CH₂CH₃ | H | —CH₃ | iso-propyl |
| J-82 | —CH₃ | H | —CH₂CH₃ | iso-propyl |
| J-83 | —CH₃ | —CH₃ | —CH₃ | iso-propyl |
| J-84 | —CH₂CH₃ | —CH₃ | —CH₃ | iso-propyl |
| J-85 | iso-propyl | —CH₃ | —CH₃ | iso-propyl |
| J-86 | iso-butyl | —CH₃ | —CH₃ | iso-propyl |
| J-87 | cyclopentyl | —CH₃ | —CH₃ | iso-propyl |
| J-88 | cyclohexyl | —CH₃ | —CH₃ | iso-propyl |
| J-89 | —CH₃ | —CH₃ | H | iso-butyl |
| J-90 | —CH₂CH₃ | —CH₂CH₃ | H | iso-butyl |
| J-91 | iso-propyl | iso-propyl | H | iso-butyl |
| J-92 | iso-butyl | iso-butyl | H | iso-butyl |

-continued

| Cpd. | R² | R³' | R³ | R⁴ = R⁵ |
|---|---|---|---|---|
| J-93 | cyclopentyl | cyclopentyl | H | iso-butyl |
| J-94 | cyclohexyl | cyclohexyl | H | iso-butyl |
| J-95 | —CH₂CH₃ | —CH₃ | H | iso-butyl |
| J-96 | —CH₃ | —CH₂CH₃ | H | iso-butyl |
| J-97 | —CH₃ | H | —CH₃ | iso-butyl |
| J-98 | —CH₂CH₃ | H | —CH₂CH₃ | iso-butyl |
| J-99 | iso-propyl | H | iso-propyl | iso-butyl |
| J-100 | iso-butyl | H | iso-butyl | iso-butyl |
| J-101 | cyclopentyl | H | cyclopentyl | iso-butyl |
| J-102 | cyclohexyl | H | cyclohexyl | iso-butyl |
| J-103 | —CH₂CH₃ | H | —CH₃ | iso-butyl |
| J-104 | —CH₃ | H | —CH₂CH₃ | iso-butyl |
| J-105 | —CH₃ | —CH₃ | —CH₃ | iso-butyl |
| J-106 | —CH₂CH₃ | —CH₃ | —CH₃ | iso-butyl |
| J-107 | iso-propyl | —CH₃ | —CH₃ | iso-butyl |
| J-108 | iso-butyl | —CH₃ | —CH₃ | iso-butyl |
| J-109 | cyclopentyl | —CH₃ | —CH₃ | iso-butyl |
| J-110 | cyclohexyl | —CH₃ | —CH₃ | iso-butyl |
| J-111 | —CH₃ | H | H | H |
| J-112 | —CH₂CH₃ | H | H | H |
| J-113 | iso-propyl | H | H | H |
| J-114 | iso-butyl | H | H | H |
| J-115 | cyclopentyl | H | H | H |
| J-116 | cyclohexyl | H | H | H |
| J-117 | —CH₃ | H | H | —CH₃ |
| J-118 | —CH₂CH₃ | H | H | —CH₃ |
| J-119 | iso-propyl | H | H | —CH₃ |
| J-120 | iso-butyl | H | H | —CH₃ |
| J-121 | cyclopentyl | H | H | —CH₃ |
| J-122 | cyclohexyl | H | H | —CH₃ |

-continued

| Cpd. | R² | R³' | R³ | R⁴ = R⁵ |
|---|---|---|---|---|
| J-123 | —CH₃ | H | H | —CH₂CH₃ |
| J-124 | —CH₂CH₃ | H | H | —CH₂CH₃ |
| J-125 | iso-propyl | H | H | —CH₂CH₃ |
| J-126 | iso-butyl | H | H | —CH₂CH₃ |
| J-127 | cyclopentyl | H | H | —CH₂CH₃ |
| J-128 | cyclohexyl | H | H | —CH₂CH₃ |
| J-129 | —CH₃ | H | H | iso-propyl |
| J-130 | —CH₂CH₃ | H | H | iso-propyl |
| J-131 | iso-propyl | H | H | iso-propyl |
| J-132 | iso-butyl | H | H | iso-propyl |
| J-133 | cyclopentyl | H | H | iso-propyl |
| J-134 | cyclohexyl | H | H | iso-propyl |
| J-135 | —CH₃ | H | H | iso-butyl |
| J-136 | —CH₂CH₃ | H | H | iso-butyl |
| J-137 | iso-propyl | H | H | iso-butyl |
| J-138 | iso-butyl | H | H | iso-butyl |
| J-139 | cyclopentyl | H | H | iso-butyl |
| J-140 | cyclohexyl | H | H | iso-butyl |

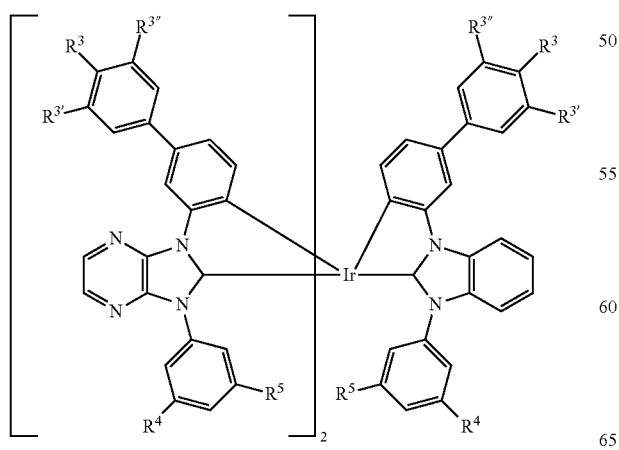

| Cpd. | R³' | R³ | R³" | R⁴ = R⁵ |
| --- | --- | --- | --- | --- |
| K-1 | —CH₃ | H | —CH₃ | H |
| K-2 | —CH₂CH₃ | H | —CH₂CH₃ | H |
| K-3 | iso-propyl | H | iso-propyl | H |
| K-4 | iso-butyl | H | iso-butyl | H |
| K-5 | cyclopentyl | H | cyclopentyl | H |
| K-6 | cyclohexyl | H | cyclohexyl | H |
| K-7 | —CH₂CH₃ | H | —CH₃ | H |
| K-8 | —CH₃ | H | —CH₂CH₃ | H |
| K-9 | —CH₃ | —CH₃ | H | H |
| K-10 | —CH₂CH₃ | —CH₂CH₃ | H | H |
| K-11 | iso-butyl | iso-butyl | H | H |
| K-12 | —CH₂CH₃ | —CH₃ | H | H |
| K-13 | —CH₃ | —CH₂CH₃ | H | H |
| K-14 | —CH₃ | H | —CH₃ | —CH₂CH₃ |
| K-15 | —CH₂CH₃ | H | —CH₂CH₃ | —CH₂CH₃ |
| K-16 | iso-propyl | H | iso-propyl | —CH₂CH₃ |
| K-17 | iso-butyl | H | iso-butyl | —CH₂CH₃ |
| K-18 | cyclopentyl | H | cyclopentyl | —CH₂CH₃ |
| K-19 | cyclohexyl | H | cyclohexyl | —CH₂CH₃ |
| K-20 | —CH₂CH₃ | H | —CH₃ | —CH₂CH₃ |
| K-21 | —CH₃ | H | —CH₂CH₃ | —CH₂CH₃ |
| K-22 | —CH₃ | —CH₃ | H | —CH₂CH₃ |
| K-23 | —CH₂CH₃ | —CH₂CH₃ | H | —CH₂CH₃ |
| K-24 | iso-butyl | iso-butyl | H | —CH₂CH₃ |
| K-25 | —CH₂CH₃ | —CH₃ | H | —CH₂CH₃ |
| K-26 | —CH₃ | —CH₂CH₃ | H | —CH₂CH₃ |
| K-27 | —CH₃ | H | —CH₃ | iso-propyl |
| K-28 | —CH₂CH₃ | H | —CH₂CH₃ | iso-propyl |
| K-29 | iso-propyl | H | iso-propyl | iso-propyl |
| K-30 | iso-butyl | H | iso-butyl | iso-propyl |
| K-31 | cyclopentyl | H | cyclopentyl | iso-propyl |
| K-32 | cyclohexyl | H | cyclohexyl | iso-propyl |
| K-33 | —CH₂CH₃ | H | —CH₃ | iso-propyl |
| K-34 | —CH₃ | H | —CH₂CH₃ | iso-propyl |
| K-35 | —CH₃ | —CH₃ | H | iso-propyl |
| K-36 | —CH₂CH₃ | —CH₂CH₃ | H | iso-propyl |
| K-37 | iso-butyl | iso-butyl | H | iso-propyl |
| K-38 | —CH₂CH₃ | —CH₃ | H | iso-propyl |
| K-39 | —CH₃ | —CH₂CH₃ | H | iso-propyl |
| K-40 | —CH₃ | H | —CH₃ | iso-butyl |
| K-41 | —CH₂CH₃ | H | —CH₂CH₃ | iso-butyl |
| K-42 | iso-propyl | H | iso-propyl | iso-butyl |
| K-43 | iso-butyl | H | iso-butyl | iso-butyl |
| K-44 | cyclopentyl | H | cyclopentyl | iso-butyl |

-continued

| Cpd. | R³' | R³ | R³" | R⁴ = R⁵ |
|---|---|---|---|---|
| K-45 | cyclohexyl | H | cyclohexyl | iso-butyl |
| K-46 | —CH₂CH₃ | H | —CH₃ | iso-butyl |
| K-47 | —CH₃ | H | —CH₂CH₃ | iso-butyl |
| K-48 | —CH₃ | —CH₃ | H | iso-butyl |
| K-49 | —CH₂CH₃ | —CH₂CH₃ | H | iso-butyl |
| K-50 | iso-butyl | iso-butyl | H | iso-butyl |
| K-51 | —CH₂CH₃ | —CH₃ | H | iso-butyl |
| K-52 | —CH₃ | —CH₂CH₃ | H | iso-butyl |
| K-53 | H | H | —CH₃ | H |
| K-54 | H | H | —CH₂CH₃ | H |
| K-55 | H | H | iso-propyl | H |
| K-56 | H | H | iso-butyl | H |
| K-57 | H | H | cyclopentyl | H |
| K-58 | H | H | cyclohexyl | H |
| K-59 | H | —CH₃ | H | H |
| K-60 | H | —CH₃ | H | H |
| K-61 | H | —CH₂CH₃ | H | H |
| K-62 | H | iso-propyl | H | H |
| K-63 | H | iso-butyl | H | H |
| K-64 | H | cyclopentyl | H | H |
| K-65 | H | cyclohexyl | H | H |
| K-66 | —CH₃ | H | —CH₃ | —CH₃ |
| K-67 | —CH₂CH₃ | H | —CH₂CH₃ | —CH₃ |
| K-68 | iso-propyl | H | iso-propyl | —CH₃ |
| K-69 | iso-butyl | H | iso-butyl | —CH₃ |
| K-70 | cyclopentyl | H | cyclopentyl | —CH₃ |
| K-71 | cyclohexyl | H | cyclohexyl | —CH₃ |
| K-72 | —CH₂CH₃ | H | —CH₃ | —CH₃ |
| K-73 | —CH₃ | H | —CH₂CH₃ | —CH₃ |
| K-74 | —CH₃ | —CH₃ | H | —CH₃ |
| K-75 | —CH₂CH₃ | —CH₂CH₃ | H | —CH₃ |
| K-76 | iso-butyl | iso-butyl | H | —CH₃ |
| K-77 | —CH₂CH₃ | —CH₃ | H | —CH₃ |
| K-78 | —CH₃ | —CH₂CH₃ | H | —CH₃ |

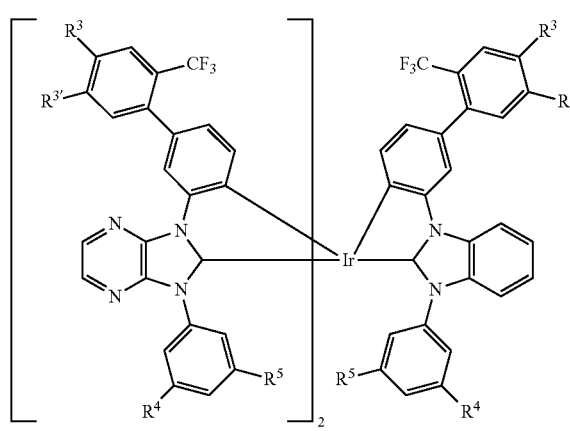

| Cpd. | R3' | R3 | R4 = R5 |
|---|---|---|---|
| L-1 | H | H | H |
| L-2 | —CH3 | H | H |
| L-3 | —CH2CH3 | H | H |
| L-4 | iso-propyl | H | H |
| L-5 | iso-butyl | H | H |
| L-6 | cyclopentyl | H | H |
| L-7 | cyclohexyl | H | H |
| L-8 | H | H | H |
| L-9 | H | —CH3 | H |
| L-10 | H | —CH2CH3 | H |
| L-11 | H | iso-propyl | H |
| L-12 | H | iso-butyl | H |
| L-13 | H | cyclopentyl | H |
| L-14 | H | cyclohexyl | H |
| L-15 | —CH3 | —CH3 | H |
| L-16 | —CH2CH3 | —CH2CH3 | H |
| L-17 | iso-propyl | iso-propyl | H |
| L-18 | iso-butyl | iso-butyl | H |
| L-19 | —CH3 | —CH2CH3 | H |
| L-20 | —CH2CH3 | —CH3 | H |
| L-21 | H | H | —CH2CH3 |
| L-22 | —CH3 | H | —CH2CH3 |
| L-23 | —CH2CH3 | H | —CH2CH3 |
| L-24 | iso-propyl | H | —CH2CH3 |
| L-25 | iso-butyl | H | —CH2CH3 |
| L-26 | cyclopentyl | H | —CH2CH3 |
| L-27 | cyclohexyl | H | —CH2CH3 |
| L-28 | H | H | —CH2CH3 |
| L-29 | H | —CH3 | —CH2CH3 |
| L-30 | H | —CH2CH3 | —CH2CH3 |
| L-31 | H | iso-propyl | —CH2CH3 |
| L-32 | H | iso-butyl | —CH2CH3 |
| L-33 | H | cyclopentyl | —CH2CH3 |
| L-34 | H | cyclohexyl | —CH2CH3 |
| L-35 | —CH3 | —CH3 | —CH2CH3 |
| L-36 | —CH2CH3 | —CH2CH3 | —CH2CH3 |
| L-37 | iso-propyl | iso-propyl | —CH2CH3 |
| L-38 | iso-butyl | iso-butyl | —CH2CH3 |
| L-39 | —CH3 | —CH2CH3 | —CH2CH3 |
| L-40 | —CH2CH3 | —CH3 | —CH2CH3 |
| L-41 | H | H | iso-propyl |
| L-42 | —CH3 | H | iso-propyl |
| L-43 | —CH2CH3 | H | iso-propyl |
| L-44 | iso-propyl | H | iso-propyl |
| L-45 | iso-butyl | H | iso-propyl |
| L-46 | cyclopentyl | H | iso-propyl |
| L-47 | cyclohexyl | H | iso-propyl |
| L-48 | H | H | iso-propyl |
| L-49 | H | —CH3 | iso-propyl |
| L-50 | H | —CH2CH3 | iso-propyl |
| L-51 | H | iso-propyl | iso-propyl |
| L-52 | H | iso-butyl | iso-propyl |
| L-53 | H | cyclopentyl | iso-propyl |
| L-54 | H | cyclohexyl | iso-propyl |
| L-55 | —CH3 | —CH3 | iso-propyl |
| L-56 | —CH2CH3 | —CH2CH3 | iso-propyl |
| L-57 | iso-propyl | iso-propyl | iso-propyl |
| L-58 | iso-butyl | iso-butyl | iso-propyl |
| L-59 | —CH3 | —CH2CH3 | iso-propyl |
| L-60 | —CH2CH3 | —CH3 | isopropyl |
| L-61 | H | H | iso-butyl |
| L-62 | —CH3 | H | iso-butyl |
| L-63 | —CH2CH3 | H | iso-butyl |
| L-64 | iso-propyl | H | iso-butyl |
| L-65 | iso-butyl | H | iso-butyl |
| L-66 | cyclopentyl | H | iso-butyl |

-continued

| Cpd. | R³' | R³ | R⁴ = R⁵ |
|---|---|---|---|
| L-67 | 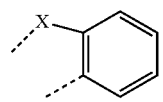 | H | iso-butyl |
| L-68 | H | H | iso-butyl |
| L-69 | H | —CH₃ | iso-butyl |
| L-70 | H | —CH₂CH₃ | iso-butyl |
| L-71 | H | iso-propyl | iso-butyl |
| L-72 | H | iso-butyl | iso-butyl |
| L-73 | H | cyclopentyl | iso-butyl |
| L-74 | H | cyclohexyl | iso-butyl |
| L-75 | —CH₃ | —CH₃ | iso-butyl |
| L-76 | —CH₂CH₃ | —CH₂CH₃ | iso-butyl |
| L-77 | iso-propyl | iso-propyl | iso-butyl |
| L-78 | iso-butyl | iso-butyl | iso-butyl |
| L-79 | —CH₃ | —CH₂CH₃ | iso-butyl |
| L-80 | —CH₂CH₃ | —CH₃ | iso-butyl |
| L-81 | H | H | CH₃ |
| L-82 | —CH₃ | H | CH₃ |
| L-83 | —CH₂CH₃ | H | CH₃ |
| L-84 | iso-propyl | H | CH₃ |
| L-85 | iso-butyl | H | CH₃ |
| L-86 | cyclopentyl | H | CH₃ |
| L-87 | cyclohexyl | H | CH₃ |
| L-88 | H | H | CH₃ |
| L-89 | H | —CH₃ | CH₃ |
| L-90 | H | —CH₂CH₃ | CH₃ |
| L-91 | H | iso-propyl | CH₃ |
| L-92 | H | iso-butyl | CH₃ |
| L-93 | H | cyclopentyl | CH₃ |
| L-94 | H | cyclohexyl | CH₃ |
| L-95 | —CH₃ | —CH₃ | CH₃ |
| L-96 | —CH₂CH₃ | —CH₂CH₃ | CH₃ |
| L-97 | iso-propyl | iso-propyl | CH₃ |
| L-98 | iso-butyl | iso-butyl | CH₃ |
| L-99 | —CH₃ | —CH₂CH₃ | CH₃ |
| L-100 | —CH₂CH₃ | —CH₃ | CH₃ |

Among the above metal carbene-complexes I-1 to I-70, J-1 to J-140, K-1 to K-78 and L-1 to L-100 the metal carbene-complexes I-1 to I-114 and J-1 to J-116 are preferred. Among these metal carbene-complexes metal carbene-complexes are more preferred, wherein $R^4$ and $R^5$ are H.

Metal carbene-complexes I-1 to I-14 and J-1 to J-116 are more preferred. Among these metal carbene-complexes metal carbene-complexes are more preferred, wherein $R^4$ and $R^5$ are H.

If $R^3$ and $R^{3'}$, or $R^1$ and $R^{3'}$ together form a group of formula

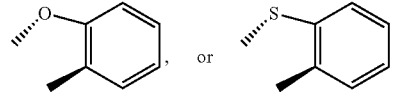

the following preferences apply:

$R^3$ and $R^{3'}$ together form a group of formula

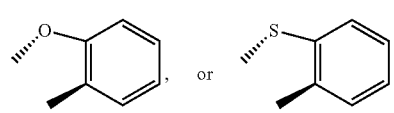

("······" indicates the $R^{3'}$ bonding, "······" indicates the $R^3$ bonding);

$R^3$ and $R^{3'}$ together form a group of formula

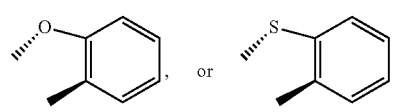

("······" indicates the $R^3$ bonding, "······" indicates the $R^{3'}$ bonding);

$R^1$ and $R^{3'}$ together form a group of formula

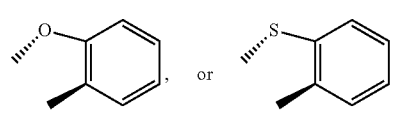

("······" indicates the $R^1$ bonding, — indicates the $R^3$ bonding):

$R^1$ and $R^{3'}$ together form a group of formula

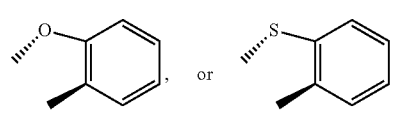

("······" indicates the $R^{3'}$ bonding, — indicates the $R^1$ bonding);

In a preferred embodiment the present invention is directed to metal complexes of formula (IVa)

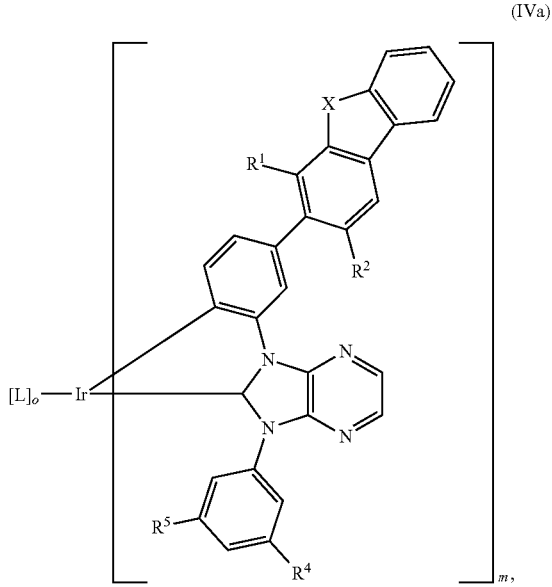

(IVb)

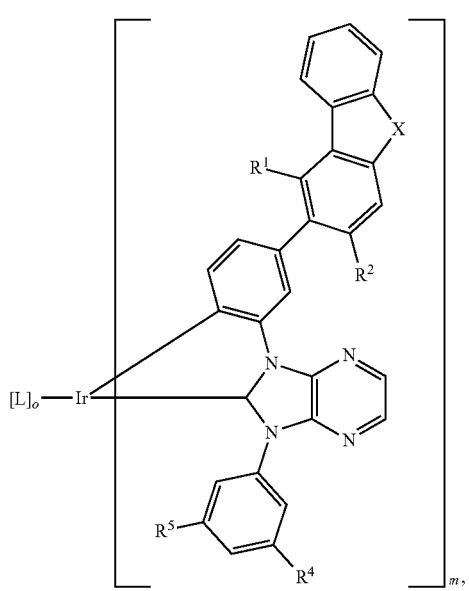

(IVc)

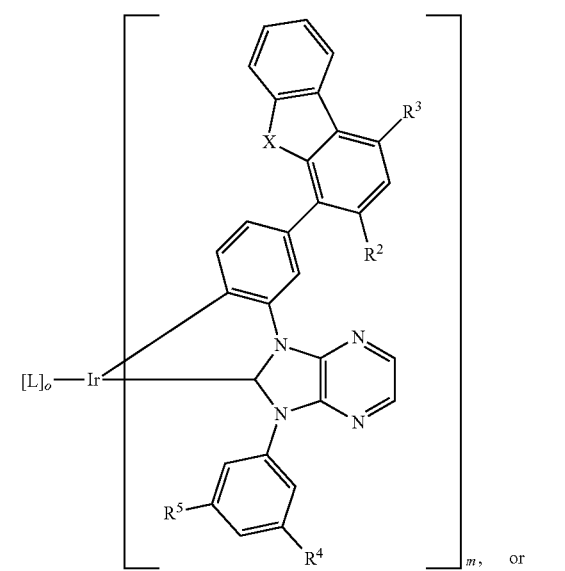

or (IVd)

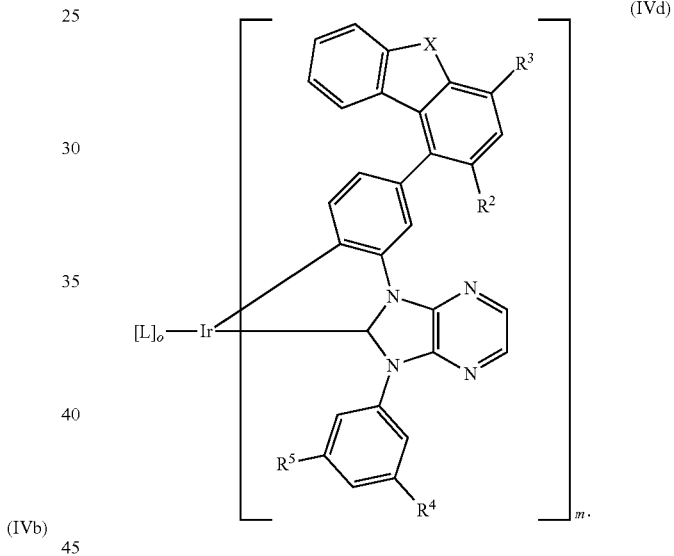

o is 0, 1, or 2 and m is 1, 2, or 3, the sum of m+o is 3.

X is O, or S, preferably O.

$R^1$ is H, $C_1$-$C_5$alkyl, cyclopentyl, or cyclohexyl; preferably $C_1$-$C_5$alkyl, more preferably methyl, ethyl, isopropyl, or isobutyl.

$R^2$ is H, $C_1$-$C_5$alkyl, cyclopentyl, or cyclohexyl; preferably $C_1$-$C_5$alkyl, more preferably methyl, ethyl, isopropyl, or isobutyl. In a preferred embodiment one of the groups $R^1$ and $R^2$ is $C_1$-$C_5$alkyl and the other group is H. In a more preferred embodiment $R^1$ and $R^2$ are $C_1$-$C_5$alkyl.

$R^3$ is H, $C_1$-$C_5$alkyl, cyclopentyl, or cyclohexyl; preferably preferably H, methyl, ethyl, isopropyl, or isobutyl, more preferably H.

$R^4$ and $R^5$ are H, $C_1$-$C_5$alkyl, especially methyl, ethyl, isopropyl, or isobutyl; cyclopentyl, or cyclohexyl; preferably H.

L is preferably a group (X-1), (X-2), (X-3), (X-4), (X-5), (X-6), (X-7), (X-8), (X-9), (X-10), (X-11), (X-12), (X-13), (X-14), (X-15), (X-16), (X-17), (X-18), (X-19), (X-20), (X-21), (X-22), (X-23), (X-24), (X-25), (X-26), or (X-27); more preferably a group (X-1), (X-2), (X-3), or (X-4).

In said embodiment metal complexes of formula
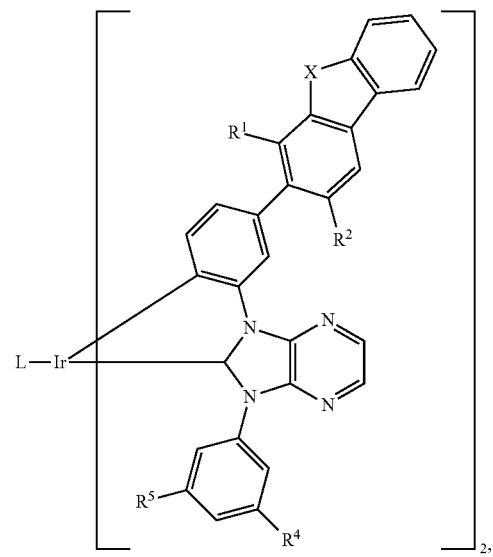
(IVa')
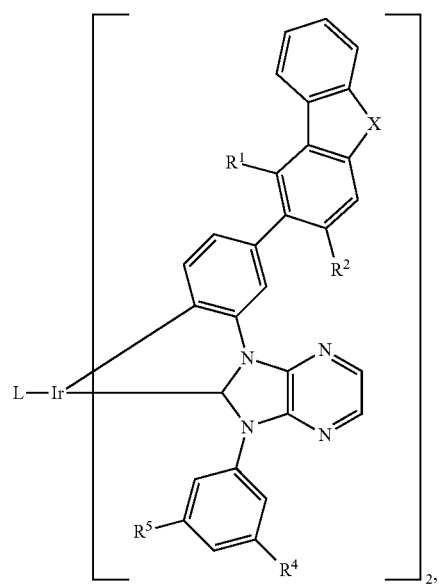
(IVb')
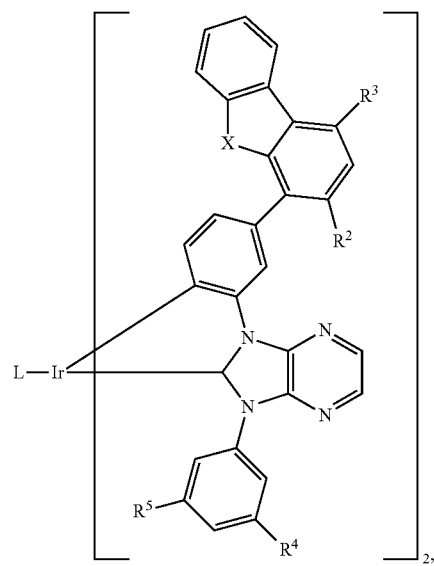
(IVc')
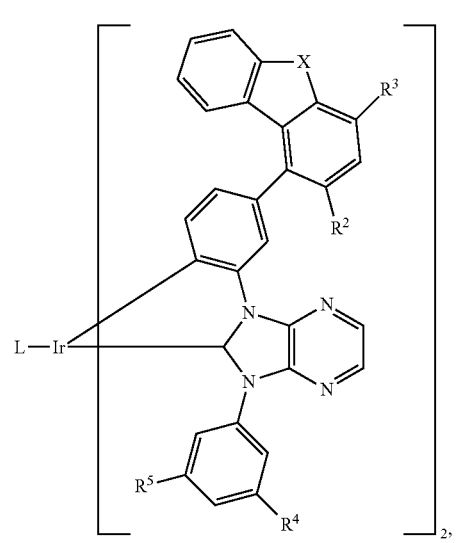
(IVd')
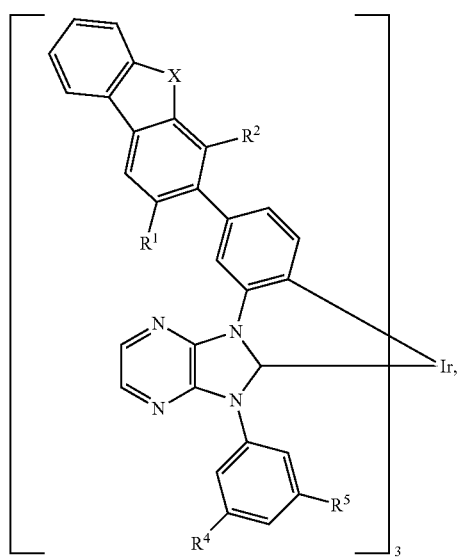
(IVe')

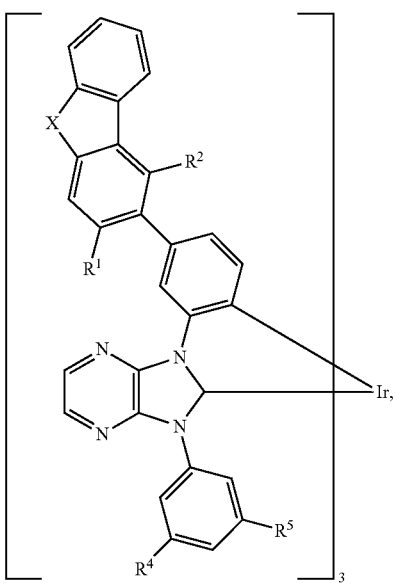

(IVf')

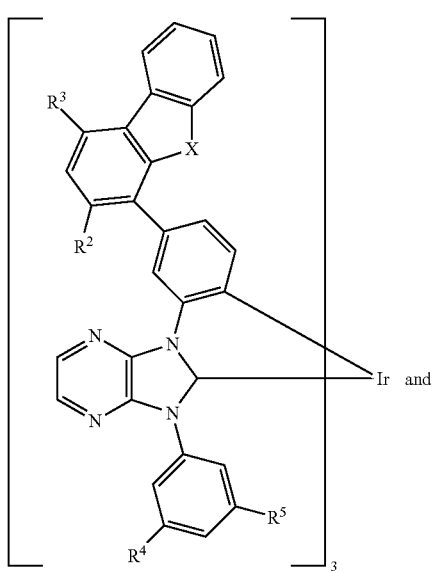

(IVg')

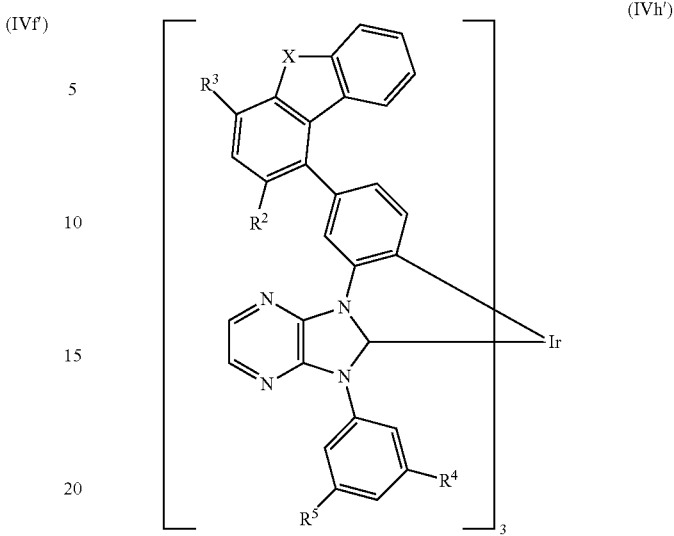

(IVh')

are more preferred, wherein X, $R^1$, $R^2$, $R^3$, $R^4$, $R^5$ and L are as defined above.

In said embodiment metal complexes of formula (IVa'), (IVb'), (IVc'), (IVd'), (IVe'), (IVf'), (IVg') and (IVh') are even more preferred, wherein the substituents have the following meanings:

X is O.

$R^1$ is $C_1$-$C_5$alkyl, cyclopentyl, or cyclohexyl; preferably $C_1$-$C_5$alkyl, more preferably methyl, ethyl, isopropyl, or isobutyl.

$R^2$ is $C_1$-$C_5$alkyl, cyclopentyl, or cyclohexyl; preferably $C_1$-$C_5$alkyl, more preferably methyl, ethyl, isopropyl, or isobutyl.

$R^3$ is H, $C_1$-$C_5$alkyl, cyclopentyl, or cyclohexyl; preferably preferably H, methyl, ethyl, isopropyl, or isobutyl, more preferably H.

$R^4$ and $R^5$ are H, $C_1$-$C_5$alkyl, especially methyl, ethyl, isopropyl, or isobutyl; cyclopentyl, or cyclohexyl; preferably H.

L is preferably a group (X-1), (X-2), (X-3), (X-4), (X-5), (X-6), (X-7), (X-8), (X-9), (X-10), (X-11), (X-12), (X-13), (X-14), (X-15), (X-16), (X-17), (X-18), (X-19), (X-20), (X-21), (X-22), (X-23), (X-24), (X-25), (X-26), or (X-27); more preferably a group (X-1), (X-2), (X-3), or (X-4).

In said embodiment metal complexes of formula (IVa'), (IVb'), (IVc'), (IVd'), (IVe'), (IVf'), (IVg') and (IVh') are most preferred, wherein the substituents have the following meanings:

X is O.

$R^1$ is $C_1$-$C_5$alkyl, more preferably methyl, ethyl, isopropyl, or isobutyl.

$R^2$ is $C_1$-$C_5$alkyl, more preferably methyl, ethyl, isopropyl, or isobutyl.

$R^3$ is H, $C_1$-$C_5$alkyl, such as methyl, ethyl, isopropyl, or isobutyl; more preferably H.

$R^4$ and $R^5$ are H.

Lisa group (X-1), (X-2), (X-3), (X-4), (X-5), (X-6), (X-7), (X-8), (X-9), (X-10), (X-11), (X-12), (X-13), (X-14), (X-15), (X-16), (X-17), (X-18), (X-19), (X-20), (X-21), (X-22), (X-23), (X-24), (X-25), (X-26), or (X-27); more preferably a group (X-1), (X-2), (X-3), or (X-4).

Examples of metal complexes of formula (IVe'), (IVf'), (IVg') and (IVh') are shown below.

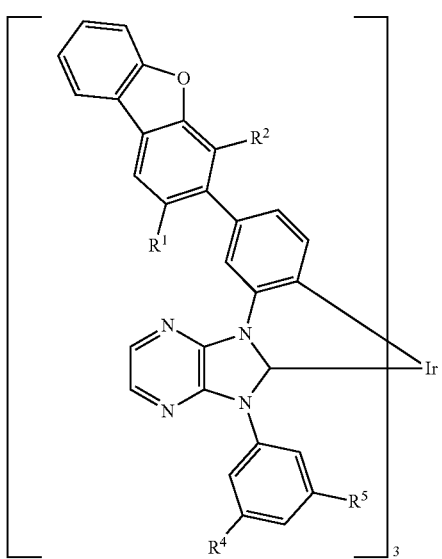

| Cpd. | R[1] | R[2] | R[4] = R[5] |
|---|---|---|---|
| M-1 | —CH₃ | —CH₃ | H |
| M-2 | —CH₂CH₃ | —CH₂CH₃ | H |
| M-3 | iso-propyl | iso-propyl | H |
| M-4 | iso-butyl | iso-butyl | H |
| M-5 | neopentyl | neopentyl | H |
| M-6 | —CH₃ | —CH₂CH₃ | H |
| M-7 | cyclopentyl | cyclopentyl | H |
| M-8 | cyclohexyl | cyclohexyl | H |
| M-9 | —CH₃ | —CH₃ | —CH₃ |
| M-10 | —CH₂CH₃ | —CH₂CH₃ | —CH₃ |
| M-11 | iso-propyl | iso-propyl | —CH₃ |
| M-12 | iso-butyl | iso-butyl | —CH₃ |
| M-13 | neopentyl | neopentyl | —CH₃ |
| M-14 | —CH₃ | —CH₂CH₃ | —CH₃ |
| M-15 | cyclopentyl | cyclopentyl | —CH₃ |
| M-16 | cyclohexyl | cyclohexyl | —CH₃ |
| M-17 | —CH₃ | —CH₃ | —CH₂CH₃ |
| M-18 | —CH₂CH₃ | —CH₂CH₃ | —CH₂CH₃ |
| M-19 | iso-propyl | iso-propyl | —CH₂CH₃ |
| M-20 | iso-butyl | iso-butyl | —CH₂CH₃ |
| M-21 | —CH₃ | —CH₂CH₃ | —CH₂CH₃ |
| M-22 | neopentyl | neopentyl | —CH₂CH₃ |
| M-23 | cyclopentyl | cyclopentyl | —CH₂CH₃ |

-continued

| Cpd. | R[1] | R[2] | R[4] = R[5] |
|---|---|---|---|
| M-24 | cyclohexyl | cyclohexyl | —CH₂CH₃ |
| M-25 | —CH₃ | —CH₃ | iso-propyl |
| M-26 | —CH₂CH₃ | —CH₂CH₃ | iso-propyl |
| M-27 | iso-propyl | iso-propyl | iso-propyl |
| M-28 | iso-butyl | iso-butyl | iso-propyl |
| M-29 | neopentyl | neopentyl | iso-propyl |
| M-30 | —CH₃ | —CH₂CH₃ | iso-propyl |
| M-31 | cyclopentyl | cyclopentyl | iso-propyl |
| M-32 | cyclohexyl | cyclohexyl | iso-propyl |
| M-33 | —CH₃ | —CH₃ | iso-butyl |
| M-34 | —CH₂CH₃ | —CH₂CH₃ | iso-butyl |
| M-35 | iso-propyl | iso-propyl | iso-butyl |
| M-36 | iso-butyl | iso-butyl | iso-butyl |
| M-37 | neopentyl | neopentyl | iso-butyl |
| M-38 | —CH₃ | —CH₂CH₃ | iso-butyl |
| M-39 | cyclopentyl | cyclopentyl | iso-butyl |
| M-40 | cyclohexyl | cyclohexyl | iso-butyl |

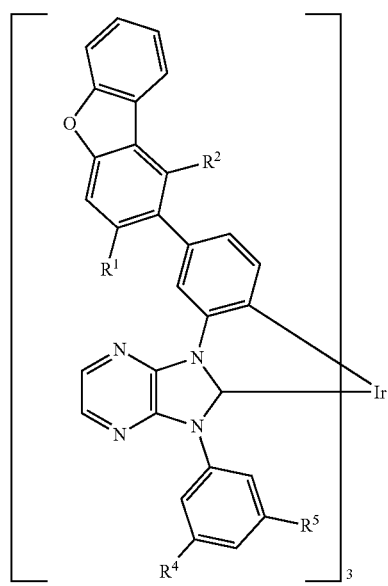

| Cpd. | R¹ | R² | R⁴ = R⁵ |
|---|---|---|---|
| N-1 | —CH₃ | —CH₃ | H |
| N-2 | —CH₂CH₃ | —CH₂CH₃ | H |
| N-3 | iso-propyl | iso-propyl | H |
| N-4 | iso-butyl | iso-butyl | H |
| N-5 | neopentyl | neopentyl | H |
| N-6 | —CH₃ | —CH₂CH₃ | H |
| N-7 | 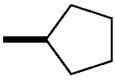 |  | H |
| N-8 | 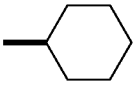 | 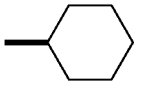 | H |
| N-9 | —CH₃ | —CH₃ | —CH₃ |
| N-10 | —CH₂CH₃ | —CH₂CH₃ | —CH₃ |
| N-11 | iso-propyl | iso-propyl | —CH₃ |
| N-12 | iso-butyl | iso-butyl | —CH₃ |
| N-13 | neopentyl | neopentyl | —CH₃ |
| N-14 | —CH₃ | —CH₂CH₃ | —CH₃ |
| N-15 | 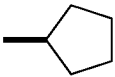 |  | —CH₃ |
| N-16 | 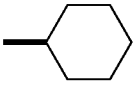 | 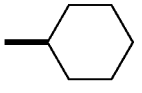 | —CH₃ |
| N-17 | —CH₃ | —CH₃ | —CH₂CH₃ |
| N-18 | —CH₂CH₃ | —CH₂CH₃ | —CH₂CH₃ |
| N-19 | iso-propyl | iso-propyl | —CH₂CH₃ |
| N-20 | iso-butyl | iso-butyl | —CH₂CH₃ |
| N-21 | —CH₃ | —CH₂CH₃ | —CH₂CH₃ |
| N-22 | neopentyl | neopentyl | —CH₂CH₃ |
| N-23 | 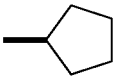 | 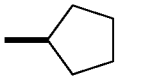 | —CH₂CH₃ |
| N-24 | 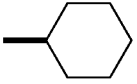 | 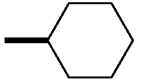 | —CH₂CH₃ |
| N-25 | —CH₃ | —CH₃ | iso-propyl |
| N-26 | —CH₂CH₃ | —CH₂CH₃ | iso-propyl |
| N-27 | iso-propyl | iso-propyl | iso-propyl |
| N-28 | iso-butyl | iso-butyl | iso-propyl |
| N-29 | neopentyl | neopentyl | iso-propyl |
| N-30 | —CH₃ | —CH₂CH₃ | iso-propyl |
| N-31 | 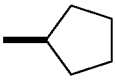 |  | iso-propyl |
| N-32 | 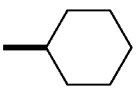 | 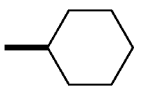 | iso-propyl |
| N-33 | —CH₃ | —CH₃ | iso-butyl |
| N-34 | —CH₂CH₃ | —CH₂CH₃ | iso-butyl |
| N-35 | iso-propyl | iso-propyl | iso-butyl |
| N-36 | iso-butyl | iso-butyl | iso-butyl |
| N-37 | neopentyl | neopentyl | iso-butyl |
| N-38 | —CH₃ | —CH₂CH₃ | iso-butyl |

-continued

| Cpd. | R¹ | R² | R⁴ = R⁵ |
|---|---|---|---|
| N-39 | 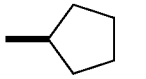 | 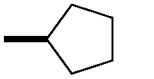 | iso-butyl |
| N-40 | 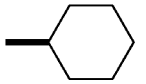 |  | iso-butyl |

| Cpd. | R¹ | R³ | R⁴ = R⁵ |
|---|---|---|---|
| O-1 | —CH₃ | —CH₃ | H |
| O-2 | —CH₂CH₃ | —CH₂CH₃ | H |
| O-3 | iso-propyl | iso-propyl | H |
| O-4 | iso-butyl | iso-butyl | H |
| O-5 | neopentyl | neopentyl | H |
| O-6 | —CH₃ | —CH₂CH₃ | H |
| O-7 | | | H |
| O-8 | | | H |
| O-9 | —CH₃ | —CH₃ | —CH₃ |
| O-10 | —CH₂CH₃ | —CH₂CH₃ | —CH₃ |
| O-11 | iso-propyl | iso-propyl | —CH₃ |
| O-12 | iso-butyl | iso-butyl | —CH₃ |
| O-13 | neopentyl | neopentyl | —CH₃ |
| O-14 | —CH₃ | —CH₂CH₃ | —CH₃ |
| O-15 | | | —CH₃ |

-continued

| Cpd. | R¹ | R³ | R⁴ = R⁵ |
|---|---|---|---|
| O-16 | cyclohexyl | cyclohexyl | —CH₃ |
| O-17 | —CH₃ | —CH₃ | —CH₂CH₃ |
| O-18 | —CH₂CH₃ | —CH₂CH₃ | —CH₂CH₃ |
| O-19 | iso-propyl | iso-propyl | —CH₂CH₃ |
| O-20 | iso-butyl | iso-butyl | —CH₂CH₃ |
| O-21 | —CH₃ | —CH₂CH₃ | —CH₂CH₃ |
| O-22 | neopentyl | neopentyl | —CH₂CH₃ |
| O-23 | cyclopentyl | cyclopentyl | —CH₂CH₃ |
| O-24 | cyclohexyl | cyclohexyl | —CH₂CH₃ |
| O-25 | —CH₃ | —CH₃ | iso-propyl |
| O-26 | —CH₂CH₃ | —CH₂CH₃ | iso-propyl |
| O-27 | iso-propyl | iso-propyl | iso-propyl |
| O-28 | iso-butyl | iso-butyl | iso-propyl |
| O-29 | neopentyl | neopentyl | iso-propyl |
| O-30 | —CH₃ | —CH₂CH₃ | iso-propyl |
| O-31 | cyclopentyl | cyclopentyl | iso-propyl |
| O-32 | cyclohexyl | cyclohexyl | iso-propyl |
| O-33 | —CH₃ | —CH₃ | iso-butyl |
| O-34 | —CH₂CH₃ | —CH₂CH₃ | iso-butyl |
| O-35 | iso-propyl | iso-propyl | iso-butyl |
| O-36 | iso-butyl | iso-butyl | iso-butyl |
| O-37 | neopentyl | neopentyl | iso-butyl |
| O-38 | —CH₃ | —CH₂CH₃ | iso-butyl |
| O-39 | cyclopentyl | cyclopentyl | iso-butyl |
| O-40 | cyclohexyl | cyclohexyl | iso-butyl |

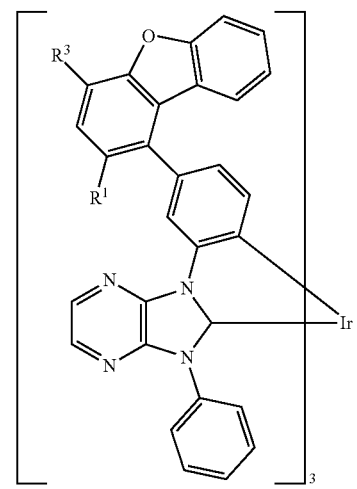

| Cpd. | R¹ | R³ | R⁴ = R⁵ |
|---|---|---|---|
| P-1 | —CH₃ | —CH₃ | H |
| P-2 | —CH₂CH₃ | —CH₂CH₃ | H |
| P-3 | iso-propyl | iso-propyl | H |
| P-4 | iso-butyl | iso-butyl | H |
| P-5 | neopentyl | neopentyl | H |
| P-6 | —CH₃ | —CH₂CH₃ | H |
| P-7 | cyclopentyl | cyclopentyl | H |
| P-8 | cyclohexyl | cyclohexyl | H |
| P-9 | —CH₃ | —CH₃ | —CH₃ |
| P-10 | —CH₂CH₃ | —CH₂CH₃ | —CH₃ |
| P-11 | iso-propyl | iso-propyl | —CH₃ |
| P-12 | iso-butyl | iso-butyl | —CH₃ |
| P-13 | neopentyl | neopentyl | —CH₃ |
| P-14 | —CH₃ | —CH₂CH₃ | —CH₃ |
| P-15 | cyclopentyl | cyclopentyl | —CH₃ |
| P-16 | cyclohexyl | cyclohexyl | —CH₃ |
| P-17 | —CH₃ | —CH₃ | —CH₂CH₃ |
| P-18 | —CH₂CH₃ | —CH₂CH₃ | —CH₂CH₃ |
| P-19 | iso-propyl | iso-propyl | —CH₂CH₃ |
| P-20 | iso-butyl | iso-butyl | —CH₂CH₃ |
| P-21 | —CH₃ | —CH₂CH₃ | —CH₂CH₃ |
| P-22 | neopentyl | neopentyl | —CH₂CH₃ |
| P-23 | cyclopentyl | cyclopentyl | —CH₂CH₃ |
| P-24 | cyclohexyl | cyclohexyl | —CH₂CH₃ |
| P-25 | —CH₃ | —CH₃ | iso-propyl |
| P-26 | —CH₂CH₃ | —CH₂CH₃ | iso-propyl |

-continued

| Cpd. | R¹ | R³ | R⁴ = R⁵ |
|---|---|---|---|
| P-27 | iso-propyl | iso-propyl | iso-propyl |
| P-28 | iso-butyl | iso-butyl | iso-propyl |
| P-29 | neopentyl | neopentyl | iso-propyl |
| P-30 | —CH₃ | —CH₂CH₃ | iso-propyl |
| P-31 | cyclopentyl | cyclopentyl | iso-propyl |
| P-32 | cyclohexyl | cyclohexyl | iso-propyl |
| P-33 | —CH₃ | —CH₃ | iso-butyl |
| P-34 | —CH₂CH₃ | —CH₂CH₃ | iso-butyl |
| P-35 | iso-propyl | iso-propyl | iso-butyl |
| P-36 | iso-butyl | iso-butyl | iso-butyl |
| P-37 | neopentyl | neopentyl | iso-butyl |
| P-38 | —CH₃ | —CH₂CH₃ | iso-butyl |
| P-39 | cyclopentyl | cyclopentyl | iso-butyl |
| P-40 | cyclohexyl | cyclohexyl | iso-butyl |

Among the above metal carbene-complexes M-1 to M-40, N-1 to N-40, O-1 to O-40 and P-1 to P-40 the metal carbene-complexes M-1 to M-8, N-1 to N-8, O-1 to O-8 and P-1 to P-8 are preferred.

In principal, L can also be a ligand

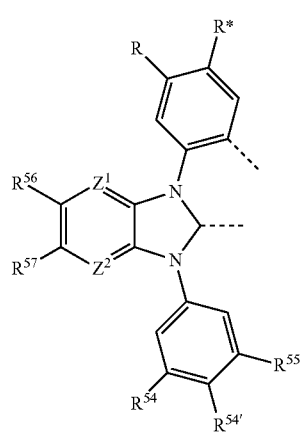

(D')

which is different from the ligand

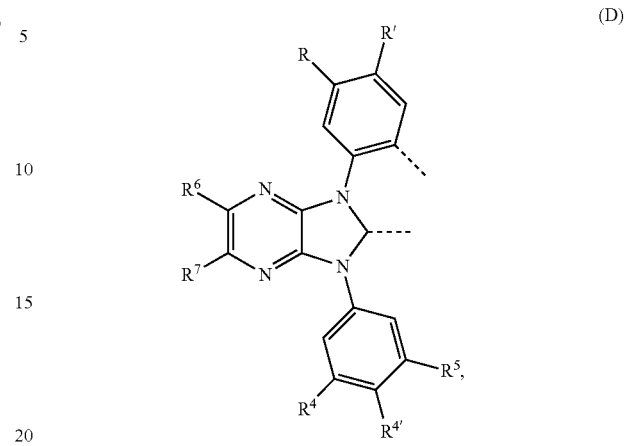

(D)

wherein $Z^1$ and $Z^2$ are N, or $Z^1$ and $Z^2$ are CH, R* has the meaning of R', $R^{54}$ has the meaning of $R^4$, $R^{54'}$ has the meaning of $R^{4'}$, $R^{55}$ has the meaning of $R^5$, $R^{56}$ has the meaning of $R^6$ and $R^{57}$ has the meaning of $R^7$ and each group R is the same within one metal-carbene complex.

In said embodiment the present invention is directed to complexes of formula D₂MD'(Va), or D₂MD'(Vb). Complexes of formula D₂MD'(Va) are preferred.

For R*, $R^{54}$, $R^{54'}$, $R^{55}$, $R^{56}$ and $R^{57}$ the same preferences apply as for R', $R^4$, $R^{4'}$, $R^5$, $R^6$ and $R^7$, respectively.

Preferably, $Z^1$ is CH, $Z^2$ is CH, R* and R' are H, $R^{54}$ is the same as $R^4$, $R^{54'}$ is the same as $R^{4'}$, $R^{55}$ is the same as $R^5$, $R^{56}$ is the same as $R^6$ and $R^{57}$ is the same as $R^7$.

Metal complexes of formula

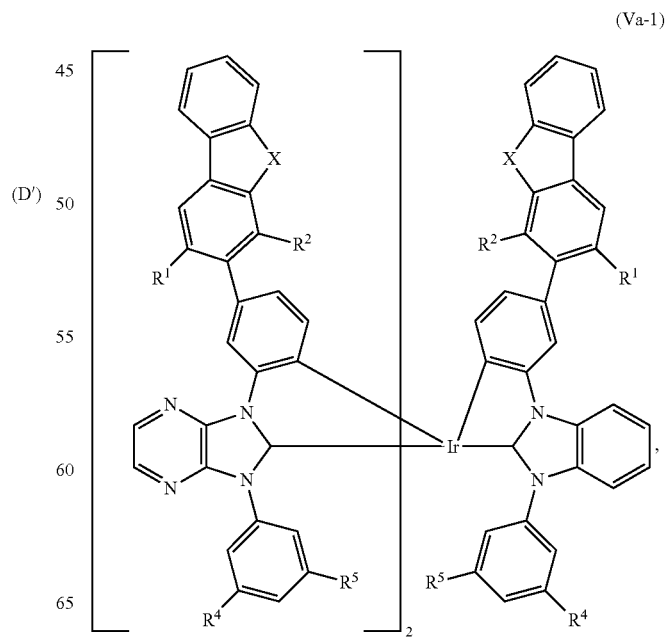

(Va-1)

-continued (Va-2)
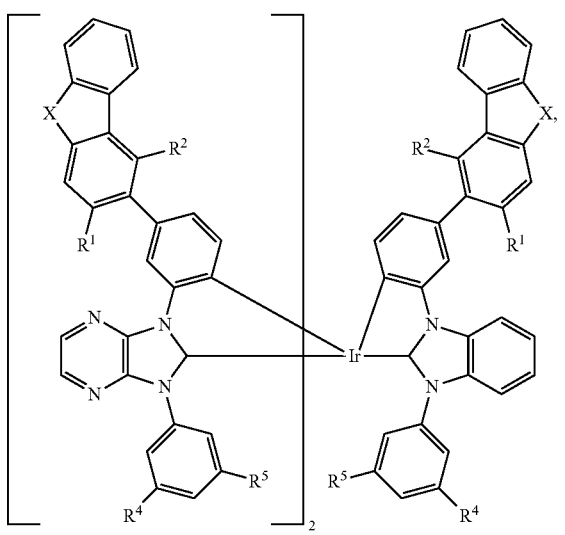

(Va-3)
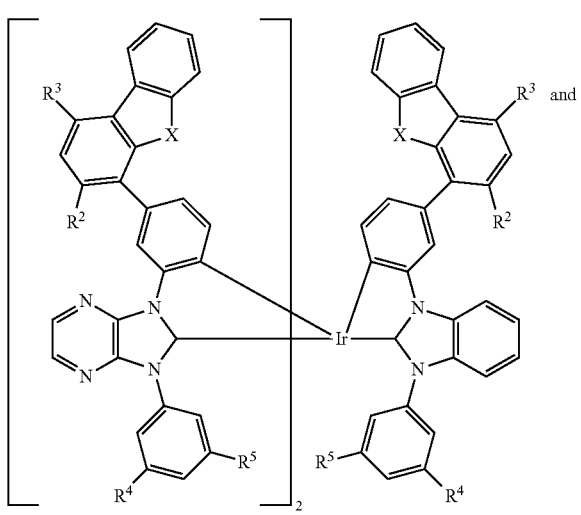

(Va-4)
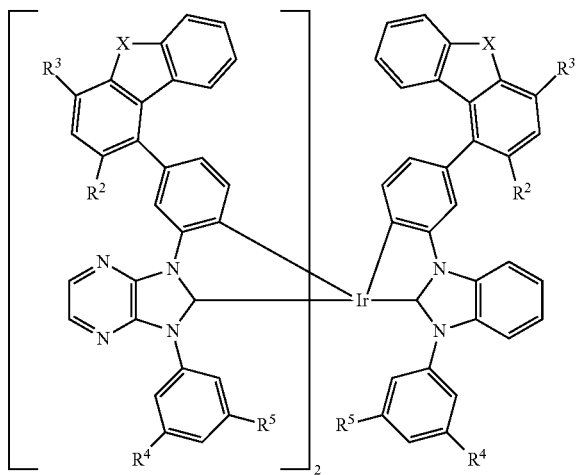

are more preferred, wherein X, $R^1$, $R^2$, $R^3$, $R^4$, $R^5$ and L are as defined above.

In said embodiment metal complexes of formula (Va-1), (Va-2), (Va-3) and (Va-4) are even more preferred, wherein the substituents have the following meanings:

X is O.

$R^1$ is $C_1$-$C_5$alkyl, cyclopentyl, or cyclohexyl; preferably $C_1$-$C_5$alkyl, more preferably methyl, ethyl, isopropyl, or isobutyl.

$R^2$ is $C_1$-$C_5$alkyl, cyclopentyl, or cyclohexyl; preferably $C_1$-$C_5$alkyl, more preferably methyl, ethyl, isopropyl, or isobutyl.

$R^3$ is H, $C_1$-$C_5$alkyl, cyclopentyl, or cyclohexyl; preferably preferably H, methyl, ethyl, isopropyl, or isobutyl, more preferably H.

$R^4$ and $R^5$ are H, $C_1$-$C_5$alkyl, especially methyl, ethyl, isopropyl, or isobutyl; cyclopentyl, or cyclohexyl; preferably H.

In said embodiment metal complexes of formula (Va-1), (Va-2), (Va-3) and (Va-4) are most preferred, wherein the substituents have the following meanings:

X is O.

$R^1$ is $C_1$-$C_5$alkyl, more preferably methyl, ethyl, isopropyl, or isobutyl.

$R^2$ is $C_1$-$C_5$alkyl, more preferably methyl, ethyl, isopropyl, or isobutyl.

$R^3$ is H, $C_1$-$C_5$alkyl, such as, for example, methyl, ethyl, isopropyl, or isobutyl; more preferably H.

$R^4$ and $R^5$ are H.

Examples of metal complexes of formula (Va-1), (Va-2), (Va-3) and (Va-4) are shown below.

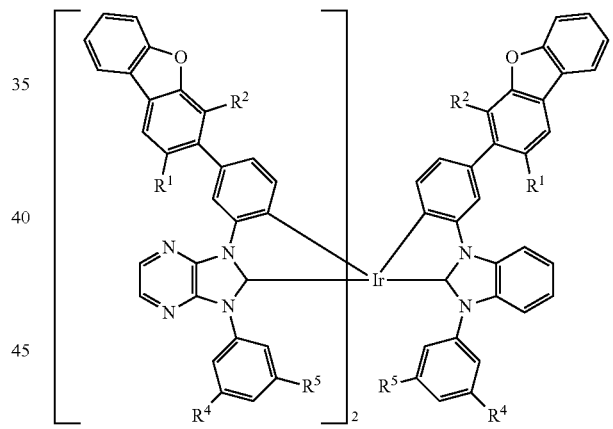

| Cpd. | $R^1$ | $R^2$ | $R^4$ = $R^5$ |
|------|-------|-------|---------------|
| Q-1 | —$CH_3$ | —$CH_3$ | H |
| Q-2 | —$CH_2CH_3$ | —$CH_2CH_3$ | H |
| Q-3 | iso-propyl | iso-propyl | H |
| Q-4 | iso-butyl | iso-butyl | H |
| Q-5 | neopentyl | neopentyl | H |
| Q-6 | —$CH_3$ | —$CH_2CH_3$ | H |
| Q-7 | cyclopentyl | cyclopentyl | H |
| Q-8 | cyclohexyl | cyclohexyl | H |

-continued

| Cpd. | R¹ | R² | R⁴ = R⁵ |
|---|---|---|---|
| Q-9 | —CH₃ | —CH₃ | —CH₃ |
| Q-10 | —CH₂CH₃ | —CH₂CH₃ | —CH₃ |
| Q-11 | iso-propyl | iso-propyl | —CH₃ |
| Q-12 | iso-butyl | iso-butyl | —CH₃ |
| Q-13 | neopentyl | neopentyl | —CH₃ |
| Q-14 | —CH₃ | —CH₂CH₃ | —CH₃ |
| Q-15 | cyclopentyl | cyclopentyl | —CH₃ |
| Q-16 | cyclohexyl | cyclohexyl | —CH₃ |
| Q-17 | —CH₃ | —CH₃ | —CH₂CH₃ |
| Q-18 | —CH₂CH₃ | —CH₂CH₃ | —CH₂CH₃ |
| Q-19 | iso-propyl | iso-propyl | —CH₂CH₃ |
| Q-20 | iso-butyl | iso-butyl | —CH₂CH₃ |
| Q-21 | —CH₃ | —CH₂CH₃ | —CH₂CH₃ |
| Q-22 | neopentyl | neopentyl | —CH₂CH₃ |
| Q-23 | cyclopentyl | cyclopentyl | —CH₂CH₃ |
| Q-24 | cyclohexyl | cyclohexyl | —CH₂CH₃ |
| Q-25 | —CH₃ | —CH₃ | iso-propyl |
| Q-26 | —CH₂CH₃ | —CH₂CH₃ | iso-propyl |
| Q-27 | iso-propyl | iso-propyl | iso-propyl |
| Q-28 | iso-butyl | iso-butyl | iso-propyl |
| Q-29 | neopentyl | neopentyl | iso-propyl |
| Q-30 | —CH₃ | —CH₂CH₃ | iso-propyl |
| Q-31 | cyclopentyl | cyclopentyl | iso-propyl |
| Q-32 | cyclohexyl | cyclohexyl | iso-propyl |
| Q-33 | —CH₃ | —CH₃ | iso-butyl |
| Q-34 | —CH₂CH₃ | —CH₂CH₃ | iso-butyl |
| Q-35 | iso-propyl | iso-propyl | iso-butyl |
| Q-36 | iso-butyl | iso-butyl | iso-butyl |
| Q-37 | neopentyl | neopentyl | iso-butyl |
| Q-38 | —CH₃ | —CH₂CH₃ | iso-butyl |
| Q-39 | cyclopentyl | cyclopentyl | iso-butyl |
| Q-40 | cyclohexyl | cyclohexyl | iso-butyl |

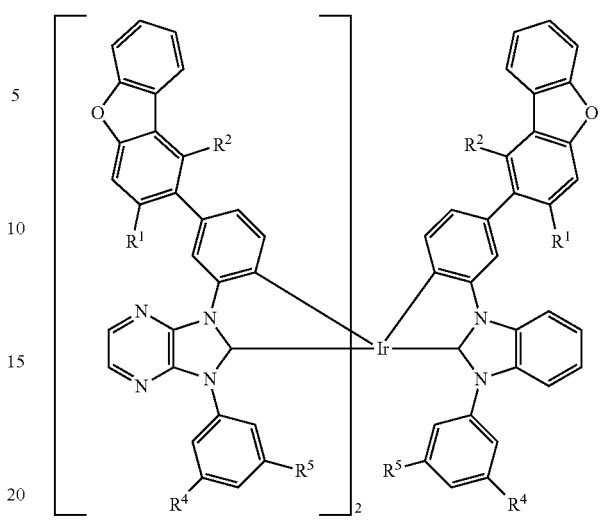

| Cpd. | R¹ | R² | R⁴ = R⁵ |
|---|---|---|---|
| R-1 | —CH₃ | —CH₃ | H |
| R-2 | —CH₂CH₃ | —CH₂CH₃ | H |
| R-3 | iso-propyl | iso-propyl | H |
| R-4 | iso-butyl | iso-butyl | H |
| R-5 | neopentyl | neopentyl | H |
| R-6 | —CH₃ | —CH₂CH₃ | H |
| R-7 | cyclopentyl | cyclopentyl | H |
| R-8 | cyclohexyl | cyclohexyl | H |
| R-9 | —CH₃ | —CH₃ | —CH₃ |
| R-10 | —CH₂CH₃ | —CH₂CH₃ | —CH₃ |
| R-11 | iso-propyl | iso-propyl | —CH₃ |
| R-12 | iso-butyl | iso-butyl | —CH₃ |
| R-13 | neopentyl | neopentyl | —CH₃ |
| R-14 | —CH₃ | —CH₂CH₃ | —CH₃ |
| R-15 | cyclopentyl | cyclopentyl | —CH₃ |
| R-16 | cyclohexyl | cyclohexyl | —CH₃ |
| R-17 | —CH₃ | —CH₃ | —CH₂CH₃ |
| R-18 | —CH₂CH₃ | —CH₂CH₃ | —CH₂CH₃ |
| R-19 | iso-propyl | iso-propyl | —CH₂CH₃ |
| R-20 | iso-butyl | iso-butyl | —CH₂CH₃ |
| R-21 | —CH₃ | —CH₂CH₃ | —CH₂CH₃ |
| R-22 | neopentyl | neopentyl | —CH₂CH₃ |
| R-23 | cyclopentyl | cyclopentyl | —CH₂CH₃ |
| R-24 | cyclohexyl | cyclohexyl | —CH₂CH₃ |
| R-25 | —CH₃ | —CH₃ | iso-propyl |

| Cpd. | R¹ | R² | R⁴ = R⁵ |
|---|---|---|---|
| R-26 | —CH₂CH₃ | —CH₂CH₃ | iso-propyl |
| R-27 | iso-propyl | iso-propyl | iso-propyl |
| R-28 | iso-butyl | iso-butyl | iso-propyl |
| R-29 | neopentyl | neopentyl | iso-propyl |
| R-30 | —CH₃ | —CH₂CH₃ | iso-propyl |
| R-31 | cyclopentyl | cyclopentyl | iso-propyl |
| R-32 | cyclohexyl | cyclohexyl | iso-propyl |
| R-33 | —CH₃ | —CH₃ | iso-butyl |
| R-34 | —CH₂CH₃ | —CH₂CH₃ | iso-butyl |
| R-35 | iso-propyl | iso-propyl | iso-butyl |
| R-36 | iso-butyl | iso-butyl | iso-butyl |
| R-37 | neopentyl | neopentyl | iso-butyl |
| R-38 | —CH₃ | —CH₂CH₃ | iso-butyl |
| R-39 | cyclopentyl | cyclopentyl | iso-butyl |
| R-40 | cyclohexyl | cyclohexyl | iso-butyl |

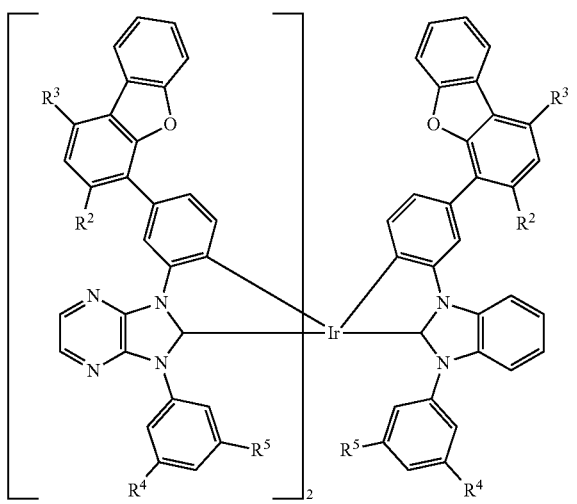

| Cpd. | R² | R³ | R⁴ = R⁵ |
|---|---|---|---|
| S-1 | —CH₃ | —CH₃ | H |
| S-2 | —CH₂CH₃ | —CH₂CH₃ | H |
| S-3 | iso-propyl | iso-propyl | H |
| S-4 | iso-butyl | iso-butyl | H |
| S-5 | neopentyl | neopentyl | H |
| S-6 | —CH₃ | —CH₂CH₃ | H |
| S-7 | cyclopentyl | cyclopentyl | H |
| S-8 | cyclohexyl | cyclohexyl | H |
| S-9 | —CH₃ | —CH₃ | —CH₃ |
| S-10 | —CH₂CH₃ | —CH₂CH₃ | —CH₃ |
| S-11 | iso-propyl | iso-propyl | —CH₃ |
| S-12 | iso-butyl | iso-butyl | —CH₃ |
| S-13 | neopentyl | neopentyl | —CH₃ |
| S-14 | —CH₃ | —CH₂CH₃ | —CH₃ |
| S-15 | cyclopentyl | cyclopentyl | —CH₃ |
| S-16 | cyclohexyl | cyclohexyl | —CH₃ |
| S-17 | —CH₃ | —CH₃ | —CH₂CH₃ |
| S-18 | —CH₂CH₃ | —CH₂CH₃ | —CH₂CH₃ |
| S-19 | iso-propyl | iso-propyl | —CH₂CH₃ |
| S-20 | iso-butyl | iso-butyl | —CH₂CH₃ |
| S-21 | —CH₃ | —CH₂CH₃ | —CH₂CH₃ |
| S-22 | neopentyl | neopentyl | —CH₂CH₃ |
| S-23 | cyclopentyl | cyclopentyl | —CH₂CH₃ |
| S-24 | cyclohexyl | cyclohexyl | —CH₂CH₃ |
| S-25 | —CH₃ | —CH₃ | iso-propyl |
| S-26 | —CH₂CH₃ | —CH₂CH₃ | iso-propyl |
| S-27 | iso-propyl | iso-propyl | iso-propyl |
| S-28 | iso-butyl | iso-butyl | iso-propyl |
| S-29 | neopentyl | neopentyl | iso-propyl |
| S-30 | —CH₃ | —CH₂CH₃ | iso-propyl |
| S-31 | cyclopentyl | cyclopentyl | iso-propyl |
| S-32 | cyclohexyl | cyclohexyl | iso-propyl |
| S-33 | —CH₃ | —CH₃ | iso-butyl |
| S-34 | —CH₂CH₃ | —CH₂CH₃ | iso-butyl |
| S-35 | iso-propyl | iso-propyl | iso-butyl |
| S-36 | iso-butyl | iso-butyl | iso-butyl |
| S-37 | neopentyl | neopentyl | iso-butyl |
| S-38 | —CH₃ | —CH₂CH₃ | iso-butyl |
| S-39 | cyclopentyl | cyclopentyl | iso-butyl |
| S-40 | cyclohexyl | cyclohexyl | iso-butyl |

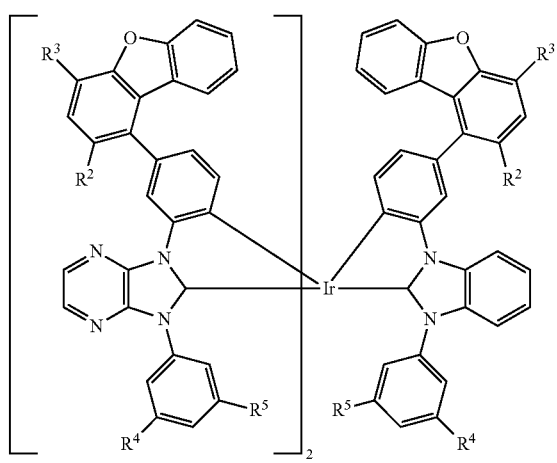

| Cpd. | R² | R³ | R⁴ = R⁵ |
|---|---|---|---|
| T-1 | —CH₃ | —CH₃ | H |
| T-2 | —CH₂CH₃ | —CH₂CH₃ | H |
| T-3 | iso-propyl | iso-propyl | H |
| T-4 | iso-butyl | iso-butyl | H |
| T-5 | neopentyl | neopentyl | H |
| T-6 | —CH₃ | —CH₂CH₃ | H |
| T-7 | cyclopentyl | cyclopentyl | H |
| T-8 | cyclohexyl | cyclohexyl | H |
| T-9 | —CH₃ | —CH₃ | —CH₃ |
| T-10 | —CH₂CH₃ | —CH₂CH₃ | —CH₃ |
| T-11 | iso-propyl | iso-propyl | —CH₃ |
| T-12 | iso-butyl | iso-butyl | —CH₃ |
| T-13 | neopentyl | neopentyl | —CH₃ |
| T-14 | —CH₃ | —CH₂CH₃ | —CH₃ |
| T-15 | cyclopentyl | cyclopentyl | —CH₃ |
| T-16 | cyclohexyl | cyclohexyl | —CH₃ |
| T-17 | —CH₃ | —CH₃ | —CH₂CH₃ |
| T-18 | —CH₂CH₃ | —CH₂CH₃ | —CH₂CH₃ |
| T-19 | iso-propyl | iso-propyl | —CH₂CH₃ |
| T-20 | iso-butyl | iso-butyl | —CH₂CH₃ |
| T-21 | —CH₃ | —CH₂CH₃ | —CH₂CH₃ |
| T-22 | neopentyl | neopentyl | —CH₂CH₃ |
| T-23 | cyclopentyl | cyclopentyl | —CH₂CH₃ |
| T-24 | cyclohexyl | cyclohexyl | —CH₂CH₃ |
| T-25 | —CH₃ | —CH₃ | iso-propyl |
| T-26 | —CH₂CH₃ | —CH₂CH₃ | iso-propyl |
| T-27 | iso-propyl | iso-propyl | iso-propyl |
| T-28 | iso-butyl | iso-butyl | iso-propyl |
| T-29 | neopentyl | neopentyl | iso-propyl |
| T-30 | —CH₃ | —CH₂CH₃ | iso-propyl |
| T-31 | cyclopentyl | cyclopentyl | iso-propyl |
| T-32 | cyclohexyl | cyclohexyl | iso-propyl |
| T-33 | —CH₃ | —CH₃ | iso-butyl |
| T-34 | —CH₂CH₃ | —CH₂CH₃ | iso-butyl |
| T-35 | iso-propyl | iso-propyl | iso-butyl |
| T-36 | iso-butyl | iso-butyl | iso-butyl |
| T-37 | neopentyl | neopentyl | iso-butyl |
| T-38 | —CH₃ | —CH₂CH₃ | iso-butyl |
| T-39 | cyclopentyl | cyclopentyl | iso-butyl |
| T-40 | cyclohexyl | cyclohexyl | iso-butyl |

Among the above metal carbene-complexes Q-1 to Q-40, R-1 to R-40, S-1 to S-40 and T-1 to T-40 the metal carbene-complexes Q-1 to Q-8, R-1 to R-8, S-1 to S-8, and T-1 to T-8 are preferred.

The at present most preferred metal carbene-complexes are metal carbene-complexes A-1 to A-14, C-1 to C-22, C-125 to C-130, C-161 to C-163, I-1 to I-14, J-1 to J-22 and J-111 to J-116. Among these metal carbene-complexes metal carbene-complexes A-2, A-3, A-4, A-6, A-14, C-126, C-127 and C-128 are even more preferred.

In the alkyl groups and aryl groups mentioned above one or more hydrogen atoms may be substituted by deuterium atoms.

A process for preparing a metal-carbene complexes of formula

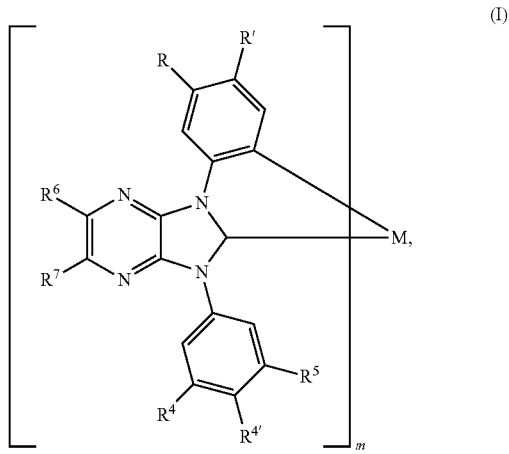

(I)

wherein M is Pt and m is 2; or M is Ir and m is 3, R is a group of formula

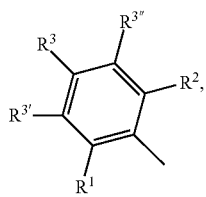

may comprise reacting a compound of formula

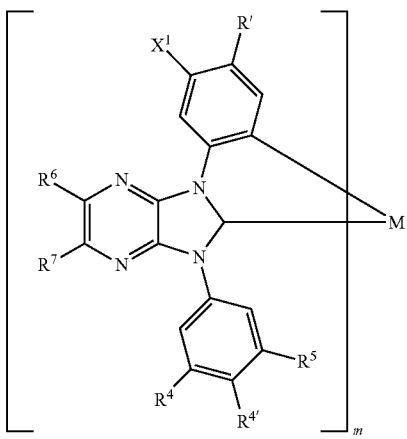

(X)

with a compound of formula

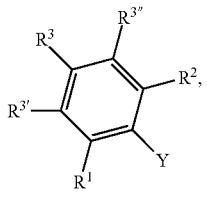

(XII)

wherein
$X^1$ is Cl, Br, or I, especially Br;
Y is —B(OH)$_2$, —B(OY$^1$)$_2$,

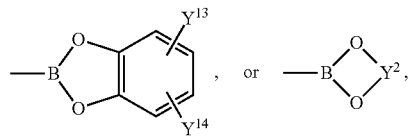

wherein $Y^1$ is independently in each occurrence a $C_1$-$C_{10}$alkyl group and $Y^2$ is independently in each occurrence a $C_2$-$C_{10}$alkylene group, such as —CY$^3$Y$^4$—CY$^5$Y$^6$—, or —CY$^7$Y$^8$—CY$^9$Y$^{10}$—CY$^{11}$Y$^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially —C(CH$_3$)$_2$C(CH$_3$)$_2$—, —CH$_2$C(CH$_3$)$_2$CH$_2$—, or —C(CH$_3$)$_2$CH$_2$C(CH$_3$)$_2$—, and $Y^{13}$ and $Y^{14}$ are independently of each other hydrogen, or a $C_1$-$C_{18}$alkyl group;
—SnR$^{307}$R$^{308}$R$^{309}$, wherein R$^{307}$, R$^{308}$ and R$^{309}$ are identical or different and are H or $C_1$-$C_8$alkyl, wherein two radicals optionally form a common ring and these radicals are optionally branched or unbranched;
ZnR$^{310}$R$^{311}$, wherein R$^{312}$ is halogen and R$^{311}$ is a $C_1$-$C_{10}$alkyl group, a $C_6$-$C_{12}$aryl group, or $C_1$-$C_{10}$alkenyl group; or
SiR$^{312}$R$^{313}$R$^{314}$, wherein R$^{312}$, R$^{313}$ and R$^{314}$ are identical or different and are halogen, or $C_1$-$C_8$alkyl; and
R, R', R$^1$, R$^2$, R$^3$, R$^{3'}$, R$^{3''}$, R$^4$, R$^{4'}$, R$^5$, R$^6$ and R$^7$ are as defined above.

The process is also suitable for producing metal-carbene complexes of formula process for preparing a metal-carbene complexes of formula

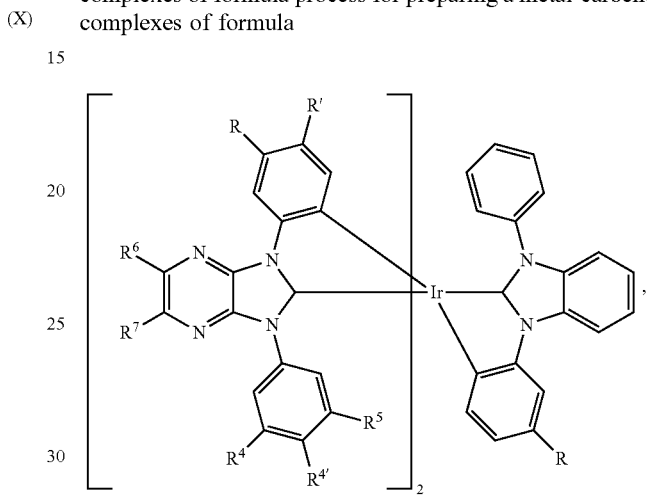

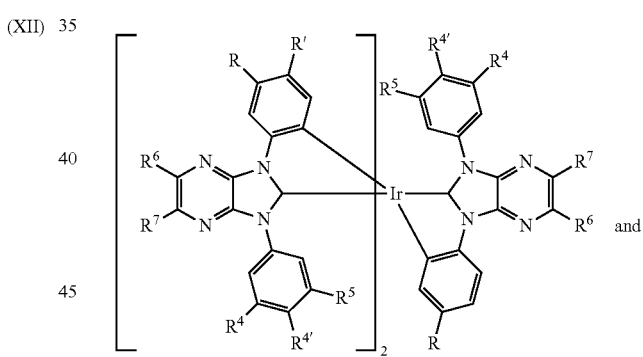

and

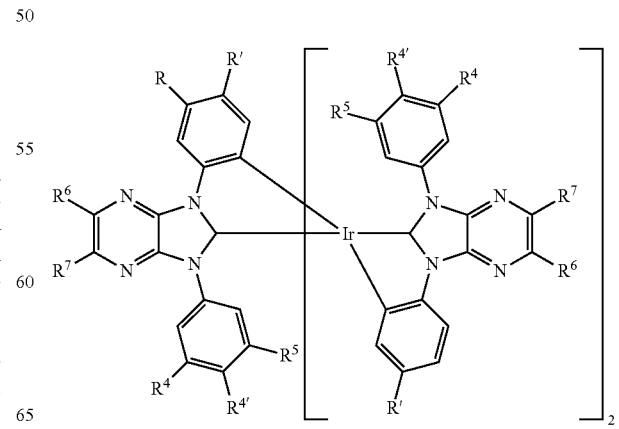

starting from

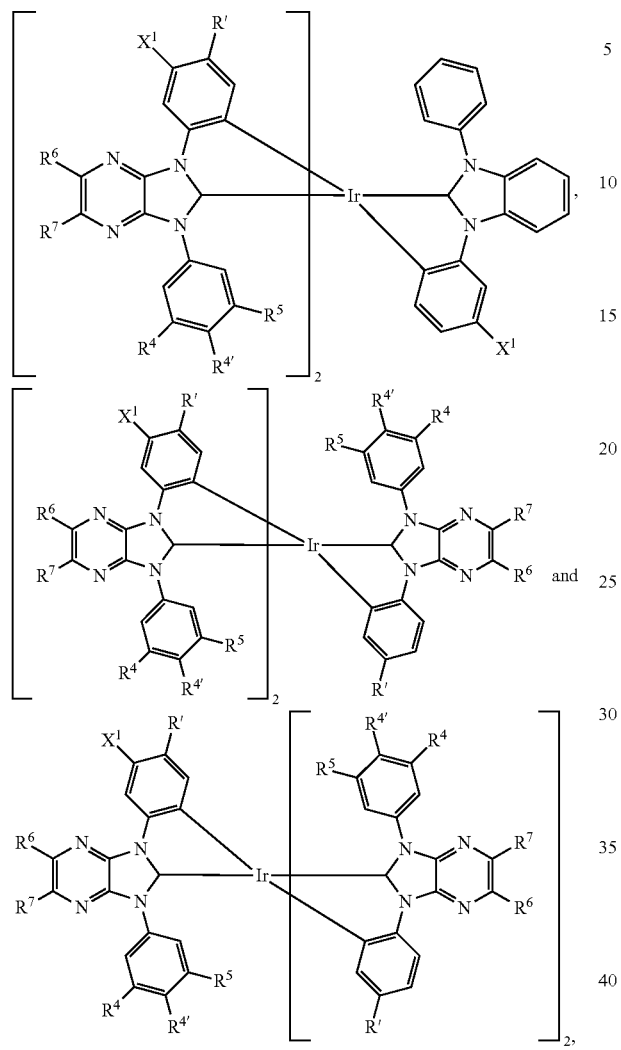

respectively.

Preferred reactions for the introduction of aryl substituents on the compound of formula (X) are in general metal catalyzed reactions and more specifically Suzuki, Ullmann, Negishi, Heck, Stille and Kumada coupling reactions (J. Hassan et al., Chemical Reviews 102 (2002) 5; L. Ackermann: "Modern Arylation Methods" (Ed.: L. Ackermann), Wiley-VCH, Weinheim, 2009).

Advantageously, the metal-carbene complexes of formula (I) can be synthesized by one of the following coupling reactions:

i) Negishi coupling reaction using a compound of formula (XII), wherein Y is $ZnR^{310}R^{311}$, wherein $R^{310}$ is halogen and $R^{311}$ is a $C_1$-$C_{18}$alkyl group, a $C_6$-$C_{12}$aryl group, or $C_1$-$C_{10}$alkenyl group. Reference is, for example, made to B. Vilas et al., Chem. Soc. Rev., 38 (2009) 1598-1607.

ii) Stille coupling reaction using a compound of formula (XII), wherein Y is —$SnR^{307}R^{308}R^{309}$, wherein $R^{307}$, $R^{308}$ and $R^{309}$ are identical or different and are H or $C_1$-$C_8$alkyl, wherein two radicals optionally form a common ring and these radicals are optionally branched or unbranched. Reference is, for example, made to J. K. Stille, Angew. Chem. 98 (1986) 504-519; P. Espinet et al., Angew. Chem. Int. Ed., 43 (2004) 4704-4734.

iii) Hiyama coupling reaction using a a compound of formula (XII), wherein Y is $SiR^{312}R^{313}R^{314}$, wherein $R^{312}$, $R^{313}$ and $R^{314}$ are identical or different and are halogen, or $C_1$-$C_8$alkyl. Reference is, for example, made to T. Hiyama et al., Pure Appl. Chem. 66 (1994) 1471-1478 and T. Hiyama et al., Synlett (1991) 845-853; and iv) Suzuki coupling reaction using a a compound of formula

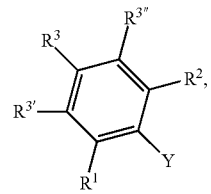

wherein Y is —$B(OH)_2$, —$B(OY^1)_2$,

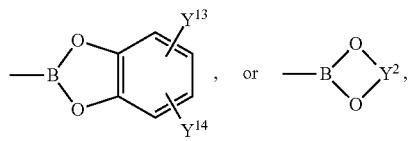

wherein $Y^1$ is independently in each occurrence a $C_1$-$C_{10}$alkyl group and $Y^2$ is independently in each occurrence a $C_2$-$C_{10}$alkylene group, such as —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially —$C(CH_3)_2C(CH_3)_2$—, —$CH_2C(CH_3)_2CH_2$—, or —$C(CH_3)_2CH_2C(CH_3)_2$—, and $Y^{13}$ and $Y^{14}$ are independently of each other hydrogen, or a $C_1$-$C_{10}$alkyl group. Reference is, for example, made to A. Suzuki et al., Chemical Reviews 95 (1995) 2457-2483, "Suzuki in Modern Arene Chemistry" (Ed.: D. Astruc), Wiley-VCH, Weinheim, 2002, pp. 53-106. More preferably Suzuki and Negishi coupling reactions are used. Suzuki type reactions are most preferred.

Preferably, the Suzuki reaction of compound (X) with compound (XII) is carried out in presence of
a) a catalyst/ligand system comprising a palladium catalyst and an organic phosphine or phosphonium compound,
b) a base,
c) a solvent or a mixture of solvents.

The organic solvent is usually an aromatic hydrocarbon, a linear, branched, or cyclic ether, or a usual polar organic solvent, such as benzene, toluene, xylene, tetrahydrofurane, or dioxane, or mixtures thereof. If desired, water can be added to the organic reaction medium, in which case, depending on the organic solvent used, the reaction can be carried out in a single phase or in a two-phase mixture.

Usually, the amount of the solvent is chosen in the range of from 1 to 10 l per mol of boronic acid derivative.

Also preferred, the reaction is carried out under an inert atmosphere such as nitrogen, or argon.

Further, it is preferred to carry out the reaction in the presence of an aqueous base, such as an alkali metal hydroxide, metal phosphate, or carbonate such as NaOH, KOH, $K_3PO_4$, $Na_2CO_3$, $K_2CO_3$, or $Cs_2CO_3$.

Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein).

Usually, the molar ratio of the base to boronic acid or boronic ester derivative is chosen in the range of from 0.5:1 to 50:1, very especially in the range of 1:1 to 5:1.

Generally, the reaction temperature is chosen in the range of from 40 to 180° C., preferably under reflux conditions.

Generally, the reaction time is chosen in the range of from 0.5 to 80 hours, preferably from 2 hours to 60 hours.

In a preferred embodiment a usual catalyst for coupling reactions or for polycondensation reactions is used, preferably Pd-based, which is described in WO2007/101820. The palladium compound is added in a ratio of from 1:10000 to 1:50, preferably from 1:5000 to 1:200, based on the number of bonds to be closed. Preference is given, for example, to the use of palladium(II) salts such as $PdOAc_2$ or $Pd_2dba_3$ and to the addition of ligands selected from the group consisting of

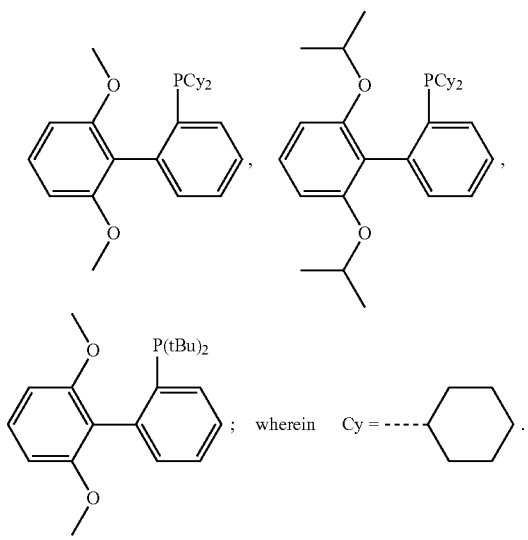

The ligand is added in a ratio of from 1:1 to 1:10, based on Pd. Also preferred, the catalyst is added as in solution or suspension. Preferably, an appropriate organic solvent such as the ones described above, preferably benzene, toluene, xylene, THF, dioxane, more preferably toluene, or mixtures thereof, is used. The amount of solvent usually is chosen in the range of from 1 to 10 l per mol of boronic acid derivative.

Other variations of reaction conditions are given by T. I. Wallow and B. M. Novak in J. Org. Chem. 59 (1994) 5034-5037; and M. Remmers, M. Schulze, G. Wegner in Macromol. Rapid Commun. 17 (1996) 239-252 and G. A. Molander and B. Canturk, Angew. Chem., 121 (2009) 9404-9425. The following reaction systems are preferred:
i) aryl boronic acid, tris(dibenzylideneacetone) dipalladium (0), SPhos (Dicyclohexylphosphino-2',6'-dimethoxybiphenyl), tripotassium phosphate (solvent toluene/water mixture);
ii) aryl boronic acid, bis(tri-t-butylphosphin)palladium(0) ($Pd[P(tBu)_3]_2$), sodium hydroxide (solvent toluene/dioxane/water mixture); and
iii) aryl boronic acid, palladium acetate ($Pd(OAc)_2$), SPhos (Dicyclohexylphosphino-2',6'-dimethoxybiphenyl), tripotassium phosphate (o-xylene mixture).

The compound of formula (X) can be obtained by reacting a compound of formula

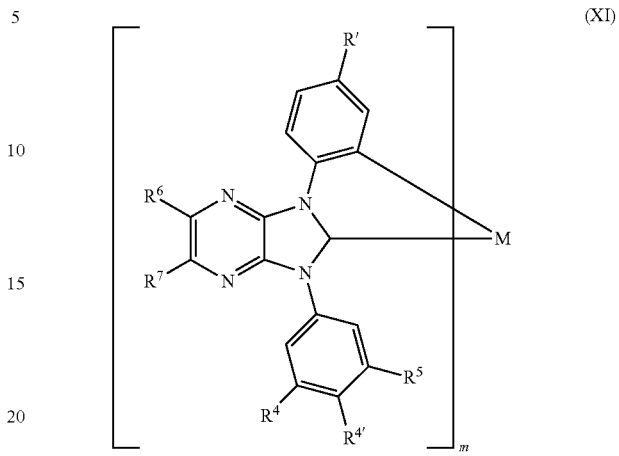

(XI)

with a halogenating agent, wherein R', $R^4$, $R^{4'}$, $R^5$, $R^6$ and $R^7$ are as defined in above. The halogenation can be performed by methods known to those skilled in the art.

Halogenating agents according to the invention are the halogens $X_2$ or the interhalogens X—X and a base in a ratio of from 1:1 to 1:100 and optionally a Lewis acid in a ratio (halogen to Lewis acid) of from 1:0.1 to 1:0.0001, for example chlorine, bromine or iodine, or chlorine fluoride, bromine fluoride, iodine fluoride, bromine chloride, iodine chloride or iodine bromide, in combination with organic bases such as amines, for example triethylamine, tri-n-butylamine, diisopropylethylamine, morpholine, N-methylmorpholine and pyridine, or salts of carboxylic acids such as sodium acetate, sodium propionate, sodium benzoate, or inorganic bases such as sodium or potassium phosphate or hydrogenphosphate, potassium or sodium hydrogencarbonate, potassium or sodium carbonate, or else organic bromine complexes such as pyridinium perbromide, optionally each in combination with a Lewis acid, e.g. boron trifluoride, boron trifluoride etherate, boron trichloride, boron tribromide, boron triiodide, aluminum trichloride, aluminum tribromide, aluminum triiodide, iron(III) chloride, iron(III) bromide, zinc(II)chloride, zinc(II)bromide, tin(IV)chloride, tin(IV)bromide, phosphorus pentachloride, arsenic pentachloride and antimony pentachloride are used.

Further halogenating agents according to the invention are organic N—X compounds, such as 1-(chloromethyl)-4-fluoro-1,4-diazoniabicyclo[2.2.2]octane bis(tetrafluoroborate), or N-halocarboxamides such as N-chloro-, N-bromo- and N-iodoacetamide, N-chloro-, N-bromo- and N-iodopropionamide, N-chloro-, N-bromo- and N-iodobenzamide, or N-halocarboximides such as N-chloro-, N-bromo- and N-iodosuccinimide, N-chloro-, N-bromo- and N-iodophthalimide, or N,N-dihalohydantoins, such as 1,3-dibromo-5,5-dimethylhydantoin, 1,3-dichloro-5,5-dimethylhydantoin, 1,3-diiodo-5,5-dimethylhydantoin or N-dihalosulfonamides such as, benzenesulfo-N-dibromamide, or N-halosulfonamide salts such as chloramine B or T. In the case of these halogenating agents, the additive use of Lewis acids, as listed above, for example, may likewise be advantageous.

Preferred halogenating agents N-halocarboxamides such as N-chloro-, N-bromo- and N-iodosuccinimide, N-chloro-, N-bromo- and N-iodophthalimide, or N,N-dihalohydantoins, such as 1,3-dibromo-5,5-dimethylhydantoin, 1,3-dichloro-5,5-dimethylhydantoin and 1,3-diiodo-5,5-dimethylhydantoin.

In the process according to the invention, a stoichiometric ratio or an excess of the halogenating agent based on the content of active halogen, to the compounds (XI) is used, and can lead selectively to the compounds (X). Preferably a stoichiometric ratio up to a ratio of 2:1 of the halogenating agent based on the content of active halogen to the compounds (XI) is used. More preferably a stoichiometric ratio is used.

Reaction media according to the invention are protic or aprotic, halogen-free or halogenated solvents, for example alcohols such as methanol, ethanol, propanol, butanol, polyhydric alcohols such as ethylene glycol, propyleneglycol, nitriles such as acetonitrile, propionitrile or benzonitrile, ethers such as diethyl ether THF or dioxane, aromatic hydrocarbons such as benzonitrile, nitrobenzene or chlorobenzene, N,N-dialkylamides such as dimethylformamide, methylacetamide or N-methylpyrroldinone, sulfoxides, such as dimethyl sulfoxide, sulfones such as dimethylsulfone or sulfolane, halogenated hydrocarbons such as dichloromethane, trichloromethanen, 1,1-dichloroethane, 1,2-dichloroethane, 1,1,2,2-tetrachloroethane. Preference is given to aromatic or chlorinated solvents.

According to the invention, the concentration of the compound of formula (XI) is in the range from 0.0005 mol/l to 2 mol/l, more preferably in the range from 0.002 mol/l to 0.1 mol/l.

According to the invention, the compound of formula (XI) may be dissolved or suspended in the reaction medium.

According to the invention, the reaction is carried out in the temperature range from −78° C. to 150° C., preferably at from 0° C. to 80° C., more preferably at from 0° C. to 40° C.

According to the invention, the reaction is carried out within from 1 h to 100 hours, preferably within from 3 h to 60 h.

Brominating in the 3 position of the cyclometallating N-aryl group of the diazabenzimidazole carbene ligand can be, for example, accomplished by reaction of the compound of formula (X) with N-bromosuccinimide in dichloromethane.

Iodinating in the 3 position of the cyclometallating N-aryl group of the diazabenzimidazole carbene ligand can be, for example, accomplished by reaction of the compound of formula (X) with N-iodosuccinimide in dichloromethane.

Carbene complexes which are suitable as starting material (XI) are, for example, specified in the following publications: WO2011/073149, US2012/0305894, WO2012/121936, and WO2012/170461.

The present invention also relates to a process for preparing the inventive metal-carbene complexes comprising one, two or three, preferably three in the case of Ir and preferably one in the case of Pt, bidentate ligands of formula

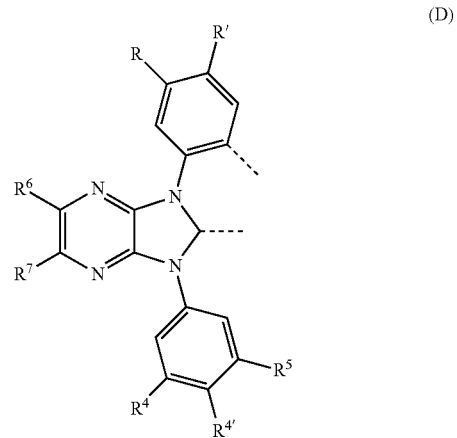

(D)

by contacting suitable compounds comprising Ir or Pt with the appropriate ligands or ligand precursors.

In one embodiment of the process according to the invention, a suitable compound comprising iridium or platinum, preferably iridium, and appropriate carbene ligands, preferably in deprotonated form as the free carbene or in the form of a protected carbene, for example as the silver-carbene complex, are contacted.

The present invention therefore relates—in one embodiment—to a process according to the invention wherein the ligand precursor used is a corresponding Ag-carbene complex.

In a further preferred embodiment of the process according to the invention, the ligand precursors used are organic compounds which are reacted with suitable Ir or Pt comprising compounds. The carbene can be released from precursors of the carbene ligands by removing volatile substances, for example lower alcohols such as methanol or ethanol, for example at elevated temperature and/or under reduced pressure and/or using molecular sieves which bind the alcohol molecules eliminated. Corresponding processes are known to those skilled in the art.

The present invention also relates to the process according to the invention wherein the ligand precursor used is a compound of the general formula

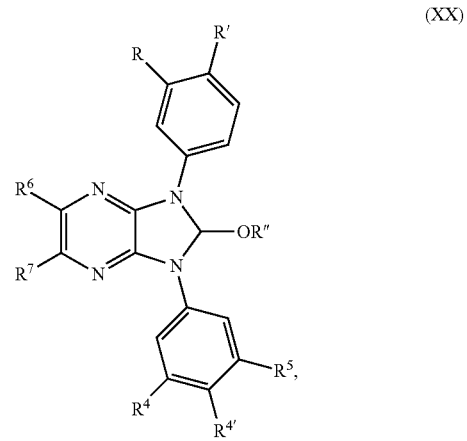

(XX)

wherein R, R', $R^4$, $R^{4'}$, $R^5$, $R^6$ and $R^7$ are as defined above, and R" is SiR¹³R¹⁴R¹⁵, aryl, heteroaryl, alkyl, cycloalkyl or heterocycloalkyl, wherein R¹³, R¹⁴ and R¹⁵ are independently of each other aryl, heteroaryl, alkyl, cycloalkyl or heterocycloalkyl.

In a particularly preferred embodiment, R" is alkyl, especially $C_1$-$C_{20}$alkyl, preferably $C_1$-$C_{10}$alkyl, more preferably $C_1$-$C_8$alkyl, for example methyl, ethyl, propyl such as n-propyl, isopropyl, butyl such as n-butyl, isobutyl, tert-butyl, pentyl, hexyl, heptyl or octyl.

R" in the compound of the general formula (XX) is most preferably methyl or ethyl.

Compounds of the general formula (XX) are generally obtainable by processes known to those skilled in the art. Compounds of the general formula (XX) can be obtained for example by reacting compounds of the general formula (XXIa)

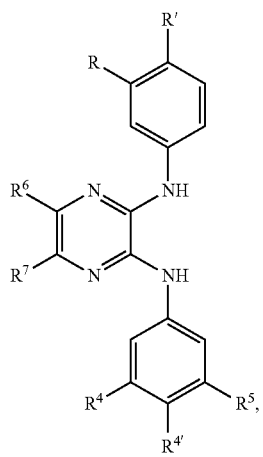

(XXIa)

or the corresponding Cl or BF₄ salt of formula

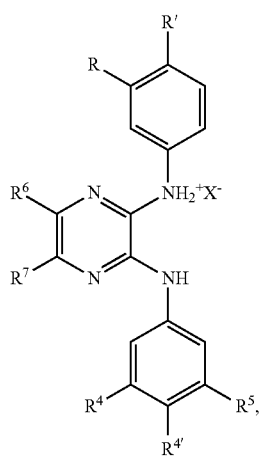

(XXIa)

wherein X is Cl or BF₄,
with compounds of the general formula HC(OR")₃ (XXII), or
by reacting compounds of the general formula (XXIa) in a first step with Vilsmeier reagent ((chloromethylene)dimethylammonium chloride) and a sodium salt selected from NaBF₄, NaCl, NaBr or NaI to obtain a compound of formula (XXIc)

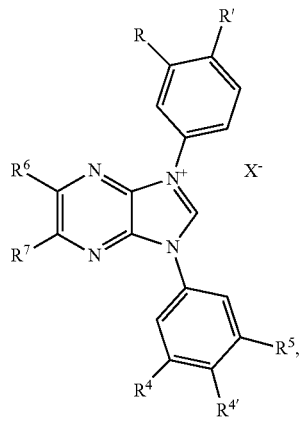

(XXIc)

wherein X is BF₄, Cl, Br or I and in a second step with R"OH or M"OR", wherein M" is an alkali metal salt, preferably Na, wherein R, R', R⁴, R⁴', R⁵, R⁶ and R⁷ are as defined above and the metal is Ir or Pt, comprising one, two or three bidentate ligands of formula (D).

This preparation of the compounds of the general formula (XX) can be effected in the presence or in the absence of a solvent. Suitable solvents are specified below. In one preferred embodiment, the compounds of the general formula (XX) are prepared in substance, or the compound of the general formula (XXII) is added in an excess, such that it functions as a solvent.

Compounds of the general formulae (XXI) and (XXII) are commercially available and/or obtainable by processes known to those skilled in the art; for example, compounds of the general formula (XXI) are obtainable by reacting the appropriate chlorides with the appropriate amines.

The compounds of the general formula (XX) are prepared generally at a temperature of 10 to 150° C., preferably 40 to 120° C., more preferably 60 to 110° C.

The reaction time is generally 2 to 48 hours, preferably 6 to 24 hours, more preferably 8 to 16 hours.

After the reaction has ended, the desired product can be isolated and purified by customary processes known to those skilled in the art, for example filtration, recrystallization, column chromatography, etc.

Appropriate compounds, especially complexes, comprising Ir or Pt, preferably iridium, are known to those skilled in the art. Particularly suitable compounds comprising platinum or iridium comprise, for example, ligands such as halides, preferably chloride, 1,5-cyclooctadiene (COD), cyclooctene (COE), phosphines, cyanides, alkoxides, pseudohalides and/or alkyl.

Particularly preferred complexes comprising the appropriate metal, especially iridium, are selected from the group consisting of [Ir(COD)Cl]₂, [Ir(COE)₂Cl]₂ IrCl₃×H₂O, Ir(acac)₃, Ir(COD)₂BF₄, Ir(COD)₂BARF (BARF=tetrakis[3,5-bis(trifluoromethyl)phenyl]borate)), Pt(COD)Cl₂, Pt(acac)₂, [Pt(C₆H₁₀)Cl₂]₂, K₂PtCl₆, Pt(pyridine)₂Cl₂, [PtMe₂(SMe₂)]₂, Pt(SMe₂)₂Cl₂, Pt(SEt₂)₂Cl₂, Pt(phenanthroline)Cl₂, Pt(NH₃)₂Cl₂ and mixtures thereof.

The carbene ligand precursors are deprotonated, preferably before the reaction, for example, by basic compounds known to those skilled in the art, for example basic metalates, basic metal acetates, acetylacetonates or alkoxides, or bases such as KOtBu, NaOᵗBu, LiOᵗBu, NaH, silylamides, Ag₂O and phosphazene bases. Particular preference is given to deprotonating with Ag₂O to obtain the corresponding Ag-carbene, which is reacted with the compound comprising M to give the inventive complexes.

Particularly preferably, the carbene can be released from precursors of the carbene ligands by removing volatile substances, for example lower alcohols.

The process according to the invention for preparing the metal-carbene complexes, wherein the metal is Ir or Pt, comprising one, two or three bidentate ligands of formula (D) according to the present invention using the compounds of the general formula (XX) has the advantage that the compounds of the general formula (XX) are stable intermediates which can be handled readily and can be isolated under standard laboratory conditions. In addition, the compounds of the general formula (XX) are soluble in customary organic solvents, such that the preparation of the inventive metal-carbene complexes, wherein the metal is Ir or Pt, comprising one, two or three bidentate ligands of formula (D) in homogeneous solution is possible, such that a workup of the desired product, i.e. of the metal-carbene complexes, wherein the metal is Ir or Pt, comprising one, two or three bidentate ligands of formula (D) is more readily possible, for example for isolation and/or purification.

The contacting is preferably effected in a solvent. Suitable solvents are known per se to those skilled in the art and are preferably selected from the group consisting of aromatic or aliphatic solvents, for example benzene, toluene, xylene or mesitylene, cyclic or acyclic ethers, for example dioxane or THF, alcohols, esters, amides, ketones, nitriles, halogenated compounds and mixtures thereof. Particularly preferred solvents are toluene, xylenes, mesitylene and dioxane.

The molar ratio of metal-noncarbene complex used to carbene ligand precursor used is generally 1:10 to 10:1, preferably 1:1 to 1:6, more preferably 1:2 to 1:5.

The contacting is generally effected at a temperature of 20 to 200° C., preferably 50 to 150° C., more preferably 60 to 150° C.

The reaction time depends on the desired carbene complex and is generally 0.02 to 50 hours, preferably 0.1 to 24 hours, more preferably 1 to 24 hours.

The metal-carbene complexes, wherein the metal is Ir or Pt, comprising one, two or three bidentate ligands of formula (D) obtained after the reaction can optionally be purified by processes known to those skilled in the art, for example washing, crystallization or chromatography, and optionally isomerized under conditions likewise known to those skilled in the art, for example with acid mediation, thermally or photochemically.

Suitable processes for preparing the metal-carbene complex comprising one, two or three, preferably three, bidentate ligands of formula (D) are for example mentioned in WO 2011/073149 and EP13174779.

The resulting complexes may yield different isomers that can be separated or converted into a form with a major isomer by isomerization of the mixture.

The inventive metal-carbene complexes can be used in electronic devices, especially OLEDs (Organic Light-Emitting Diodes), for example, as emitter, matrix material, charge transport material and/or charge or exciton blocker.

The inventive metal-carbene complexes are generally notable for improved device performance such as high external quantum efficiency, high luminous efficacy and low voltage, blue emission, decreased lifetime of the luminescence ti (higher radiation rate $k_{rad}$), reduced color-shift (e.g. CIE-y shift) with increasing doping concentration, or long device lifetime and/or excellent thermal stability.

The inventive metal-carbene complexes are therefore suitable with particular preference as emitter material in OLEDs.

The inventive metal-carbene complexes can be used in electronic devices, for example organic electronic devices selected from switching elements such as organic light-emitting diodes (OLEDs), organic photovoltaic cells (OPVs), organic field-effect transistors (OFETs) and light-emitting electrochemical cells (LEECs), preference being given to using the metal-carbene complexes of the formula (I) in OLEDs.

The inventive metal-carbene complex is preferably a compound of formula (IIIa) to (IIIe), especially a compound of formula (IIIa-1) to (IIIe-1), very especially a compound (A-1) to (A-70) and (C-1) to (C-110), (C-125) to (C-154), and (C-161) to (C-163), wherein those compounds are particularly preferred, wherein $R^4$ and $R^5$ are H, i.e. compounds (A-1) to (A-14), (C-1) to (C-22), (C-125) to (C-130) and (C-161) to (C-163).

In a preferred embodiment, the organic electronic device is an OLED comprising a light-emitting layer comprising at least one inventive metal-carbene complex.

In addition, the inventive metal-carbene complexes can be used as matrix material, charge transport material, especially hole transport material, and/or charge blocker.

The inventive metal-carbene complexes are preferably used as an emitter and/or charge transport material and/or matrix material, more preferably as an emitter.

Particular properties of the inventive metal-carbene complexes are particularly good efficiencies, good CIE color loci and long lifetimes when used in OLEDs.

The present application therefore further provides an OLED comprising at least one inventive metal-carbene complex. The inventive metal-carbene complex is used in the OLED preferably as an emitter, matrix material, charge transport material, especially hole transport material, and/or charge blocker, more preferably as an emitter and/or hole transport material, most preferably as an emitter.

The present application also provides for the use of the inventive metal-carbene complexes in OLEDs, preferably as an emitter, matrix material, charge transport material, especially hole transport material, and/or charge blocker, more preferably as an emitter and/or hole transport material, most preferably as an emitter.

Organic light-emitting diodes are in principle formed from a plurality of layers, e.g.:
(a) an anode,
(b) optionally a hole injection layer,
(c) optionally a hole transport layer,
(d) optionally an exciton blocking layer
(e) a light-emitting layer, comprising
(f) optionally a hole/exciton blocking layer
(g) optionally an electron transport layer,
(h) optionally an electron injection layer, and
(i) a cathode.

It is, however, also possible that the OLED does not have all of the layers mentioned; for example, an OLED comprising layers (a) (anode), (e) (light-emitting layer) and (i) (cathode) is likewise suitable, in which case the functions of layers (c) (hole-transport layer) and (g) (electron-transport layer) are assumed by the adjoining layers. OLEDs having layers (a), (c), (e), (g) and (i) or (a), (c), (e) and (i) or layers (a), (e), (g) and (i) are likewise suitable.

The inventive metal-carbene complexes are preferably used as emitter molecules and/or matrix materials in the light-emitting layer (e). The inventive metal-carbene complexes may—in addition to use as emitter molecules and/or matrix materials in the light-emitting layer (e) or instead of use in the light-emitting layer—also be used as a charge transport material in the hole-transport layer (c) or in the electron-transport layer (g) and/or as a charge blocker, preference being given to use as a charge transport material in the hole-transport layer (c) (hole transport material).

The present application therefore further provides a light-emitting layer comprising at least one of the inventive metal-carbene complexes, preferably as emitter material and/or matrix material, more preferably as emitter material. Preferred inventive metal-carbene complexes have already been specified above.

The light-emitting layer comprises preferably at least one metal-carbene complex according to the invention, especially used as emissive material, and a host material.

In a further embodiment, the present invention relates to a light-emitting layer consisting of at least one inventive metal-carbene complex.

The inventive metal-carbene complexes used in accordance with the invention may be present in the light-emitting layer in substance, i.e. without further additions. However, it is also possible that, in addition to the metal-carbene complexes used in accordance with the invention, further compounds are present in the light-emitting layer. In addition, a diluent material (matrix material) may be used. This diluent material may be a polymer, for example poly(N-vinylcarbazole) or polysilane. The diluent material may, however, likewise be a small molecule, for example 4,4'-N,N'-dicarbazolebiphenyl (CDP) or tertiary aromatic amines. When a diluent material is used, the proportion of the inventive metal-carbene complexes in the light-emitting layer is generally less than 40% by weight, preferably 3 to 30% by weight. The inventive metal-carbene complexes are preferably used in a matrix. The light-emitting layer thus preferably comprises at least one inventive metal-carbene complex and at least one matrix material.

Preferred further phosphphosphorescence emitters are carbene complexes. Carbene complexes which are suitable phosphorescent blue emitters are specified in the following publications: WO 2006/056418 A2, WO 2005/113704, WO 2007/115970, WO 2007/115981, WO 2008/000727, WO2009050281, WO2009050290, WO2011051404, US2011/057559 WO2011/073149, WO2012/121936A2, US2012/0305894A1, WO2012170571, WO2012170461, WO 2012170463, WO2006121811, WO2007095118, WO2008156879, WO2008156879, WO2010068876, US20110057559, WO2011106344, US20110233528, WO2012048266 and WO2012172482.

Suitable matrix materials are in principle the materials specified hereinafter as hole and electron transport materials, and also carben complexes, for example, the inventive metal-carbene complexes, or the carbene complexes mentioned in WO 2005/019373. Particularly suitable are carbazole derivatives, for example 4,4'-bis(carbazol-9-yl)-2,2'-dimethylbiphenyl (CDBP), 4,4'-bis(carbazol-9-yl)biphenyl (CBP), 1,3-bis(N-carbazolyl)benzene (mCP), and the matrix materials specified in the following applications: WO2008/034758, WO2009/003919.

Further suitable matrix materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co)polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446, WO06128800, WO2012014621, WO2012105310, WO2012/130709 and European patent applications EP12175635.7 and EP12185230.5, EP12191408.9 (in particular page 25 to 29 of EP12191408.9), WO2012048266, WO2012145173, WO2012162325, and EP2551932.

In a particularly preferred embodiment, one or more compounds of the general formula (X) specified hereinafter are used as matrix material.

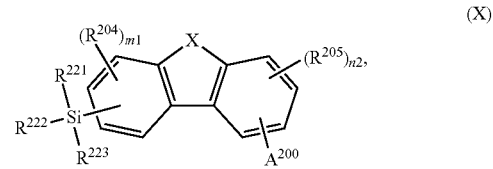

wherein
X is NR, S, O or PR;
R is aryl, heteroaryl, alkyl, cycloalkyl, or heterocycloalkyl;
$A^{200}$ is $-NR^{206}R^{207}$, $-P(O)R^{208}R^{209}$, $-PR^{210}R^{211}$, $-S(O)_2R^{212}$, $-S(O)R^{213}$, $-SR^{214}$, or $-OR^{215}$;
$R^{221}$, $R^{222}$ and $R^{223}$ are independently of each other aryl, heteroaryl, alkyl, cycloalkyl, or heterocycloalkyl, wherein at least on of the groups $R^{221}$, $R^{222}$, or $R^{223}$ is aryl, or heteroaryl;
$R^{224}$ and $R^{225}$ are independently of each other alkyl, cycloalkyl, heterocycloalkyl, aryl, heteroaryl, a group $A^1$, or a group having donor, or acceptor characteristics;
n2 and m1 are independently of each other 0, 1, 2, or 3;
$R^{206}$, $R^{207}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and $R^{208}$, $R^{209}$, $R^{210}$, $R^{211}$, $R^{212}$, $R^{213}$, $R^{214}$ and $R^{215}$ are independently of each other aryl, heteroaryl, alkyl, cycloalkyl, or heterocycloalkyl.

Compounds of formula (X) and their preparation processes, such as, for example,

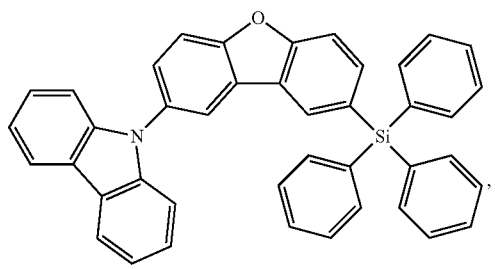
(SH-4)

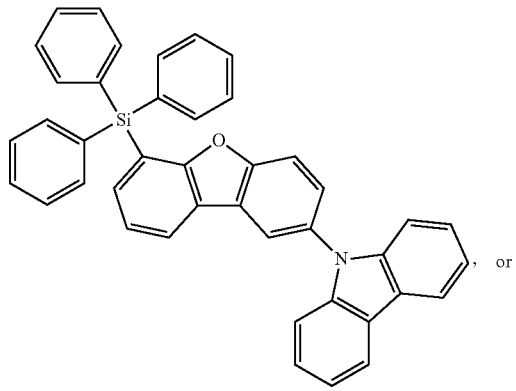
(SH-5)

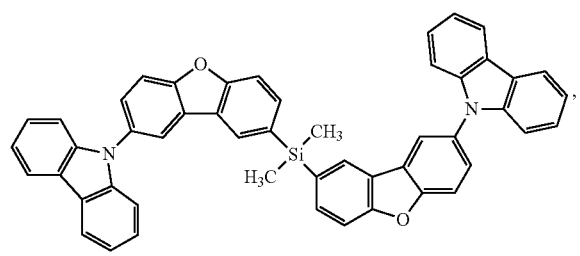
(SH-6)

are described in WO2010/079051 (in particular pages on 19 to 26 and in tables on pages 27 to 34, pages 35 to 37 and pages 42 to 43).

Additional host materials on basis of dibenzofurane are, for example, described in US 2009066226, EP1885818, EP1970976, EP1998388 and EP2034538. Examples of particularly preferred host materials are shown below:

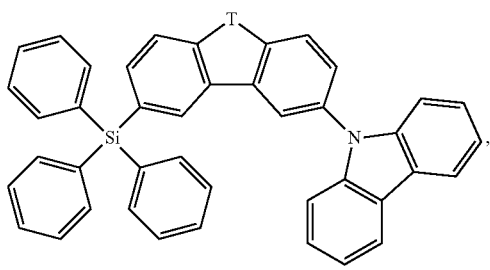

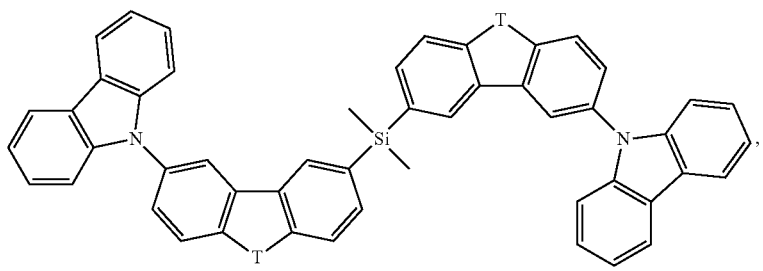

-continued
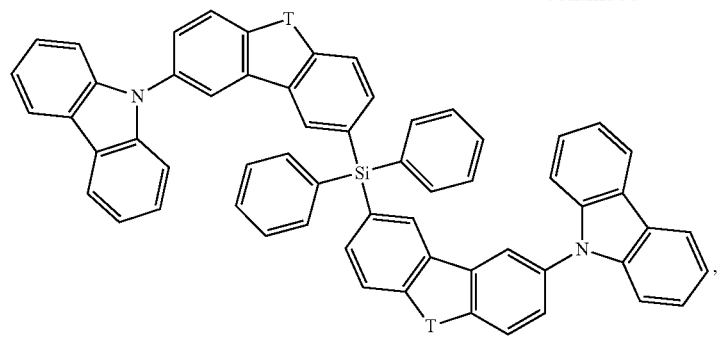
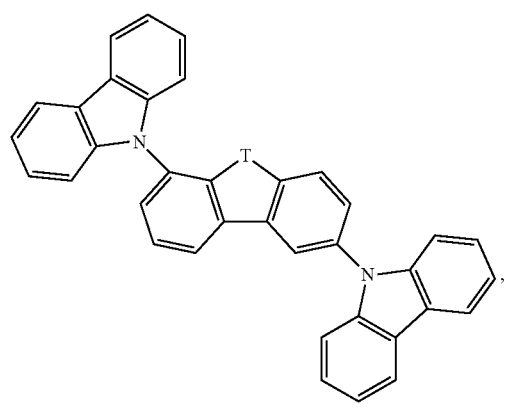
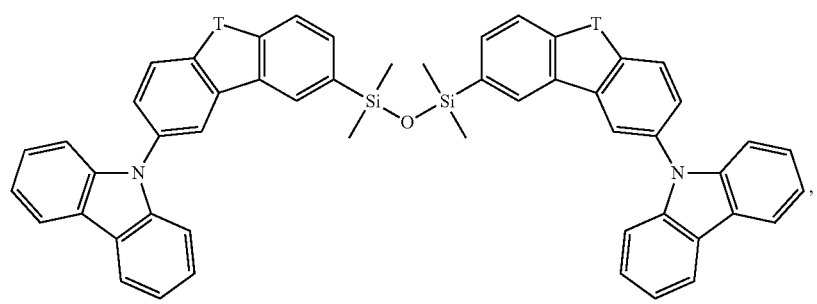
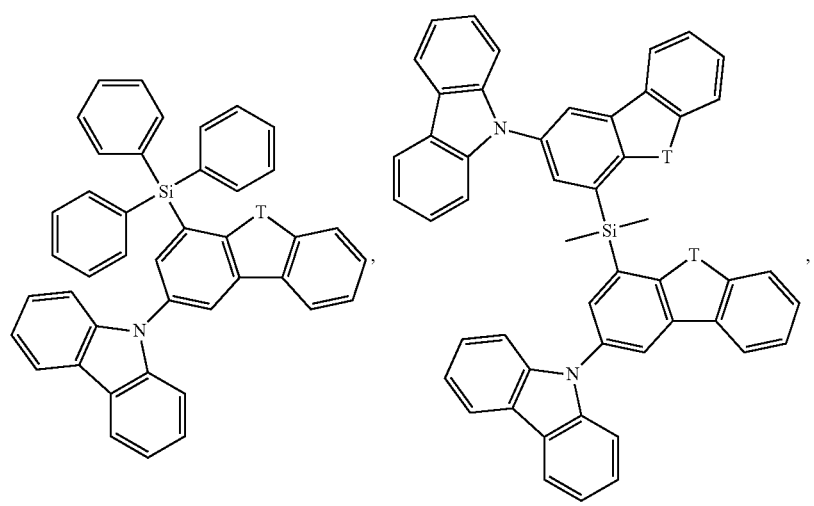

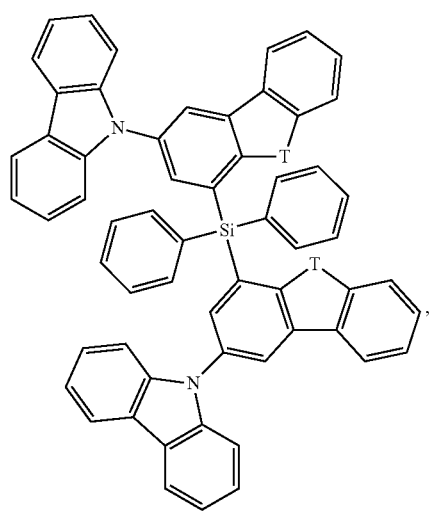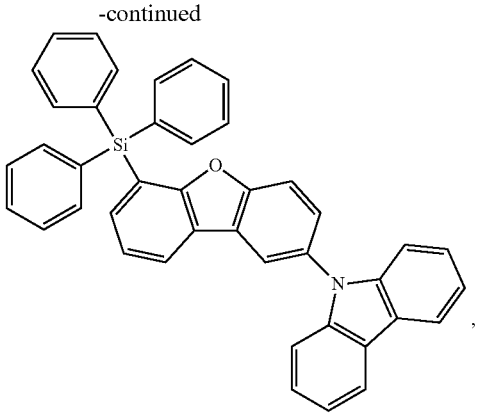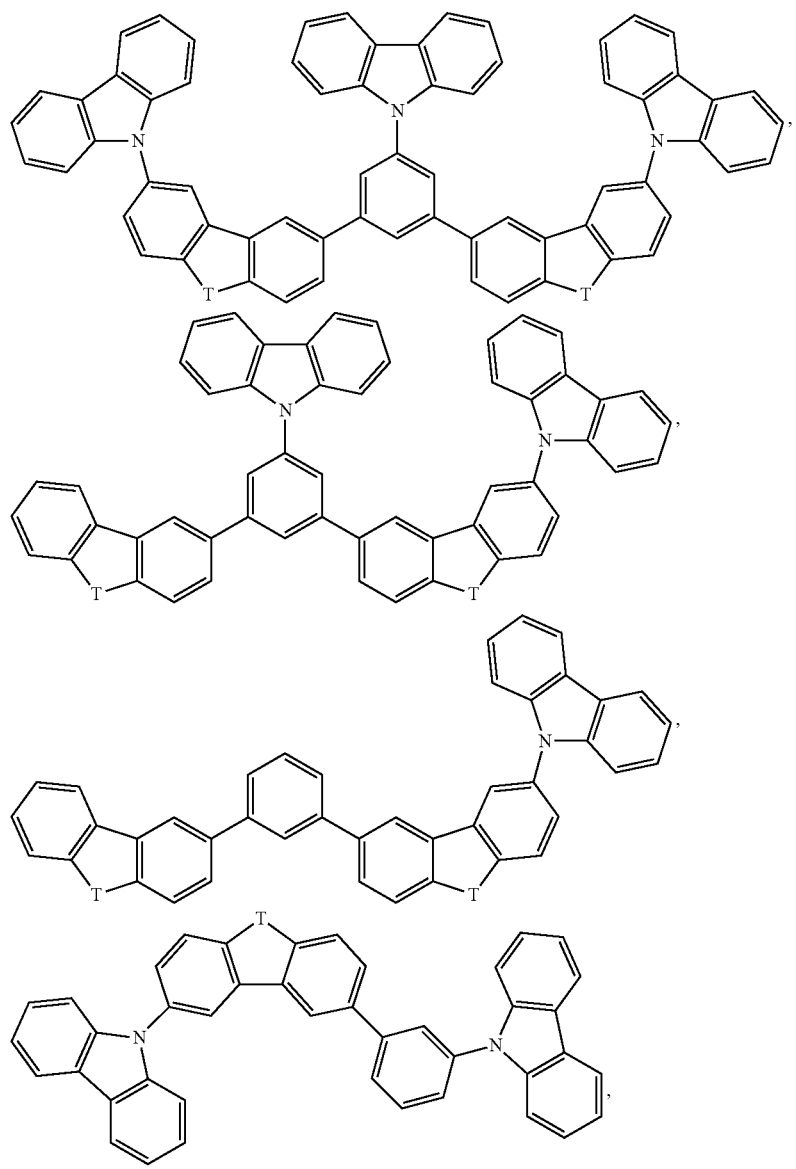

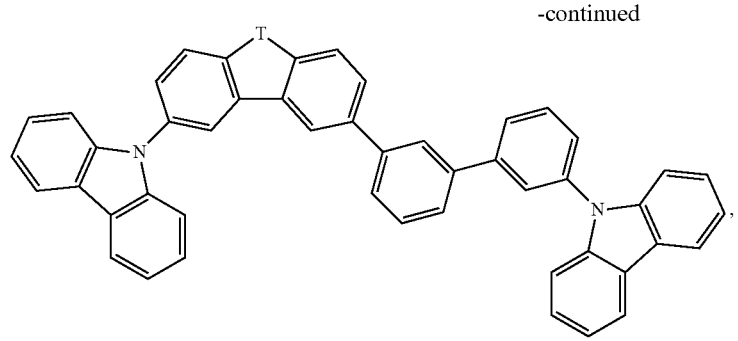
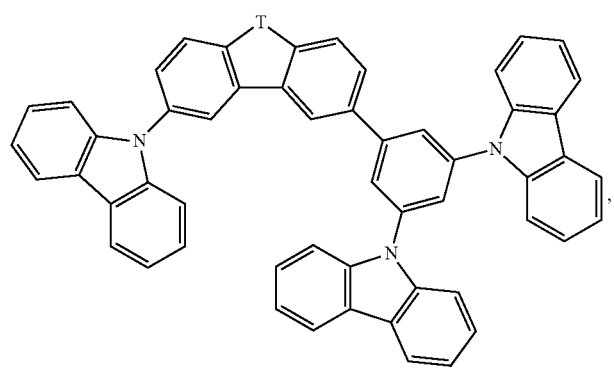
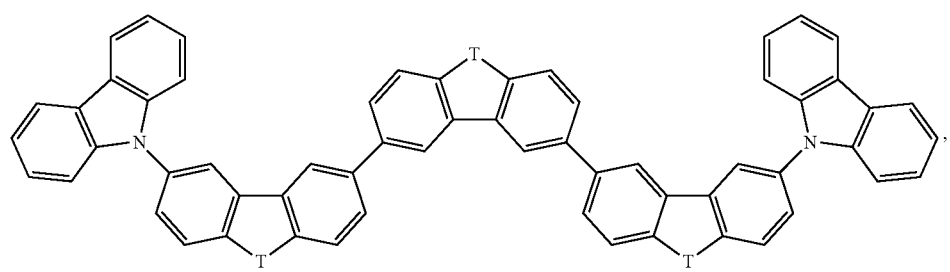
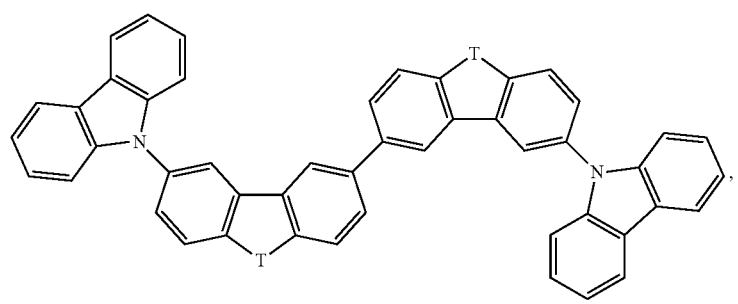
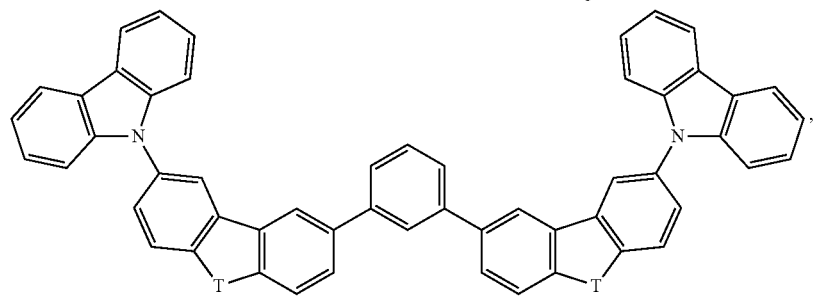

-continued
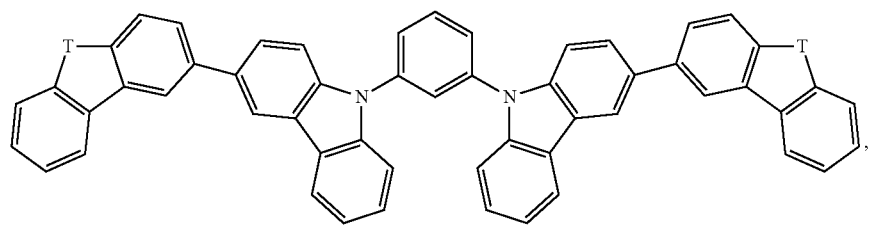
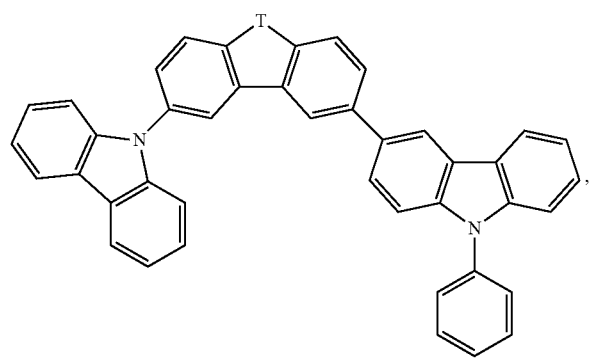
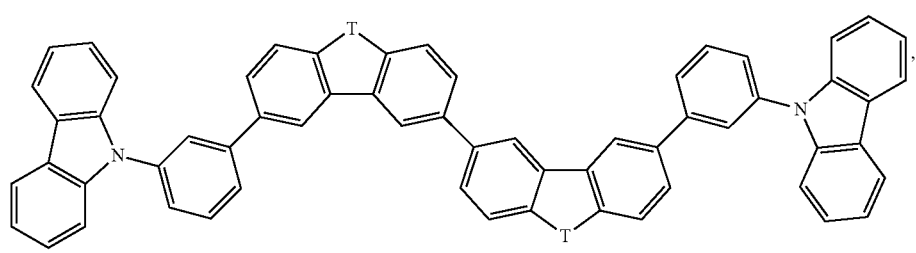
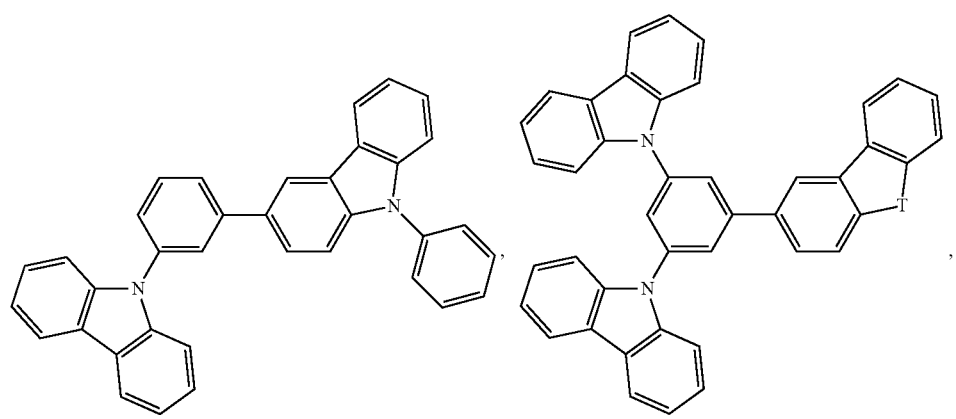
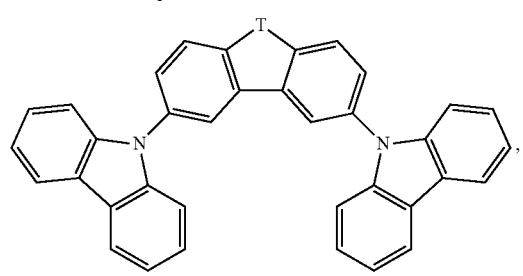

-continued
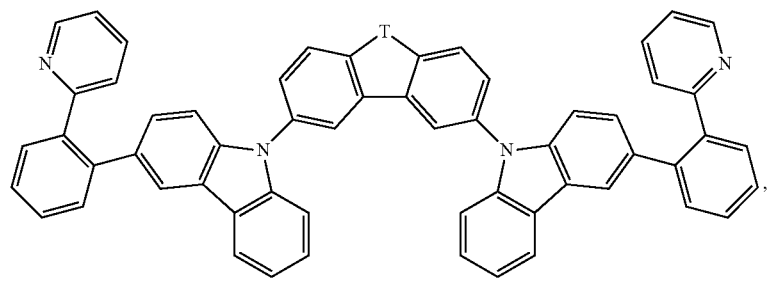
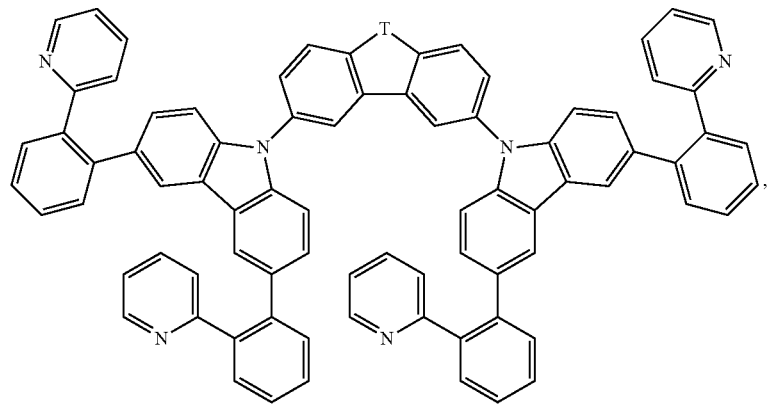
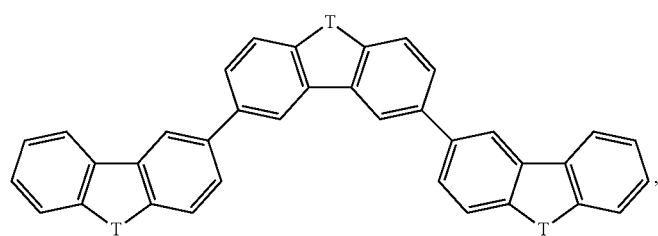
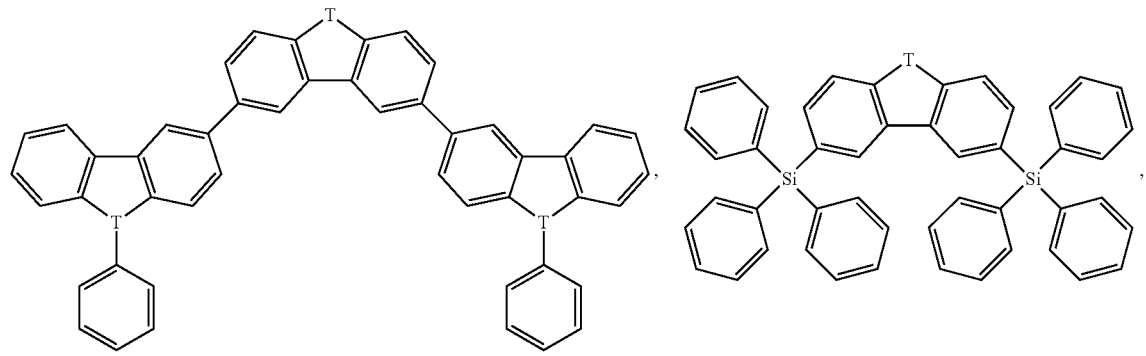
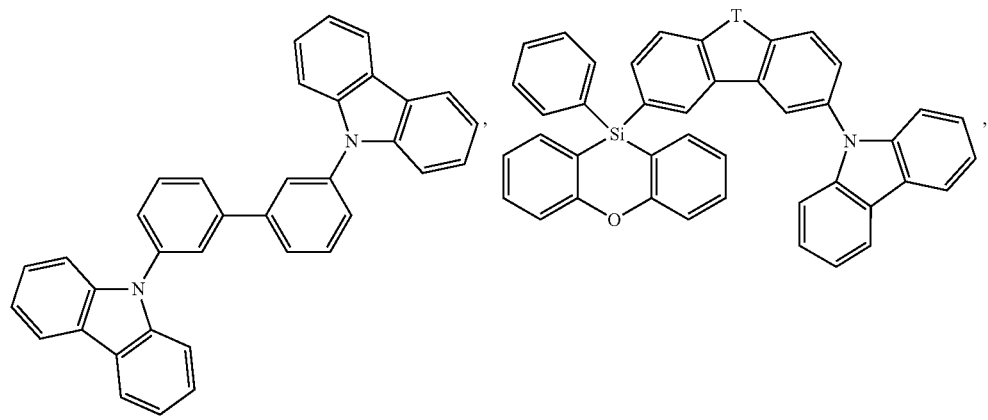

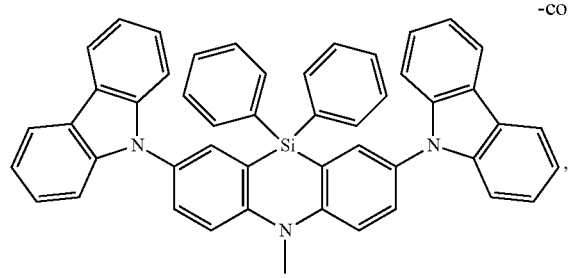
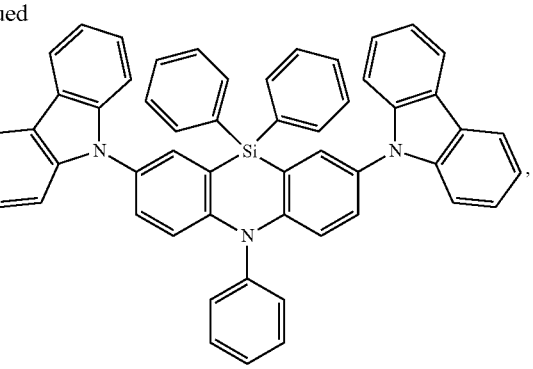
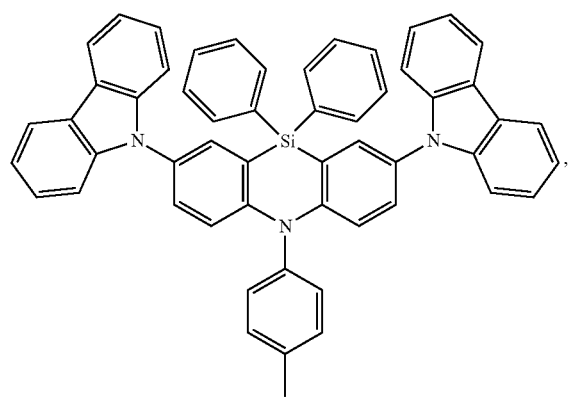
, and
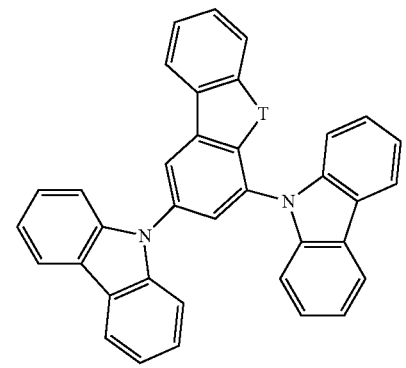
In the above-mentioned compounds T is O, or S, preferably O. If T occurs more than one time in a molecule, all groups T have the same meaning.
The more preferred host compounds are shown below:
(SH-1)
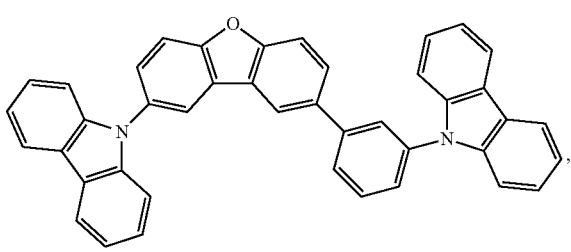
(SH-2)
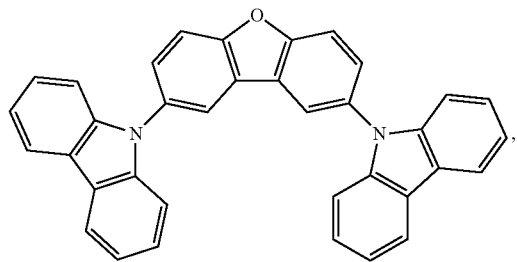
-continued
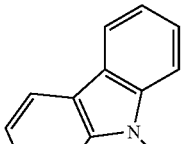
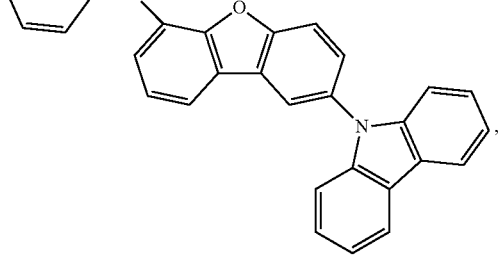
(SH-3), (SH-4), (SH-5), (SH-6)    (SH-7a)
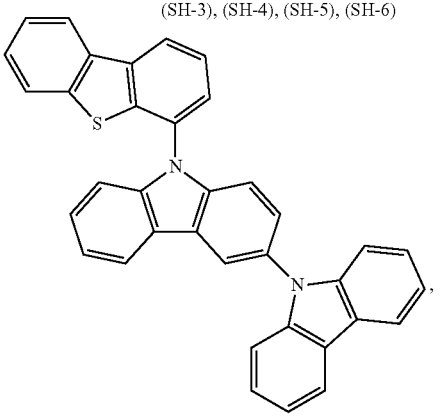

(SH-7b)
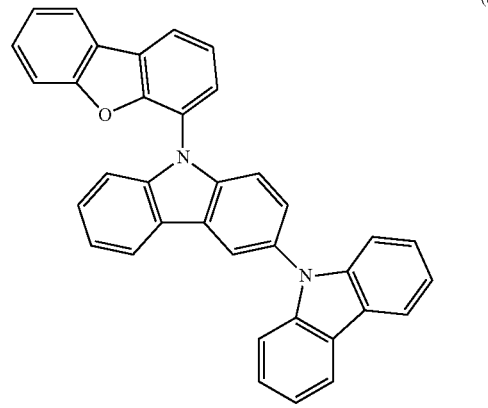
(SH-8a)
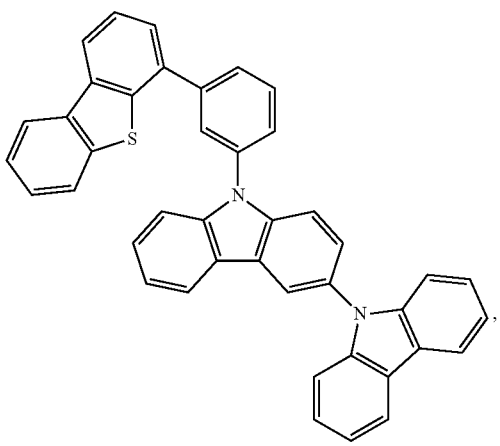
(SH-8b)
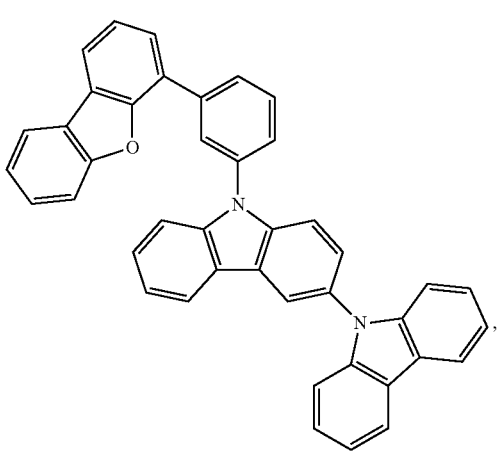
(SH-9)
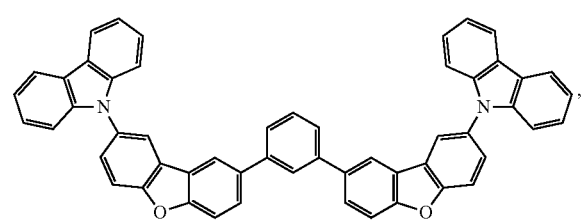
(SH-10)
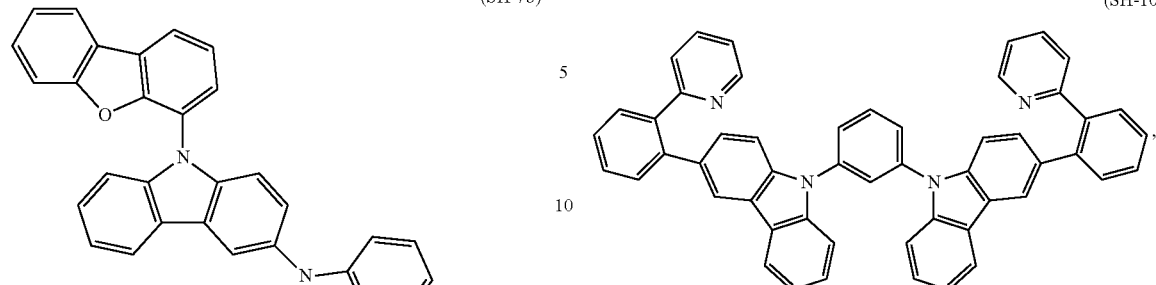
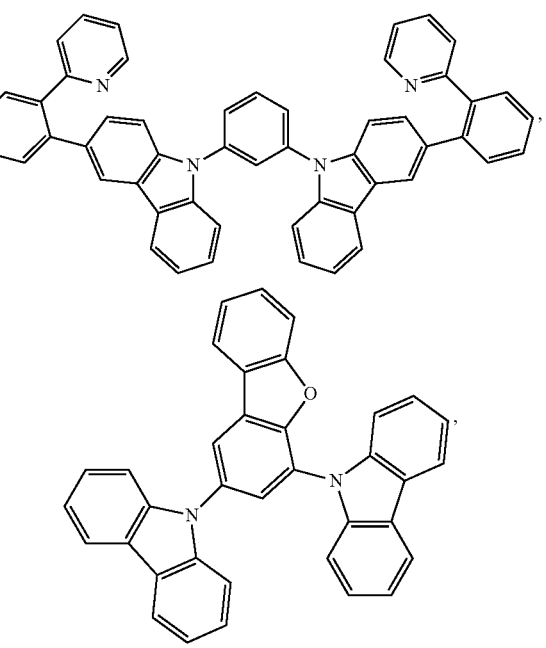
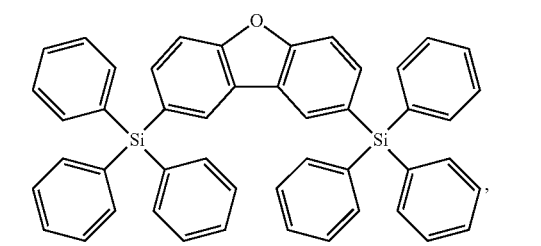
(SH-11)
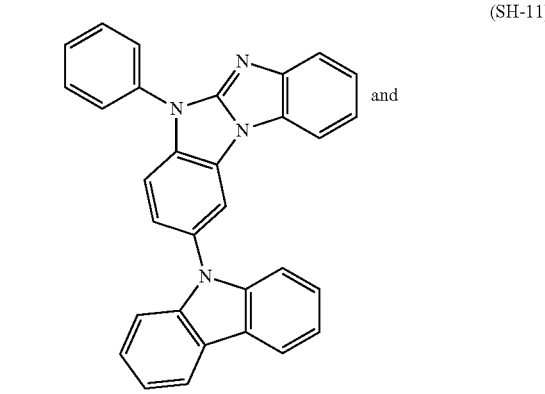
and
(SH-12)
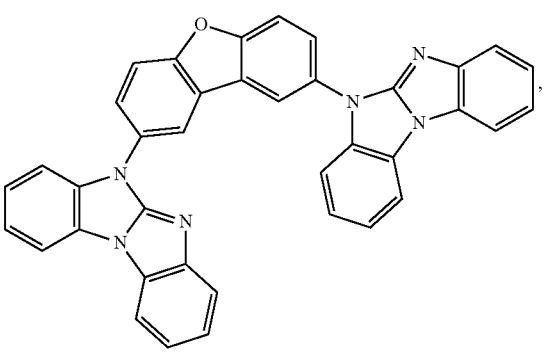

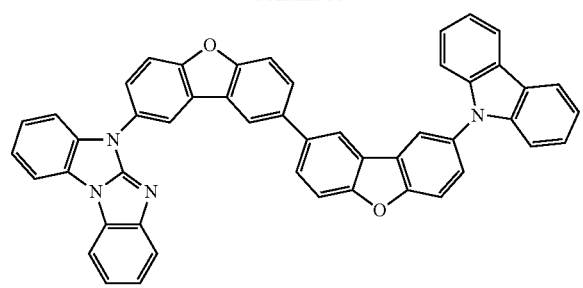
(published in WO2012/130709)
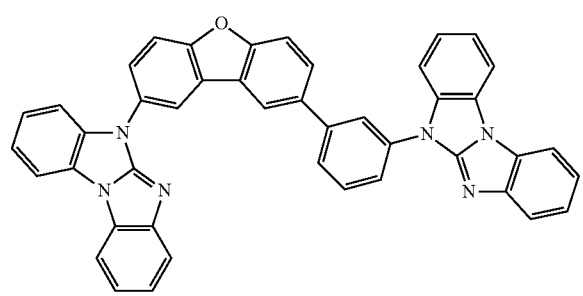 [SMILES: c1cc(-c2ccc3oc4ccc(-n5c6ccccc6n6c7ccccc7nc56)cc4c3c2)cc(-n2c3ccccc3n3c4ccccc4nc23)c1]
(published in WO2012/130709),
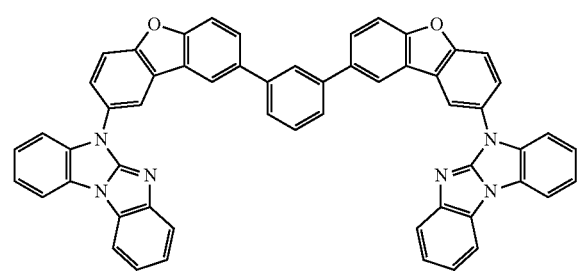 [SMILES: c1cc(-c2ccc3oc4ccc(-n5c6ccccc6n6c7ccccc7nc56)cc4c3c2)cc(-c2ccc3oc4ccc(-n5c6ccccc6n6c7ccccc7nc56)cc4c3c2)c1]
(published in WO2012/130709)
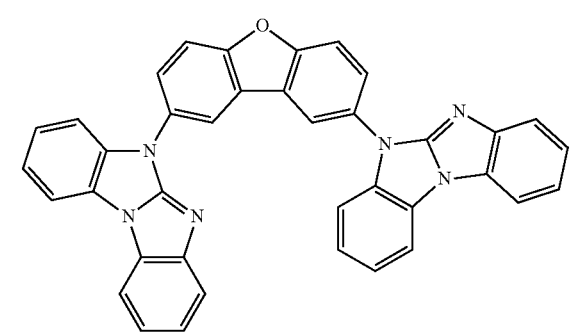 [SMILES: c1ccc2c(c1)nc1n(-c3ccc4oc5ccc(-n6c7ccccc7n7c8ccccc8nc67)cc5c4c3)c3ccccc3n21]
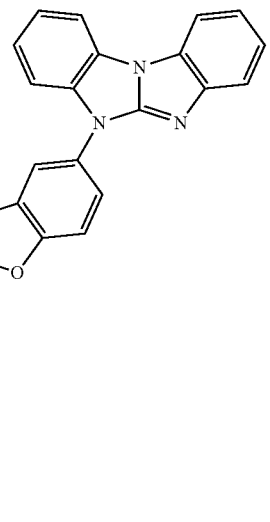
(published in WO2012/130709)
(published in WO2012/130709),
(published in WO2012/130709);
as well as the host materials published in WO2012048266, WO2012145173, WO2012162325, and EP2551932.

The most preferred host compounds are shown below:

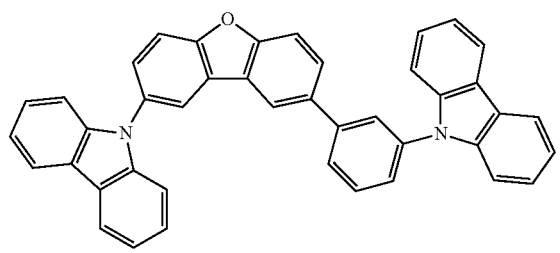 [SMILES: c1cc(-c2ccc3oc4ccc(-n5c6ccccc6c6ccccc65)cc4c3c2)cc(-n2c3ccccc3c3ccccc32)c1]

(SH-1; published in WO 2009/008100, example 4),

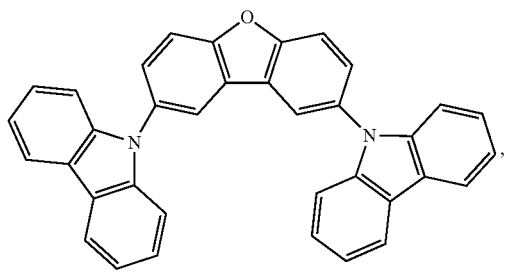

(SH-2)

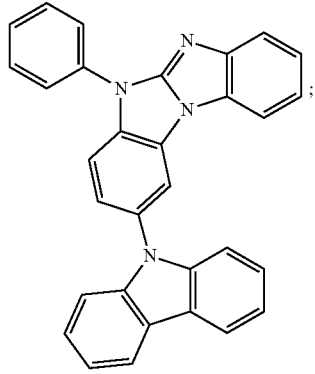

(SH-11)

disclosed in EP12175635.7 and U.S. 61/669,677),

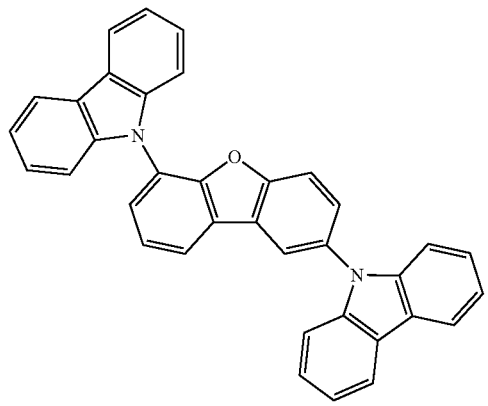 [SMILES: c1cc(-n2c3ccccc3c3ccccc32)c2oc3ccc(-n4c5ccccc5c5ccccc54)cc3c2c1]

(published in WO 2011/004639, compound I-1, synthesis described in [0163]),

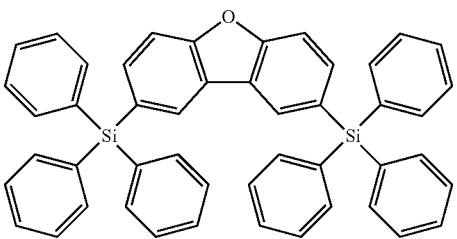 [SMILES: c1ccc([Si](c2ccccc2)(c2ccccc2)c2ccc3oc4ccc([Si](c5ccccc5)(c5ccccc5)c5ccccc5)cc4c3c2)cc1]

(published in WO2009/003898, compound 4g),

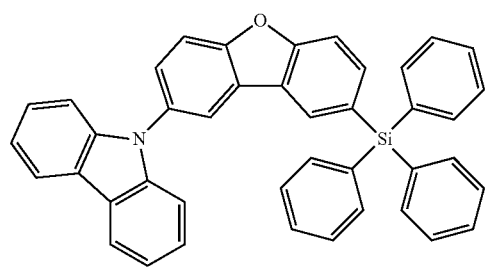 [SMILES: c1ccc([Si](c2ccccc2)(c2ccccc2)c2ccc3oc4ccc(-n5c6ccccc6c6ccccc65)cc4c3c2)cc1]

(SH-4, published in WO 2010/079051, compound 14),

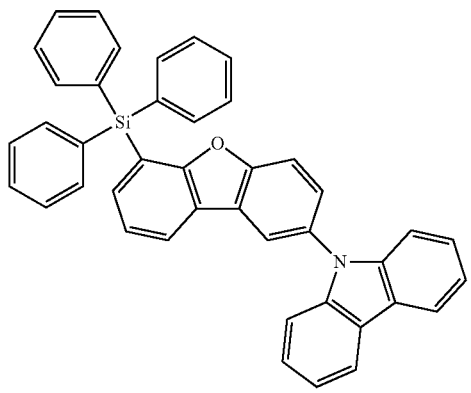 [SMILES: c1ccc([Si](c2ccccc2)(c2ccccc2)c2cccc3c2oc2ccc(-n4c5ccccc5c5ccccc54)cc23)cc1]

(SH-5, published in WO 2010/079051, structure on page 22, X=O)
and

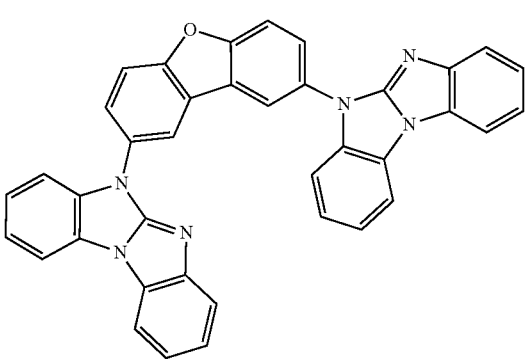 [SMILES: c1ccc2c(c1)nc1n(-c3ccc4oc5ccc(-n6c7ccccc7n7c8ccccc8nc67)cc5c4c3)c3ccccc3n21]

(SH-12; published in WO 2012/130709).

In a preferred embodiment, the light-emitting layer is formed from 2 to 40% by weight, preferably 5 to 35% by weight, of at least one of the inventive metal carbene complexes and 60 to 98% by weight, preferably 65 to 95% by weight, of at least one of the aforementioned matrix materials, where the sum total of the emitter material and of the matrix material adds up to 100% by weight.

In particularly preferred embodiment, the light-emitting layer comprises a matrix material, such as, for example, compound (SH-1), or (SH-2) and two carbene complexes, such as for example, compound (A-17) and

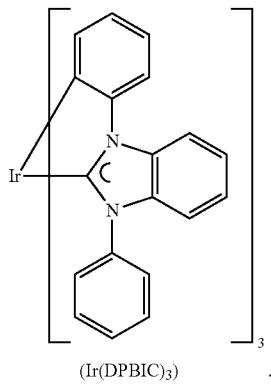

(Ir(DPBIC)₃)

In said embodiment, the light-emitting layer is formed from 2 to 40% by weight, preferably 5 to 35% by weight, of (A-17 and 60 to 98% by weight, preferably 65 to 95% by weight, of SH-1 and Ir(DPBIC)₃, where the sum total of the carben complexes and SH-1 adds up to 100% by weight.

Suitable metal complexes for use as matrix material and/or hole/exciton blocker material and/or electron/exciton blocker material and/or hole injection material and/or electron injection material and/or hole transport material and/or electron transport material, preferably as matrix material and/or hole/exciton blocker material, in OLEDs are thus, for example, also carbene complexes as described in WO 2005/019373 A2, WO 2006/056418 A2, WO 2005/113704, WO 2007/115970, WO 2007/115981 and WO 2008/000727. Explicit reference is made here to the disclosure of the WO applications cited, and these disclosures shall be considered to be incorporated into the content of the present application.

Preferably, the light-emitting layer (e) comprises at least one emitter material and at least one host material. Suitable and preferred emitter materials as well as suitable and preferred host materials are mentioned above.

The individual layers among the aforementioned layers of the OLED may in turn be formed from two or more layers. For example, the hole-transport layer may be formed from one layer, into which holes are injected from the electrode, and a layer which transports the holes away from the hole-injecting layer into the light-emitting layer. The electron-transport layer may likewise consist of a plurality of layers, for example of a layer in which electrons are injected through the electrode and a layer which receives electrons from the electron-injecting layer and transports them into the light-emitting layer. These layers mentioned are each selected according to factors such as energy level, thermal resistance and charge carrier mobility, and also energy difference of the layers mentioned with the organic layers or the metal electrodes. The person skilled in the art is capable of selecting the construction of the OLEDs such that it is matched optimally to the inventive metal-carbene complexes used as emitter substances in accordance with the invention.

In order to obtain particularly efficient OLEDs, the HOMO (highest occupied molecular orbital) of the hole-transport layer should be aligned to the work function of the anode, and the LUMO (lowest unoccupied molecular orbital) of the electron-transport layer should be aligned to the work function of the cathode.

The present application further provides an OLED comprising at least one inventive light-emitting layer. The further layers in the OLED may be formed from any material which is typically used in such layers and is known to those skilled in the art.

Suitable materials for the aforementioned layers (anode, cathode, hole and electron injection materials, hole and electron transport materials and hole and electron blocker materials, matrix materials, fluorescence and phosphorescence emitters) are known to those skilled in the art and are specified, for example, in H. Meng, N. Herron, *Organic Small Molecule Materials for Organic Light-Emitting Devices in Organic Light-Emitting Materials and Devices*, eds: Z. Li, H. Meng, Taylor & Francis, 2007, Chapter 3, pages 295 to 411.

Anode (a)

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

The anode materials mentioned above are commercially available and/or prepared by processes known by a person skilled in the art.

Hole Transport Layer (c)

Suitable hole transport materials for layer (c) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole-transport material. Customarily used hole-transporting molecules are selected from the group consisting of

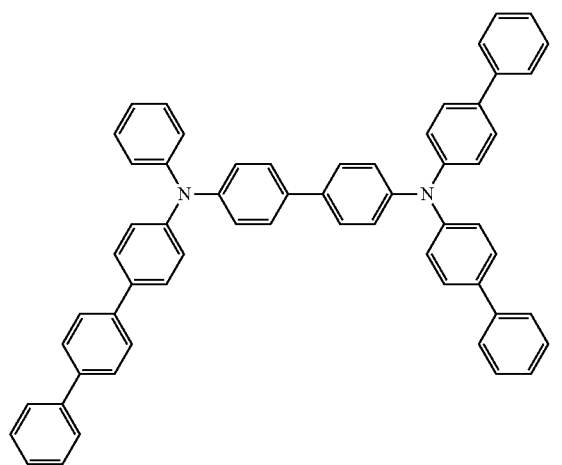 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]

(4-phenyl-N-(4-phenylphenyl)-N-[4-[4-(N-[4-(4-phenyl-phenyl)phenyl]anilino)phenyl]phenyl]aniline),

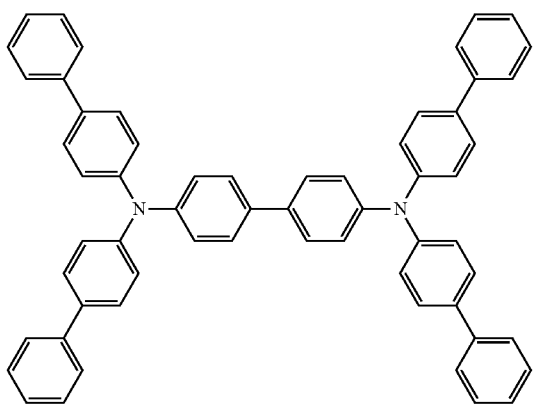 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

(4-phenyl-N-(4-phenylphenyl)-N-[4-[4-(4-phenyl-N-(4-phenylphenyl)anilino)phenyl]phenyl]aniline),

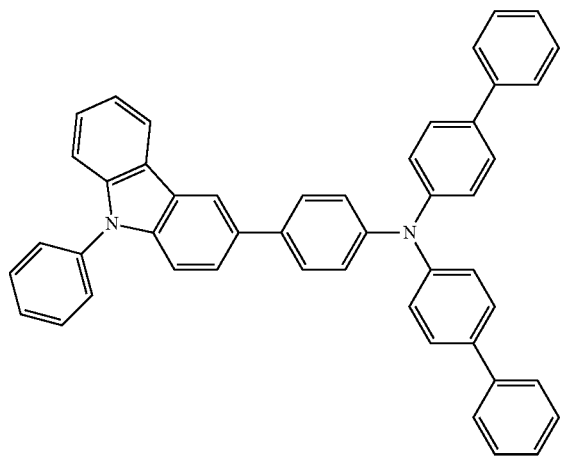 [SMILES: c1ccc(-c2ccc(N(c3ccc(-c4ccccc4)cc3)c3ccc(-c4ccc5c(c4)c4ccccc4n5-c4ccccc4)cc3)cc2)cc1]

(4-phenyl-N-[4-(9-phenylcarbazol-3-yl)phenyl]-N-(4-phenylphenyl)aniline),

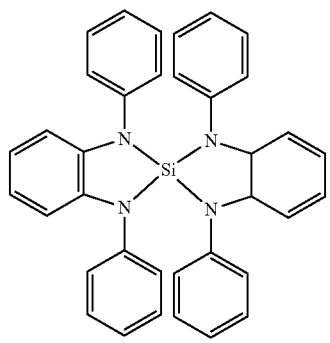 [SMILES: C1=CC2C(C=C1)N(c1ccccc1)[Si]1(N(c3ccccc3)c3ccccc3N1c1ccccc1)N2c1ccccc1]

1,1',3,3'-tetraphenylspiro[1,3,2-benzodiazasilole-2,2'-3a,7a-dihydro-1,3,2-b enzodiazasilole],

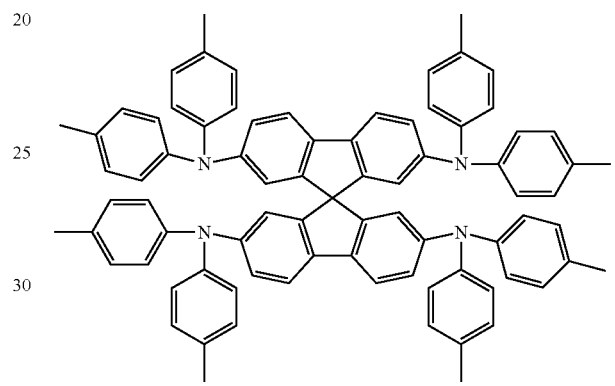

(N2,N2,N2',N2',N7,N7,N7',N7'-octa-kis(p-tolyl)-9,9'-spirobi[fluorene]-2,2',7,7'-tetramine), 4,4'-bis[N-(1-naphthyl)-N-phenyl-amino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)-biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra (N,N-di-tolyl)amino-9,9-spirobifluorene (spiro-TTB), N,N'-bis(naphthalen-1-yl)-N,N'-bis(phenyl)-9,9-spirobifluorene (spiro-NPB) and 9,9-bis(4-(N,N-bis-biphenyl-4-yl-amino)phenyl-9H-fluorene, benzidine compounds such as N,N'-bis(naphthalen-1-yl)-N,N'-bis(phenyl)-benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

In addition—in one embodiment—it is possible to use metal carbene complexes as hole conductor materials, in which case the band gap of the at least one hole conductor material is generally greater than the band gap of the emitter material used. In the context of the present application, band gap is understood to mean the triplet energy. Suitable carbene complexes are, for example, metal carbene complexes as described in WO2005/019373A2, WO2006/056418 A2, WO2005/113704, WO2007/115970, WO2007/115981 and WO2008/000727. One example of a suitable carbene complex is Ir(DPBIC)$_3$ with the formula:

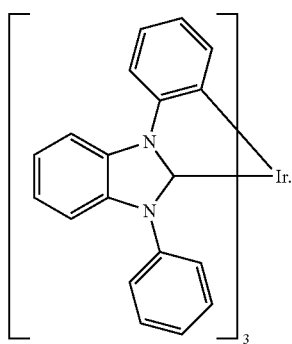

Another example of a suitable carbene complex is Ir(DPABIC)$_3$

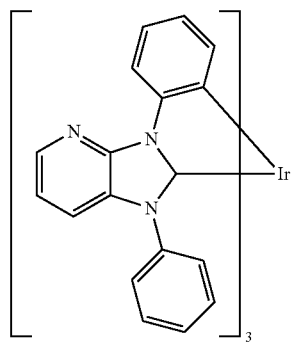

The preparation of Ir(DPABIC)$_3$ is for example mentioned in WO2012/172182 (as complex fac-Em1; synthesis: example 1)). The hole-transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transport layer, in particular mixtures which lead to electrical p-doping of the hole-transport layer. p-Doping is achieved by the addition of oxidizing materials. These mixtures may, for example, be the following mixtures: mixtures of the abovementioned hole transport materials with at least one metal oxide, for example MoO$_2$, MoO$_3$, WO$_N$, ReO$_3$ and/or V$_2$O$_5$, preferably MoO$_3$ and/or ReO$_3$, more preferably ReO$_3$ or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane (F$_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquino-dimethane, 2,5-difluoro-7,7,8,8-etracyanoquinodimethane, dicyanomethylene-1,3,4,5,7,8-hexafluoro-6H-naphthalen-2-ylidene)malononitrile (F$_6$-TNAP), Mo(tfd)$_3$ (from Kahn et al., J. Am. Chem. Soc. 2009, 131 (35), 12530-12531), compounds as described in EP1988587 and in EP2180029 and quinone compounds as mentioned in EP2401254.

Electron-Transport Layer (g)

Electron transport layer may include a material capable of transporting electrons. Electron transport layer may be intrinsic (undoped), or doped. Doping may be used to enhance conductivity. Suitable electron-transport materials for layer (g) of the inventive OLEDs comprise metals chelated with oxinoid compounds, such as tris(8-hydroxyquinolato)aluminum (Alq$_3$), compounds based on phenanthroline such as 2,9-dimethyl-4,7-diphenyl-1,10phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). Layer (g) may serve both to ease the electron transport and as a buffer layer or as a barrier layer in order to prevent quenching of the exciton at the interfaces of the layers of the OLED. Layer (g) preferably improves the mobility of the electrons and reduces quenching of the exciton. The electron-transport materials mentioned above are commercially available and/or prepared by processes known by a person skilled in the art.

It is likewise possible to use mixtures of at least two materials in the electron-transport layer, in which case at least one material is electron-conducting. Preferably, in such mixed electron-transport layers, at least one phenanthroline compound is used, preferably BCP (in combination with Cs$_2$CO$_3$), or at least one pyridine compound according to the formula (VIII) below, preferably a compound of the formula (VIIIaa) below. More preferably, in mixed electron-transport layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula VII). Reference is made to WO2011/157779.

The electron-transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transport layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $Rb_2CO_3$, dipotassium phthalate, $W(hpp)_4$ from EP 1786050, or with compounds as described in EP1837926B1.

In a preferred embodiment, the electron-transport layer comprises at least one compound of the general formula (VII)

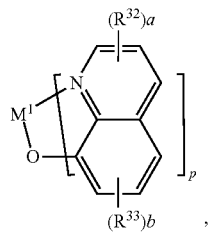

in which $R^{32}$ and $R^{33}$ are each independently F, $C_1$-$C_8$-alkyl, or $C_6$-$C_{14}$-aryl, which is optionally substituted by one or more $C_1$-$C_8$-alkyl groups, or two $R^{32}$ and/or $R^{33}$ substituents together form a fused benzene ring which is optionally substituted by one or more $C_1$-$C_8$-alkyl groups;

a and b are each independently 0, or 1, 2 or 3, $M^1$ is an alkaline metal atom or alkaline earth metal atom, p is 1 when $M^1$ is an alkali metal atom, p is 2 when $M^1$ is an alkali metal atom.

A very particularly preferred compound of the formula (VII) is

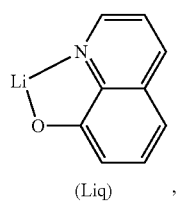

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transport layer comprises at least one compound of the formula (VIII),

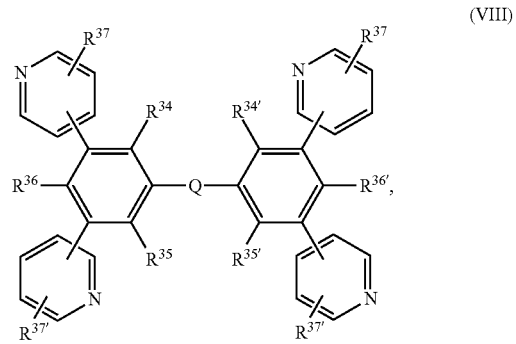

in which $R^{34}$, $R^{35}$, $R^{36}$, $R^{37}$, $R^{34'}$, $R^{35'}$, $R^{36'}$ and $R^{37'}$ are each independently H, $C_1$-$C_{18}$-alkyl, $C_1$-$C_{18}$-alkyl which is substituted by E and/or interrupted by D, $C_6$-$C_{24}$-aryl, $C_6$-$C_{24}$-aryl which is substituted by G, $C_2$-$C_{20}$-heteroaryl or $C_2$-$C_{20}$-heteroaryl which is substituted by G, Q is an arylene or heteroarylene group, each of which is optionally substituted by G;

D is —CO—; —COO—; —S—; —SO—; —SO$_2$—; —O—; —NR$^{40}$—; —SiR$^{45}$R$^{46}$—; —POR$^{47}$—; —CR$^{38}$=CR$^{39}$—; or —C≡C—;

E is —OR$^{44}$; —SR$^{44}$; —NR$^{40}$R$^{41}$; —COR$^{43}$; —COOR$^{42}$; —CONR$^{40}$R$^{41}$; —CN; or F;

G is E, $C_1$-$C_{18}$-alkyl, $C_1$-$C_{18}$-alkyl which is interrupted by D, $C_1$-$C_{18}$-perfluoroalkyl, $C_1$-$C_{18}$-alkoxy, or $C_1$-$C_{18}$-alkoxy which is substituted by E and/or interrupted by D, in which $R^{38}$ and $R^{39}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;

$R^{40}$ and $R^{41}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or $R^{40}$ and $R^{41}$ together form a 6-membered ring;

$R^{42}$ and $R^{43}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{44}$ is $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{45}$ and $R^{46}$ are each independently $C_1$-$C_{18}$-alkyl, $C_6$-$C_{18}$-aryl or $C_6$-$C_{18}$-aryl which is substituted by $C_1$-$C_{18}$-alkyl, $R^{47}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (VIII) are compounds of the formula (VIIIa)

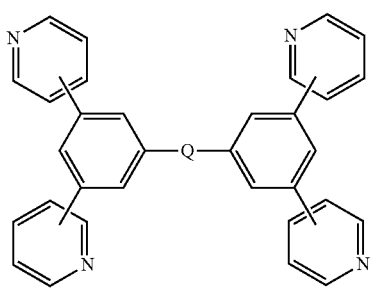

(VIIIa)

in which Q is:

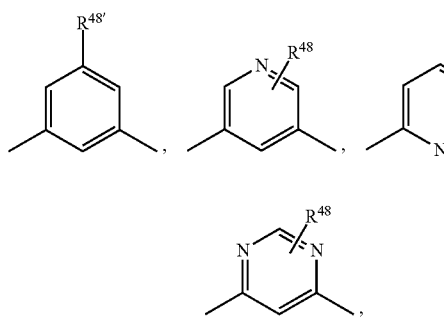

$R^{48}$ is H or $C_1$-$C_{18}$-alkyl and

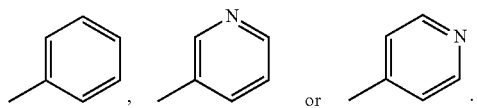

$R^{48'}$ is H, $C_1$-$C_{18}$-alkyl or

Particular preference is given to a compound of the formula (VIIIaa)

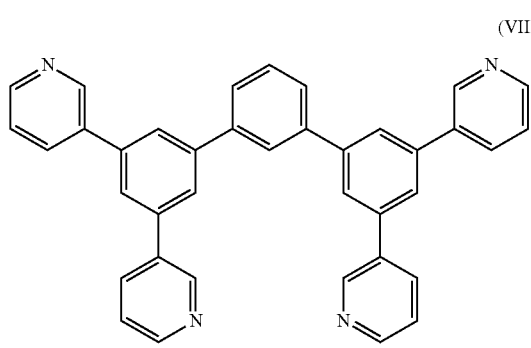

(VIIIaa)

In a further, very particularly preferred embodiment, the electron-transport layer comprises a compound of the formula

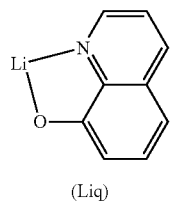

(Liq)

and a compound of the formula

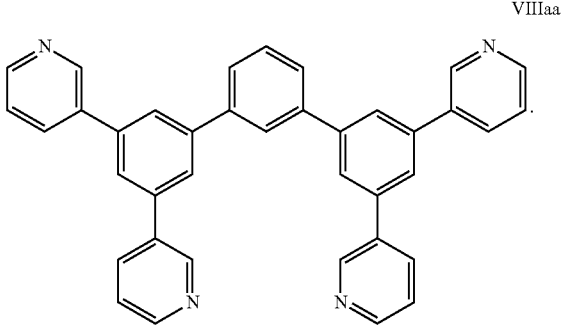

VIIIaa (ETM-1)

In a preferred embodiment, the electron-transport layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008-127326, or the compounds can be prepared analogously to the processes disclosed in the aforementioned documents.

It is likewise possible to use mixtures of alkali metal hydroxyquinolate complexes, preferably Liq, and dibenzofuran compounds in the electron-transport layer. Reference is made to WO2011/157790. Dibenzofuran compounds A-1 to A-36 and B-1 to B-22 described in WO2011/157790 are preferred, wherein dibenzofuran compound

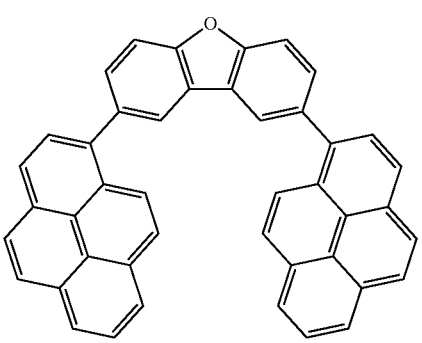

(A-10; = ETM-2)

is most preferred.

In a preferred embodiment, the electron-transport layer comprises Liq in an amount of 99 to 1% by weight, preferably 75 to 25% by weight, more preferably about 50% by weight, where the amount of Liq and the amount of the dibenzofuran compound(s), especially compound A-10, adds up to a total of 100% by weight.

In a preferred embodiment, the invention relates to an inventive OLED wherein the electron-transport layer comprises at least one phenanthroline derivative and/or pyridine derivative.

In a further preferred embodiment, the invention relates to an inventive OLED wherein the electron-transport layer comprises at least one phenanthroline derivative and/or pyridine derivative and at least one alkali metal hydroxyquinolate complex.

In a further preferred embodiment, the invention relates to an inventive OLED wherein the electron-transport layer comprises at least one phenanthroline derivative and/or pyridine derivative and 8-hydroxyquinolatolithium.

In a further preferred embodiment, the electron transport layer comprises at least one of the dibenzofuran compounds A-1 to A-36 and B-1 to B-22 described in WO2011/157790, especially A-10.

In a further preferred embodiment, the electron transport layer comprises a compound described in WO 2012/111462, WO 2012/147397 and US 2012/0261654, such as, for example, a compound of formula

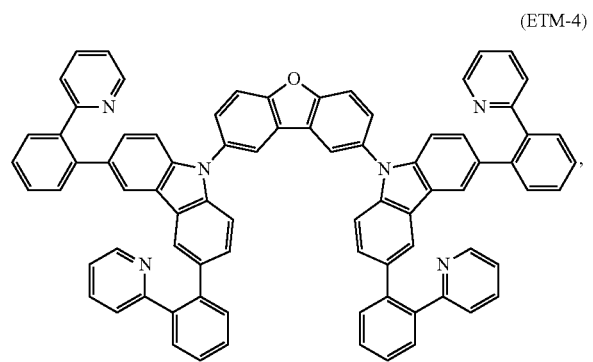 [SMILES: c1ccc(-c2ccccc2-c2ccc3c(c2)c2cc(-c4ccccc4-c4ccccn4)ccc2n3-c2ccc3oc4ccc(-n5c6ccc(-c7ccccc7-c7ccccn7)cc6c6cc(-c7ccccc7-c7ccccn7)ccc65)cc4c3c2)nc1]

(ETM-4)

WO 2012/115034, such as for example, such as, for example, a compound of formula

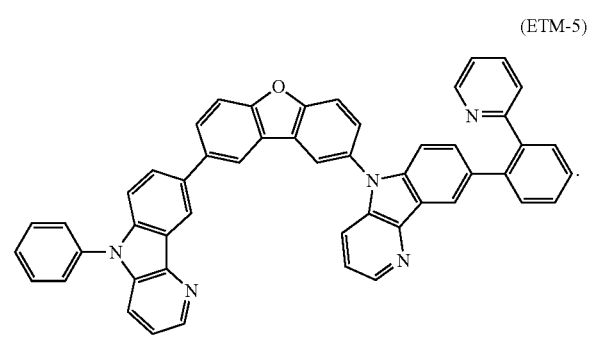 [SMILES: c1ccc(-n2c3ccc(-c4ccc5oc6ccc(-n7c8ccc(-c9ccccc9-c9ccccn9)cc8c8ncccc87)cc6c5c4)cc3c3ncccc32)cc1]

(ETM-5)

Some of the materials mentioned above as hole transport materials and electron-transport materials can fulfill several functions. For example, some of the electron-transport materials are simultaneously hole-blocking materials if they have a low-lying HOMO.

Cathode (i)

The cathode (i) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. The cathode materials mentioned above are commercially available and/or prepared by processes known by a person skilled in the art.

Hole Injection Layer (b)

Generally, injection layers are comprised of a material that may improve the injection of charge carriers from one layer, such as an electrode or a charge generating layer, into an adjacent organic layer. Injection layers may also perform a charge transport function. The hole injection layer (b) may be any layer that improves the injection of holes from anode into an adjacent organic layer. A hole injection layer may comprise a solution deposited material, such as a spin-coated polymer, or it may be a vapor deposited small molecule material, such as, for example, CuPc or MTDATA. Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

The hole injection materials mentioned above are commercially available and/or prepared by processes known by a person skilled in the art.

Electron Injection Layer (h)

The electron injection layer (h) may be any layer that improves the injection of electrons into an adjacent organic layer. Lithium-comprising organometallic compounds such as 8-hydroxyquinolatolithium (Liq), CsF, NaF, KF, $Cs_2CO_3$ or LiF may be applied between the electron transport layer (g) and the cathode (i) as an electron injection layer in order to reduce the operating voltage.

The electron injection materials mentioned above are commercially available and/or prepared by processes known by a person skilled in the art.

Those skilled in the art know how suitable materials have to be selected (for example on the basis of electrochemical investigations). Suitable materials for the individual layers are known to those skilled in the art and disclosed, for example, in WO00/70655.

In addition, it is possible that some or all of the layers (b) to (h) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass, inorganic materials such as ITO or IZO or polymer films. For the vapor deposition, customary techniques may be used, such as thermal evaporation, chemical vapor deposition (CVD), physical vapor deposition (PVD) and others.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform. In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof.

It is possible that the layers of the OLED are all produced by the same coating method. Furthermore, it is likewise possible to conduct two or more different coating methods to produce the layers of the OLED.

In general, the different layers in the inventive OLED, if present, have the following thicknesses:

anode (a): 50 to 500 nm, preferably 100 to 200 nm;
hole injection layer (b): 5 to 100 nm, preferably 20 to 80 nm;
hole-transport layer (c): 5 to 100 nm, preferably 10 to 80 nm;
electron/exciton blocking layer (d): 1 to 50 nm, preferably 5 to 10 nm,
light-emitting layer (e): 1 to 100 nm, preferably 5 to 60 nm;
hole/exciton blocking layer (f): 1 to 50 nm, preferably 5 to 10 nm,
electron-transport layer (g): 5 to 100 nm, preferably 20 to 80 nm;
electron injection layer (h): 1 to 50 nm, preferably 2 to 10 nm;
cathode (i): 20 to 1000 nm, preferably 30 to 500 nm.

In addition to the compounds of the formula (X), according to the present invention, it is also possible to use crosslinked or polymeric materials comprising repeat units based on the general formula (X) in crosslinked or polymerized form together with at least one inventive metal-carbene complex. Like the compounds of the general formula (X), the latter are preferably used as matrix materials.

The crosslinked or polymeric materials have outstanding solubility in organic solvents, excellent film-forming properties and relatively high glass transition temperatures. In addition, high charge carrier mobilities, high stabilities of color emission and long operating times of the corresponding components can be observed when crosslinked or polymeric materials according to the present invention are used in organic light-emitting diodes (OLEDs).

The crosslinked or polymerized materials are particularly suitable as coatings or in thin films since they are thermally and mechanically stable and relatively defect-free.

The crosslinked or polymerized materials comprising repeating units based on the general formula (X) can be prepared by a process comprising steps (a) and (b):

(a) preparation of a crosslinkable or polymerizable compound of the general formula (X) where at least one of the m1 $R^{204}$ radicals or at least one of the n2 $R^{205}$ radicals is a crosslinkable or polymerizable group attached via a spacer, and (b) crosslinking or polymerization of the compound of the general formula (X) obtained from step (a).

The crosslinked or polymerized materials may be homopolymers, which means that exclusively units of the general formula (X) are present in crosslinked or polymerized form. They may also be copolymers, which means that further monomers are present in addition to the units of the general formula (X), for example monomers with hole-conducting and/or electron-conducting properties, in crosslinked or polymerized form.

In a further preferred embodiment of the inventive OLED, it comprises an emission layer comprising at least one inventive metal-carbene complex, at least one matrix material of the formula (X), and optionally at least one further hole-transport matrix material.

The inventive OLEDs can be used in all devices in which electroluminescence is useful. Suitable devices are preferably selected from stationary and mobile visual display units and illumination means. The present invention therefore also relates to a device selected from the group consisting of stationary visual display units and mobile visual display units and illumination means, comprising an inventive OLED.

Stationary visual display units are, for example, visual display units of computers, televisions, visual display units in printers, kitchen appliances and advertising panels, illuminations and information panels. Mobile visual display units are, for example, visual display units in cellphones, laptops, tablet PCs, digital cameras, mp-3 players, smartphones, vehicles, and destination displays on buses and trains.

The inventive metal-carbene complexes can additionally be used in OLEDs with inverse structure. In these inverse OLEDs, the inventive complexes are in turn preferably used in the light-emitting layer. The structure of inverse OLEDs and the materials typically used therein are known to those skilled in the art.

The present invention further provides a white OLED comprising at least one inventive metal-carbene complex. In a preferred embodiment, the inventive metal-carbene complexes are used as emitter material in the white OLED. Preferred embodiments of the inventive metal-carbene complexes have been specified above. In addition to the at least one inventive metal-carbene complex, the white OLED may comprise (i) at least one compound of the formula (X). The compound of the formula (X) is preferably used as matrix material. Preferred compounds of the formula (X) have been specified above; and/or (ii) at least one compound of the formula (VII) and/or (IX). The compounds of the formula (VII) and/or (IX) are preferably used as electron transport material. Preferred compounds of the formulae (VII) and (IX) have been specified above.

In order to obtain white light, the OLED must generate light which colors the entire visible range of the spectrum.

However, organic emitters normally emit only in a limited portion of the visible spectrum—i.e. are colored. White light can be generated by the combination of different emitters. Typically, red, green and blue emitters are combined. However, the prior art also discloses other methods for formation of white OLEDs, for example the triplet harvesting approach. Suitable structures for white OLEDs or methods for formation of white OLEDs are known to those skilled in the art.

In one embodiment of a white OLED, several dyes are layered one on top of another in the light-emitting layer of an OLED and hence combined (layered device). This can be achieved by mixing all dyes or by direct series connection of different-colored layers. The expression "layered OLED" and suitable embodiments are known to those skilled in the art.

In a further embodiment of a white OLED, several different-colored OLEDs are stacked one on top of another (stacked device). For the stacking of two OLEDs, what is called a charge generation layer (CG layer) is used. This CG layer may be formed, for example, from one electrically n-doped and one electrically p-doped transport layer. The expression "stacked OLED" and suitable embodiments are known to those skilled in the art.

In further embodiments of this "stacked device concept", it is also possible to stack only two OLEDs or to stack more than three OLEDs.

In a further embodiment of white OLEDs, the two concepts mentioned for white light generation can also be combined. For example, a single-color OLED (for example blue) can be stacked with a multicolor layered OLED (for example red-green). Further combinations of the two concepts are conceivable and known to those skilled in the art.

The inventive metal-carbene complexes can be used in any of the layers mentioned above in white OLEDs. In a preferred embodiment, it is used in one or more or all light-emitting layer(s) of the OLED(s), in which case the structure of the invention metal-carbene complex is varied as a function of the use of the complex. Suitable and preferred components for the further layers of the light OLED(s) or materials suitable as matrix material in the light-emitting layer(s) and preferred matrix materials are likewise specified above.

The present invention also relates to an organic electronic device, preferably an organic light-emitting diode (OLED), organic photovoltaic cell (OPV), organic field-effect transistor (OFET) or light-emitting electrochemical cell (LEEC), comprising at least one inventive metal-carbene complex.

The examples which follow, more particularly the methods, materials, conditions, process parameters, apparatus and the like detailed in the examples, are intended to support the present invention, but not to restrict the scope of the present invention.

EXAMPLES

A variety of representations are used to depict the bonding in metal-carbenes, including those in which a curved line is used to indicate partial multiple bonding between the carbene carbon and the adjacent heteroatom(s):

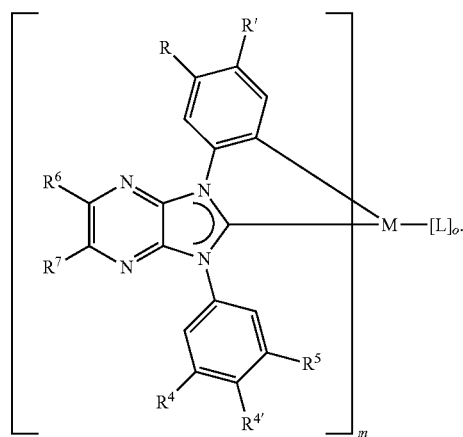

In the figures and structures herein, a metal-carbene bond is depicted as C-M, as, for example,

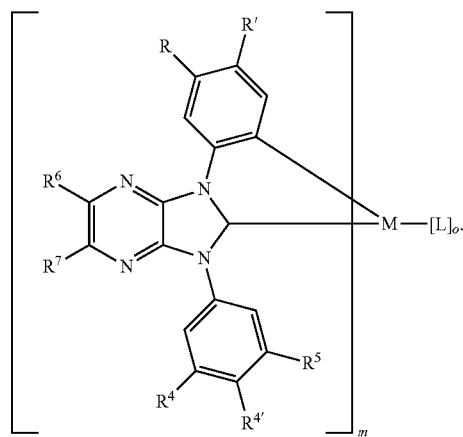

All experiments are carried out in protective gas atmosphere. The percentages and ratios mentioned in the examples below—unless stated otherwise—are % by weight and weight ratios.

I. Synthesis Examples

Synthesis Example 1

Synthesis of Complex (A-1)

a) Synthesis of 1,3-dimethyl-2-(3-nitrophenyl)benzene

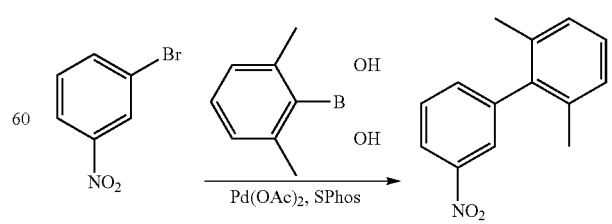

40.8 g (0.20 mol) of 1-bromo-3-nitrobenzene together with 34.0 g (0.22 mol) of 2,6-dimethylphenylboronic acid, 230 g (1.00 mol) of potassium phosphate tribasic monohydrate, 1.23 g (3.0 mmol)) of 2-dicyclohexylphosphino-2',6'-dimethoxybiphenyl, and 0.22 g (1.0 mmol) of palladium(II) acetate are suspended in 300 ml of toluene at room temperature under argon. The suspension is three times evacuated and backfilled with argon, followed by heating under reflux for three hours. The beige suspension is filtered through a layer of Hyflo® filter aid and the filter aid rinsed with 200 ml of toluene. The filtrate is three times washed with 200 ml of water, the combined organic phases dried over sodium sulfate, concentrated under vacuum, and further purified by chromatography (silica gel, heptane), giving the title product as a light yellow oil (yield: 36.5 g (80%)).

$^1$H-NMR (400 MHz, CDCl$_3$): □=2.06 (s, 6 H), 7.17 (d, 2 H), 7.22-7.30 (m, 1 H), 7.51-7.58 (m, 1 H), 7.62-7.69 (m, 1 H), 8.07-8.12 (m, 1 H), 8.23-8.29 (m, 1 H).

b) Synthesis of 3-(2,6-dimethylphenyl)aniline

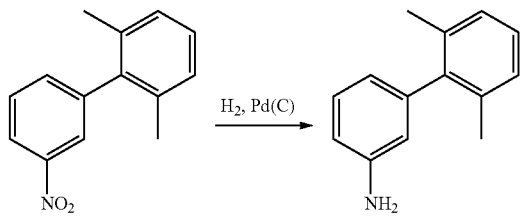 [SMILES: Cc1cccc(C)c1-c1cccc([N+](=O)[O-])c1 ; Cc1cccc(C)c1-c1cccc(N)c1]

30.0 g (0.132 mol) of 1,3-dimethyl-2-(3-nitrophenyl)benzene and 3.0 g of 5 wt %-palladium on carbon are reacted under 3 bar hydrogen pressure at 35° C. during 21 hours. The reaction mixture is filtered through a layer of Hyflo® filter aid and rinsed with additional ethanol, followed by concentration under vacuum. The yellow oil is further purified by chromatography (silica gel, heptane/ethyl acetate 9:1) giving the title product as a light yellow solid (yield: 19.3 g (74%)).

$^1$H-NMR (400 MHz, CD$_2$Cl$_2$): δ=2.09 (s, 6 H), 2.86-4.20 (br. s, 2 H), 6.47-6.57 (m, 2 H), 6.67-6.73 (m, 1 H), 7.08-7.20 (m, 3 H), 7.21-7.27 (m, 1 H).

c) Synthesis of 3-chloro-N-phenyl-pyrazin-2-amine

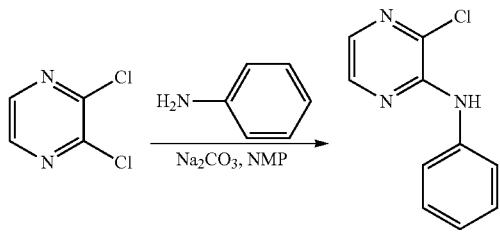

59.6 g (0.40 mol) of 2,3-dichloropyrazine, 37.3 g (0.40 mol) of aniline, and 42.4 g (0.40 mol) of sodium carbonate are suspended in 250 ml of 1-methyl-pyrrolidone and heated at 151° C. during 24 hours. The black suspension is cooled down to 100° C., filtered, and the solid residue further washed with ethyl acetate. The filtrate is concentrated under vacuum and the residual oil further purified by distillation (125-128° C., 0.3 mbar) giving the title product as light yellow solid (yield: 58.3 g (71%)).

$^1$H-NMR (300 MHz, CDCl$_3$): δ=7.05-7.22 (m, 2 H), 7.32-7.45 (m, 2 H), 7.57-7.68 (m, 2 H), 7.75 (d, 1 H), 8.05 (d, H).

d) Synthesis of N3-[3-(2,6-dimethylphenyl)phenyl]-N2-phenyl-pyrazine-2,3-diamine

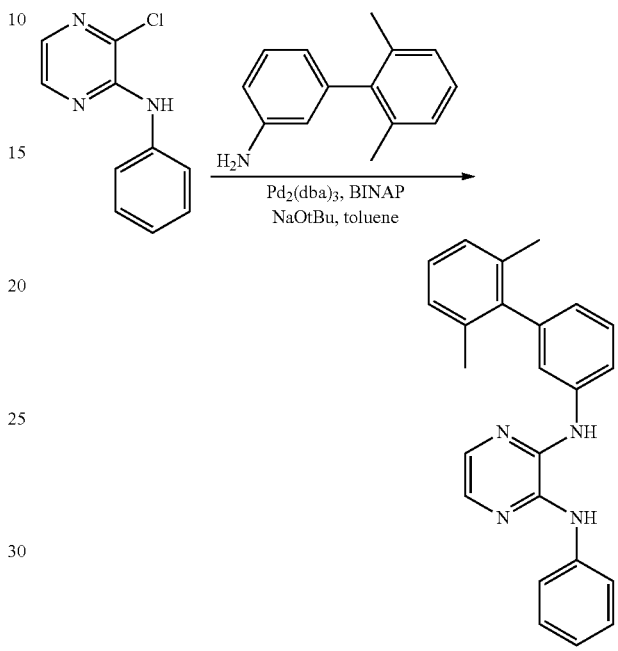

9.38 g (45.6 mmol) of 3-chloro-N-phenyl-pyrazin-2-amine, and 9.00 g (45.6 mmol) of 3-(2,6-dimethylphenyl)aniline, and 0.21 g (0.23 mmol) of tris(dibenzylideneacetone)dipalladium(0), and 0.43 g (0.69 mmol) of 2,2'-bis(diphenylphosphino)-1,1'-binaphthalene, and 6.14 g (63.9 mmol) of sodium tert-butoxide are suspended in 100 ml of toluene at room temperature under argon. The red-brown suspension is three times evacuated and backfilled with argon, followed by heating under reflux for 49 hours. An additional 0.21 g (0.23 mmol) of tris(dibenzylideneacetone)dipalladium(0), and 0.43 g (0.69 mmol) 2,2'-bis(diphenylphosphino)-1,1'-binaphthalene are added and heating continued for 23 hours. An additional 0.11 g (0.12 mmol) of tris(dibenzylideneacetone)dipalladium(0), and 0.22 g (0.35 mmol) 2,2'-bis(diphenylphosphino)-1,1'-binaphthalene are added and heating continued for 6 hours giving a beige suspension. The reaction mixture is cooled down to room temperature and 200 ml of hexane are added followed by filtration. The solid residue is further washed with hexane and taken up in 200 ml of water followed by filtration and washing with plenty of water. The solid is taken up in 300 ml of 5%-ammonia solution, stirred during 30 minutes, followed by filtration and washing with 200 ml of water. The brown solid is dissolved in 300 ml ethyl acetate and filtered through a 4 cm layer of silica gel followed by rinsing the silica gel layer with ethyl acetate. The combined ethyl acetate fractions are concentrated under vacuum and the resulting brown viscous oil dissolved in dichloromethane followed by filtration through a 4 cm layer of silica gel and additional rinsing of the silica gel layer with dichloromethane. The combined eluents are concentrated under vacuum giving the title product as beige solid (yield: 8.9 g (53%)).

$^1$H-NMR (400 MHz, d$_6$-DMSO): δ=2.05 (s, 6 H), 6.73-6.78 (m, 1 H), 6.96-7.02 (m, 1 H), 7.09-7.20 (m, 3 H), 7.29-7.35 (m, 2 H), 7.41 (t, 1 H), 7.45-7.48 (m, 1 H), 7.56-7.60 (m, 2 H), 7.63-7.72 (m, 3 H), 8.53 (br. s, 1 H), 8.58 (br. s, 1 H).

e) Synthesis of (3-anilinopyrazin-2-yl)-[3-(2,6-dimethylphenyl)phenyl]ammonium chloride

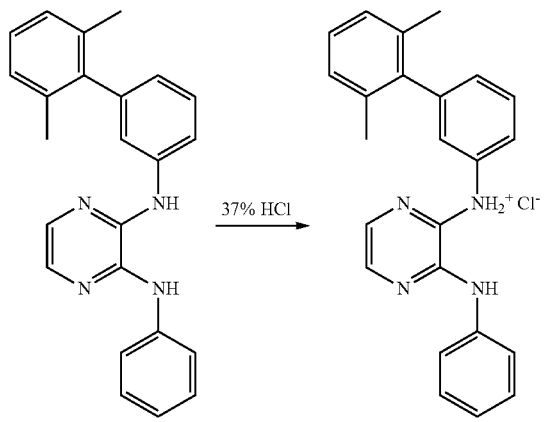

A beige suspension of 5.0 g (13.6 mmol) of N3-[3-(2,6-dimethylphenyl)phenyl]-N2-phenyl-pyrazine-2,3-diamine and 100 ml of 37% hydrochloric acid is stirred at room temperature during 21 hours. The suspension is filtered and further washed with 37% hydrochloric acid and plenty of hexane, followed by drying in a vacuum oven, giving the title product as a beige solid (yield: 5.4 g (99%)).

$^1$H-NMR (400 MHz, d$_6$-DMSO): δ=2.04 (s, 6 H), 6.87 (d, 1 H), 7.09-7.20 (m, 4 H), 7.37-7.49 (m, 4 H), 7.52 (d, 1 H), 7.61-7.65 (m, 1 H), 7.73 (d, 2 H), 7.84-7.90 (m, 1 H), 10.37 (br. s, 1 H), 10.59 (br. s, 1 H).

f) Synthesis of 3-[3-(2,6-dimethylphenyl)phenyl]-2-ethoxy-1-phenyl-2H-imidazo[4,5-b]-pyrazine

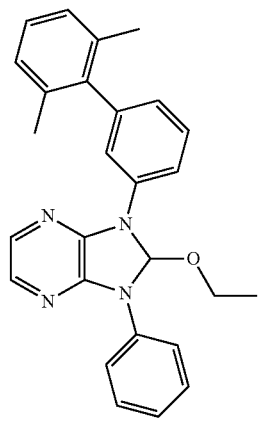

5.0 g (12.4 mmol) of (3-anilinopyrazin-2-yl)-[3-(2,6-dimethylphenyl)phenyl]ammonium chloride and 90 g (0.61 mol) of triethyl orthoformate are heated up under argon at 100° C. during one hour. The light brown solution is filtered through a layer of Hyflo® filter aid and the filter aid rinsed with 10 ml of triethyl orthoformate. The filtrate is concentrated under vacuum giving the title product as off-white solid (yield: 5.1 g (97%)).

$^1$H-NMR (400 MHz, d$_6$-DMSO): δ=0.89 (t, 3 H), 2.04 (s, 6 H), 3.20 (q, 2 H), 6.96 (d, 1 H), 7.12-7.23 (m, 4 H), 7.42-7.49 (m, 2 H), 7.50-7.60 (m, 3 H), 7.76-7.79 (m, 1 H), 7.87 (s, 1 H), 8.03-8.08 (m, 2 H), 8.18-8.24 (m, 1 H).

g) Synthesis of Complex (A-1)

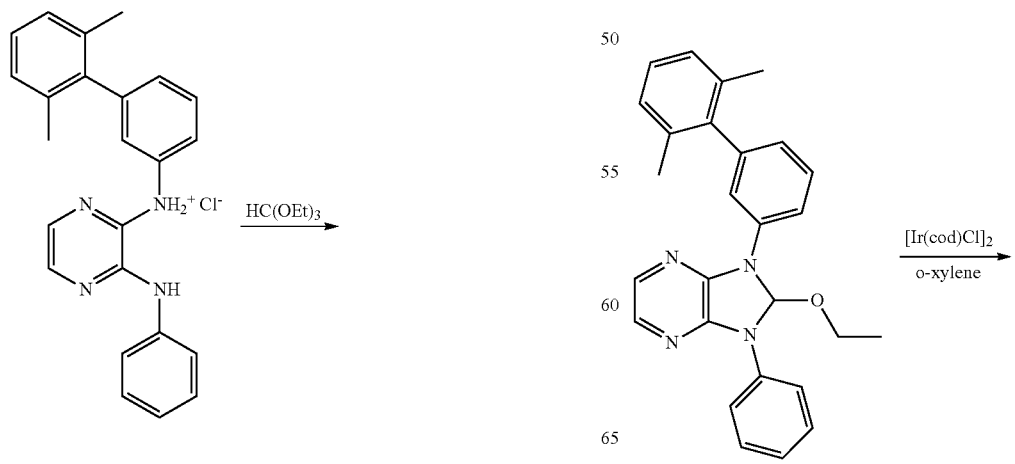

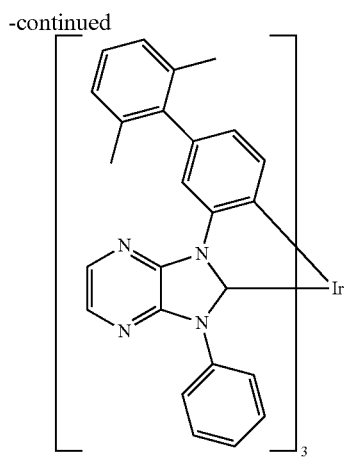

3.2 g (7.6 mmol) of 3-[3-(2,6-dimethylphenyl)phenyl]-2-ethoxy-1-phenyl-2H-imidazo[4,5-b]-pyrazine and 0.62 g (0.92 mmol) of chloro(1,5-cyclooctadiene)iridium(I) dimer are suspended under argon in 30 ml of o-xylene. The suspension is four times evacuated and backfilled with argon, followed by heating at 135° C. during 19 hours. The dark brown solution is cooled down to room temperature, diluted with 50 ml of dichloromethane and filtered through a 3 cm layer of silica gel followed by rinsing the silica gel layer with 200 ml of dichloromethane. The filtrate is concentrated and further suspended in 75 ml of hot ethanol providing precipitation of some solid. The filtrate is several times re-concentrated and treated by ethanol and hexane to provide further precipitation, giving a fraction of 0.51 g product mixture. The yellow powder is further purified by chromatography (silica gel, hexane/ethyl acetate) giving the title product as yellow solid (yield: 89.7 mg (4%)). APCI-LC-MS (positive, m/z): exact mass of $C_{75}H_{57}IrN_{12}$=1318.44. found 1319.6 [M+1]$^+$.

Synthesis Example 2

Synthesis of Complex (A-15)

a) Synthesis of
3-chloro-N-(3,5-dimethylphenyl)pyrazin-2-amine

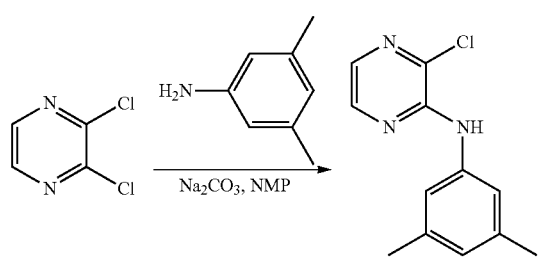

74.5 g (0.50 mol) of 2,3-dichloropyrazine, 60.6 g (0.50 mol) of 3,5-dimethylaniline and 53.0 g (0.50 mol) of sodium carbonate are suspended in 250 ml of 1-methyl-pyrrolidone and heated at 151° C. during 48 hours. The brown suspension is cooled down to room temperature, poured into 2 l of water, stirred during 30 minutes and filtered. The solid residue is washed with 2 l of water and dried under vacuum at 50° C. The solid is dissolved in 600 ml of ethyl acetate and filtered through a 7 cm layer of silica gel followed by rinsing the silica gel with plenty of ethyl acetate. The filtrate is concentrated under vacuum and dissolved in 500 ml of hot ethanol giving a brown solution. The solution is cooled down to ice-bath temperature and stirred at the same temperature during one hour. The resulting precipitate is further washed with ethanol and dried under vacuum at 50° C., giving the title product as a beige solid (yield: 47.9 g (41%)).

$^1$H-NMR (400 MHz, $d_6$-DMSO): δ=2.26 (s, 6 H), 6.73 (s, 1 H), 7.29 (s, 2 H), 7.79 (d, 1 H), 8.13 (d, 1 H), 8.59 (s, 1 H).

b) Synthesis of N3-(3,5-dimethylphenyl)-N2-[3-(2,6-dimethylphenyl)phenyl]-pyrazine-2,3-diamine

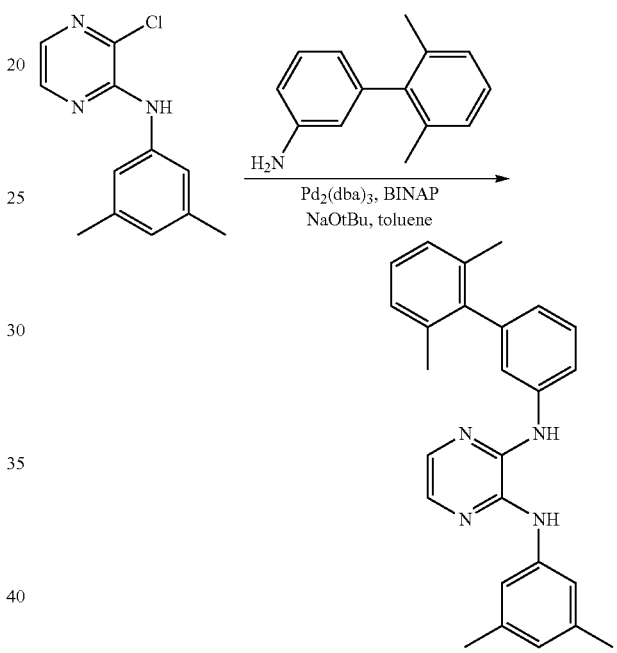

11.9 g (50.7 mmol) of 3-chloro-N-(3,5-dimethylphenyl)pyrazin-2-amine, and 10.0 g (50.7 mmol) of 3-(2,6-dimethylphenyl)aniline, and 0.23 g (0.25 mmol) of tris(dibenzylidene-acetone)dipalladium(0), and 0.47 g (0.75 mmol) 2,2'-bis(diphenylphosphino)-1,1'-binaphthalene, and 6.82 g (71.0 mmol) of sodium tert-butoxide are suspended in 125 ml of toluene at room temperature under argon. The brown suspension is three times evacuated and backfilled with argon, followed by heating under reflux for seven hours. The reaction mixture is cooled down to room temperature and filtered through a layer of Hyflo® filter aid and the filter aid rinsed with toluene. The filtrate is diluted with heptane (volume ratio 1:1) giving a precipitate which is filtered and washed with heptane, followed by three times washing with water. The solid is dried under vacuum at 50° C. and further dissolved in 500 ml of hot ethanol. The turbid solution is filtered through a 3 cm layer of Hyflo® filter aid and the filter aid rinsed with 30 ml of hot ethanol. The filtrate is cooled down to room temperature giving a beige suspension which is further stirred at ice-bath temperature for one hour. The suspension is filtered, the solid washed with 100 ml of cold ethanol and further dried under vacuum, giving the title product as a beige solid (yield: 9.6 g (48%)).

¹H-NMR (400 MHz, d₆-DMSO): δ=2.04 (s, 6 H), 2.26 (s, 6 H), 6.64 (s, 1 H), 6.73-6.78 (m, 1 H), 7.10-7.20 (m, 3 H), 7.29 (s, 2 H), 7.40 (t, 1 H), 7.44-7.48 (m, 1 H), 7.56 (d, 1 H), 7.59 (d, 1 H), 7.66-7.72 (m, 1 H), 8.39 (br. s, 1 H), 8.57 (br. s, 1 H).

c) Synthesis of [3-(3,5-dimethylanilino)pyrazin-2-yl]-[3-(2,6-dimethylphenyl)phenyl]-ammonium chloride

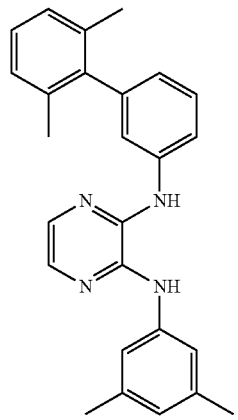

37% HCl →

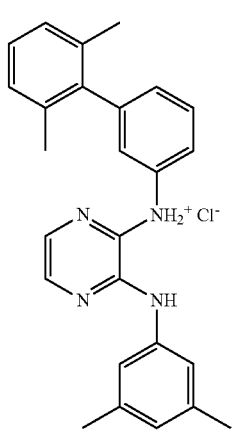

A suspension of 9.0 g (22.8 mmol) N3-(3,5-dimethylphenyl)-N2-[3-(2,6-dimethylphenyl)-phenyl]pyrazine-2,3-diamine and 180 ml of 37% hydrochloric acid is stirred at room temperature during 20 hours. The resulting dark viscous oil is separated from the liquid phase by decantation and directly used for the next step.

d) Synthesis of 3-(3,5-dimethylphenyl)-1-[3-(2,6-dimethylphenyl)phenyl]-2-ethoxy-2H-imidazo[4,5-b]pyrazine

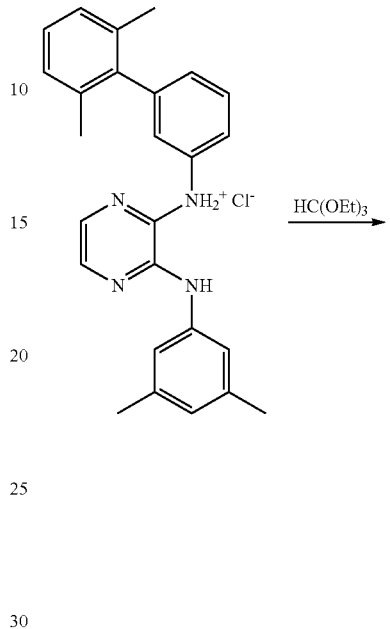

HC(OEt)₃ →

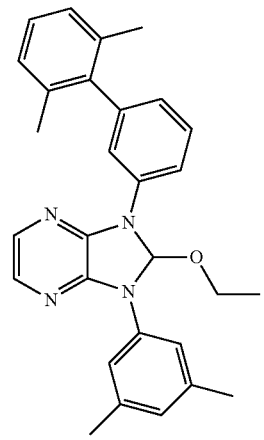

The crude product mixture of the former reaction step and 135 g (0.91 mol) of triethyl orthoformate are heated up under argon at 100° C. during two hours. The brown solution is filtered through a layer of Hyflo® filter aid and the filter aid rinsed with 10 ml of triethyl orthoformate. The filtrate is concentrated under vacuum and dissolved in 80 ml of hot heptane giving a turbid solution which is further filtered through a layer of Hyflo® filter aid followed by rinsing the filter aid with heptane. The filtrate is concentrated under vacuum giving the title product as off-white solid (yield: 6.1 g (59%)).

¹H-NMR (400 MHz, d₆-DMSO): δ=0.89 (t, 3 H), 2.03 (s, 3 H), 2.05 (s, 3H), 2.32 (s, 6 H), 3.18 (q, 2 H), 6.83 (s, 1 H), 6.96 (d, 1 H), 7.11-7.23 (m, 3 H), 7.49-7.59 (m, 3 H), 7.68 (s, 2 H), 7.74 (s, 1 H), 7.83 (s, 1 H), 8.22-8.28 (m, 1 H).

e) Synthesis of Complex (A-15)

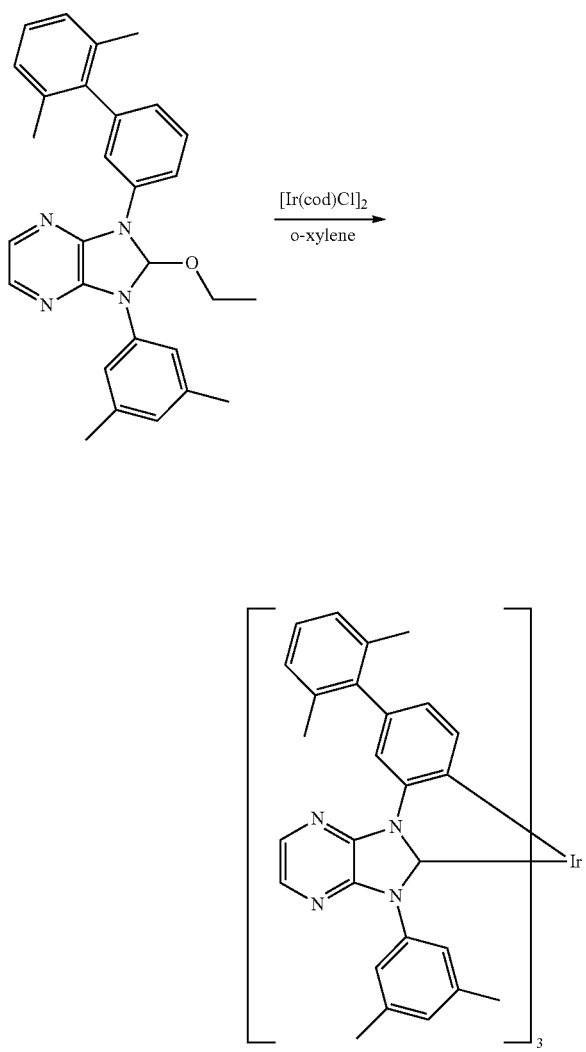

3.0 g (6.7 mmol) of 3-(3,5-dimethylphenyl)-1-[3-(2,6-dimethylphenyl)-phenyl]-2-ethoxy-2H-imidazo[4,5-b]pyrazine and 0.56 g (0.83 mmol) of chloro(1,5-cyclooctadiene)iridium(I) dimer are suspended under argon in 25 ml of o-xylene. The suspension is three times evacuated and backfilled with argon, followed by heating at 126° C. during 18 hours. The brown suspension is cooled down to room temperature, diluted with 50 ml of heptane and filtered. The solid is three times suspended in 20 ml of ethanol followed by filtration and washing of the solid with ethanol, and a final washing with heptane. The resulting solid is dried under vacuum at 50° C., suspended in 30 ml of ethyl acetate followed by irradiation in an ultrasonic bath during 30 minutes. The yellow solid is separated and suspended in 20 ml of 2-butanone and 3 ml of 1M HCl. The suspension is heated at 100° C. during 30 hours, followed by filtration and washing with ethanol and heptane. The solid is dried under vacuum at 50° C. giving the title product as a yellow solid (yield: 0.75 g (32%)).

APCI-LC-MS (positive, m/z): exact mass of $C_{81}H_{69}IrN_{12}$=1402.54. found 1403.4 $[M+1]^+$.

$^1$H-NMR (400 MHz, $CDCl_3$): δ=1.89 (s, 9 H), 2.15 (s, 9 H), 2.17 (s, 9 H), 2.40 (s, 9 H), 6.02 (s, 3 H), 6.42 (s, 3 H), 6.67-6.74 (m, 3 H), 6.90 (d, 3 H), 7.06 (s, 3 H), 7.09-7.22 (m, 9 H), 8.06 (d, 3 H), 8.19 (d, 3 H), 8.58 (d, 3 H).

Synthesis Example 3

Synthesis of Complex (B-15)

a) Synthesis of Complex Intermediate (I-1)

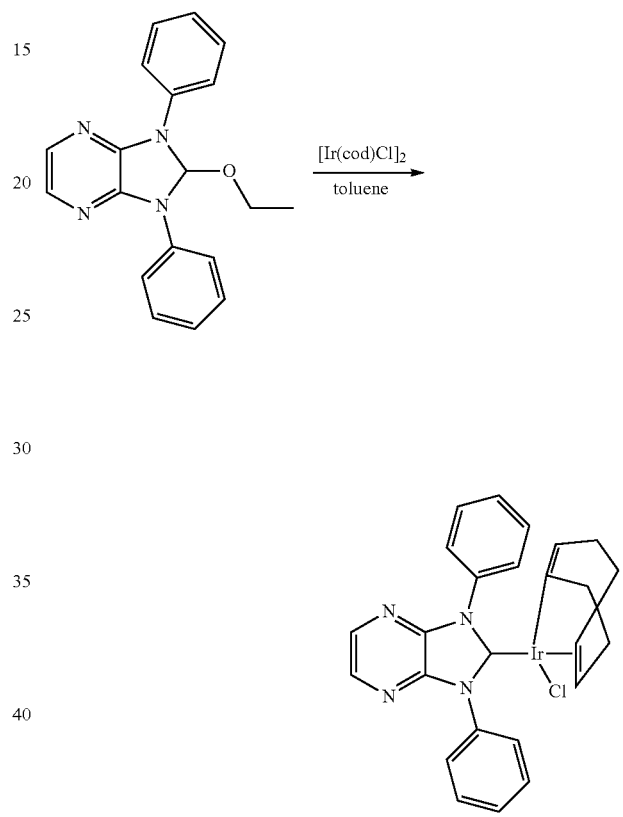

5.27 g (7.85 mmol) of chloro(1,5-cyclooctadiene)iridium (I) dimer are suspended in 250 ml of toluene and three times evacuated and backfilled with argon. 5.00 g (15.7 mmol) of 2-ethoxy-1,3-diphenyl-2H-imidazo[4,5-b]pyrazine are added in small portions at 66° C. during 20 minutes. Heating is continued at 66° C. and the generated ethanol continuously removed by using a distillation bridge. The yellow-brown suspension is cooled down to room temperature and diluted with 200 ml of ethanol, and cooling is continued until 5° C. is reached. Stirring is continued at this temperature for 30 minutes, followed by filtration and washing with 50 ml of cold ethanol and 50 ml of heptane. The resulting solid is dried under vacuum giving the title product as a yellow solid (yield: 4.1 g (43%)).

$^1$H-NMR (400 MHz, $CDCl_3$): δ=1.31-1.42 (m, 2 H), 1.43-1.64 (m, 4 H), 1.73-1.86 (m, 2 H), 2.50-2.59 (m, 2 H), 4.68-4.78 (m, 2 H), 7.57-7.69 (m, 6 H), 8.15-8.22 (m, 4 H), 8.33 (s, 2 H).

b) Synthesis of Complex (B-15)

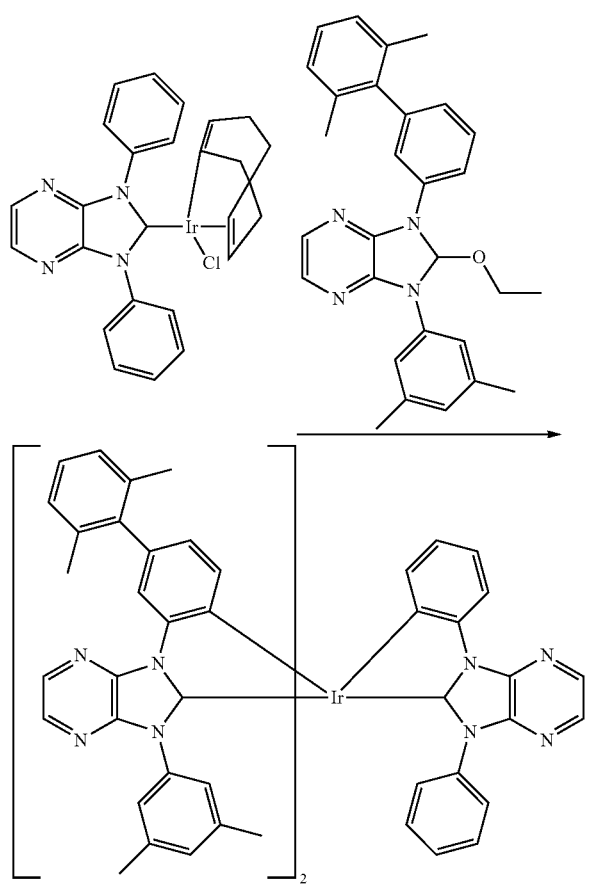

1.9 g (3.1 mmol) of intermediate complex (I-1) and 2.69 g (5.97 mmol) of 3-(3,5-dimethyl-phenyl)-1-[3-(2,6-dimethylphenyl)phenyl]-2-ethoxy-2H-imidazo[4,5-b]pyrazine are dissolved under argon in 130 ml of toluene. The yellow-brown solution is three times evacuated and backfilled with argon, followed by heating at 107° C. during 21 hours. Toluene is distilled off and replaced by 90 ml of o-xylene, and heating continued at 133° C. during six hours. The yellow-brown solution is diluted with 200 ml of heptane, filtered and the filtrate concentrated under vacuum. The dark resin is suspended in ethanol, filtered, and washed with ethanol and heptane. The yellow solid is suspended in ethyl acetate, filtered, washed with ethyl acetate and heptane, and further purified by chromatography (silica gel, heptane/ethyl acetate 7:3), giving the title product as a bright yellow solid (yield: 0.19 g (5%)).

APCI-LC-MS (positive, m/z): exact mass of $C_{71}H_{57}IrN_{12}$=1270.45. found 1271.3 $[M+1]^+$.

$^1$H-NMR (400 MHz, CDCl$_3$): δ=1.73-1.88 (s and br. s, 6 H), 2.10 (s, 3 H), 2.14 (s, 3 H), 2.17 (s, 3 H), 2.23 (s, 3 H), 2.33 (br. s, 3 H), 2.42 (s, 3 H), 5.96 (br. s, 1 H), 6.06 (s, 1 H), 6.43-7.36 (m, 23 H), 8.04 (d, 1 H), 8.07 (d, 1 H), 8.11 (d, 1 H), 8.18 (d, 1 H), 8.23 (d, 1 H), 8.32 (d, 1 H), 8.54 (d, 1 H), 8.62 (d, 1 H), 8.76-8.81 (d, 1 H).

Synthesis Example 4

Synthesis of Complex (A-17)

a) Synthesis of 2-bromo-1,3-diisopropyl-benzene

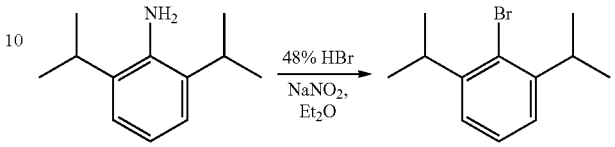

181 ml of 47% HBr solution (1.57 mol) are slowly added to 35.5 g (0.20 mol) of 2,6-diiodopropylaniline at room temperature during 15 minutes. The white suspension is cooled down to −56° C. and 23.6 g (0.34 mol) of sodium nitrite are added in portions during 10 minutes and stirring continued at the same temperature during one hour. 250 ml of ice-cold diethyl ether are slowly added during 10 minutes and the temperature let slowly rising to −15° C. during two hours until no more gas evolved. The temperature is decreased again to −56° C. and 24 ml of water are added first followed by the addition of 118.5 g (0.41 mol) of sodium carbonate decahydrate giving a brown suspension. The temperature is let raising to room temperature during three hours with evolution of gas starting at −32° C. The resulting orange suspension is further stirred at room temperature during 16 hours. The water phase is separated and the organic phase three times washed with water, dried and concentrated under vacuum. Further purification is done by chromatography (silica gel, heptane) giving the title product as colorless oil (yield: 38.7 g (80%)).

$^1$H-NMR (400 MHz, CDCl$_3$): δ=1.33 (d, 12 H), 3.54-3.66 (m, 2 H), 7.19-7.23 (m, 2 H), 7.30-7.35 (m, 1 H).

b) Synthesis of 1,3-diisopropyl-2-(3-nitrophenyl)benzene

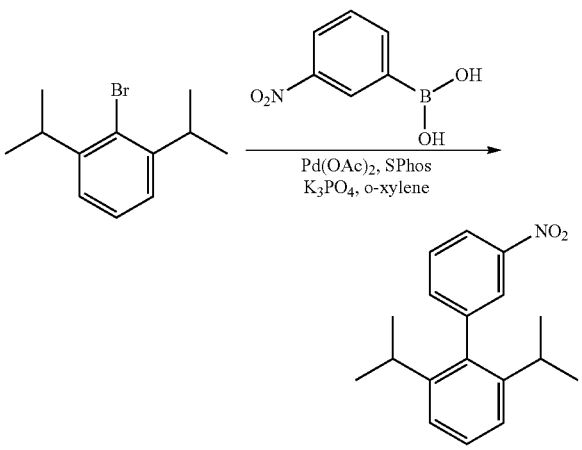

4.07 g (24.4 mmol) of 3-nitrobenzeneboronic acid, 5.0 g (20.7 mmol) of 2-bromo-1,3-diisopropyl-benzene, 21.3 g (0.10 mol) of tripotassium phosphate, 248 mg (0.60 mmol) of 2-dicyclohexylphosphino-2',6'-dimethoxybiphenyl, and 45 mg (0.20 mmol) of palladium(II) acetate are suspended in 50 ml of toluene, and three times evacuated and backfilled with argon. The beige suspension is heated under reflux during 19 hours and 0.75 ml of water are added. Heating is continued under reflux during eight hours and the hot suspension filtered through a 3 cm layer of Hyflo® filter aid followed by rinsing the filter aid with 200 ml of toluene. The filtrate is three times extracted with 200 ml of water, the organic phase dried over sodium sulfate, and concentrated under vacuum. The resulting solid is suspended in heptane, filtered and dried under vacuum, and further purified by chromatography (silica gel, heptane/ethyl acetate 95:5), giving the title product as a light yellow solid (yield: 3.8 g (67%)).

$^1$H-NMR (400 MHz, CDCl$_3$): δ=1.11 (d, 6 H), 1.13 (d, 6 H), 2.45-2.57 (m, 2 H), 7.27 (d, 2 H), 7.40-7.46 (m, 1 H), 7.53-7.58 (m, 1 H), 7.61-7.67 (m, 1 H), 8.09-8.13 (m, 1 H), 8.25-8.30 (m, 1 H).

c) Synthesis of 3-(2,6-diisopropylphenyl)aniline

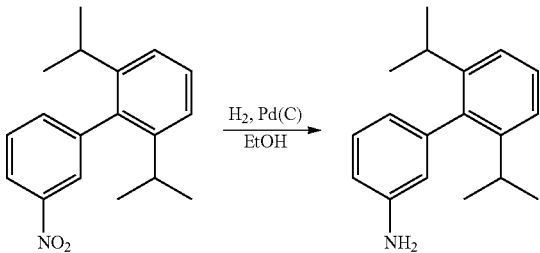 [SMILES: "EtOH" ; CC(C)c1cccc(C(C)C)c1-c1cccc([N+](=O)[O-])c1 ; CC(C)c1cccc(C(C)C)c1-c1cccc(N)c1]

11.0 g (38.8 mmol) of 1,3-diisopropyl-2-(3-nitrophenyl)benzene and 1.0 g of 5 wt %-palladium on carbon are reacted under 3 bar hydrogen pressure at 35° C. during six hours. The reaction mixture is filtered through a 3 cm layer of Hyflo® filter aid and rinsed with additional ethanol, followed by concentration under vacuum. The beige solid is further purified by recrystallization from heptane giving the title product as a white solid (yield: 9.1 g (93%)).

$^1$H-NMR (400 MHz, CDCl$_3$): δ=1.11 (d, 6 H), 1.13 (d, 6 H), 2.67-2.79 (m, 2 H), 3.71 (br. s, 2 H), 6.51-6.55 (m, 1 H), 6.58-6.62 (m, 1 H), 6.69-6.74 (m, 1 H), 7.18-7.25 (m, 3 H), 7.32-7.38 (m, 1 H).

d) Synthesis of N2-[3-(2,6-diisopropylphenyl)phenyl]-N3-(3,5-dimethyl-phenyl)pyrazine-2,3-diamine

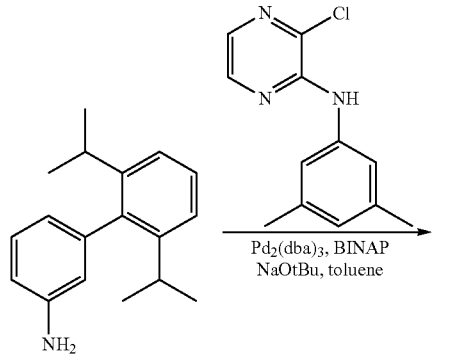

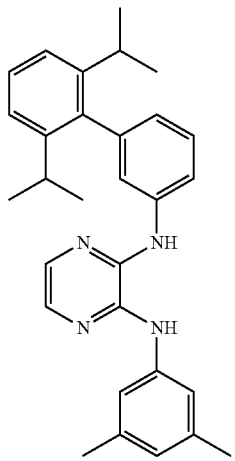

5.5 g (21.7 mmol) of 3-(2,6-diisopropylphenyl)aniline, 5.07 g (21.7 mmol) of 3-chloro-N-(3,5-dimethylphenyl)pyrazin-2-amine, 0.10 g (0.11 mmol) of tris(dibenzylideneacetone)dipalladium(0), and 0.20 g (0.32 mmol) of 2,2'-bis(diphenylphosphino)-1,1'-binaphthalene, and 2.92 g (30.4 mmol) of sodium tert-butoxide are suspended in 80 ml of toluene at room temperature under argon. The brown suspension is three times evacuated and backfilled with argon, followed by heating under reflux for nine hours. The brown suspension is cooled down to room temperature and diluted with 20 ml of water followed by filtration through a 3 cm layer of Hyflo® filter aid and rinsing the filter aid with toluene. The filtrate is three times extracted with 50 ml of water, followed by extraction with 50 ml of 5% aqueous ammonia solution, and two times with 50 ml of water. The organic phase is dried over sodium sulfate and concentrated under vacuum giving a solid which is further stirred in 200 ml of hot ethanol. Filtration and washing with cold ethanol gives the title product as light beige solid (yield: 7.3 g (75%)).

$^1$H-NMR (400 MHz, CDCl$_3$): δ=1.09 (d, 6 H), 1.11 (d, 6 H), 2.30 (s, 6 H), 2.65-2.77 (m, 2 H), 6.20 (s, 1 H), 6.29 (s, 1 H), 6.71 (s, 1 H), 6.84-6.94 (m, 3 H), 7.08 (s, 1 H), 7.19-7.24 (m, 2 H), 7.33-7.40 (m, 3 H), 7.76-7.83 (m, 2 H).

e) Synthesis of [3-(2,6-diisopropylphenyl)phenyl]-[3-(3,5-dimethylanilino)pyrazin-2-yl]-ammonium chloride

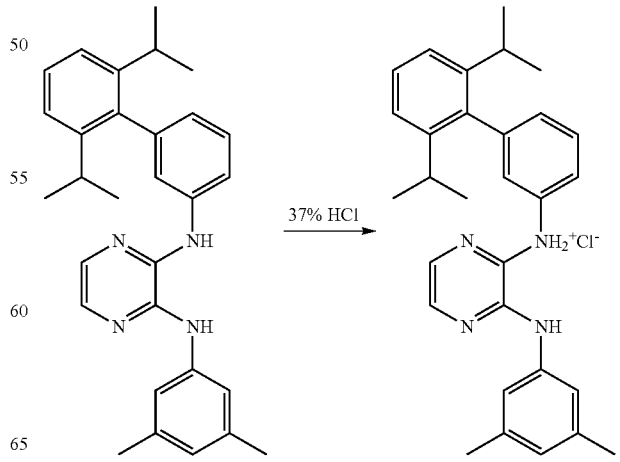

A suspension of 5.0 g (11.1 mmol) of N2-[3-(2,6-diisopropyl-phenyl)phenyl]-N3-(3,5-dimethylphenyl)pyrazine-2,3-diamine and 100 ml of 37% hydrochloric acid is stirred at room temperature during 22 hours. The resulting beige suspension is filtered and the solid washed with 37% hydrochloric acid and hexane, and dried after washing on the filter funnel under vacuum, giving the title product as a beige solid (yield: 5.39 g (>99%)).

$^1$H-NMR (400 MHz, d$_6$-DMSO): δ=1.07 (t, 12 H), 2.27 (s, 6 H), 2.61-2.73 (m, 2 H), 6.68 (s, 1 H), 6.78 (d, 1 H), 7.22 (d, 2 H), 7.28-7.43 (m, 4 H), 7.69-7.75 (m, 1 H), 8.88 (br. s, 1 H), 8.96 (br. s, 1 H).

f) Synthesis of 1-[3-(2,6-diisopropylphenyl)phenyl]-3-(3,5-dimethylphenyl)-2-ethoxy-2H-imidazo[4,5-b]pyrazine

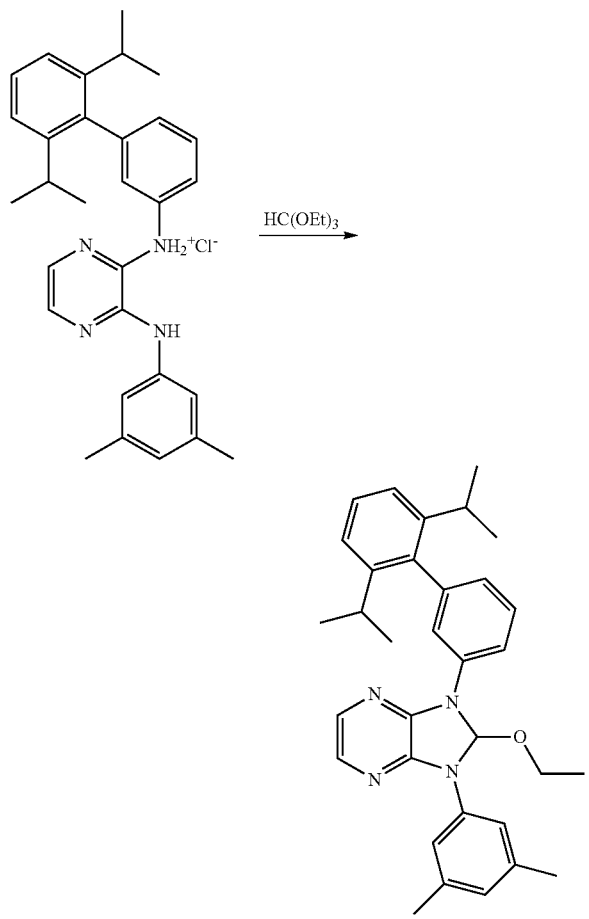

A yellow suspension of 7.0 g (14.4 mmol) of [3-(2,6-diisopropyl-phenyl)phenyl]-[3-(3,5-dimethylanilino)pyrazin-2-yl]ammonium chloride and 135 g (0.91 mol) of triethyl orthoformate is heated up under argon at 100° C. during two hours. The resulting brown solution is filtered and the small amount of solid residue rinsed with 10 ml of triethyl orthoformate. The filtrate is concentrated under vacuum, dissolved in 80 ml warm heptane and filtered through a layer of Hyflo® filter aid and the filter aid rinsed with a small amount of heptane. The solution is cooled down to ice-bath temperature and the resulting suspension stirred during one hour, followed by filtration and washing with cold heptane, giving the title product as off-white solid (yield 4.2 g (58%)).

$^1$H-NMR (400 MHz, d$_6$-DMSO): δ=0.88 (t, 3 H), 0.99-1.18 (br. d, 12 H), 2.32 (s, 6 H), 2.54-2.71 (m, 2 H), 3.13-3.25 (m, 2 H), 6.84 (s, 1 H), 6.93-7.03 (m, 1 H), 7.19-7.31 (m, 2 H), 7.31-7.42 (m, 1 H), 7.43-7.61 (m, 3 H), 7.62-7.92 (m, 4 H), 8.13-8.32 (m, 1 H).

g) Synthesis of Complex (A-17)

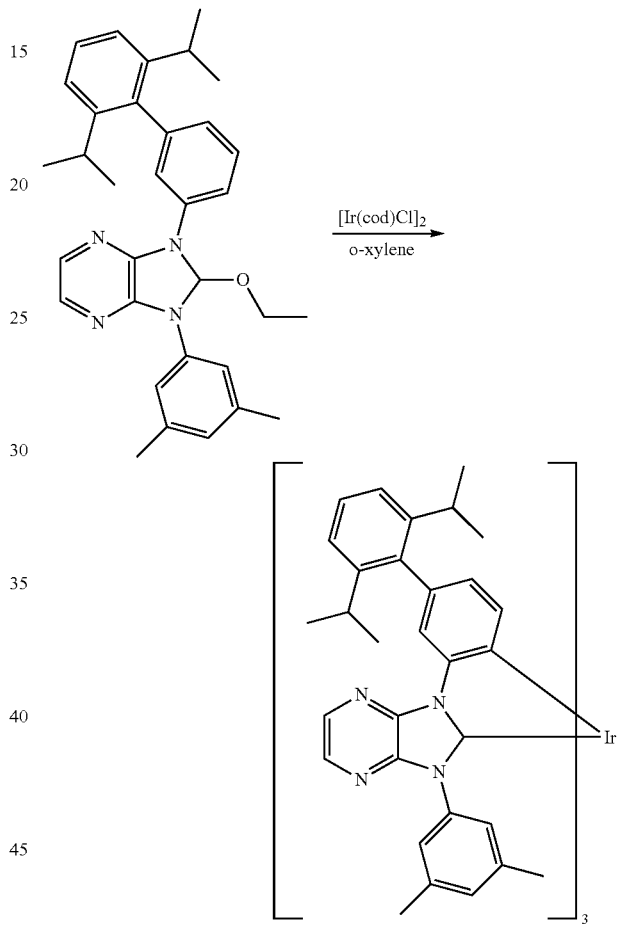

3.0 g (5.9 mmol) of 1-[3-(2,6-diisopropylphenyl)phenyl]-3-(3,5-dimethylphenyl)-2-ethoxy-2H-imidazo[4,5-b]pyrazine and 0.50 g (0.74 mmol) of chloro(1,5-cyclooctadiene)iridium(I) dimer are suspended under argon in 25 ml of o-xylene.

The suspension is three times evacuated and backfilled with argon, followed by heating at 137° C. during 21 hours. The brown solution is cooled down to room temperature and diluted with 200 ml of ethanol followed by stirring at ice-bath temperature during 30 minutes. The resulting suspension is filtered and the solid two times washed with 50 ml of ethanol followed by washing with additional ethanol and 30 ml of heptane. The yellow solid is dissolved in dichloromethane and filtered through a 3 cm layer of silica gel and the silica gel layer rinsed with 20 ml of dichloromethane. The collected dichloromethane fractions are diluted with 25 ml of ethanol and the solution slowly concentrated under vacuum until precipitation occurred. The resulting solid is filtered off and washed with ethanol and heptane, and further purified by chromatography (silica gel, heptane/ethyl acetate), giving the title product as yellow solid (yield: 0.8 g (35%)).

APCI-LC-MS (positive, m/z): exact mass of $C_{93}H_{93}IrN_{12}$=1570.73. found 1571.7 $[M+1]^+$.

$^1$H-NMR (400 MHz, CDCl$_3$): δ=1.00 (d, 9 H), 1.15 (d, 9 H), 1.16 (d, 18 H), 1.77 (s, 9 H), 2.45 (s, 9 H), 2.86-3.04 (m, 6 H), 6.12 (s, 3 H), 6.48 (s, 3 H), 6.69-6.76 (m, 3 H), 6.79-6.90 (m, 6 H), 7.21-7.32 (m, 6 H), 7.34-7.41 (m, 3 H), 8.07 (d, 3 H), 8.18 (d, 3 H), 8.68 (d, 3 H).

Synthesis Example 5

Synthesis of Complex (B-43)

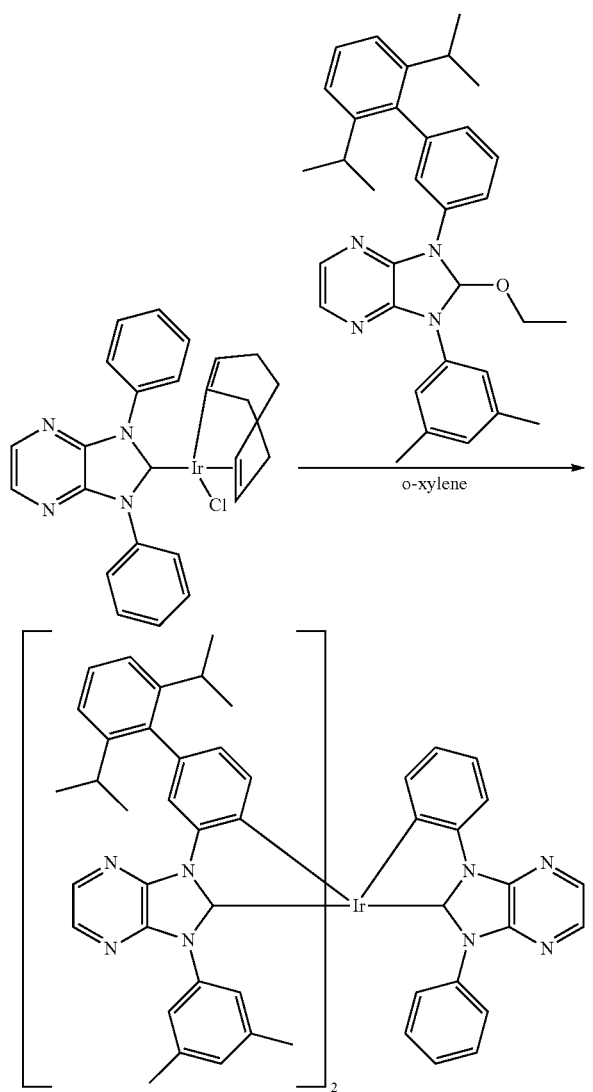

1.30 g (2.15 mmol) of intermediate complex (I-1) and 2.07 g (4.09 mmol) of 1-[3-(2,6-diisopropylphenyl)phenyl]-3-(3,5-dimethylphenyl)-2-ethoxy-2H-imidazo[4,5-b]pyrazine are dissolved under argon in 130 ml of toluene. The yellow-brown solution is three times evacuated and back-filled with argon, followed by heating at 107° C. during 2 hours. Some toluene is distilled off and replaced by 25 ml of o-xylene and heating continued at 133° C. during 17 hours. The yellow-brown solution is diluted with 200 ml of heptane and filtered. The solution is filtered through a 3 cm layer of Hyflo® filter aid and the filter aid rinsed with toluene, followed by concentration under vacuum. Further purification is done by chromatography (silica gel, heptane/ethyl acetate). The isolated solid is dissolved in 10 ml of dichloromethane, 20 ml of ethanol are added, and the resulting solution slowly concentrated under vacuum until precipitation occurs. The suspension is stirred during 30 minutes and filtered. Dissolution and precipitation using dichloromethane and ethanol is repeated twice, followed by filtration and drying under vacuum, giving the title product as a bright yellow solid (yield: 0.37 g (14%)).

APCI-LC-MS (positive, m/z): exact mass of $C_{79}H_{73}IrN_{12}$=1382.57. found 1383.6 $[M+1]^+$.

$^1$H-NMR (400 MHz, CDCl$_3$): δ=0.96 (d, 6 H), 1.04-1.32 (m, 18 H), 1.70 (s, 3 H), 1.74 (br. s, 3 H), 2.40 (br. s, 3 H), 2.46 (s, 3 H), 2.68-2.80 (m, 1 H), 2.92-3.08 (m, 2 H), 3.70-3.80 (m, 1 H), 5.98 (br. s, 1 H), 6.13 (s, 1 H), 6.3-7.44 (m, 22 H), 8.04 (d, 1 H), 8.07 (d, 1 H), 8.12 (d, 1 H), 8.17 (d, 1 H), 8.20 (d, 1 H), 8.33 (d, 1 H), 8.59 (d, 1 H), 8.72 (d, 1 H), 8.77-8.83 (m, 1 H).

Synthesis Example 6

Synthesis of Bromo-Complex Intermediate (HI-1)

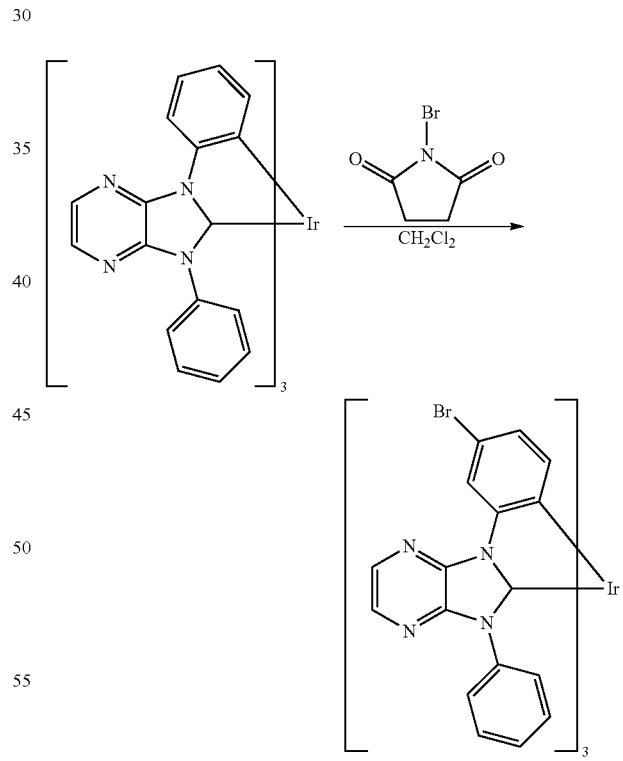

3.22 g (3.2 mmol) of iridium complex (see synthesis in WO2011/073149, example fac-EM1) are dissolved in 350 ml of dichloromethane. 3.42 g (19.2 mmol) of N-bromosuccinimide are added to the solution and the reaction is stirred under argon atmosphere at room temperature under exclusion of light. The progress is monitored via HPLC and N-bromosuccinimide (1.71 g 9.6 mmol) is added every two days until full conversion of the starting material into the desired product is achieved. After completion, 160 mL of a 10% water solution of sodium metabisulfite are added and the mixture is stirred for 3 hours. The phases are separated and the organic solution is extracted with water and dried over magnesium sulphate. The title product is isolated after precipitation in cyclohexane from dichloromethane as a yellow solid (yield: 3.64 g (92%)).

$^1$H-NMR (400 MHz, CD$_2$Cl$_2$): δ=8.92 (d, 3H, J=1.8 Hz), 8.37 (d, 3H, J=2.8 Hz), 8.11 (d, 3H, J=2.8 Hz), 7.80-5.95 (m, 21H).

Synthesis Example 7

Synthesis of Iodo-Complex Intermediate (HI-2)

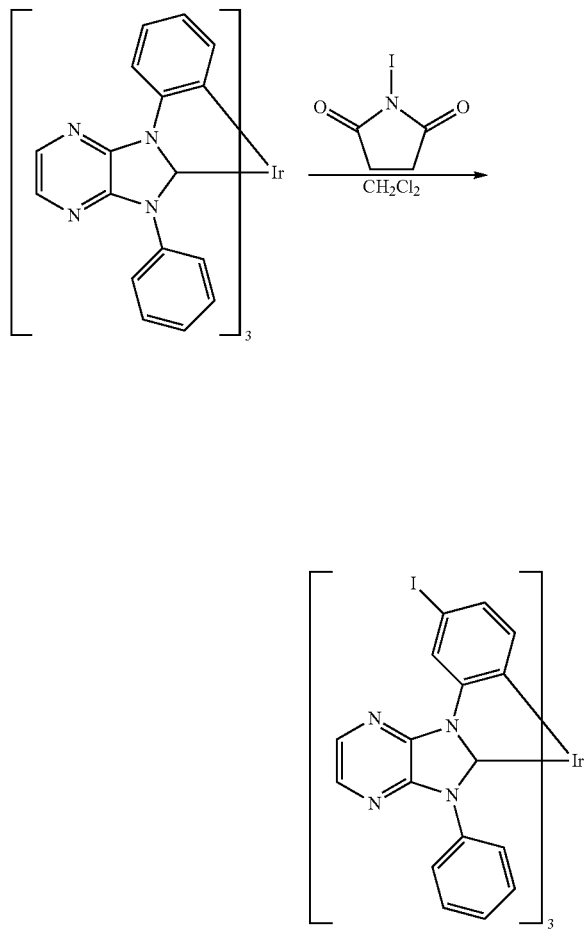

200 mg (0.20 mmol) of iridium complex (see synthesis in WO2011/073149, example fac-EM1) is dissolved in 20 ml of dichloromethane at room temperature and 268 mg (1.20 mmol) of N-iodosuccinimide are added. The reaction mixture is stirred at room temperature for 48 hours, the solvent is removed under vacuum and further purified by chromatography (silica gel, dichloromethane/ethyl acetate 9:1) giving the title product (yield 88%). $^1$H-NMR (400 MHz, CD$_2$Cl$_2$): δ=9.08 (s, 1 H), 8.37 (d, 1 H), 8.10 (d, 1 H), 8.00 (broad signal, 4 H), 7.11 (d, 1 H), 6.42 (d, 1 H), 6.86 (t, 1 H).

Synthesis Example 8

Synthesis of Bromo-Complex Intermediate (HI-3)

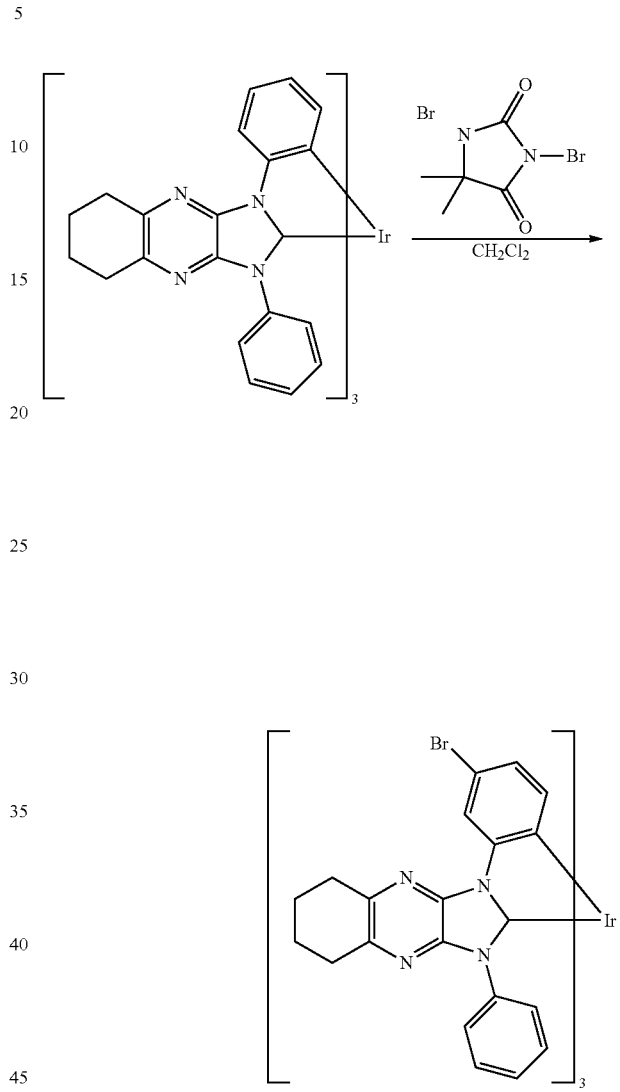

0.73 g (0.62 mmol) of iridium complex (see synthesis in EP13162776.2, Synthesis of complex BE-12) and 0.27 g (0.94 mmol) of 1,3-dibromo-5,5-dimethylhydantoin are suspended in 100 ml dichloromethane at room temperature. The suspension is stirred at 0° C. for 24 hours. The reaction mixture is treated with aqueous sodium thiosulfate and the temperature raised to 20° C. The organic phase is two times washed with water and dried over sodium sulfate and filtered. The light yellow solution is poured into 200 ml of methanol and the resulting suspension further stirred at ice-bath temperature. The light yellow suspension is filtered and the solid washed with methanol followed by drying under vacuum, giving the title product as a light yellow solid (yield: 0.74 g (84%)).

APCI-LC-MS (positive, m/z): exact mass of $C_{63}H_{48}Br_3IrN_{12}$=1402.13. found 1405.3.

$^1$H-NMR (400 MHz, CD$_2$Cl$_2$): δ=1.88-2.11 (m, 12 H), 2.70-2.95 (m, 6 H), 3.14-3.31 (m, 6 H), 6.27-7.37 (br. m, 21 H), 8.93 (d, 3 H).

Example 9

Synthesis of Complex (E-1)

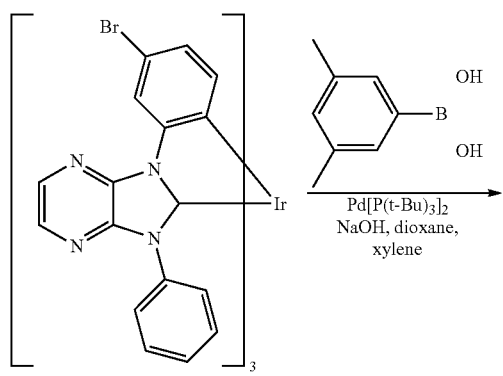

NaOH (0.144 g of a 50% water solution), 50 ml of 1,4-dioxane and 50 ml of xylene are mixed together under argon atmosphere. Successively bromo-complex product (HI-1) of synthesis example 6 (0.25 g, 0.2 mmol) is added and argon is bubbled through the solution for 15 minutes. After adding 3,5-dimethylphenylboronic acid (0.18 g, 1.2 mmol) and bis(tri-t-butylphosphine)palladium(0) (11 mg, 0.021 mmol), the solution is purged for another 15 minutes with argon and then heated to 85° C. for 3 days. After completion, the reaction is cooled down to room temperature, the precipitate filtered and washed with 1,4-dioxane. The solid is dried under vacuum and dissolved in dichloromethane and extracted with water. The organic phase is dried over sodium sulfate, the solvent removed under vacuum and the resulting solid further purified by column chromatography (silica gel, dichloromethan/ethyl acetate 6/4). The title product is isolated as a yellow solid (yield: 0.21 g (80%)).

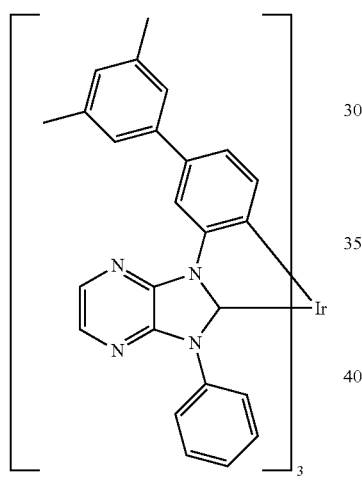

$^1$H-NMR (400 MHz, CD$_2$Cl$_2$): δ=8.57 (d, 3H, J=1.5 Hz), 8.36 (d, 3H, J=2.9 Hz), 8.26 (d, 3H, J=2.9 Hz), 7.55-6.21 (m, 30H), 2.17 (s, 9H), 2.08 (s, 9H).

Synthesis Example 10

Synthesis of Complex (A-1)

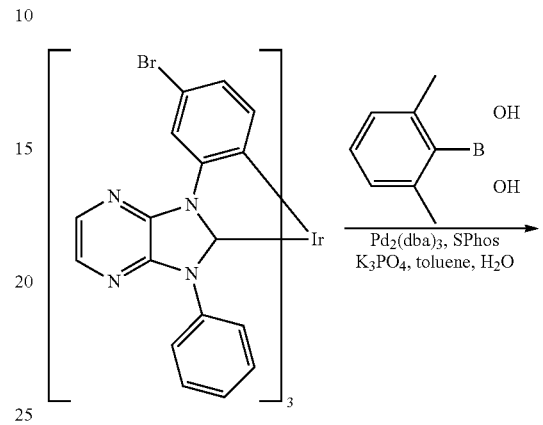

Bromo-complex product (HI-1) of synthesis example 6 (0.30 g, 0.24 mmol), 2,6-dimethylphenylboronic acid (0.16 g, 1.08 mmol), and K$_3$PO$_4$ (0.31 g, 1.44 mmol) are suspended in 150 ml of toluene and 36 ml of water. Argon is bubbled through the solution for 30 minutes and then tris-(dibenzylidenacetone)-dipalladium(0) (10 mg, 0.01 mmol) and Sphos (18 mg, 0.04 mmol) are added. The solution is purged with argon for 15 minutes and then heated to reflux under inert atmosphere overnight. After cooling to room temperature the precipitate is filtered and purified via column chromatography (silica, dichloromethane/ethyl acetate 9/1). The title product is isolated as yellow solid (yield: 0.22 g (70%)).

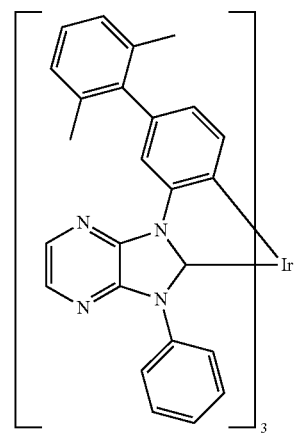

$^1$H-NMR (400 MHz, CD$_2$Cl$_2$): δ=9.09 (d, 3H, J=1.8 Hz), 8.40 (d, 3H, J=2.9 Hz), 8.09 (d, 3H, J=2.9 Hz), 7.60-6.21 (m, 30H), 2.39 (s, 18H).

Synthesis Example 11

Synthesis of Complex (C-125)

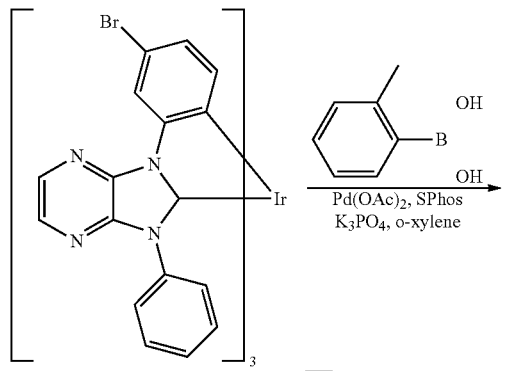

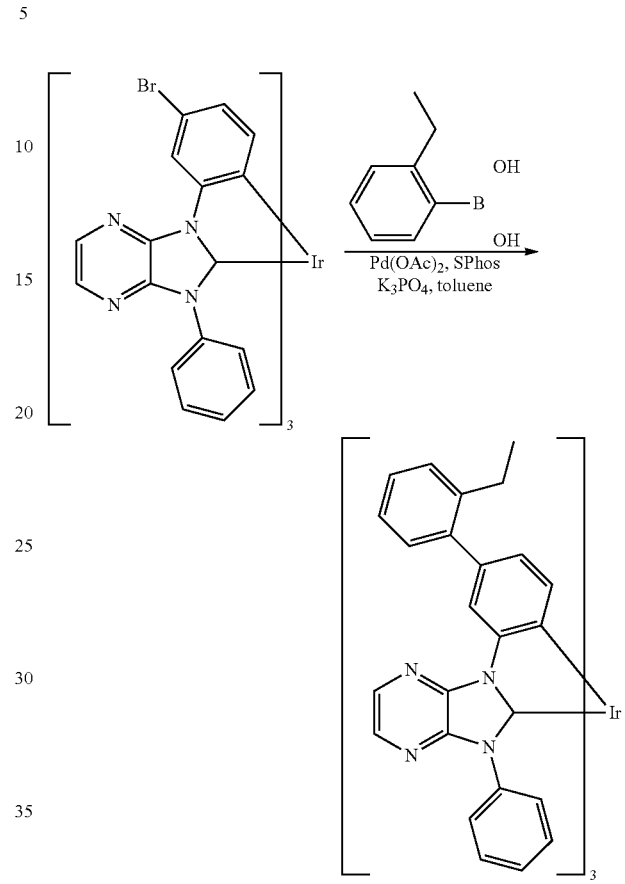

1.00 g (0.80 mmol) of bromo-complex product (HI-1) of synthesis example 6, 0.50 g (3.68 mmol) o-tolylboronic acid, and 1.03 g (4.85 mmol) of tripotassium phosphate are suspended under argon in 50 ml of toluene. The suspension is three times evacuated and backfilled with argon and treated with 9.0 mg (0.04 mmol) of palladium(II) acetate and 33.0 mg (0.08 mmol) of 2-dicyclohexylphosphino-2',6'-dimethoxybiphenyl. The beige-yellow suspension is heated at 94° C. during 2.5 hours, the turbid solution cooled down to room temperature, diluted with 200 ml of dichloromethane and filtered through a 3 cm layer of of Hyflo® filter aid. The filtrate is concentrated under vacuum, dissolved in dichloromethane and passed through a 4 cm layer of silica gel followed by rinsing the silica gel layer with dichloromethane. 30 ml of ethanol are added and dichloromethane is slowly evaporated under vacuum until precipitation occurs. The solid is filtered off, washed with ethanol and dried under vacuum. The resulting solid is dissolved in 75 ml of hot DMF, cooled down to room temperature and diluted with 25 ml of ethanol providing a suspension which is filtered, and the solid washed with ethanol and heptane giving the title product as a yellow solid (yield: 0.83 g (81%)).

APCI-LC-MS (positive, m/z): exact mass of $C_{72}H_{51}IrN_{12}$=1276.40. found 1277.1 $[M+1]^+$.

$^1$H-NMR (400 MHz, CDCl$_3$): δ=2.42 (s, 9 H), 6.25-7.56 (very broad signal, 9 H), 6.82-6.89 (t, 3 H), 6.91 (s, 6 H), 7.24-7.34 (m, 12 H), 7.39-7.44 (m, 3 H), 8.09 (d, 3 H), 8.30 (d, 3 H), 8.85 (s, 3 H).

Synthesis Example 12

Synthesis of Complex (C-126)

1.00 g (0.80 mmol) of bromo-complex product (HI-1) of synthesis example 6, 0.56 g (3.73 mmol) 2-ethylphenylboronic acid, and 1.03 g (4.59 mmol) of tripotassium phosphate are suspended under argon in 50 ml of toluene. The suspension is three times evacuated and backfilled with argon and treated with 9.0 mg (0.04 mmol) of palladium(II) acetate and 33.0 mg (0.08 mmol) of 2-dicyclohexylphosphino-2',6'-dimethoxybiphenyl. The brown-yellow suspension is heated at 76° C. during 30 minutes. The resulting yellow suspension is cooled down to room temperature and filtered through a 4 cm layer of silica gel followed by rinsing the silica gel layer with dichloromethane. The filtrate is slowly concentrated under vacuum until dichloromethane is removed. The solution is diluted with 50 ml of heptane and filtered.

The solid is washed with ethanol and heptane followed by drying under vacuum, giving the title product as a yellow solid (0.89 g (84%)).

APCI-LC-MS (positive, m/z): exact mass of $C_{75}H_{57}IrN_{12}$=1318.45. found 1319.5 $[M+1]^+$.

$^1$H-NMR (400 MHz, CDCl$_3$): δ=1.20 (t, 9 H), 2.78 (q, 6 H), 6.25-7.51 (very broad signal, 9 H), 6.86 (t, 3 H), 6.92 (s, 6 H), 7.23-7.44 (m, 12 H), 8.09 (s, 3 H), 8.29 (s, 3 H), 8.86 (s, 3 H).

Synthesis Example 13

Synthesis of Complex (C-127)

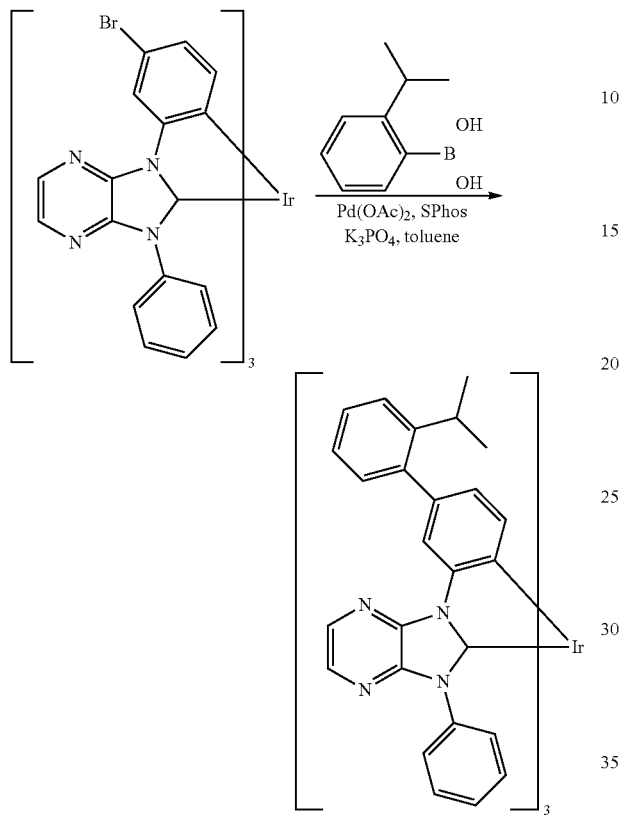

2.00 g (1.61 mmol) of bromo-complex product (HI-1) of synthesis example 6, 1.22 g (7.44 mmol) 2-isopropylphenylboronic acid, and 2.05 g (9.66 mmol) of tripotassium phosphate are suspended under argon in 100 ml of toluene. The suspension is three times evacuated and backfilled with argon and treated with 18.0 mg (0.08 mmol) of palladium(II) acetate and 66.0 mg (0.16 mmol) of 2-dicyclohexylphosphino-2',6'-dimethoxybiphenyl. The brown-yellow suspension is heated at 74° C. during 45 minutes, cooled down to room temperature, diluted with 150 ml of dichloromethane and filtered through a 3 cm layer of Hyflo® filter aid. The filtered is rinsed with 200 ml of dichloromethane and the filtrated concentrated to 50 ml volume. 50 ml of ethanol are added and the resulting suspension filtered and the solid washed with ethanol and heptane. 1.50 g of a yellow solid are obtained which are reacted again under the same conditions as before with 0.31 g (1.89 mmol) 2-isopropylphenylboronic acid, 0.51 g (2.40 mmol) of tripotassium phosphate, 9.0 mg (0.04 mmol) of palladium(II) acetate, 33.0 mg (0.08 mmol) of 2-dicyclohexylphosphino-2',6'-dimethoxybiphenyl and 50 ml of toluene. The reaction mixture is heated at 76° C. during three hours, followed by work-up and purification as described before, giving the title product as a light yellow solid (yield: 1.68 g (77%)).

APCI-LC-MS (positive, m/z): exact mass of $C_{78}H_{63}IrN_{12}$=1360.49. found 1361.5 $[M+1]^+$.

$^1$H-NMR (400 MHz, $CD_2Cl_2$): δ=1.19 (d, 9 H), 1.29 (d, 9 H), 3.28-3.41 (m, 3 H), 6.14-7.55 (very broad signal, 15 H), 6.89 (s, 6 H), 7.21-7.30 (t, 3 H), 7.32-7.41 (d, 6 H), 7.41-7.49 (d, 3 H), 8.10 (s, 3 H), 8.32 (s, 3 H), 8.82 (s, 3 H).

Synthesis Example 14

Synthesis of Complex (G-1)

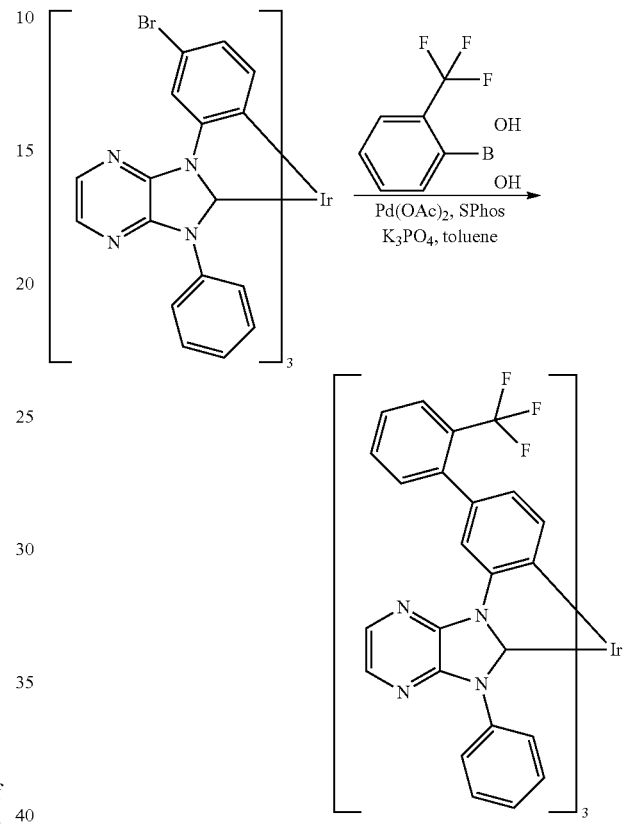

1.00 g (0.80 mmol) of bromo-complex product (HI-1) of synthesis example 6, 0.70 g (3.69 mmol) 2-(trifluoromethyl)phenylboronic acid, and 1.03 g (4.59 mmol) of tripotassium phosphate are suspended under argon in 50 ml of toluene. The suspension is three times evacuated and backfilled with argon and treated with 9.0 mg (0.04 mmol) of palladium(II) acetate and 33.0 mg (0.08 mmol) of 2-dicyclohexylphosphino-2',6'-dimethoxybiphenyl. The brown-yellow suspension is heated at 93° C. during 15 minutes. The resulting beige-yellow suspension is cooled down to room temperature and filtered. The solid is washed with toluene and ethanol and three times washed with water, filtered, and washed again with ethanol. The resulting solid is dissolved in 75 ml of hot DMF and filtered through a 3 cm layer of Hyflo® filter aid followed by rinsing the filter aid with a small amount of DMF. The filtrate is cooled down to room temperature and diluted with 30 ml of ethanol. The suspension is filtered and the resulting solid washed with DMF, ethanol and heptane and further dried under vacuum giving the title product as a yellow solid (yield: 0.83 g (76%)).

APCI-LC-MS (positive, m/z): exact mass of $C_{72}H_{42}F_9IrN_{12}$=1438.31. found 1439.1 $[M+1]^+$.

$^1$H-NMR (400 MHz, $CD_2Cl_2$): δ=6.08-7.75 (very broad signal, 15 H), 6.88 (s, 6 H), 7.47-7.68 (m, 9 H), 7.80 (d, 3 H), 8.10 (br. s, 3 H), 8.31 (br. s, 3 H), 8.83 (s, 3 H).

Synthesis Example 15

Synthesis of Complex (A-85)

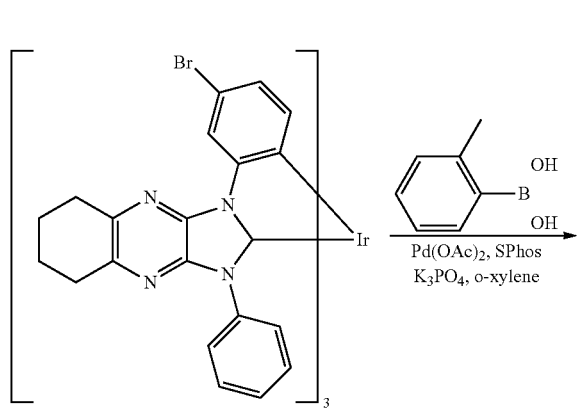

0.73 g (0.52 mmol) of bromo-complex product (HI-3) of synthesis example 8, 0.28 g (2.06 mmol) o-tolylboronic acid, and 0.55 g (2.59 mmol) of tripotassium phosphate are suspended under argon in 30 ml of toluene. The suspension is three times evacuated and backfilled with argon and treated with 5.8 mg (0.03 mmol) of palladium(II) acetate and 21.3 mg (0.05 mmol) of 2-dicyclohexylphosphino-2',6'-dimethoxybiphenyl. The brown suspension is heated at 100° C. during 20 hours and cooled down to room temperature. 1 g of sodium cyanide is dissolved in 20 ml warm water and poured into the reaction mixture. The reaction mixture and purified as described for complex C-126, giving the title product as a light yellow solid (yield: 0.36 g (48%)).

APCI-LC-MS (positive, m/z): exact mass of $C_{84}H_{69}IrN_{12}$=1438.54. found 1439.7.

$^1$H-NMR (400 MHz, $CD_2Cl_2$): δ=1.86-2.10 (m, 12 H), 2.46 (s, 9 H), 2.70-2.95 (m, 6 H), 3.04-3.24 (m, 6 H), 6.47-7.49 (br. m, 33 H), 8.85 (s, 3 H).

Synthesis Example 16

Synthesis of Complex (A-3)

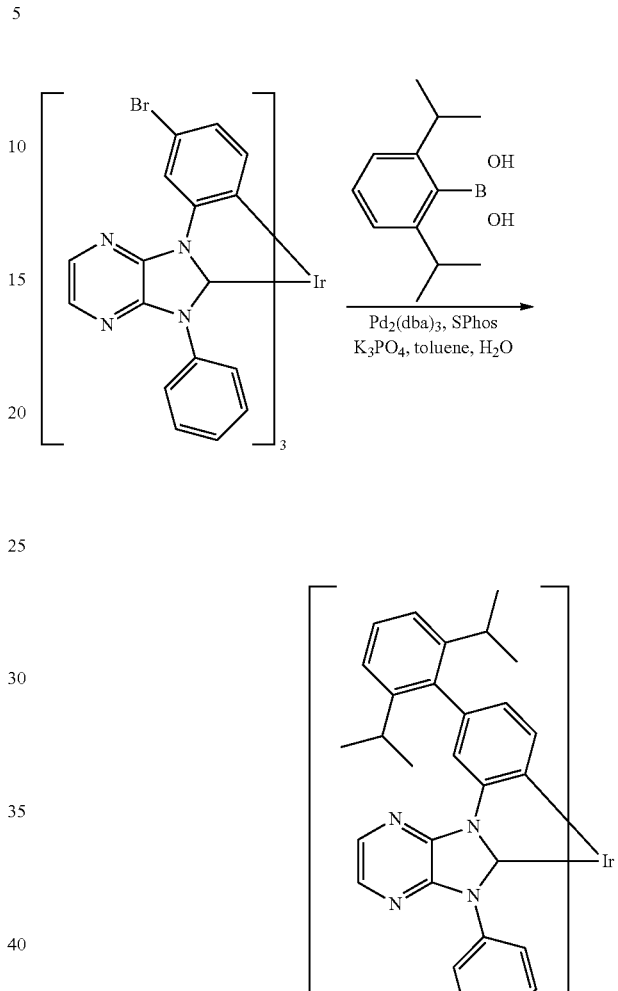

Bromo-complex product (HI-1) of synthesis example 6 (0.30 g, 0.24 mmol), 2,6-diisopropylphenylboronic acid (0.22 g, 1.08 mmol), and $K_3PO_4$ (0.31 g, 1.44 mmol) are suspended in 180 ml of toluene and 36 ml of water. Argon is bubbled through the solution for 30 minutes and then tris-(dibenzylidenacetone)-dipalladium(0) (10 mg, 0.01 mmol) and Sphos (18 mg, 0.04 mmol) are added. The solution is purged with argon for 15 minutes and then heated to reflux under inert atmosphere overnight. After cooling to room temperature, phases are separated, the organic phase collected and the solvent removed. The solid is then purified via column chromatography (silica, cyclohexane/ethyl acetate). The title product is isolated as yellow solid (yield: 0.27 g (67%)).

$^1$H-NMR (400 MHz, $CD_2Cl_2$): δ=8.64 (d, 3H, J=1.6 Hz), 8.25 (d, 3H, J=2.9 Hz), 8.05 (d, 3H, J=2.9 Hz), 7.47-7.30 (m, 6H), 7.21 (t, 6H, J=7.5), 7.16-7.00 (br m, 3H), 6.87 (d, 3H, J=7.4 Hz), 6.78 (t, 3H, J=7.5 Hz), 6.74 (d, 3H, J=7.6 Hz), 6.65-6.20 (br m, 6H), 3.00 (sep, 3H, J=6.9), 2.77 (sep, 3H, J=6.9 Hz), 1.20-1.12 (m, 18 H), 1.10 (d, 9H, J=6.9 Hz), 1.01 (d, 9H, J=6.9 Hz).

Synthesis Example 17

Synthesis of Complex (A-14)

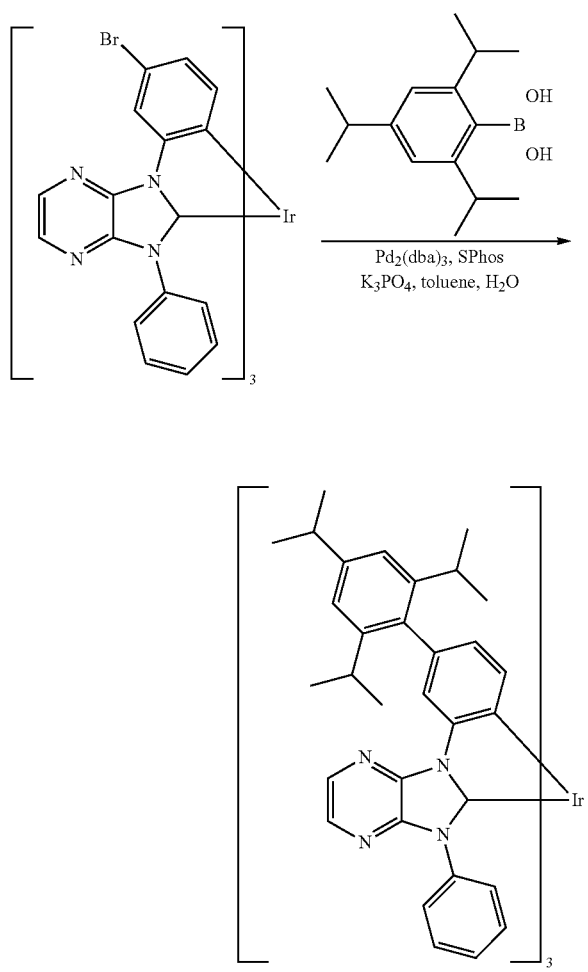

Bromo-complex product (HI-1) of synthesis example 6 (0.20 g, 0.16 mmol), 2,6-dimethylphenylboronic acid (0.18 g, 0.72 mmol), and K$_3$PO$_4$ (0.21 g, 0.96 mmol) are suspended in 120 ml of toluene and 24 ml of water. Argon is bubbled through the solution for 30 minutes and then tris-(dibenzylidenacetone)-dipalladium(0) (7 mg, 0.01 mmol) and Sphos (12 mg, 0.03 mmol) are added. The solution is purged with argon for 15 minutes and then heated to reflux under inert atmosphere overnight. After cooling to room temperature, phases are separated, the organic phase collected and the solvent removed. The solid is then purified via column chromatography (silica, cyclohexane/ethyl acetate). The title product is isolated as yellow solid (yield: 0.25 g (97%)).

$^1$H-NMR (400 MHz, CD$_2$Cl$_2$): δ=8.62 (d, 3H, J=1.4 Hz), 8.24 (d, 3H, J=2.9 Hz), 8.04 (d, 3H, J=2.9 Hz), 7.41-7.18 (br m, 3H), 7.18-7.05 (m, 6H, J=7.5), 7.01 (s, 6H), 6.86 (d, 3H, J=7.4 Hz), 6.79 (t, 3H, J=7.6 Hz), 6.73 (d, 3H, J=7.6 Hz), 6.65-6.20 (br m, 6H), 3.05-2.75 (m, 9H), 1.31 (d, 6H, J=6.9 Hz), 1.18-1.14 (m, 18 H), 1.10 (d, 9H, J=6.9 Hz), 0.97 (d, 9H, J=6.9 Hz).

Synthesis Example 18

Synthesis of Complex (C-161)

a) Synthesis of 1-bromo-2-tert-butyl-benzene

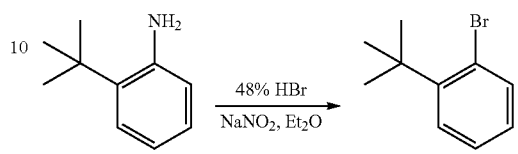

176 ml of 48% HBr solution (1.57 mol) are slowly added to 30.5 g (0.20 mol) of 2-tert-butylaniline at room temperature during 20 minutes. The beige suspension is cooled down to −56° C. and 23.8 g (0.34 mol) of sodium nitrite are added in small portions during 20 minutes and stirring continued at the same temperature during one hour. 250 ml of ice-cold diethyl ether are slowly added during 15 minutes and the temperature let slowly rising to −8° C. during two hours until no more gas evolved. The temperature is decreased again to −56° C. and 25 ml of water are added first followed by the addition of 118.5 g (0.41 mol) of sodium carbonate decahydrate giving a brown suspension. The temperature is let raising to room temperature during three hours with evolution of gas starting at −28° C. The resulting brown suspension is further stirred at room temperature during 16 hours. The water phase is separated and the organic phase three times washed with water, dried over sodium sulfate and concentrated under vacuum giving a brown oil. Further purification is done by chromatography (silica gel, heptane), followed by distillation of resulting oil under vacuum (97° C., 16 mbbar), giving the title product as colorless oil (yield: 17.9 g (41%)).

$^1$H-NMR (400 MHz, CDCl$_3$): δ=1.58 (s, 9 H), 7.07 (dt, 1 H), 7.29 (dt, 1 H), 7.50 (dd, 1 H), 7.64 (dd, 1 H).

b) Synthesis of (2-tert-butylphenyl)boronic acid

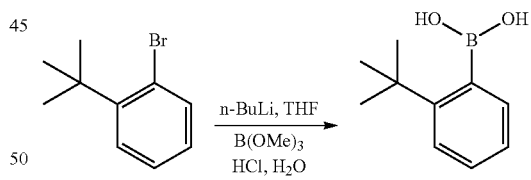

33.0 ml (87 mmol) of 2.7M n-butyl lithium solution in heptane is slowly treated at −73° C. with 16.0 g (72.8 mmol) of 1-bromo-2-tert-butyl-benzene in 100 ml of THF under argon atmosphere, letting the temperature not rise above −70° C. Addition is completed after 90 minutes, and stirring continued at −73° C. during one hour, giving a pink solution. 12.3 ml (109 mmol) of trimethylborate are slowly added during 75 minutes at −73° C., letting the temperature not rise above −70° C. Stirring is continued at −73° C. during one hour first, and the temperature let raising to room temperature during three hours. The colorless solution is further stirred at room temperature during 16 hours, followed by the slow addition of 30 ml of 10% aqueous hydrochloric acid solution during 10 minutes. Stirring is continued at room temperature during 30 minutes, and THF distilled off under vacuum at 80° C., followed by the addition of 50 ml of heptane and stirring at ice-bath temperature during one hour. The resulting suspension is filtered and the solid washed with 20 ml of heptane, giving the title product as an off-white solid (yield 7.7 g (58%)).

$^1$H-NMR (400 MHz, CDCl$_3$): δ=1.44 (s, 9 H), 4.67 (s, 2 H), 7.20 (td, 1 H), 7.32-7.40 (m, 2 H), 7.47 (d, 1 H).

c) Synthesis of Complex (C-161)

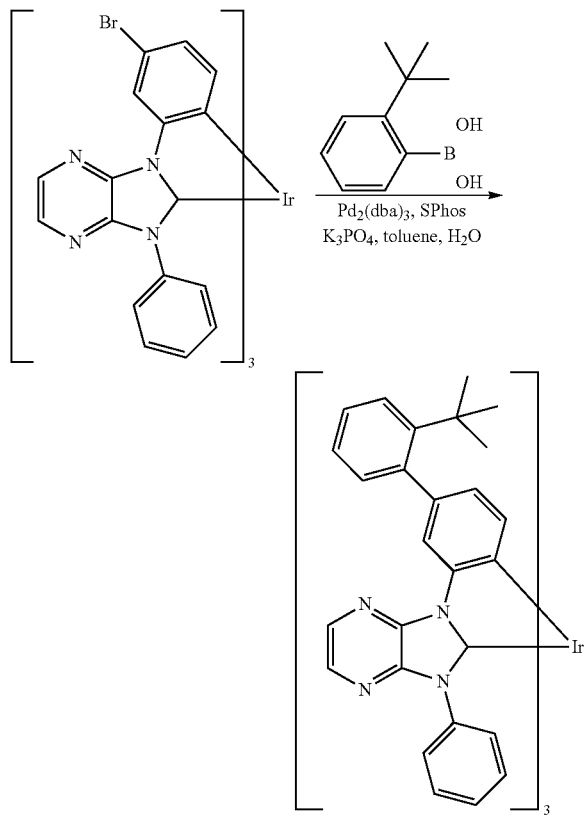

3.00 g (2.41 mmol) of bromo-complex product (HI-1) of synthesis example 6, 1.93 g (10.8 mmol) (2-tert-butylphenyl)boronic acid, and 3.07 g (14.5 mmol) of tripotassium phosphate are suspended under argon in 700 ml of toluene and 100 ml of water. The suspension is three times evacuated and backfilled with argon and treated with 110 mg (0.12 mmol) of tris(dibenzylideneacetone)dipalladium(0) and 180 mg (0.44 mmol) of 2-dicyclohexylphosphino-2',6'-dimethoxybiphenyl. The red-brown suspension is heated at 84° C. during three hours accompanied by a color change to yellow-brown, followed by direct filtration through a 3 cm layer of Hyflo® filter aid, and rinsing the filter aid with plenty of toluene. The toluene phase is separated and treated with 50 ml of 5% aqueous sodium cyanide solution and vigorously stirred during one hour, followed by the addition of 600 ml of dichloromethane. The mixture is further vigorously stirred at room temperature during 30 minutes, the organic phase separated and dried over sodium sulfate. 20 ml of ethanol are added and the mixture filtered through a 3 cm layer of silica gel followed by rinsing the silica gel with dichloromethane. The solution is concentrated under vacuum to ca. 50 ml volume and the precipitated solid separated. followed by drying under vacuum, giving the title product as a yellow solid (yield: 2.02 g (60%)).

$^1$H-NMR (400 MHz, CD$_2$Cl$_2$): δ=1.06-1.41 (broad signal, 27 H), 6.24-7.49 (very broad signal, 30 H), 7.59 (d, 3 H), 8.08 (d, 3 H), 8.28 (d, 3 H), 8.77 (br. s, 3 H).

APCI-LC-MS (positive, m/z): exact mass of C$_{81}$H$_{69}$IrN$_{12}$=1402.54. found 1403.2 [M+1]$^+$.

Synthesis Example 19

Synthesis of Complex (C-130)

a) Synthesis of (2-cyclohexylphenyl)boronic acid

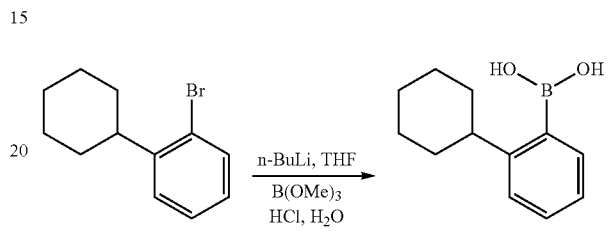

46.7 ml (117 mmol) of 2.5M n-butyl lithium solution in hexane is slowly treated at −73° C. with 24.0 g (97.3 mmol) of 1-bromo-2-cyclohexyl-benzene in 200 ml of THF under argon atmosphere, letting the temperature not rise above −70° C. Addition is completed after 90 minutes, giving a white suspension, and stirring continued at −73° C. during 30 minutes. 15.3 g (147 mmol) of trimethylborate are slowly added during 20 minutes at −73° C., letting the temperature not rise above −70° C. The colorless solution is further stirred at −74° C. during one hour, and the temperature let raising to room temperature during three hours. The colorless solution is further stirred at room temperature during 16 hours, followed by the slow addition of 30 ml of 10% aqueous hydrochloric acid solution during 15 minutes. Stirring is continued at room temperature during three hours, and the reaction mixture two times extracted with 100 ml of ethyl acetate. The organic phase is dried over sodium sulfate, concentrated under vacuum, and further purified by chromatography (silica gel, heptane/ethyl actate 4:1), giving the title product as an off-white solid (yield: 10.1 g (51%)).

$^1$H-NMR (400 MHz, CDCl$_3$): δ=1.24-2.11 (m, 10 H), 3.72-3.91 (m, 1 H), 7.33 (dt, 1 H), 7.49 (d, 1 H), 7.56 (dt, 1 H), 8.26 (dd, 1 H).

b) Synthesis of Complex (C-130)

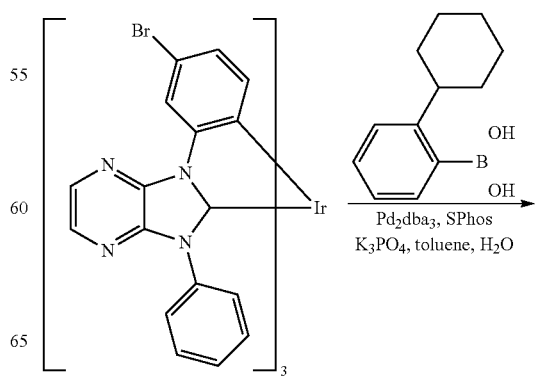

-continued

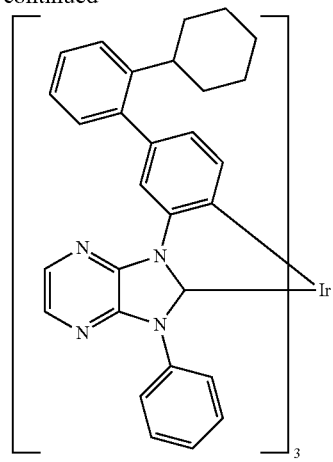

1.00 g (0.80 mmol) of bromo-complex product (HI-1) of synthesis example 6, 0.74 g (3.62 mmol) (2-cyclohexylphenyl)boronic acid, and 1.03 g (4.85 mmol) of tripotassium phosphate are suspended under argon in 250 ml of toluene and 50 ml of water. The suspension is three times evacuated and backfilled with argon and treated with 36.8 mg (0.04 mmol) of tris(dibenzylideneacetone)dipalladium(0) and 59.5 mg (0.14 mmol) of 2-dicyclohexylphosphino-2',6'-dimethoxybiphenyl. The yellow suspension is heated at 87° C. during three hours. The brown solution is cooled down to room temperature, followed by filtration and extraction of the organic phase with water (two times 100 ml). The organic phase is dried over sodium sulfate, concentrated under vacuum, and the resulting solid dissolved in dichloromethane. The solution is filtered through a 3 cm layer of silica gel followed by rinsing the silica gel layer with dichloromethane, and addition of 30 ml of ethanol. The combined eluents are diluted with 30 ml of ethanol and dichloromethane distilled off under vacuum. The resulting suspension is filtered and the solid washed with ethanol, and further purified by chromatography (silica gel, cyclohexane/ethyl acetate), giving the title product as an off-white solid (yield: 0.61 g (49%)).

$^1$H-NMR (400 MHz, $CD_2Cl_2$): δ=0.94-2.02 (m, 30 H), 2.97 (m, 3 H), 6.32-7.66 (very broad signal, 12 H), 6.84-6.97 (m, 9 H), 7.24 (dt, 3 H), 7.31-7.45 (m, 9 H), 8.10 (d, 3 H), 8.32 (d, 3 H), 8.85 (d, 3 H).

APCI-LC-MS (positive, m/z): exact mass of $C_{87}H_{75}IrN_{12}$=1480.59. found 1481.7 $[M+1]^+$.

Synthesis Example 20

Synthesis of Complex (C-128)

a) Synthesis of 2-isobutylaniline

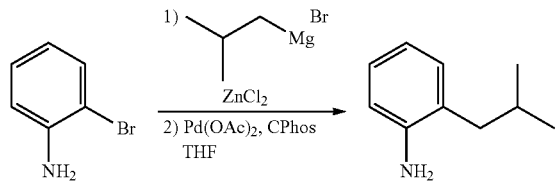

14.59 g (0.60 mol) of magnesium shavings are suspended under argon in 50 ml of tetrahydrofuran. 90.4 g (0.66 mol) of 1-bromo-2-methylpropane in 200 ml of tetrahydrofuran are slowly added during 45 minutes by carefully regulating the exothermy of the Grignard reaction by cooling with an ice-bath keeping the reaction temperature at a maximum of 55° C. The grey suspension is further stirred during 50 minutes and allowed to cool down to room temperature, giving a grey-brown solution. A colorless solution of 40.89 g (0.30 mol) of anhydrous zinc chloride in 200 ml of tetrahydrofuran is added during 10 minutes and the released exothermy carefully regulated with an ice-bath keeping the temperature at a maximum of 39° C. The resulting grey thick suspension is further stirred during 95 minutes until the temperature reaches 26° C., and slowly added during 30 minutes to a red-brown solution of 26.3 g (150 mmol) of 2-bromoaniline, 1.31 g (3.00 mmol) of 2-dicyclohexylphosphino-2',6'-bis(N,N-dimethylamino)biphenyl (=CPhos), 0.34 g (1.51 mmol) of palladium(II) acetate in 200 ml of THF, by carefully controlling the exothermy at a maximum of 32° C. using a water-bath. 50 ml of water are first carefully added under cooling keeping the temperature at a maximum of 33° C., followed by the addition of 500 ml of water and 200 ml of saturated ethylenediaminetetraacetic acid trisodium salt hydrate (EDTA-$Na_3$), and by stirring for 30 minutes. The suspension is filtered through a layer of Hyflo® filter aid and the filter aid rinsed with 500 ml of toluene. The organic phase is separated and washed with 100 ml of EDTA-$Na_3$ and 100 ml of saturated sodium chloride, followed by drying over sodium sulfate and concentration under vacuum. The oil is further distilled (120° C., 0.1 mbar) giving the title product as a colorless oil (yield: 16.5 g (74%)).

$^1$H-NMR (400 MHz, $CD_2Cl_2$): δ=1.00 (d, 6 H), 1.96 (dq, 1 H), 2.42 (d, 2 H), 3.64 (br. s, 2 H), 6.72 (m, 2 H), 7.04 (m, 2 H).

b) Synthesis of 1-bromo-2-isobutyl-benzene

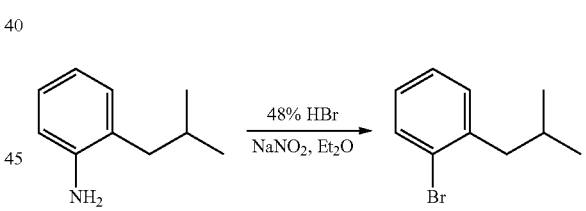

88.0 ml (0.79 mol) of 48% HBr solution are slowly added to 14.9 g (0.10 mol) of 2-isobutylaniline at room temperature during 15 minutes by carefully controlling the temperature. The white suspension is cooled down to −55° C. and 11.8 g (0.17 mol) of sodium nitrite are carefully added in small portions at a maximum temperature of −48° C. during 15 minutes. 100 ml of ice-cold diethyl ether are slowly added to the dark suspension during 15 minutes and the suspension further stirred during 90 minutes at −53° C. The temperature is slowly let rising first to 8° C. during 30 minutes carefully controlling the amount of gas evolution, then to room temperature during 75 minutes until no more gas evolved. The temperature is decreased again to −43° C. and 60 g (0.21 mol) of sodium carbonate decahydrate are added. The temperature is let raising to room temperature during one hour. The water phase is separated and the organic phase diluted with 100 ml of heptane, then three times washed with water, dried over sodium sulfate and concentrated under vacuum giving a dark oil. Further purification is done by chromatography (silica gel, heptane), giving the title product as colorless oil (yield: 5.3 g (25%)). GC-MS (CI): exact mass of $C_{10}H_{13}Br$=212.02. found 212.0 $[M]^+$.

c) Synthesis of (2-isobutylphenyl)boronic acid

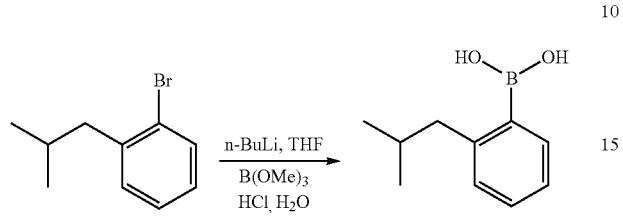

10.5 ml (28.4 mmol) of 2.7M n-butyl lithium solution in heptane is slowly treated at −70° C. with 5.00 g (23.5 mmol) of 1-bromo-2-isobutyl-benzene in 50 ml of THF under argon atmosphere, letting the temperature not rise above −70° C. Addition is completed after 30 minutes, and stirring continued at −72° C. during 30 minutes, giving a colorless solution. 3.66 g (35.2 mmol) of trimethylborate are slowly added during one hour at −72° C., letting the temperature not rise above −68° C. The temperature is let raising to room temperature during two hours, and stirring continued for one hour. The colorless solution is slowly treated with 5 ml of water and 20 ml of 10% aqueous hydrochloric acid solution. THF is distilled off under vacuum, followed by the addition of 30 ml of heptane, and stirring at ice-bath temperature during one hour. The resulting suspension is filtered and the solid washed with a small amount of cold heptane, then dried under vacuum, giving the title product as an off-white solid (yield 1.75 g (42%)).

$^1$H-NMR (400 MHz, CDCl$_3$): δ=0.93 (dd, 6 H), 1.89 (m, 1 H), 2.71, 3.11 (2d, 2 H), 6.32 (br. s, 2 H), 7.16-7.40 (m, 2 H), 7.45-7.58 (m, 1 H), 8.23 (dd, 1 H).

d) Synthesis of Complex (C-128)

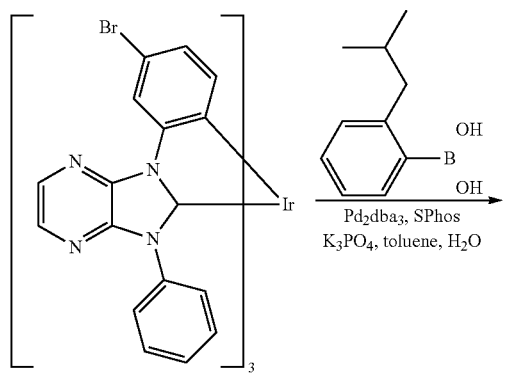

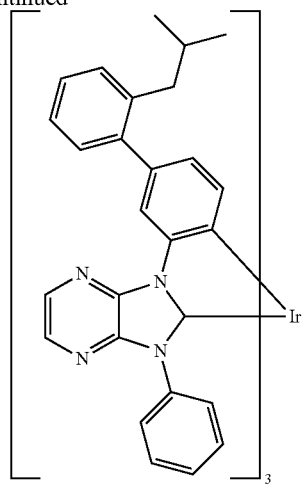

1.50 g (1.21 mmol) of bromo-complex product (HI-1) of synthesis example 6, 1.29 g (7.25 mmol) (2-isobutylphenyl) boronic acid, and 1.54 g (7.25 mmol) of tripotassium phosphate are suspended under argon in 70 ml of toluene and 20 ml of water. The suspension is three times evacuated and backfilled with argon and treated with 55 mg (0.06 mmol) of tris(dibenzylideneacetone)dipalladium(0) and 90 mg (0.22 mmol) of 2-dicyclohexylphosphino-2',6'-dimethoxybiphenyl. The light beige suspension is heated at 83° C. during 22 hours followed by the addition of 0.30 g (1.69 mmol) of (2-isobutylphenyl)boronic acid. Heating is continued for five hours, 100 ml of toluene are added, followed by direct filtration through a 3 cm layer of Hyflo® filter aid, and rinsing the filter aid with plenty of toluene. The toluene phase is separated and treated with 5% aqueous sodium cyanide solution, and the resulting mixture vigorously stirred during 30 minutes. The organic phase is separated and washed with water, dried over sodium sulfate and concentrated under vacuum. The yellow residue is dissolved in dichloromethane and filtered through a 3 cm layer of silica gel followed by rinsing the silica gel layer with a dichloromethane/ethanol 95:5 solvent mixture. Dichloromethane is distilled off under vacuum, the precipitated solid filtered off, washed with ethanol and dried under vacuum. The solid is further purified by chromatography (silica gel, dichloromethane/methanol), giving the title product as a light yellow solid (yield: 0.67 g (40%)).

$^1$H-NMR (400 MHz, CD$_2$Cl$_2$): δ=0.72 (d, 9 H), 0.73 (d, 9 H), 1.74 (m, 3 H), 2.62 (dd, 3 H), 6.12-7.78 (very broad signal, 12 H), 6.86 (m, 9 H), 7.29 (m, 9 H), 7.36 (m, 3 H), 8.10 (d, 3 H), 8.33 (d, 3 H), 8.83 (d, 3 H).

APCI-LC-MS (positive, m/z): exact mass of $C_{81}H_{69}IrN_{12}$=1402.54. found 1403.6 $[M+1]^+$.

Synthesis Example 21

Synthesis of Complex (A-6)

a) Synthesis of (2-ethyl-6-methyl-phenyl)boronic acid

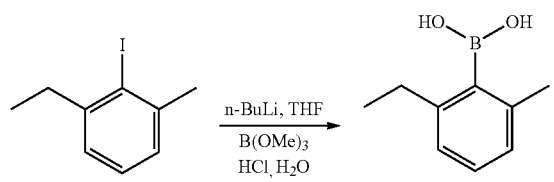

45.9 ml (115 mmol) of 2.5M n-butyl lithium solution in hexane is slowly treated at −73° C. with 24.0 g (23.5 mmol) of 1-ethyl-2-iodotoluene in 200 ml of THF under argon atmosphere, letting the temperature not rise above −70° C. Addition is completed after 90 minutes, and stirring continued at −73° C. during one hour, giving a white suspension. 15.9 ml (142 mmol) of trimethylborate are slowly added during one hour at −73° C., letting the temperature not rise above −70° C. The temperature is let raising to room temperature during two hours (aspect: clear and colorless solution), and stirring continued for 18 hours. The slightly turbid solution is slowly treated with water by intermittent cooling with an ice-bath, followed by the addition of 30 ml of 10% aqeuous hydrochloric acid solution at room temperature. The organic solvents are distilled off at a bath-temperature of 80° C. Heptane is added and the mixture stirred at 0° C. during one hour. The resulting suspension is filtered and the solid washed with a small amount of ice-cold water and heptane, followed by drying under vacuum, giving the title product as an off-white solid (yield: 12.9 g (81%)).

$^1$H-NMR (400 MHz, CDCl$_3$): δ=1.26 (t, 3 H), 2.38 (s, 3 H), 2.67 (q, 2 H), 5.03 (s, 2 H), 7.01 (d, 1 H), 7.05 (d, 1 H), 7.05 (d, 1 H), 7.21 (d, 1 H).

Synthesis of Complex (A-6)

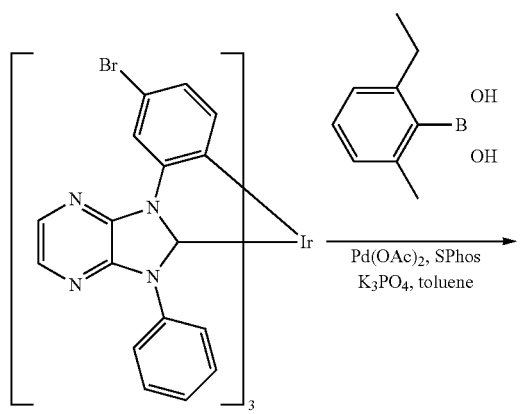

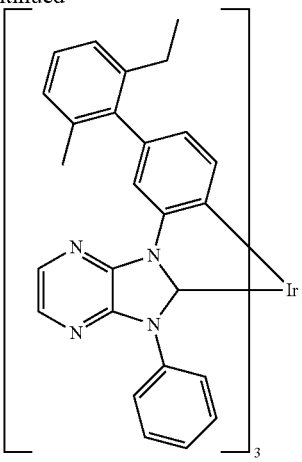

b) 1.00 g (0.80 mmol) of bromo-complex product (HI-1) of synthesis example 6, 0.59 g (3.60 mmol) (2-ethyl-6-methyl-phenyl)boronic acid, and 1.03 g (4.59 mmol) of tripotassium phosphate are suspended under argon in 50 ml of toluene. The suspension is three times evacuated and backfilled with argon and treated with 9.0 mg (0.04 mmol) of palladium(II) acetate and 33.0 mg (0.08 mmol) of 2-dicyclohexylphosphino-2',6'-dimethoxybiphenyl. The brown-yellow suspension is heated at 97° C. during 30 minutes, and five hours at 107° C. The brown suspension is cooled down to room temperature, diluted with dichloromethane and filtered over a 3 cm layer of silica gel followed by rinsing the silica gel with dichloromethane mixed with a small amount of methanol. Dichloromethane is removed under vacuum until precipitation started. The yellow suspension is filtered and the solid dried under vacuum. The isolated product (0.45 g) is reacted and worked up in a second step under the same reaction conditions, with 0.20 g of (2-ethyl-6-methyl-phenyl)boronic acid, 5 mg of palladium(II) acetate, 16 mg of 2-dicyclohexylphosphino-2',6'-dimethoxybiphenyl and 0.50 g of tripotassium phosphate in 20 ml toluene, giving the title product as a light yellow solid (yield: 0.38 g (35%)).

$^1$H-NMR (400 MHz, CD$_2$Cl$_2$): δ=1.03-1.14 (m, 9 H), 2.11, 2.19 (2s, 9 H), 2.39-2.50 (m, 3 H), 2.53-2.65 (m, 3 H), 6.17-7.84 (very broad signal, 12 H), 6.70-6.77 (m, 3 H), 6.81-6.95 (2 m, 6 H), 7.11-7.27 (m, 9 H), 8.09 (m, 3 H), 8.29 (m, 3 H), 8.64 (m, 3 H).

APCI-LC-MS (positive, m/z): exact mass of C$_{78}$H$_{63}$IrN$_{12}$=1360.49. found 1361.6 [M+1]$^+$.

Synthesis Example 22

Synthesis of Complex (A-2)

a) Synthesis of 2-bromo-1,3-diethyl-benzene

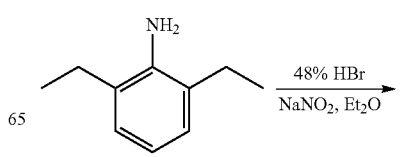

-continued

265 g (1.57 mol) of 48% HBr solution are slowly added to 30.5 g (0.20 mol) of 2,6-diethylaniline at room temperature during 15 minutes by carefully controlling the temperature. The beige suspension is cooled down to −55° C. and 23.8 g (0.34 mol) of sodium nitrite are carefully added in small portions at a maximum temperature of −48° C. during 40 minutes. The brown suspension is further stirred at −53° C. during 50 minutes. 250 ml of pre-cooled diethyl ether are slowly added during 15 minutes and the temperature slowly increased to −18° C. during 30 minutes until no more gas is released (careful control of gas evolution). The brown suspension is cooled down to −54° C. and slowly treated with 25 g of water and 119 g (0.41 mol) of sodium carbonate decahydrate. The temperature is let rising to room temperature during four hours carefully controlling the amount of gas released. The suspension is further stirred at room temperature during 19 hours. The organic phase is separated, extracted with water (2×100 ml), dried over sodium sulfated and concentrated under vacuum. The crude product is further purified by chromatography (silica gel, heptane) giving the title product as a yellow oil (yield: 36.3 g (83%)).

$^1$H-NMR (400 MHz, CD$_2$Cl$_2$): δ=1.35 (t, 6 H), 2.91 (q, 4 H), 7.17 (d, 2 H), 7.27 (dd, 1 H).

b) Synthesis of (2,6-diethylphenyl)boronic acid

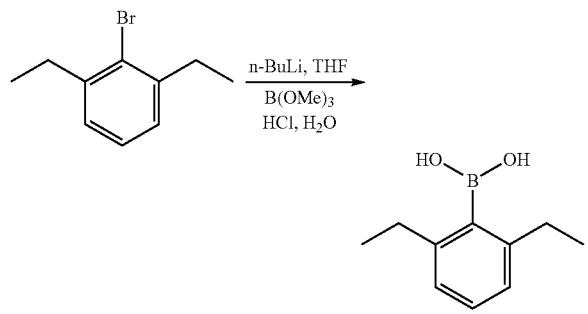

48.0 ml (0.12 mol) of 2.7M n-butyl lithium solution in heptane is slowly treated at −73° C. with 22.0 g (0.10 mol) of 2-bromo-1,3-diethyl-benzene in 200 ml of THF under argon atmosphere, letting the temperature not rise above −70° C. Addition is completed after 70 minutes, and stirring continued at −73° C. during one hour, giving a white suspension. 15.7 g (0.15 mol) of trimethylborate are slowly added during 25 minutes at −73° C., letting the temperature not rise above −70° C. Stirring is continued at −73° C. during one hour first, and the temperature let raising to room temperature during two hours. The colorless solution is further stirred at room temperature during 16 hours, followed by the slow addition of 30 ml of 10% aqueous hydrochloric acid solution during 15 minutes. Stirring is continued at room temperature during 30 minutes, and THF distilled off under vacuum at 80° C., followed by the addition of 50 ml of heptane and stirring at ice-bath temperature during one hour. The resulting suspension is filtered and the solid washed with 30 ml of heptane, giving the title product as an off-white solid.

$^1$H-NMR (400 MHz, CDCl$_3$): δ=1.27 (t, 6 H), 2.69 (q, 4 H), 4.73 (s, 2 H), 7.07 (d, 2 H), 7.27 (t, 1 H).

c) Synthesis of Complex (A-2)

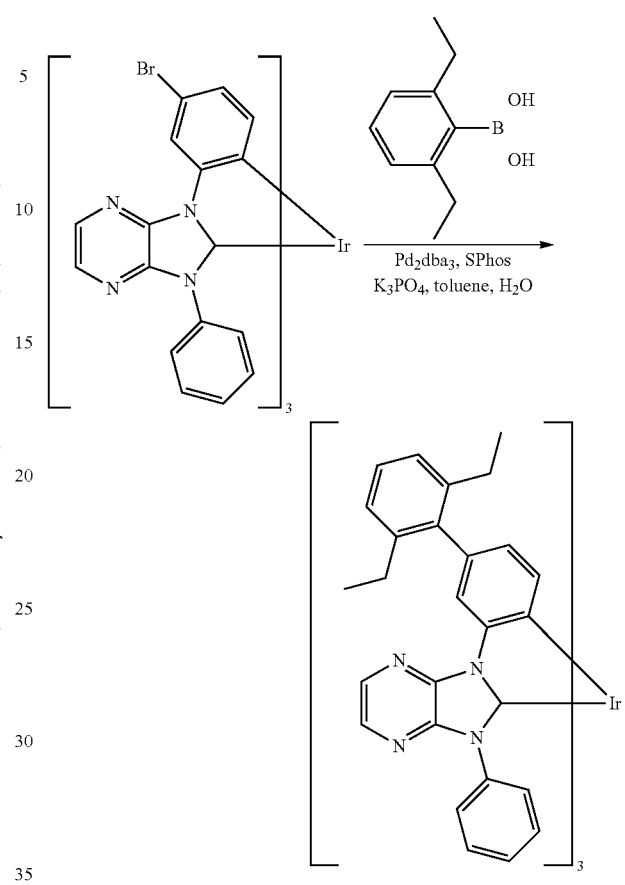

1.00 g (0.80 mmol) of bromo-complex product (HI-1) of synthesis example 6, 645 mg (3.62 mmol) (2,6-diethylphenyl)boronic acid, and 1.03 g (4.83 mmol) of tripotassium phosphate are suspended under argon in 250 ml of toluene and 50 ml of water. The suspension is three times evacuated and backfilled with argon and treated with 37 mg (0.04 mmol) of tris(dibenzylideneacetone)dipalladium(0) and 60 mg (0.15 mmol) of 2-dicyclohexylphosphino-2',6'-dimethoxybiphenyl. The greenish brown suspension is heated at 87° C. during six hours, directly filtered through a 3 cm layer of Hyflo® filter aid, and the filter aid rinsed with plenty of toluene. The organic phase is extracted with water (2×100 ml), dried over sodium sulfate and concentrated under vacuum. The solid residue is dissolved in dichloromethane and filtered through a 3 cm layer of silica gel followed by rinsing the silica gel with dichloromethane. The combined filtrates are treated with 30 ml of ethanol and dichloromethane distilled off under vacuum. The suspension is filtered and the solid washed with ethanol and further purified by chromatography (silica gel, cyclohexane/ethyl acetate). The product fractions are collected and concentrated under vacuum until precipitation occurred. The solid is separated and washed with cyclohexane and ethanol, further dried under vacuum, giving the title product as a light yellow solid (yield: 0.81 g (72%)).

$^1$H-NMR (400 MHz, CD$_2$Cl$_2$): δ=1.04-1.15 (m, 18 H), 2.37-2.51 (m, 6 H), 2.51-2.65 (m, 6 H), 6.23-7.70 (very broad signal, 12 H), 6.76 (dd, 3 H), 6.85 (t, 3 H), 6.91 (d, 3 H), 7.18 (t, 6 H), 7.28 (t, 3 H), 8.09 (d, 3 H), 8.29 (d, 3 H), 8.68 (d, 3 H).

APCI-LC-MS (positive, m/z): exact mass of $C_{81}H_{69}IrN_{12}$=1402.54. found 1403.6 [M+1]$^+$.

Synthesis Example 23

Synthesis of Bromo-Complex Intermediate (HI-4)

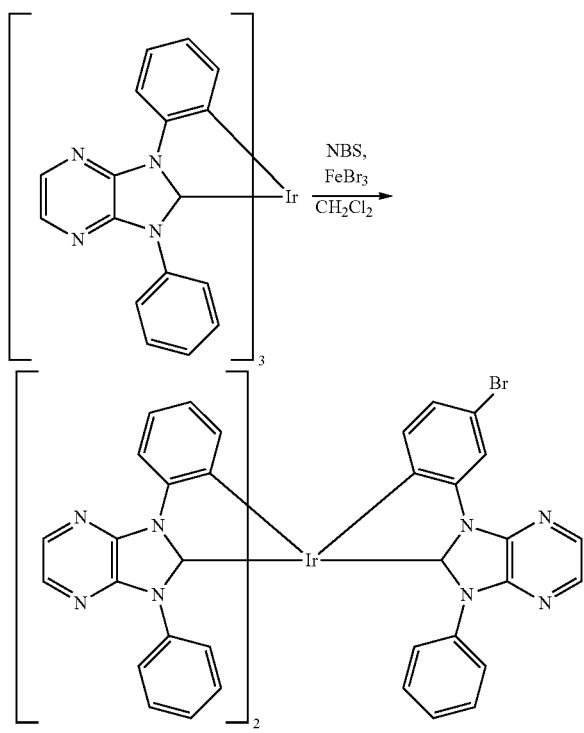

1.00 g (1.0 mmol) of iridium complex (see synthesis in WO2011/073149, example fac-EM1) are dissolved in 100 ml of dichloromethane at room temperature under argon atmosphere. 1.60 mg (0.01 mmol) of iron(III) bromide are added first followed by the slow addition of 178 mg (1.0 mmol) of N-bromosuccinimide in 100 ml of dichloromethane during 90 minutes. Stirring is continued during 16 hours. 20 ml of ethanol are added and the mixture filtered through a 3 cm layer of silica gel, followed by rinsing the silica gel with dichloromethane/EtOH 95:5 eluent. The combined eluents are concentrated under vacuum and further purified by chromatography (silica gel, dichloromethane/ethyl acetate). The combined product fractions are concentrated under vacuum and the resulting solid dissolved in dichloromethane, followed by the addition of ethanol. Dichloromethane is removed under vacuum and the resulting precipitate filtered and further washed with ethanol, giving the title product as a yellow solid (yield: 0.6 g (56%)).

$^1$H-NMR (400 MHz, CD$_2$Cl$_2$): δ=6.09-7.57 (very broad signal, 12 H), 6.59 (d, 1 H), 6.65-6.74 (m, 3 H), 6.83-6.92 (m, 3 H), 6.96 (dd, 1 H), 7.17-7.25 (m, 3 H), 8.11 (m, 3 H), 8.38 (m, 3 H), 8.81 (d, 2 H), 8.95 (d, 1 H).

APCI-LC-MS (positive, m/z): exact mass of C$_{51}$H$_{32}$BrIrN$_{12}$=1084.17. found 1085.3 [M+1]$^+$.

Synthesis Example 24

Synthesis of Complex (X-1)

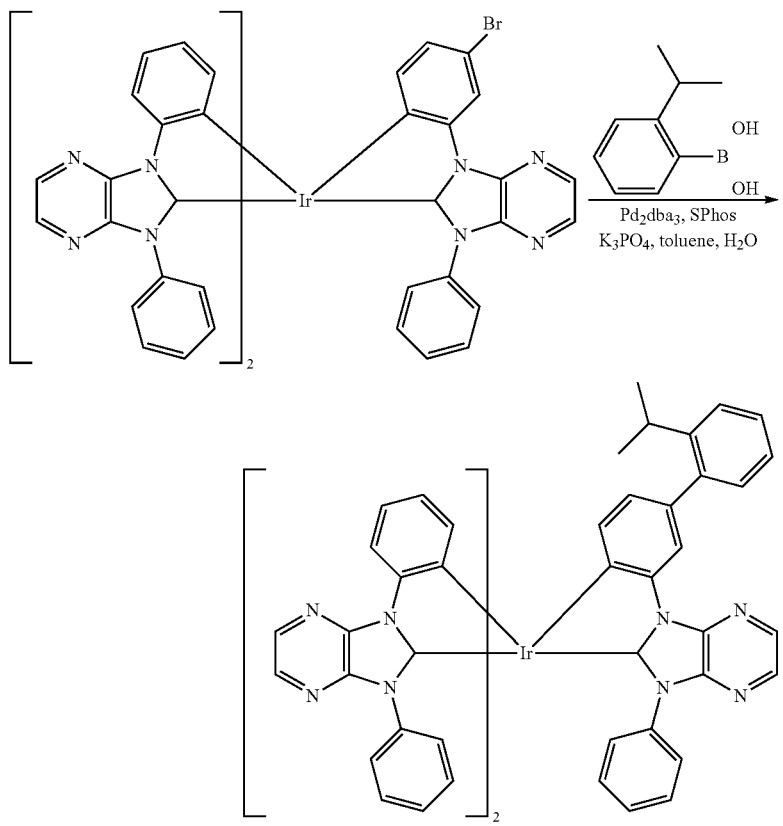

150 mg (0.14 mmol) of the bromo complex intermediate (HI-4) of synthesis example 23 are reacted according to synthesis example 20 d) (PM2119-isobutyl) with 43 mg (0.26 mmol) of (2-isopropylphenyl)boronic acid, 170 mg (0.80 mmol) of tripotassium phosphate, 6 mg (0.007 mmol) of tris(dibenzylideneacetone)dipalladium(0), and 10 mg (0.02 mmol) of 2-dicyclohexylphosphino-2',6'-dimethoxybiphenyl, in 20 ml of toluene and 5 ml of water, with a reaction time of four hours at 88° C. The resulting brown suspension is diluted with 10 ml of toluene and the organic phase stirred with 5 ml of 5% aqueous sodium cyanide solution. The light yellow organic phase is separated and filtered through a 3 cm layer of silica gel followed by rinsing the silica gel with dichloromethane. The combined eluents are concentrated under vacuum and the resulting solid three times dissolved in 20 ml of dichloromethane and 3 ml of ethyl acetate followed by removal of dichloromethane under vacuum until precipitation of a solid is each time initiated. The resulting solid is washed with heptane and dried under vacuum, giving the title product as a light yellow solid (yield: 122 mg (78%)).

$^1$H-NMR (400 MHz, CD$_2$Cl$_2$): δ=1.18 (d, 3 H), 1.27 (d, 3 H), 3.32 (m, 1 H), 6.21-7.58 (m and very broad signal, 27 H), 8.06 (d, 1 H), 8.10 (m, 2 H), 8.28 (d, 1 H), 8.37 (dd, 2 H), 8.81 (m, 3 H).

APCI-LC-MS (positive, m/z): exact mass of C$_{60}$H$_{43}$IrN$_{12}$=1124.34 found 1125.5 [M+1]$^+$.

Synthesis Example 25

Synthesis of Complex (X-2)

200 mg (0.18 mmol) of the of the bromo complex intermediate (HI-4) of synthesis example 23 are reacted according to synthesis example 14 with 69 mg (0.36 mmol) of (2-trifluoromethylphenyl)boronic acid, 230 mg (1.08 mmol) of tripotassium phosphate, 2 mg (0.009 mmol) of palladium(II) acetate, and 8 mg (0.02 mmol) of 2-dicyclohexylphosphino-2',6'-dimethoxybiphenyl, in 20 ml of toluene, with a reaction time of five hours at 93° C. The resulting brown suspension is diluted with 10 ml of and filtered through a 3 cm layer of silica gel followed by rinsing the silica gel with dichloromethane/ethyl acetate 9:1 mixture. The combined eluents are concentrated under vacuum and the resulting yellow dissolved in 30 ml of dichloromethane and 10 ml of ethanol. Dichloromethan is removed under vacuum until precipitation starts, giving the title product as a light yellow solid (yield: 64 mg (30%)).

$^1$H-NMR (400 MHz, CD$_2$Cl$_2$): δ=6.09-7.68 (br. signal, 12 H), 6.73 (m, 2 H), 6.78-6.95 (m, 7 H), 7.21 (m, 2 H), 7.52 (m, 2 H), 7.63 (d, 1 H), 7.80 (d, 1 H), 8.07 (d, 1 H), 8.11 (t, 2 H), 8.28 (d, 1 H), 8.37 (dd, 2 H), 8.78 (dd, 1 H), 8.83 (m, 2 H).

APCI-LC-MS (positive, m/z): exact mass of C$_{58}$H$_{36}$F$_3$IrN$_{12}$=1150.28 found 1551.4 [M+1]$^+$.

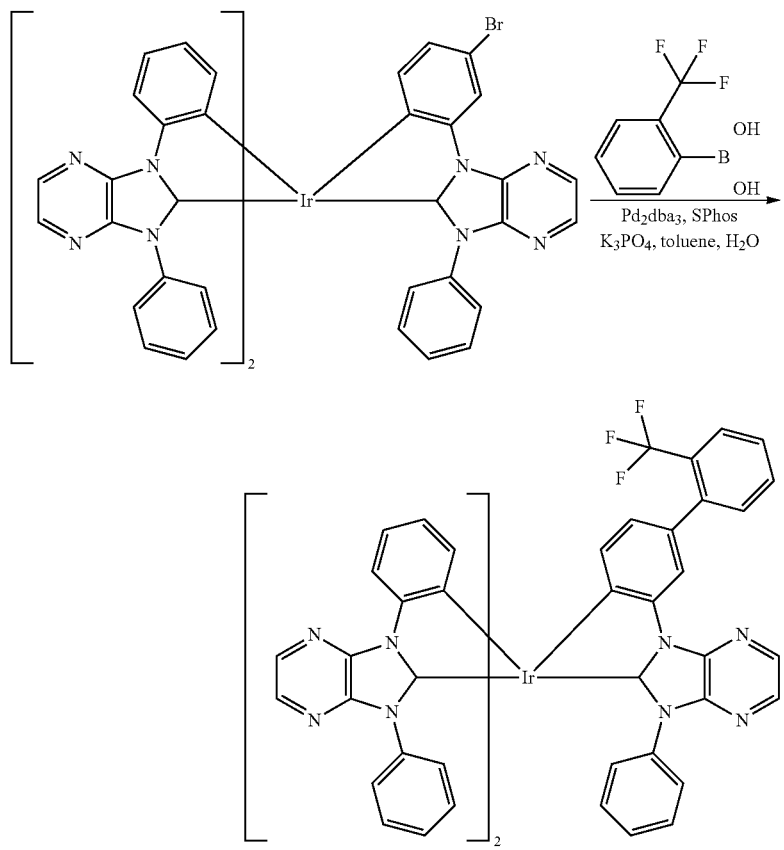

Synthesis Example 26

Synthesis of Bromo-Complex Intermediate (HI-5)

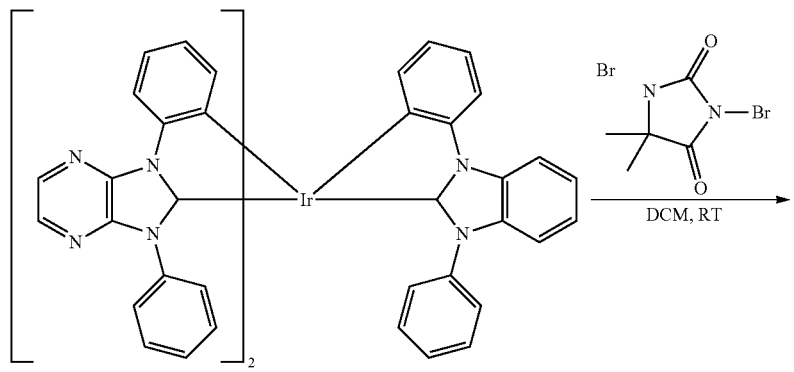

0.50 g (0.50 mmol) of iridium complex (see synthesis in WO2011/073149, complex Em8) and 0.43 g (1.50 mmol) of 1,3-dibromo-5,5-dimethylhydantoin are suspended in 100 ml dichloromethane at room temperature. The yellow solution is stirred during 23 hours and ethanol is added. Dichloromethane is removed under vacuum leading to precipitation of the product. The solid is separated and dried under vacuum, giving the title product as a light yellow solid (yield: 0.53 g (86%)).

$^1$H-NMR (400 MHz, CDCl$_3$): δ=6.02-7.63 (broad signal, 8 H), 6.31 (d, 1 H), 6.39 (d, 1 H), 6.43 (m, 2 H), 6.53 (d, 1 H), 6.59 (dd, 2 H), 6.83 (m, 3H), 6.97 (m, 3 H), 7.11 (t, 1 H), 7.26 (dd, 1 H), 7.38 (m, 1 H), 8.10 (m, 4 H), 8.32 (d, 1 H), 8.36 (d, 1 H), 8.88 (d, 1 H), 8.96 (d, 1 H).

Synthesis Example 27

Synthesis of Complex (J-113)

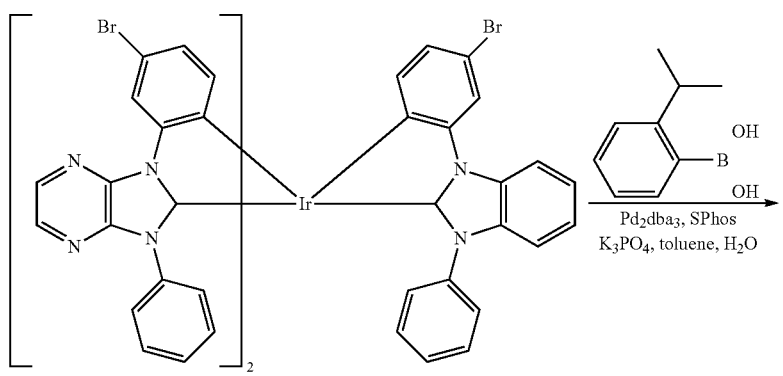

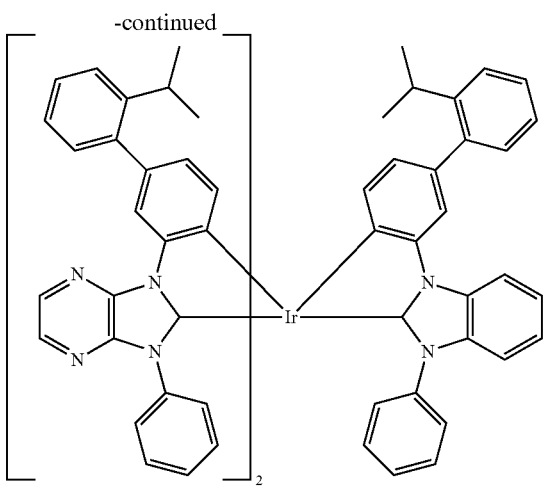

300 mg (0.24 mmol) of the bromo complex intermediate (HI-5) of synthesis example 26 are reacted according to synthesis example 20 d) with 178 mg (1.09 mmol) of (2-isopropylphenyl)boronic acid, 307 mg (1.45 mmol) of tripotassium phosphate, 11 mg (0.012 mmol) of tris(dibenzylideneacetone)dipalladium(0), and 18 mg (0.04 mmol) of 2-dicyclohexylphosphino-2',6'-dimethoxybiphenyl, in 30 ml of toluene and 5 ml of water, with a reaction time of four hours at 88° C. The resulting brown suspension is diluted with 10 ml of dichloromethane and the organic phase stirred with 5 ml of 5% aqueous sodium cyanide solution. The light yellow organic phase is separated and filtered through a 3 cm layer of silica gel followed by rinsing the silica gel with dichloromethane. The combined eluents are concentrated under vacuum and the resulting solid separated and washed with ethanol and heptane, followed by drying under vacuum, giving the title product as a light yellow solid (yield: 221 mg (67%)).

$^1$H-NMR (400 MHz, CDCl$_3$): δ=1.19 (m, 9 H), 1.27 (m, 9 H), 3.36 (m, 3 H), 6.30-7.70 (broad signal and m, 36 H), 7.94 (d, 1 H), 8.04 (d, 1 H), 8.08 (d, 1 H), 8.15 (d, 1 H), 8.23 (d, 1 H), 8.77 (d, 1 H), 8.84 (d, 1 H).

Synthesis Example 28

Synthesis of Complex (L-1)

500 mg (0.40 mmol) of the bromo complex intermediate (HI-5) of synthesis example 26 are reacted according to synthesis example 20 d) with 460 mg (2.42 mmol) of (2-trifluoromethylphenyl)boronic acid, 513 mg (2.42 mmol) of tripotassium phosphate, 18.5 mg (0.020 mmol) of tris(dibenzylideneacetone)dipalladium(0), and 30 mg (0.07 mmol) of 2-dicyclohexylphosphino-2',6'-dimethoxybiphenyl, in 40 ml of toluene and 10 ml of water, with a reaction time of five hours at 88° C. The resulting brown suspension is diluted with 30 ml of dichloromethane and the organic phase stirred with 5 ml of 5% aqueous sodium cyanide solution. The organic phase is separated and concentrated under vacuum. The solid residue is dissolved in 20 ml of dichloromethane and 10 ml of toluene. Dichloromethane is distilled off and the suspension filtered, the solid washed with ethanol and heptane and dried under vacuum, giving the title product as a light yellow solid (yield: 476 mg (82%)).

$^1$H-NMR (400 MHz, CD$_2$Cl$_2$): δ=6.15-7.74 (very broad signal, 8 H), 6.40 (d, 1 H), 6.52 (d, 1 H), 6.59 (t, 1 H), 6.74-6.96 (m, 8 H), 7.16 (m, 3 H), 7.31 (m, 3 H), 7.46-7.70 (m, 8 H), 7.90 (m, 3 H), 8.08 (m, 4 H), 8.27 (dd, 2 H), 8.78 (s, 1 H), 8.84 (s, 1 H).

APCI-LC-MS (positive, m/z): exact mass of C$_{74}$H$_{44}$F$_9$IrN$_{10}$=1436.32. found 1437.4 [M+1]$^+$.

Synthesis Example 29

Synthesis of Complex (Y-1)

a) Synthesis of N2,N3-bis(4-ethylphenyl)pyrazine-2,3-diamine

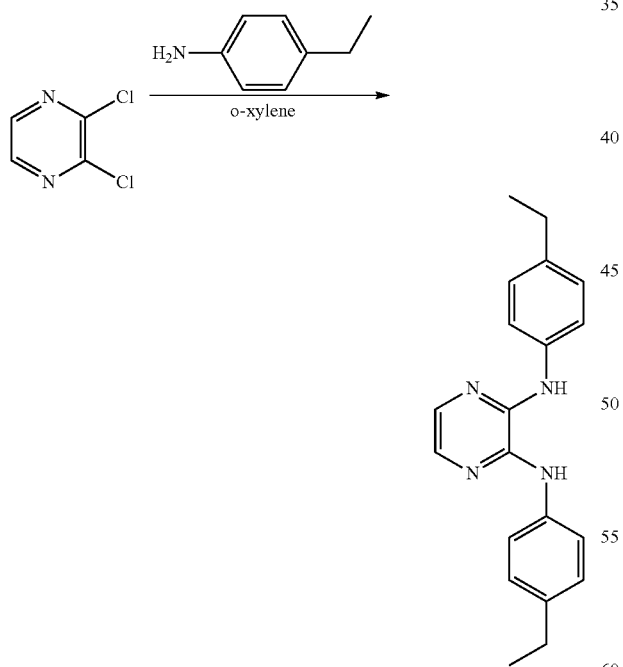

27.9 g (0.19 mol) of 2,3-dichloropyrazine and 50.0 g (0.41 mol) of 4-ethylaniline in 200 ml of mesitylene are heated at 164° C. during three hours. The black suspension is cooled down to room temperature, diluted with 50 ml of toluene and stirring continued during 90 minutes. The suspension is filtered and the solid washed with toluene and heptane. The solid is suspended in 500 ml of water, and 200 ml of 25% aqueous ammonia solution are added under stirring, and stirring continued for 30 minutes. The suspension is filtered and the solid washed with water (2×250 ml), followed by washing with cyclohexane (2×200 ml). The solid is suspended in 400 ml of cyclohexane and heated under reflux during one hour, cooled down to room temperature and further stirred during one hour. The suspension is filtered and washed with hexane and dried under vacuum, giving the title product as a light yellow solid (yield: 28.3 g (47%)).

$^1$H-NMR (400 MHz, d$_4$-MeOD): δ=1.25 (t, 6 H), 2.64 (q, 4 H), 7.18 (d, 4 H), 7.46 (d, 6 H).

b) Synthesis of [3-(4-ethylanilino)pyrazin-2-yl]-(4-ethylphenyl)ammonium chloride

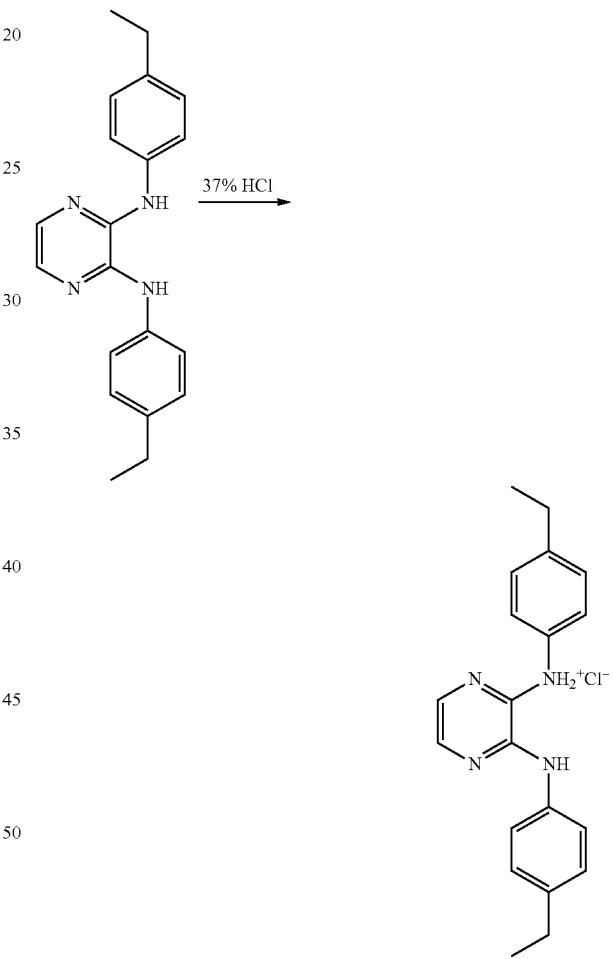

A yellow suspension of 28.3 g (88.9 mmol) of N2,N3-bis(4-ethylphenyl)pyrazine-2,3-diamine and 300 ml of 37% aqueous hydrochloric acid solution is stirred at room temperature during one hour. The suspension is diluted with water and stirring continued. The suspension is filtered and the solid washed with 100 ml of water. The yellow solid is three times suspended with 100 ml of cyclohexane and filtered, followed by drying on the filter under vacuum first, followed by drying at room temperature in the vacuum oven during two days, giving the title product as a light yellow solid (yield: 41.3 g, still wet).

$^1$H-NMR (400 MHz, d$_6$-DMSO): δ=1.20 (t, 6 H), 2.61 (q, 4 H), 7.24 (d, 4 H), 7.41 (s, 2 H), 7.63 (d, 4 H), 10.08 (br. s, 2 H).

c) Synthesis of 2-ethoxy-1,3-bis(4-ethylphenyl)-2H-imidazo[4,5-b]pyrazine

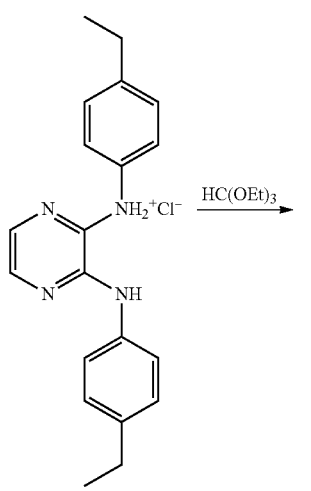

40.0 g (ca. 88 mmol, still including residual water) of [3-(4-ethylanilino)pyrazin-2-yl]-(4-ethylphenyl)ammonium chloride and 300 ml (1.8 mol) of triethyl orthoformate heated under argon at 100° C. during 18 hours. The light orange solution is cooled down to room temperature and filtered. The filrated is concentrated under vacuum giving and the resulting suspension filtered and washed with heptane, giving the title product as a light pink solid (yield: 23.7 g).

$^1$H-NMR (300 MHz, d$_6$-DMSO): δ=0.89 (t, 3 H), 1.20 (t, 6 H), 2.61 (q, 4 H), 3.16 (q, 2 H), 7.29 (d, 4 H), 7.47 (s, 2 H), 7.67 (s, 1 H), 7.93 (m, 4 H).

d) Synthesis of Complex Intermediate (CI-1)

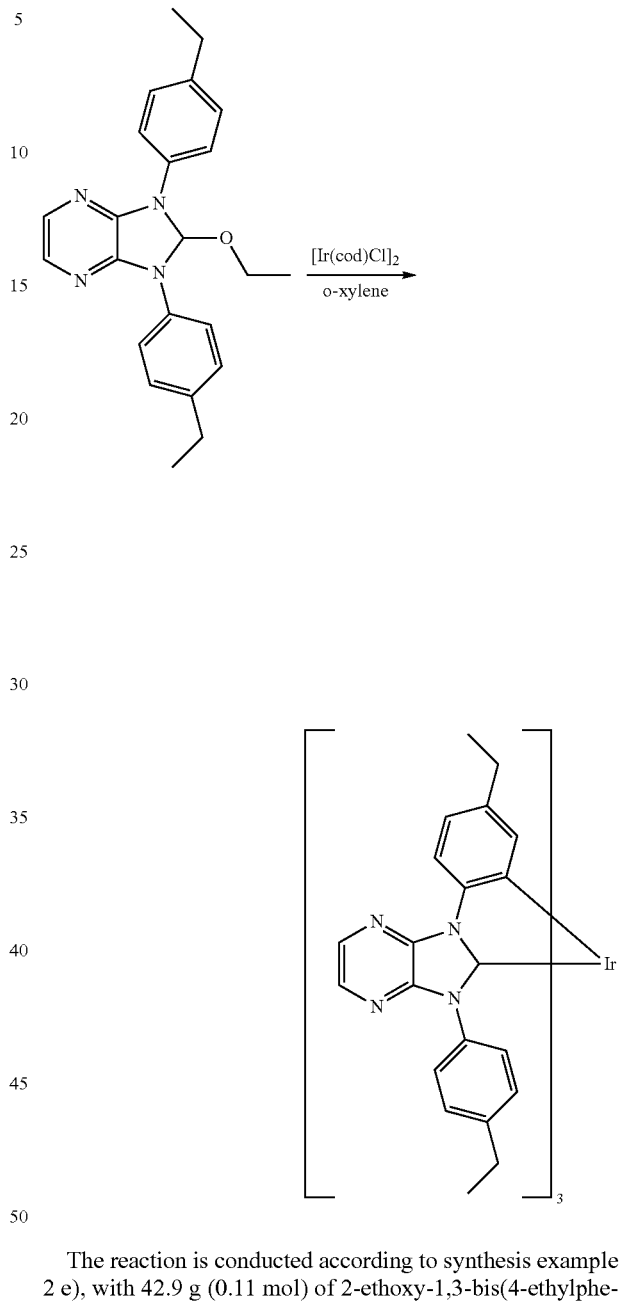

The reaction is conducted according to synthesis example 2 e), with 42.9 g (0.11 mol) of 2-ethoxy-1,3-bis(4-ethylphenyl)-2H-imidazo[4,5-b]pyrazine, 7.00 g (10.4 mmol) of chloro(1,5-cyclooctadiene)iridium(I) dimer in 400 ml of o-xylene, at 138° C. during eight hours. The resulting dark suspension is poured into 1800 ml of methanol and stirred during 30 minutes. The suspension is filtered and the solid washed with 150 ml of methanol. The solid is dissolved in dichloromethane and filtered over silica gel (2×8 cm filter) using a dichloromethane/toluene eluent with a small amount of added ethanol. The combined filtrates are diluted with 300 ml of methanol until precipitation started. The suspension is stirred for one hour, then filtered and the solid washed with methanol (3×15 ml), followed by drying under vacuum, giving the title product as a light yellow solid (yield: 8.49 g (35%)).

e) Synthesis of Bromo-Complex Intermediate (HI-6)

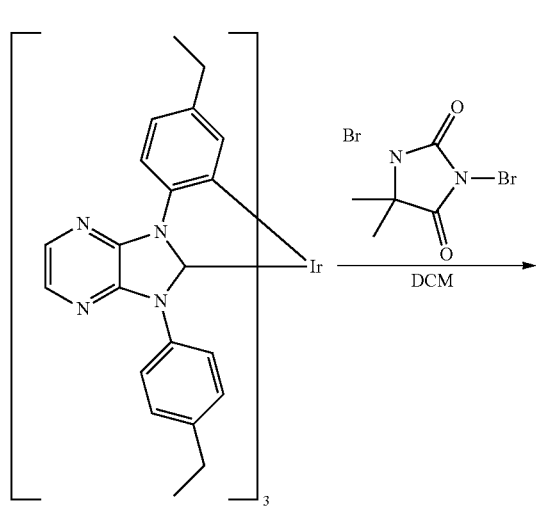

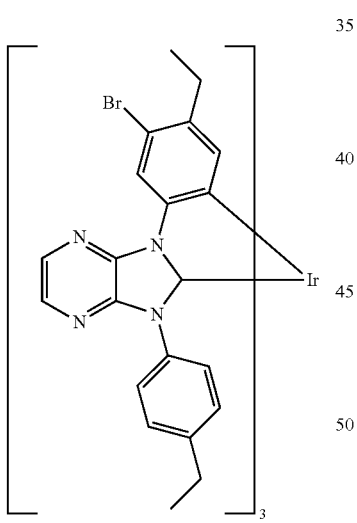

The reaction is conducted according to synthesis example 8, with 1.30 g (1.11 mmol) of the product of the synthesis example 29 d), 483 mg (1.69 mmol) of 1,3-dibromo-5,5-dimethylhydantoin in 100 ml of dichloromethane at 0° C. during 17 hours, giving the title product as a light yellow solid (yield: 1.52 g (97%)).

$^1$H-NMR (400 MHz, CD$_2$Cl$_2$): δ=1.00 (m, 18 H), 2.28 (q, 6 H), 2.42 (m, 3 H), 2.66 (m, 3 H), 5.83-7.72 (2 very broad signals, 12 H), 6.55 (s, 3 H), 8.10 (d, 3 H), 8.39 (d, 3 H), 8.92 (s, 3 H).

f) Synthesis of Complex (Y-1)

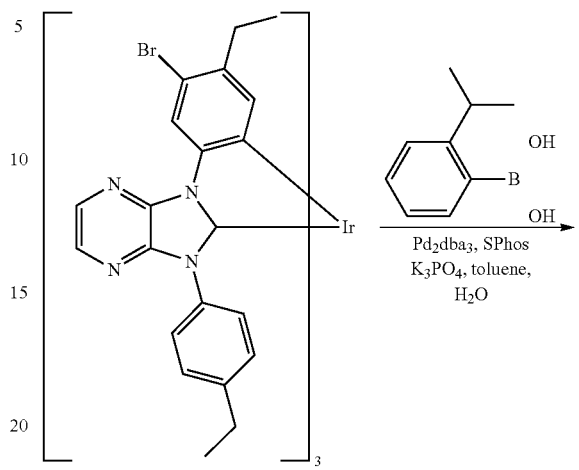

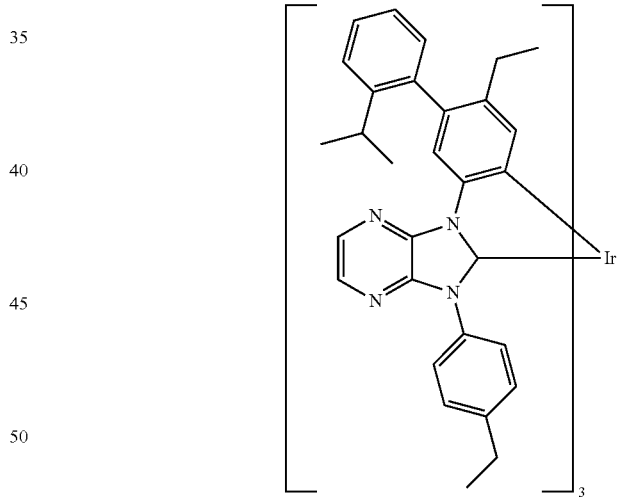

760 mg (0.54 mmol) of the product HI-6 of synthesis example 29 e) are reacted according to synthesis example 20 d) with 398 mg (2.43 mmol) of (2-isopropylphenyl)boronic acid, 686 mg (3.23 mmol) of tripotassium phosphate, 24.7 mg (0.03 mmol) of tris(dibenzylideneacetone)dipalladium (0), and 39.8 mg (0.10 mmol) of 2-dicyclohexylphosphino-2',6'-dimethoxybiphenyl, in 200 ml of toluene and 40 ml of water, with a reaction time of 17 hours at 98° C., giving the title product as a light yellow solid (yield: 0.49 g (59%)).

$^1$H-NMR (400 MHz, CD$_2$Cl$_2$): δ=0.90 (m, 9 H), 1.01 (m, 9 H), 1.19 (m, 18 H), 2.09-2.38 (m, 12 H), 2.85, 3.07 (2m, 3 H), 5.98-7.68 (very broad signal, 9 H), 6.51 (br. s, 3 H), 6.76 (m, 3 H), 7.23 (m, 6 H), 7.41 (m, 6 H), 8.05 (m, 3 H), 8.29 (m, 3 H), 8.54 (m, 3 H).

Synthesis Example 30

Synthesis of Complex (Y-2)

a) Synthesis of N2,N3-bis(4-isopropylphenyl)pyrazine-2,3-diamine

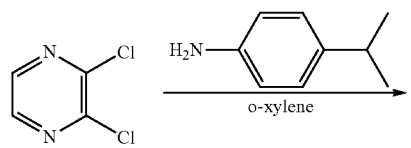

16.0 g (0.11 mol) of 2,3-dichloropyrazine are reacted according to synthesis example 29 a) with 32.0 g (0.24 mol) of 4-isopropylaniline in 200 ml of o-xylene under reflux during 12 hours, giving after workup and purification the title product as a yellow solid (yield: 34.5 g (93%)).

$^1$H-NMR (300 MHz, d$_4$-MeOD): δ=1.14 (d, 12 H), 4.46 (s, 2 H), 7.08 (d, 4 H), 7.34 (m, 6 H).

b) Synthesis of [3-(4-isopropylanilino)pyrazin-2-yl]-(4-isopropylphenyl)ammonium chloride

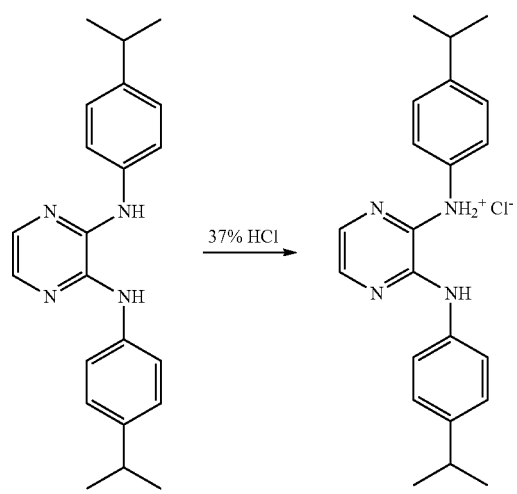

34.5 g (0.10 mol) of N2,N3-bis(4-isopropylphenyl)pyrazine-2,3-diamine are reacted according to synthesis example 29 b) with 300 ml of 37% aqueous hydrochloric, giving the title product as a light yellow solid (yield: 34.2 g, still wet)

$^1$H-NMR (400 MHz, d$_6$-DMSO): δ=1.23 (d, 12 H), 2.91 (m, 2 H), 7.32 (d, 4 H), 7.36 (s, 2 H), 7.62 (d, 4 H), 10.78 (br. s, 2 H).

c) Synthesis of 2-ethoxy-1,3-bis(4-isopropylphenyl)-2H-imidazo[4,5-b]pyrazine

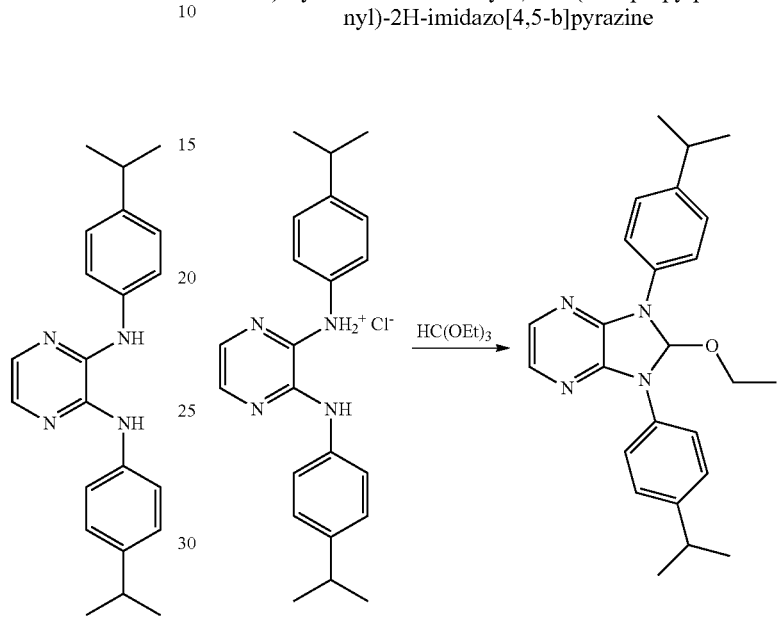

34.2 g (ca. 89 mmol, still including some residual water) of [3-(4-isopropylanilino)-pyrazin-2-yl]-(4-isopropylphenyl)ammonium chloride are reacted are reacted according to synthesis example 29 c) with 300 ml (1.8 mol) of triethyl orthoformate heated under argon at 100° C. during 18 hours, giving the title product as a light yellow solid (yield: 26.9 g (75%)).

$^1$H-NMR (300 MHz, d$_6$-DMSO): δ=0.91 (t, 3 H), 1.23 (d, 12 H), 2.91 (m, 2 H), 3.18 (m, 2 H), 7.34 (d, 4 H), 7.47 (s, 2 H), 7.67 (s, 1 H), 7.93 (d, 4 H).

d) Synthesis of Complex Intermediate (CI-2)

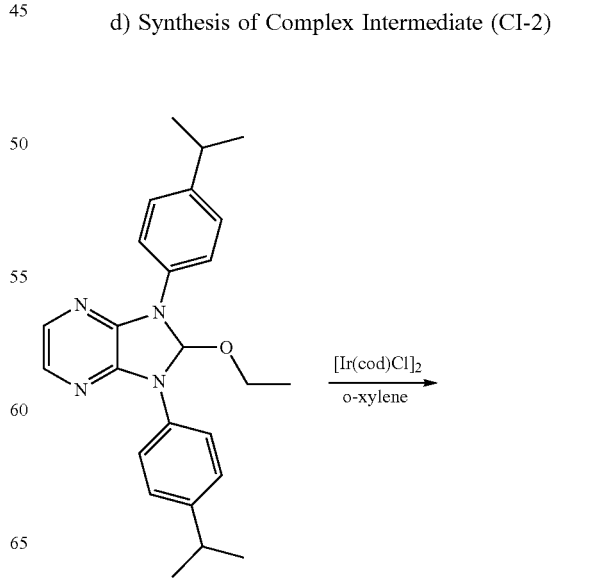

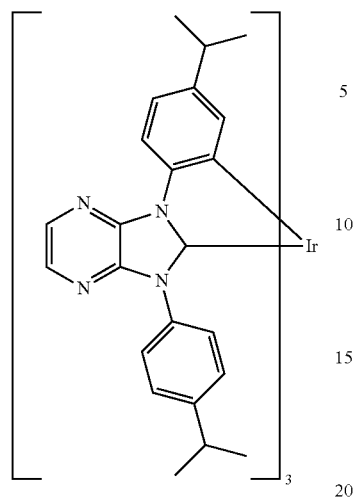

5.75 g (14.3 mmol) of 2-ethoxy-1,3-bis(4-isopropylphenyl)-2H-imidazo[4,5-b]pyrazine are reacted according to synthesis example 29 d) with 1.20 g (1.8 mmol) of chloro(1,5-cyclooctadiene)iridium(I) dimer in 100 ml of o-xylene under reflux during eight hours, giving the title product as a yellow solid (yield: 2.03 g (45%)).

e) Synthesis of Bromo-Complex Intermediate (HI-7)

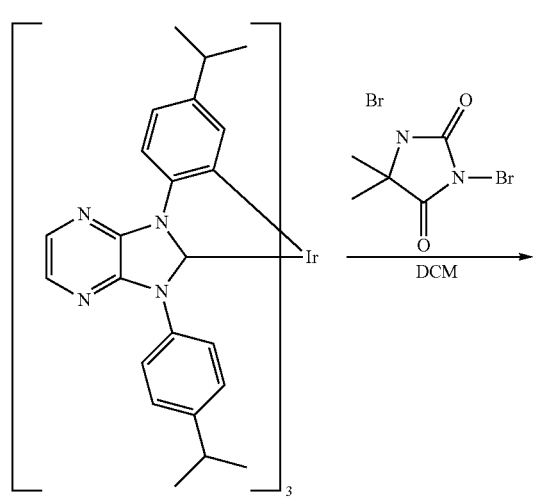

0.93 g (0.74 mmol) of the product of the synthesis example 30 d), are reacted according to synthesis example 29 e) with 320 mg (1.12 mmol) of 1,3-dibromo-5,5-dimethylhydantoin in 100 ml of dichloromethane at 0° C. during 16 hours, giving the title product as a light yellow solid (yield: 0.94 g (85%)).

$^1$H-NMR (400 MHz, CD$_2$Cl$_2$): δ=0.88 (d, 9 H), 1.04 (m, 27 H), 2.57 (m, 3 H), 3.23 (m, 3 H), 5.88-7.69 (3 broad signals, 12 H), 6.53 (s, 3 H), 8.12 (d, 3 H), 8.41 (d, 3 H), 8.94 (s, 3 H).

f) Synthesis of Complex (Y-2)

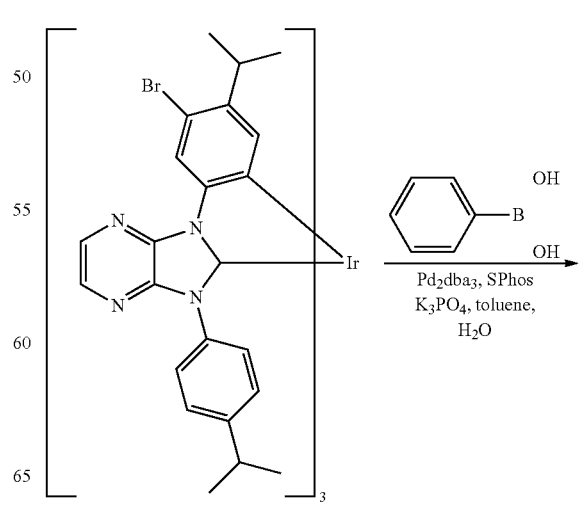

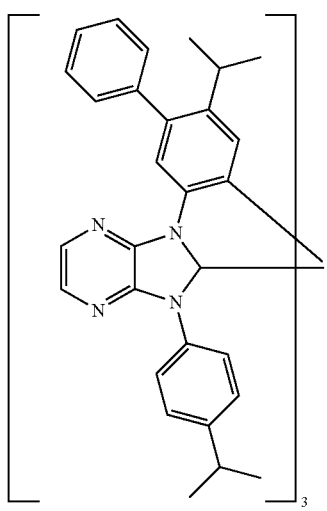

389 mg (0.54 mmol) of the product, HI-7, of synthesis example 30 e) are reacted according to to synthesis example 29 e) with 140 mg (1.15 mmol) of phenylboronic acid, 0.32 g (1.5 mmol) of tripotassium phosphate, 11.6 mg (0.01 mmol) of tris(dibenzylideneacetone)dipalladium(0), and 19 mg (0.05 mmol) of 2-dicyclohexylphosphino-2',6'-dimethoxybiphenyl, in 95 ml of toluene and 19 ml of water, with a reaction time of 23 hours under reflux, giving the title product as a light yellow solid (yield: 0.15 g (39%)).

$^1$H-NMR (400 MHz, CD$_2$Cl$_2$): δ☐=0.89 (d, 9 H), 0.99 (d, 9 H), 1.03 (d, 9 H), 1.10 (d, 9 H), 2.59 (m, 3 H), 2.96 (m, 3 H), 5.90-7.72 (3 broad signals, 12 H), 6.72 (m, 3 H), 7.38 (m, 3 H), 7.46 (m, 12 H), 8.08 (d, 3 H), 8.32 (d, 3 H), 8.61 (s, 3 H).

Synthesis Example 31

Synthesis of Bromo-Complex Intermediates HI-5 (Isomer 1, Isomer 2, Isomer 3 and Isomer 4)

a) Synthesis of CC-5 (Isomer 1, Isomer 2, Isomer 3 and Isomer 4)

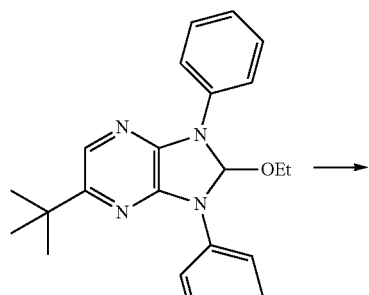

Intermediate G

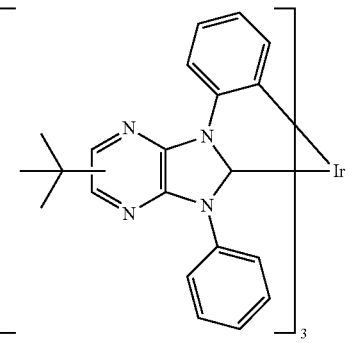

A mixture of 5.0 g (13 mmol) intermediate G and 0.9 g (1.3 mmol) [Ir(cod)Cl]$_2$ in o-xylene (300 ml) is stirred at reflux for 5 h. The solvent is removed, the residue is taken up in a 1:1 mixture of acetonitrile and acetone (100 ml) and stirred for 16 h. The solid (containing CC-5 (Isomer 1, Isomer 2, Isomer 3 and Isomer 4)) is isolated by filtration. The synthesis of CC-5 (Isomer 1, Isomer 2, Isomer 3 and Isomer 4) is described in more detail in PCT/EP2014/064054.

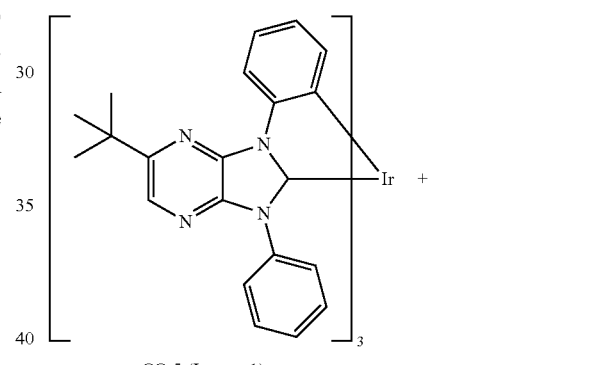

CC-5 (Isomer 1)

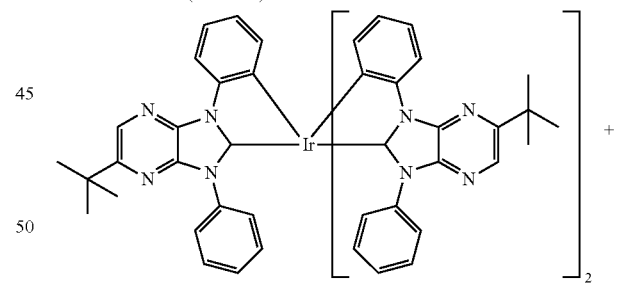

CC-5 (Isomer 2)

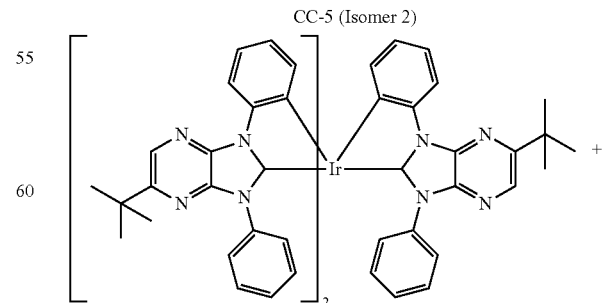

CC-5 (Isomer 3)

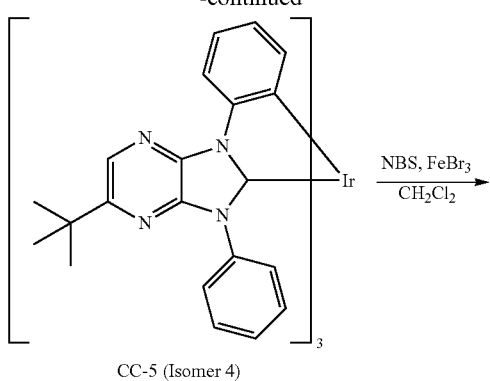

CC-5 (Isomer 4)

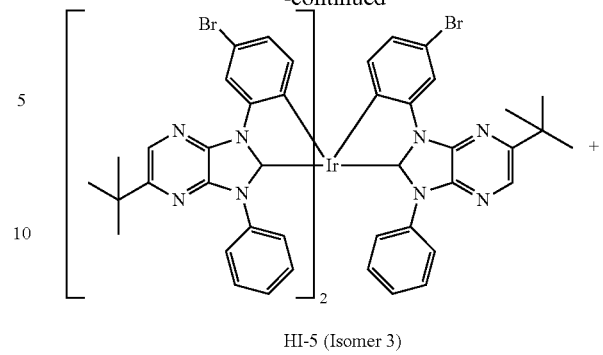

HI-5 (Isomer 3)

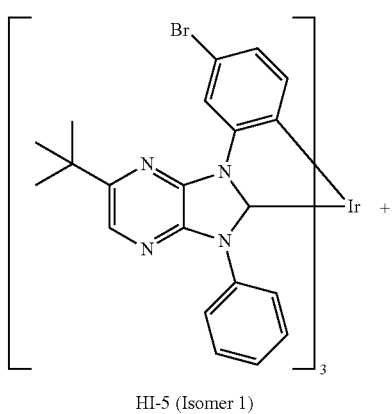

HI-5 (Isomer 1)

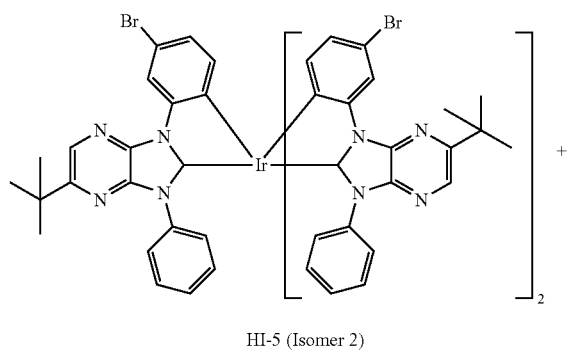

HI-5 (Isomer 4)

The mixture of Isomer-1, Isomer-2, Isomer-3 and Isomer-4 of CC-5 (0.86 g, 0.74 mmol) and iron(III) bromide (12.0 mg, 0.04 mmol) are dissolved in 180 ml of dichloromethane under inert atmosphere. After cooling the system to 0° C., N-bromo succinimide (0.40 g, 2.22 mmol) is added and the solution is stirred in the absence of light for 7 hours. A 10% water solution of sodium bisulfite (6 ml) is added to the reaction mixture and stirred. After pouring the solution into water, the phases are separated and the organic portion dried over anhydrous sodium sulfate. After filtering, the solvent is evaporated and the solid residue purified by column chromatography ($SiO_2$, dichloromethane/toluene) providing four product isomers as yellow solids which have been further assigned by $^1$H-NMR analysis (combined yield of all four product isomers 1-4: 0.99 g (82%)).

HI-5 (Isomer 1): $^1$H-NMR (400 MHz, $CD_2Cl_2$): δ=8.89 (d, 3H, J=1.96 Hz), 8.43 (s, 3H), 8.03 (d, 3H, J=2.88 Hz), 7.65-5.85 (br m, 21 H), 1.30 (s, 27 H)

HI-5 (Isomer 2): $^1$H-NMR (400 MHz, $CD_2Cl_2$): δ=8.96 (d, 1H, J=1.97 Hz), 8.90 (d, 1H, J=1.97 Hz), 8.87 (d, 1H, J=1.97 Hz), 8.44 (s, 1H), 8.42 (s, 1H), 8.15 (s, 1H), 7.49-6.04 (br m, 21 H), 1.56 (s, 9H), 1.32 (s, 9H), 1.29 (s, 9H)

HI-5 (Isomer 3): $^1$H-NMR (400 MHz, $CD_2Cl_2$): δ=8.98 (d, 1H, J=1.95 Hz), 8.95 (d, 1H, J=1.95 Hz), 8.88 (d, 1H, J=1.95 Hz), 8.43 (s, 1H), 8.16 (s, 1H), 8.14 (s, 1H), 7.70-6.07 (br m, 21 H), 1.58 (s, 9H), 1.55 (s, 9H), 1.31 (s, 9H)

HI-5 (Isomer 4): $^1$H-NMR (400 MHz, $CD_2Cl_2$): δ=8.95 (d, 3H, J=1.96 Hz), 8.16 (s, 3H), 7.75-5.98 (br m, 21 H), 1.56 (s, 27 H).

Synthesis Example 32

Synthesis of Complex (C'113 (Isomer 3))

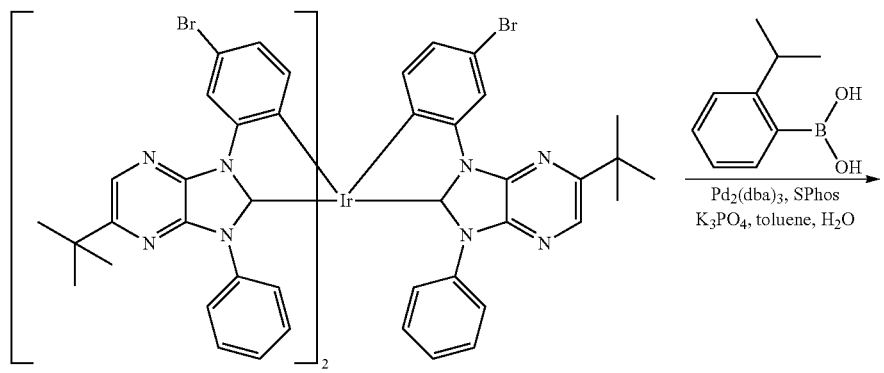

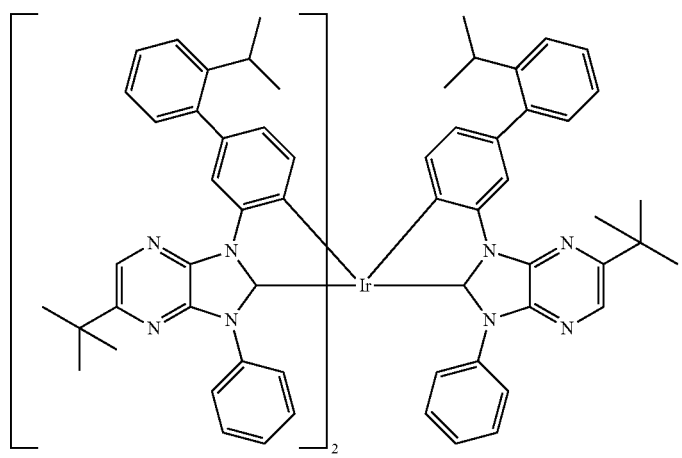

HI-5 (Isomer 3) of synthesis example 31 (0.26 g, 0.18 mmol), 2,6-diisopropylphenylboronic acid (0.13 g, 0.81 mmol), and $K_3PO_4$ (0.23 g, 1.08 mmol) are suspended in 150 ml of toluene and 30 ml of water. Argon is bubbled through the solution for 30 minutes and then tris-(dibenzylidenacetone)-dipalladium(0) (8.0 mg, 0.03 mmol) and S-phos (13 mg, 0.03 mmol) are added. The solution is purged with argon for 15 minutes and then heated to reflux under inert atmosphere overnight. After cooling to room temperature, phases are separated, the organic phase collected and the solvent removed. The solid is then purified via column chromatography (silica, first purification toluene/dichloromethane, second purification cyclohexane/ethyl acetate). The title product is isolated as a yellow solid (yield: 0.15 g (54%)).

$^1$H-NMR (500 MHz, $CD_2Cl_2$): δ=8.82 (d, J=1.7 Hz, 1H), 8.80 (d, J=1.7 Hz, 1H), 8.74 (d, J=1.7 Hz, 1H), 8.33 (s, 1H), 8.12 (s, 1H), 8.11 (s, 1H), 7.40 (d, J=8.2 Hz, 3H), 7.34-7.29 (m, 6H), 7.20 (td, J=7.4, 1.5 Hz, 3H), 7.14-6.29 (m, 21H), 3.40 (h, J=6.8 Hz, 2H), 3.31 (h, J=6.7 Hz, 1H), 1.48 (s, 9H), 1.47 (s, 9H), 1.30 (s, 9H), 1.25-1.20 (m, 9H), 1.16-1.11 (m, 9H).

Synthesis Example 33

Synthesis of Complex (M-4)

a) Synthesis of 3-aminodibenzofuran

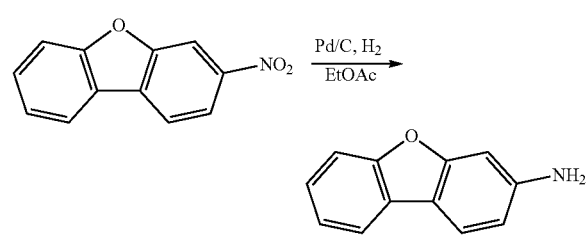

Reference is made to preparation of compound (3) in WO2012/020327.

$^1$H-NMR (300 MHz, $CDCl_3$): δ=3.92 (br. s, 2 H), 6.71 (dd, 1 H), 6.87 (d, 1 H), 7.32 (m, 2 H), 7.50 (d, 1 H), 7.71 (d, 1 H), 7.82 (d, 1 H).

b) Synthesis of 2,4-dibromodibenzofuran-3-amine

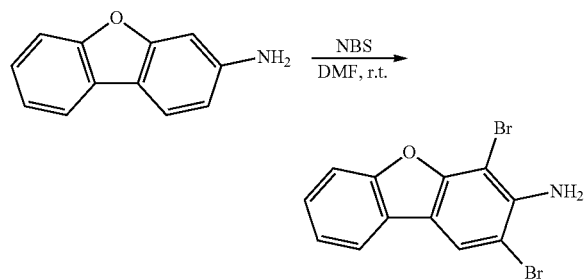

21.7 g (118 mmol) of 3-aminodibenzofuran are dissolved in 200 ml of DMF and cooled down to ice-bath temperature under argon atmosphere. 43.0 g (242 mmol) of N-bromosuccinimide are added in small portions during 90 minutes, letting the temperature not rise above 10° C. 100 ml of additional DMF are added at 8° C. and the temperature let rising to room temperature during one hour under stirring. The dark solution is treated with 30 ml aqueous sodium thiosulfate solution and diluted with water up to a volume of 2000 ml, followed by stirring during 20 minutes. The resulting suspension is filtered and the solid mixed with 200 ml of ethanol and stirred during 15 minutes. The suspension is filtered and the resulting solid washed with ethanol and dried under vacuum, giving the title product as a light yellow solid (yield: 39.8 g (98%)).

$^1$H-NMR (400 MHz, d$_6$-DMSO): δ=4.80 (br. s, 2 H), 7.34 (td, 1 H), 7.41 (td, 1 H), 7.59 (d, 1 H), 7.78 (m, 1 H), 7.96 (s, 1 H).

c) Synthesis of 2,4-diisobutyldibenzofuran-3-amine

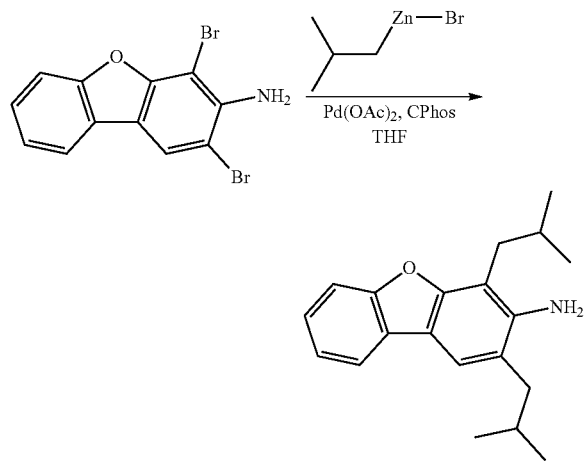

15.6 g (45.7 mmol) of 2,4-dibromodibenzofuran-3-amine are dissolved under in 220 ml of THF and 50 mg (0.22 mmol) of palladium(II) acetate and 200 mg (0.46 mmol) of 2-dicyclohexylphosphino-2',6'-bis(N,N-dimethylamino)biphenyl (=CPhos) are added. The violet-brown solution is three times evacuated and backfilled with argon and cooled down to 0° C. 220 ml (0.11 mol) 0.5M isobutylzinc bromide solution slowly added during ohne hour, and stirring continued during 30 minutes at 0° C. The temperature is let rising to room temperature and the dark brown solution further stirred during 17 hours. 100 ml of water are added together with 10 g of Hyflo® filter aid, and stirred during 30 minutes. The brown suspension is filtered through a 3 cm layer of Hyflo® filter aid followed by washing the filter aid with toluene. The combined filtrates are concentrated. The brown residue is diluted with 500 ml of toluene and the water phase separated. The organic phase is extracted with 200 ml of 2% aqueous 3-amino-1-propanol solution, followed by extraction with 200 ml of water and 100 ml of saturated sodium chloride. The organic phase is dried over sodium sulfate, filtered and concentrated under vacuum, giving the title product as a red oil, which was used in the next step without further purification (12.3 g, product content of 84% according to GC measurement).

d) Synthesis of 3-iodo-2,4-diisobutyl-dibenzofuran

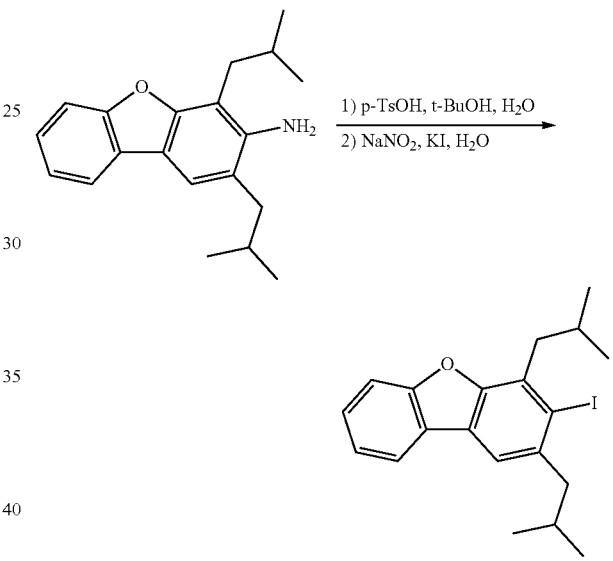

3.79 g (10.8 mmol) of 2,4-diisobutyldibenzofuran-3-amine are dissolved in 200 ml of tert-butanol followed by fast addition of a solution of 9.26 g (48.7 mmol) of p-toluenesulfonic acid in 50 ml of water. The light yellow solution is stirred at room temperature during 15 minutes, and cooled down to 5° C. 2.25 g (32.6 mmol) and 6.70 g (40.4 mmol) of potassium iodide are dissolved in 100 ml of water and added to the reaction mixture slowly at a maximum temperature of 5° C. during one hour. The dark suspension is stirred at 0° C. during 30 minutes and the temperature let rising to room temperature, followed by heating at 40° C. during 30 minutes. The reddish suspension is cooled down and 40 ml of 20% aqueous sodium bicarbonate solution are added followed by the addition of 100 ml of 10% aqueous sodium thiosulfate solution. The colorless suspension is poured onto 800 ml of an ice-water mixture under stirring. The light grey suspension is filtered and he solid is washed with water and ethanol, followed by drying under vacuum, giving the title product as a white solid (yield: 2.79 g (64%)).

$^1$H-NMR (400 MHz, CDCl$_3$): δ=1.04 (t, 12 H), 2.11 (m, 1 H), 2.29 (m, 1 H), 2.86 (d, 2 H), 3.10 (d, 2 H), 7.35 (td, 1 H), 7.49 (td, 1 H), 7.59 (d, 1 H), 7.62 (s, 1 H), 7.95 (d, 1 H).

e) Synthesis of (1,3-diisobutyldibenzofuran-2-yl)boronic acid

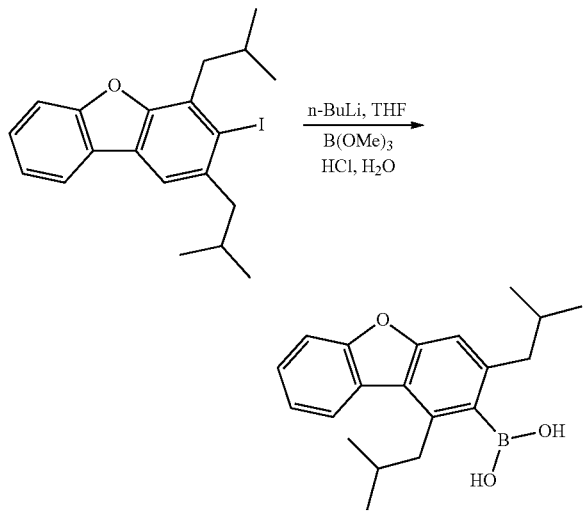

1.45 g (3.5 mmol) of 3-iodo-2,4-diisobutyl-dibenzofuran are dissolved in 20 ml of THF under argon atmosphere and slowly treated with 1.68 ml (4.2 mmol) of 2.5M n-butyl lithium solution in hexane at −77° C., letting the temperature not rise above −70° C. during addition. The light yellow solution is stirred at −78° C. during one hour. 0.70 g (6.7 mmol) of trimethylborate are slowly added during 35 minutes, letting the temperature not rise above −70° C., and stirring continued for one hour at −78° C. The temperature is let rising to room temperature under stirring and the yellow solution slowly treated with 20 ml of water. 6 ml of 6% aqueous hydrochloric acid are added and THF distilled off under vacuum at 80° C., followed by the addition of 15 ml of heptane and stirring at ice-bath temperature during ohne hour. The suspension is filtered and the solid washed with heptane giving the title product as a beige solid (yield: 1.11 g (98%)).

$^{1}$H-NMR (400 MHz, $d_6$-DMSO): δ=0.91 (d, 12 H), 1.98 (m, 1 H), 2.14 (m, 1 H), 2.65 (d, 2 H), 2.84 (d, 2 H), 7.34 (td, 1 H), 7.46 (td, 1 H), 7.66 (m, 2 H), 8.07 (d, 1 H), 8.22 (s, 2 H).

f) Synthesis of Complex (M-4)

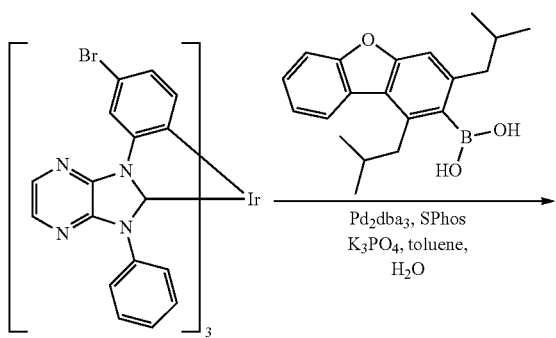

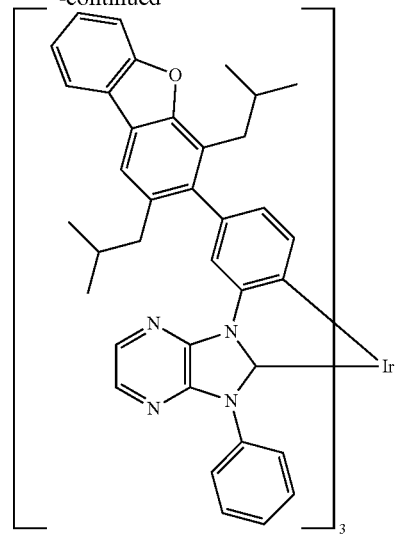

1.10 g (0.89 mmol) of bromo-complex product (HI-1) of synthesis example 6, are reacted according to synthesis example 20 d) with 1.12 g (3.45 mmol) of (1,3-diisobutyldibenzofuran-2-yl)boronic acid, 1.16 g (5.41 mmol) of tripotassium phosphate, 41 mg (0.04 mmol) of tris(dibenzylideneacetone)dipalladium(0), and 67 mg (0.16 mmol) of 2-dicyclohexylphosphino-2',6'-dimethoxybiphenyl, in 70 ml of toluene and 16 ml of water, with a reaction time of 17 hours at 90° C. The resulting orange emulsion is diluted with 30 ml of dichloromethane and the organic phase stirred with 15 ml of 5% aqueous sodium cyanide solution. The light yellow organic phase is separated and filtered through a 3 cm layer of silica gel followed by rinsing the silica gel with dichloromethane. The combined eluents are concentrated under vacuum and the resulting solid separated and washed with ethanol and heptane, followed by drying under vacuum, giving the title product as a light yellow solid (yield: 1.23 g (78%)).

$^{1}$H-NMR (400 MHz, $CD_2Cl_2$): δ=0.65 (m, 18 H), 0.86 (m, 18 H), 1.83 (m, 3 H), 2.05 (m, 3 H), 2.38-2.98 (m, 12 H), 6.27-7.90 (broad signal, 12 H), 6.77 (m, 3 H), 6.90 (t, 3 H), 7.01 (d, 3 H), 7.38 (t, 3 H), 7.48 (t, 3 H), 7.61 (dd, 3 H), 7.75 (d, 3 H), 8.02 (m, 3 H), 8.10 (t, 3 H), 8.30 (d, 3 H), 8.77 (d, 3 H).

II. Photoluminescence Examples

Determination of the Photoluminescence Spectra (2% Film in PMMA Matrix)

The photoluminescence (PL) spectra of the complexes are measured on thin polymer films doped with the respective complexes. The thin films are prepared by the following procedure: a 10%-w/w polymer solution is made by dissolving 1 g of the polymer "PMMA 6N" (Evonik) in 9 g of dichloromethane, followed by stirring for one hour. 2 mg of the respective complexes are added to 0.098 g of the PMMA solution, and stirring continued for one minute. The solutions are casted by doctor-blading with a film applicator (Model 360 2082, Erichsen) with a 60 μm gap onto quartz substrates providing thin doped polymer films (thickness ca. 6 μm). The PL spectra and quantum-yields (Q.Y.) of these films are measured with the integrating-sphere method using the Absolute PL Quantum Yield Measurement System (Hamamatsu, Model C9920-02) (excitation wavelength: 370 nm).

Determination of the Lifetime of Luminescence $\tau_V$

The lifetime ($\tau_V$) of the luminescence of the complexes in the prepared films are measured by the following procedure: For excitation of the emission a sequence of short laser pulses (THG Nd-YAG, 355 nm, 1 nsec pulse length, 1 kHz repetition rate) is used. The emissions are detected by the time-resolved photon-counting technique in the multi-channel scaling modus using a combination of photomultiplier, discriminator and a multiscaler card (FAST ComTec GmbH, Model P7888).

The PL Q.Y., $\lambda_{max}$, CIE x, y, and $\tau_V$ values of the photoluminescence measurements are included in the following tables.

| Cpd. | Formula | PL Q.Y. | $\lambda_{max}$ (nm) | CIE x, y | $\tau_V$ (µs) |
|---|---|---|---|---|---|
| CC-1 | 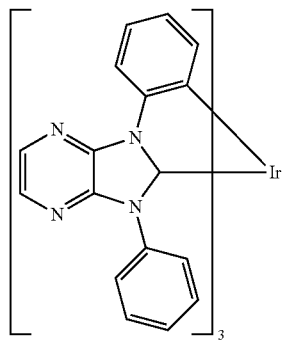 (WO2011073149 (complex fac-EM1)) | 93% | 474 | 0.15, 0.25 | 2.37 |
| A-17 | 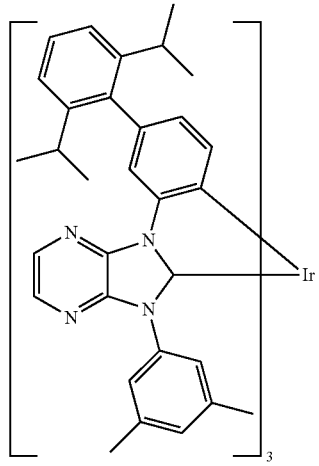 | 95% | 476 | 0.16, 0.28 | 1.95 |
| B-43 | 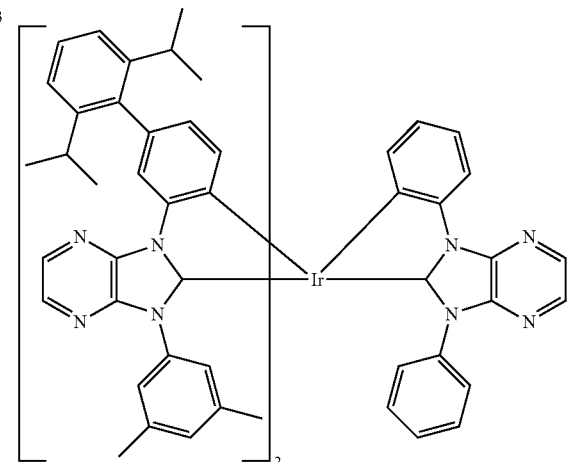 | 95% | 476 | 0.16, 0.27 | 1.94 |

-continued

| Cpd. | Formula | PL Q.Y. | λ$_{max}$ (nm) | CIE x, y | τ$_v$ (μs) |
|---|---|---|---|---|---|
| A-15 | | 88% | 476 | 0.16, 0.28 | 1.95 |
| B-15 | | 96% | 478 | 0.16, 0.27 | 1.99 |
| E-1 | | 79% | 485 | 0.18, 0.37 | 1.84 |

-continued

| Cpd. | Formula | PL Q.Y. | $\lambda_{max}$ (nm) | CIE x, y | $\tau_v$ (µs) |
|---|---|---|---|---|---|
| A-1 | | 87% | 477 | 0.16, 0.28 | 1.78 |
| C-125 | | 91% | 480 | 0.16, 0.31 | 1.65 |
| C-126 | | 94% | 477 | 0.16, 0.28 | 1.67 |

| Cpd. | Formula | PL Q.Y. | λ$_{max}$ (nm) | CIE x, y | τ$_v$ (μs) |
|---|---|---|---|---|---|
| C-127 | | 94% | 478 | 0.16, 0.29 | 1.69 |
| G-1 | | 88% | 464 | 0.15, 0.16 | 2.16 |
| C-161 | | 98% | 477 | 0.16, 0.28 | 1.78 |

-continued

| Cpd. | Formula | PL Q.Y. | λ_max (nm) | CIE x, y | τ_v (μs) |
|---|---|---|---|---|---|
| C-130 | | 93% | 477 | 0.16, 0.28 | 1.86 |
| C-128 | | 87% | 477 | 0.16, 0.28 | 1.41 |
| A-6 | | 95% | 478 | 0.16, 0.29 | 1.81 |

-continued

| Cpd. | Formula | PL Q.Y. | λ$_{max}$ (nm) | CIE x, y | τ$_v$ (μs) |
|---|---|---|---|---|---|
| A-2 | | 94% | 477 | 0.16, 0.28 | 1.82 |
| Y-1 | | 92% | 484 | 0.17, 0.34 | 1.96 |
| Y-2 | | 96% | 485 | 0.17, 0.36 | 1.90 |

-continued

| Cpd. | Formula | PL Q.Y. | $\lambda_{max}$ (nm) | CIE x, y | $\tau_v$ (µs) |
|---|---|---|---|---|---|
| M-4 | | 95% | 473 | 0.15, 0.24 | 1.97 |
| A-3 | | 90% | 475 | 0.16, 0.26 | 1.77 |
| A-14 | | 87% | 479 | 0.16, 0.30 | 1.64 |

The inventive metal carbene complexes show a blue emission, with very high absolute quantum efficiency, and with improved (=shorter) lifetime of luminescence in comparison with comparative compound CC-1.

| Cpd. | Formula | PL Q.Y. | $\lambda_{max}$ (nm) | CIE x, y | $\tau_v$ (µs) |
|---|---|---|---|---|---|
| CC-2 | (PCT/EP2014/055520 ((complex BE-12)) | 95% | 473 | 0.15, 0.23 | 5.74 |
| A-85 | | 91% | 474 | 0.15, 0.25 | 4.12 |

The inventive metal carbene complex A-85 shows a blue emission, with very high absolute quantum efficiency, and with improved (=shorter) lifetime of luminescence in comparison with comparative compound CC-2.

| Cpd. | Formula | PL Q.Y. | $\lambda_{max}$ (nm) | CIE x, y | $\tau_v$ (µs) |
|---|---|---|---|---|---|
| CC-3 | (WO2011/073149 (complex Em8)) | 89% | 482 | 0.17, 0.32 | 2.43 |

| Cpd. | Formula | PL Q.Y. | λ_max (nm) | CIE x, y | τ_v (μs) |
|---|---|---|---|---|---|
| J-113 | | 89% | 485 | 0.18, 0.36 | 1.84 |
| L-1 | | 94% | 476 | 0.15, 0.26 | 1.96 |

The inventive metal carbene complexes, J-113 and L-1, show a blue emission, with very high absolute quantum efficiency, and with improved (=shorter) lifetime of luminescence in comparison with comparative compound CC-3.

| Cpd. | | PL Q.Y. | λ_max (nm) | CIE x, y | τ_v (μs) |
|---|---|---|---|---|---|
| CC-5 | | 99% | 467 | 0.14, 0.19 | 2.90 |

| Cpd. | | PL Q.Y. | λ_max (nm) | CIE x, y | τ_v (μs) |
|---|---|---|---|---|---|
| C'-113 (Isomer 3) | | 84% | 469 | 0.15, 0.21 | 1.84 |

The inventive metal carbene complex, C'-113 (Isomer 3), shows a blue emission, with very high absolute quantum efficiency, and with improved (=shorter) lifetime of luminescence in comparison with comparative compound CC-5 (Isomer 3) of Synthesis Example 31 a)).

Determination of the Photoluminescence Spectra (4% Film in Host SH-5)

SH-5:

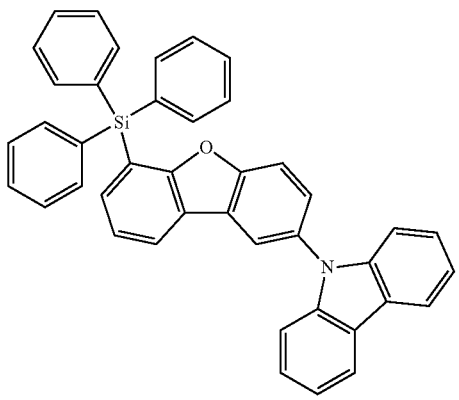

SH-5 described in WO2010/079051, structure on page 22 (X=O); synthesis as in example 17 in EP1885818 on page 104 in US2013/0119360.

The photoluminescence (PL) spectra of the iridium complexes are measured on thin SH-5 films doped with 4%-w/w of the respective iridium complexes. The thin film samples are prepared by the following procedure: 1 mg of the the respective iridium complexes and 24 mg of SH-5 are added to 2.5 mL of dichloromethane and the mixtures stirred for 1-5 minutes. The resulting solutions are casted by doctor-blading with a film applicator (Model 360 2082, Erichsen) with a 30 μm gap onto quartz substrates. The PL spectra are measured as described for the PMMA films (excitation wavelength: 370 nm). The lifetime ($\tau_V$) of the phosphorescence of the iridium complexes in the prepared films are measured as described for the PMMA films The PL Q.Y., $\lambda_{max}$, CIE x, y and FWHM of the iridium complex doped α-NPD films are shown in the table below:

The PL Q.Y., $\lambda_{max}$, CIE x, y, and $\tau_V$ values of the photoluminescence measurements are included in the following tables.

| Cpd. | Formula | PL Q.Y. | λ_max (nm) | CIE x, y | τ_v (μs) |
|---|---|---|---|---|---|
| CC-1 | (WO2011073149 (complex fac-EM1)) | 90% | 473 | 0.15, 0.24 | 1.82 |

-continued

| Cpd. | Formula | PL Q.Y. | λ_max (nm) | CIE x, y | τ_v (µs) |
|---|---|---|---|---|---|
| A-17 | | 94% | 473 | 0.14, 0.24 | 1.37 |
| B-43 | | 87% | 476 | 0.15, 0.25 | 1.49 |
| A-15 | | 79% | 476 | 0.15, 0.26 | 1.33 |

-continued

| Cpd. | Formula | PL Q.Y. | $\lambda_{max}$ (nm) | CIE x, y | $\tau_v$ (μs) |
|---|---|---|---|---|---|
| B-15 | | 93% | 479 | 0.15, 0.27 | 1.58 |
| C-125 | | 82% | 480 | 0.15, 0.30 | 1.23 |
| C-126 | | 88% | 479 | 0.15, 0.29 | 1.24 |

-continued

| Cpd. | Formula | PL Q.Y. | λ_max (nm) | CIE x, y | τ_v (μs) |
|---|---|---|---|---|---|
| C-127 | | 83% | 477 | 0.15, 0.27 | 1.26 |
| C-161 | | 96% | 479 | 0.15, 0.28 | 1.18 |
| C-130 | | 82% | 478 | 0.15, 0.27 | 1.33 |

-continued
| Cpd. | Formula | PL Q.Y. | λ_max (nm) | CIE x, y | τ_v (μs) |
|---|---|---|---|---|---|
| A-6 | 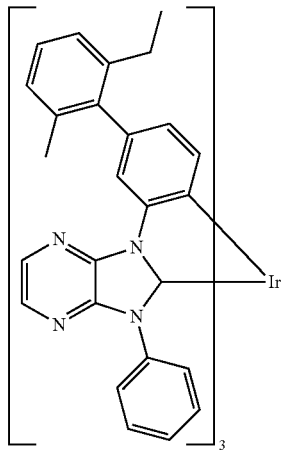 | 85% | 479 | 0.15, 0.28 | 1.34 |
| A-2 | 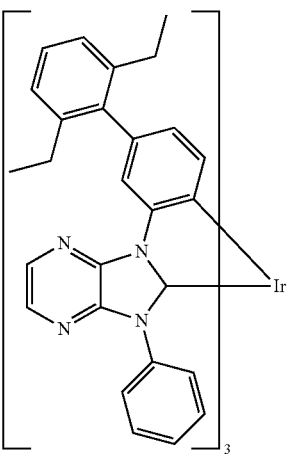 | 88% | 478 | 0.15, 0.26 | 1.31 |
| X-1 | 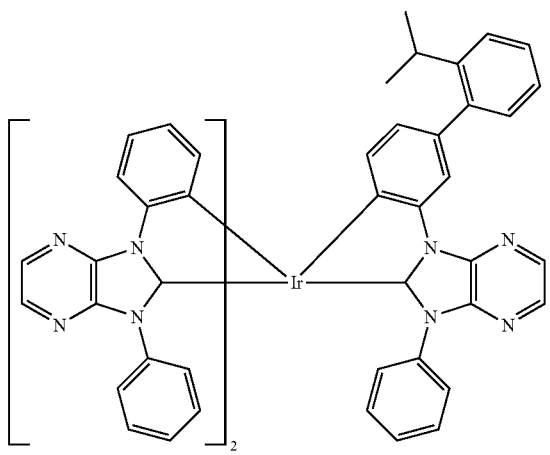 | 79 | 476 | 0.15, 0.27 | 1.40 |

-continued

| Cpd. | Formula | PL Q.Y. | λ_max (nm) | CIE x, y | τ_v (μs) |
|---|---|---|---|---|---|
| X-2 | | 87 | 473 | 0.14, 0.24 | 1.59 |
| Y-1 | | 87% | 483 | 0.15, 0.32 | 1.45 |
| Y-2 | | 95% | 481 | 0.16, 0.31 | 1.70 |

-continued

| Cpd. | Formula | PL Q.Y. | $\lambda_{max}$ (nm) | CIE x, y | $\tau_v$ (µs) |
|---|---|---|---|---|---|
| M-4 | | 77% | 472 | 0.15, 0.23 | 1.30 |
| A-2 | | 79% | 475 | 0.15, 0.24 | 1.39 |
| A-14 | | 81% | 474 | 0.15, 0.25 | 1.22 |

The inventive metal carbene complexes show a blue emission, with very high absolute quantum efficiency, and with improved (=shorter) lifetime of luminescence in comparison with comparative compound CC-1.

III. Device Examples
Production of an OLED (General Procedure)

The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the hole injection layer (40 nm) AJ20-1000 from Plexcore is spun on from solution.

Thereafter, the organic materials specified below are applied by vapor deposition to the cleaned substrate at about $10^{-7}$-$10^{-9}$ mbar at a rate of approx. 0.5-5 nm/min. The hole conductor and exciton blocker applied to the substrate is Ir(DPBIC)$_3$ (devices 1 to 3) with a thickness of 20 nm, of which the first 10 nm are doped with MoO$_x$ (50 wt.-%: 50 wt.-%) to improve the conductivity.

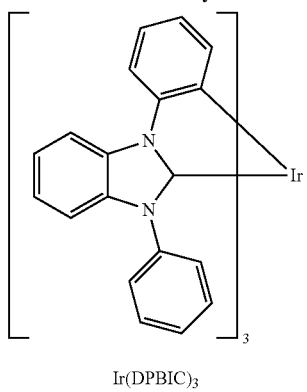

Ir(DPBIC)$_3$ (for preparation of Ir(DPBIC)$_3$ see Ir complex (7) in the application WO2005/019373).

Subsequently, a mixture of emitter, Ir(DPBIC)$_3$ and a host material (the emitter (A-17 or B-15), the host material (SH-1, SH-2, or SH-5) and the relative amounts in % by weight are given in the specific device examples) is applied by vapor deposition with a thickness of 40 nm (devices 1 to 3). Subsequently, the host material is applied by vapor deposition with a thickness of 5 nm as an exciton and hole blocker.

Host Material:

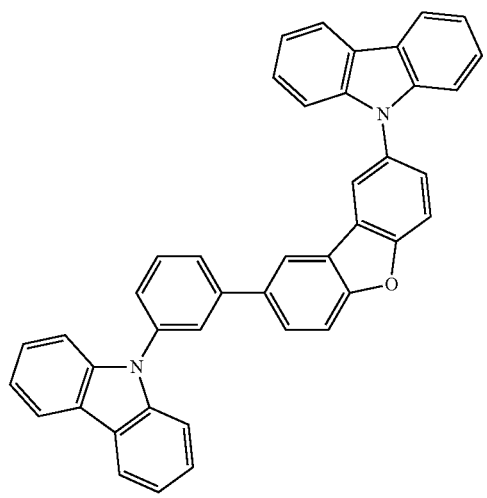

SH-1

(described in WO2009/008100, example 4)

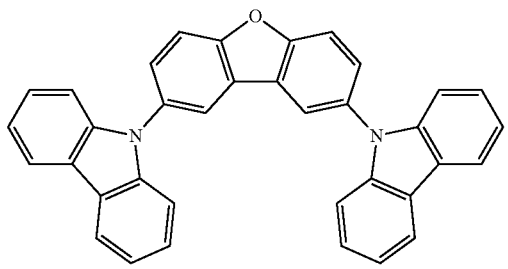

SH-2

(compound "3-1" in "Synthetic example 2" in US2009/066226)

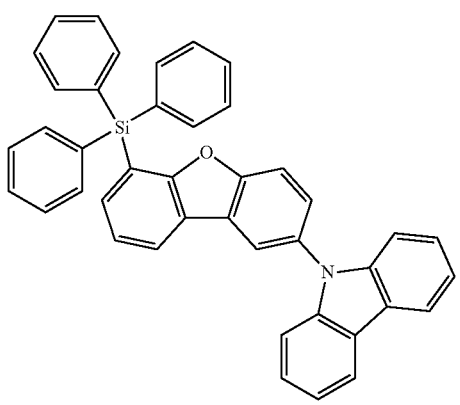

SH-5 described in WO2010/079051, structure on page 22 (X=O); synthesis as in example 17 in EP1885818 on page 104 in US2013/0119360.

Next, as an electron transporter, a mixture of Liq and ETM (ETM-1 as specified in the specific device examples) (50 wt.-%:50 wt.-%) is applied by vapor deposition in a thickness of 25 nm; then a 4 nm LiF layer is applied; and finally a 100 nm-thick Al electrode is applied. All components are adhesive-bonded to a glass lid in an inert nitrogen atmosphere.

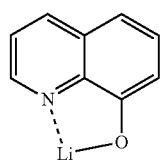

Liq

Electron Transport Material:

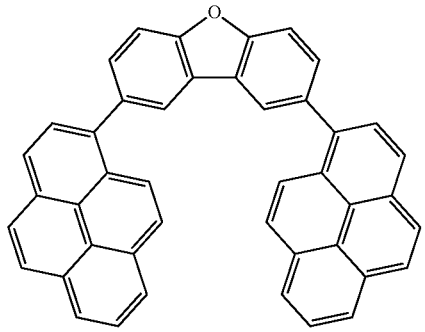

ETM-2

(compound A1 in WO 2011/157779; compound A-10 in WO2006/128800)

To characterize the OLED, electroluminescence spectra are recorded at different currents and voltages. In addition, the current-voltage characteristic is measured in combination with the light output emitted. The light output can be converted to photometric parameters by calibration with a photometer. The $CIE_{x,y}$ coordinates are extracted from the spectra according to CIE 1931 as known in the art.

Device 1:
HIL Plexcore AJ20-1000—10 nm Ir(DPBIC)$_3$:MoO$_3$ (50:50)—10 nm Ir(DPBIC)$_3$—40 nm blue emitter/SH-2/Ir(DPBIC)$_3$ (10:80:10)—5 nm SH-2—25 nm ETM-2:Liq (50:50)—4 nm KF—100 nm Al Device 2:
HIL Plexcore AJ20-1000—10 nm Ir(DPBIC)$_3$:MoO$_3$ (50:50)—10 nm Ir(DPBIC)$_3$—40 nm blue emitter/SH-1/Ir(DPBIC)$_3$ (10:80:10)—5 nm SH-1—25 nm ETM-2:Liq (50:50)—4 nm KF—100 nm Al Device 3:
HIL Plexcore AJ20-1000—10 nm Ir(DPBIC)$_3$:MoO$_3$ (50:50)—10 nm Ir(DPBIC)$_3$—40 nm blue emitter/SH-5/Ir(DPBIC)$_3$ (10:80:10)—5 nm SH-5—25 nm ETM-2:Liq (50:50)—4 nm KF—100 nm Al For the different emitters and different host materials in the above-described OLED structure, the following electrooptical data are obtained (all data at 300 nits):

|  | Blue emitter | Voltage [V] | currEff [cd/A] | LumEff [lm/W] | EQE [%] | CIE x, y |
|---|---|---|---|---|---|---|
| Device 1.1 | A-17 | 5.1 | 27.7 | 17.0 | 13.9 | 0.16, 0.30 |
| Device 1.2 | B-15 | 4.4 | 29.9 | 21.3 | 14.5 | 0.17, 0.32 |
| Device 2 | A-17 | 5.4 | 29.0 | 16.9 | 14.8 | 0.16, 0.30 |
| Device 3 | B-15 | 4.1 | 29.5 | 22.5 | 15.3 | 0.16, 0.29 |

The devices comprising the inventive metal carbene complexes show a blue emission color with high efficiency and low voltage.

Device 4:
80 nm Ir(DPBIC)$_3$:MoO$_3$ (90:10)—10 nm Ir(DPBIC)$_3$—40 nm blue emitter/SH-2/Ir(DPBIC)$_3$ (20:70:10)—5 nm SH-2—25 nm ETM-2:Liq (50:50)—4 nm KF—100 nm Al Device 5:
100 nm Ir(DPBIC)$_3$:MoO$_3$ (90:10)—10 nm Ir(DPBIC)$_3$—20 nm blue emitter/SH-2/Ir(DPBIC)$_3$ (20:70:10)—5 nm SH2—35 nm ETM-2:Liq (50:50)—4 nm KF—100 nm Al The device lifetime $LT_{70}$ of the diode is defined by the time taken for the luminance to fall to 70% of its initial value. The lifetime is measured at $LT_{70}$ at 4000 cd/m$^2$ and then calculated back to $LT_{70}$ at 300 cd/m$^2$ using the experimentally observed acceleration factor. The lifetime measurement is carried out at a constant current. All other data are obtained directly at 300 nits.

For the different emitters in the above-described OLED structures, the following electrooptical data are obtained, wherein the measured values of voltage, current efficiency, luminance efficacy, EQE and lifetime of the device 4.1 are set to 100 and the values of the devices 4.2, 5.1 and 5.2 are specified in relation to those of device 4.1:

|  | Blue emitter | CIE x, y | $\lambda_{max}$ [nm] | Rel. Voltage [%] | Rel. currEff [%] | Rel. LumEff [%] | Rel. EQE[1] [%] | Rel. Lifetime[2] (%) |
|---|---|---|---|---|---|---|---|---|
| Device 4.1 | CC-1 | 0.16, 0.29 | 498 | 100 | 100 | 100 | 100 | 100 |
| Device 4.2 | C-127 | 0.16, 0.31 | 500 | 110 | 109 | 98 | 104 | 168 |
| Device 5.1 | CC-1 | 0.16, 0.28 | 497 | 75 | 108 | 145 | 110 | 101 |
| Device 5.2 | C-127 | 0.16, 0.30 | 499 | 81 | 111 | 141 | 111 | 173 |

[1] External quantum efficiency (EQE) is # a of generated photons escaped from a substance or a device/# of electrons flowing through it.
[2] Drop to 70% of initial luminance.

The devices 4.2 and 5.2 comprising the inventive metal carbene complex C-127 show a blue emission color with high efficiency and low voltage, together with increased device lifetime $LT_{70}$ in comparison to the devices comprising the comparative metal carbene complex CC-1. Reference is made to FIG. 1, which provides a plot of the EL intensity of compounds CC-1 and C-127 as a function of wavelength.

The invention claimed is:

1. A metal-carbene complex of the Formula (I):

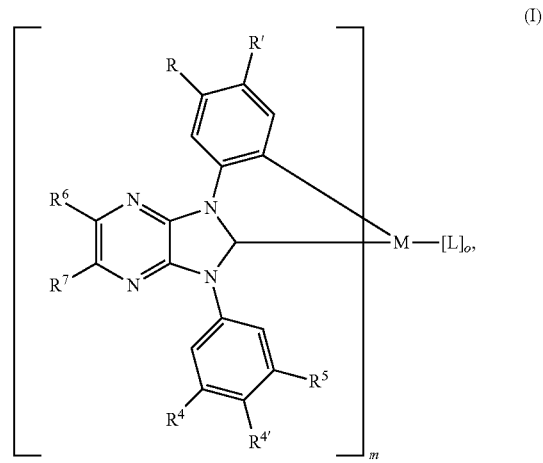

wherein:

M is Ir;

m is 1, 2, or 3;

o is 0, 1, or 2; and the sum of m and o is 3;

with the proviso that, if o is 2, the ligands L may be the same or different;

L is a monoanionic bidentate ligand of formaula (A),(B), or(C):

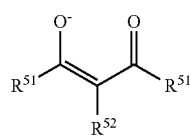

(A)

wherein in formula (A):

$R^{51}$ is in each case independently a linear or branched $C_1$-$C_8$alkyl group; a substituted or unsubstituted $C_6$-$C_{18}$aryl radical; or a substituted or unsubstituted $C_6$-$C_{12}$heteroaryl; and $R^{52}$ is hydrogen; a linear or branched $C_1$-$C_6$alkyl group; or a substituted or unsubstituted $C_6$-$C_{18}$aryl radical;

wherein each substituent is independently a $C_1$-$C_8$alkyl group;

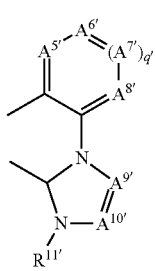

(B)

wherein in formula (B):

$A^{9'}$ is $CR^{12'}$ or N;

$A^{10'}$ is $CR^{13'}$ or N;

$R^{11'}$ is a linear or branched, substituted or unsubstituted alkyl radical having 1 to 20 carbon atoms, optionally interrupted by at least one heteroatom selected from O, S and N; a substituted or unsubstituted cycloalkyl radical having 3 to 18 carbon atoms; a substituted or unsubstituted heterocycloalkyl radical interrupted by at least one heteroatom selected from O, S and N, and having 3 to 18 carbon atoms and/or heteroatoms; a substituted or unsubstituted aryl radical having 6 to 30 carbon atoms; or a substituted or unsubstituted heteroaryl radical interrupted by at least one heteroatom selected from O, S and N and having a total of 5 to 30 carbon atoms and/or heteroatoms;

$R^{12'}$ and $R^{13'}$ are each independently hydrogen; deuterium; a linear or branched, substituted or unsubstituted alkyl radical having 1 to 20 carbon atoms, optionally interrupted by at least one heteroatom selected from O, S and N; a substituted or unsubstituted cycloalkyl radical having 3 to 18 carbon atoms; a substituted or unsubstituted heterocycloalkyl radical interrupted by at least one heteroatom selected from O, S and N, and having 3 to 18 carbon atoms and/or heteroatoms; or a substituted or unsubstituted aryl radical having 6 to 30 carbon atoms; a substituted or unsubstituted heteroaryl radical interrupted by at least one heteroatom selected from O, S and N and having a total of 5 to 30 carbon atoms and/or heteroatoms;

if $A^{9'}$ is $CR^{12'}$ and $A^{10'}$ is $CR^{13'}$, $CR^{12'}$ and $CR^{13'}$ together may form, a saturated, unsaturated, or aromatic, optionally substituted ring, which is optionally interrupted by at least one heteroatom selected from O, S and N, has a total of from 5 to 18 carbon atoms and/or heteroatoms, and may optionally be fused to at least one further optionally substituted saturated, unsaturated, or aromatic ring, optionally interrupted by at least one heteroatom selected from O, S and N, and having a total of from 5 to 18 carbon atoms and/or heteroatoms;

$A^{5'}$ is $CR^{14'}$ or N;

$A^{6'}$ is $CR^{15'}$ or N;

$A^{7'}$ is $CR^{16'}$ or N;

$A^{8'}$ is $CR^{17'}$ or N; and $R^{14'}$, $R^{15'}$, $R^{16'}$ and $R^{17'}$ are each independently hydrogen; deuterium; a linear or branched, substituted or unsubstituted alkyl radical having 1 to 20 carbon atoms, optionally interrupted by at least one heteroatom selected from O, S and N; a substituted or unsubstituted cycloalkyl radical having 3 to 18 carbon atoms; a substituted or unsubstituted heterocycloalkyl radical interrupted by at least one heteroatom, selected from O, S and N, and having 3 to 18 carbon atoms and/or heteroatoms; a substituted or unsubstituted aryl radical having 6 to 30 carbon atoms; or a substituted or unsubstituted heteroaryl radical interrupted by at least one heteroatom, selected from O, S and N and having a total of 5 to 30 carbon atoms and/or heteroatoms; or $R^{14'}$ and $R^{15'}$, $R^{15'}$ and $R^{16'}$, or $R^{16'}$ and $R^{17'}$ may form together with the carbon atoms to which they are bonded, a saturated or unsaturated or aromatic, optionally substituted ring, which is optionally interrupted by at least one heteroatom, selected from O, S and N, has a total of from 5 to 18 carbon atoms and/or heteroatoms, and may optionally be fused to at least one further optionally substituted saturated or unsaturated or aromatic ring, optionally interrupted by at least one heteroatom, selected from O, S and N, and having a total of from 5 to 18 carbon atoms and/or heteroatoms; or if $A^{9'}$ is $CR^{12'}$, $R^{12'}$ and $R^{17'}$ together may form a saturated or unsaturated, linear or branched bridge optionally comprising heteroatoms, selected from O, S and N, to which is optionally fused a substituted or unsubstituted, 5- to 8-membered ring comprising carbon atoms and/or heteroatoms selected from O, S and N, and which are optionally substituted with aromatic units, or heteroaromatic units wherein each substituent is independently selected from the group consisting of a $C_1$-$C_{18}$alkyl group, which can optionally be substituted by E and/or interrupted by D; a $C_3$-$C_{12}$cycloalkyl group, which can optionally be substituted by G; a $C_3$-$C_{10}$heterocycloalkyl radical which is interrupted by at least one of O, S and $NR^{65}$ and/or substituted by E; a $C_6$-$C_{14}$aryl group, which can optionally be substituted by G; a $C_2$-$C_{30}$heteroaryl group, which can optionally be substituted by G; a halogen atom; a fluoro$C_1$-$C_4$alkyl group; CN; or $SiR^{80}R^{81}R^{82}$;

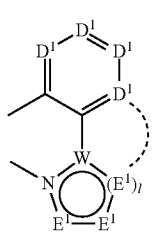

wherein in formula (C):
$D^1$ is at each independent occurrence $CR^{34'''}$ or N;
W is C or N;
$E^1$ is at each independent occurrence $CR^{35'''}$, N, $NR^{36'''}$ or O;
l is 1 or 2;
$R^{34'''}$, $R^{35'''}$, and $R^{36'''}$ are each independently hydrogen; substituted, unsubstituted, or branched alkyl; substituted, unsubstituted aryl; or substituted or unsubstituted heteroaryl; or
in each case two $R^{34'''}$, $R^{35'''}$, or $R^{36'''}$ radicals together form a fused ring which may optionally comprise at least one heteroatom selected from O, S and N;
where the dotted line means an optional bridge between one of the D groups and one of the E groups; where the bridge may be defined as follows: alkylene, arylene, heteroarylene, alkynylene, alkenylene, $N^{R38'''}$, O, S, $SiR^{41'''}$, $R^{42'''}$, and $(CR^{43'''}R^{44'''})_v$, where one or more nonadjacent $(CR^{43'''}R^{44'''})$ groups may be replaced by $NR^{38'''}$, O, S, $SiR^{41'''}R^{42'''}$, where v is 2, 3, 4, 5, 6, 7, 8, 9 or 10; and $R^{38'''}$, $R^{41'''}$, $R^{42'''}$, $R^{43'''}$, and $R^{44'''}$ are each hydrogen; alkyl; aryl; or heteroaryl
wherein each substituent is independently selected from the group consisting of a $C_1$-$C_8$alkyl group; a $C_6$-$C_{14}$aryl group, which is optionally substituted with one or more $C_1$-$C_5$alkyl groups; and a $C_3$-$C_{12}$cycloalkyl group;
R is a group of formula

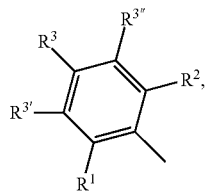

R' is hydrogen, a $C_1$-$C_5$alkyl group, or a fluoro$C_1$-$C_4$alkyl group;
$R^1$ is hydrogen, a $C_1$-$C_5$alkyl group, a fluoro$C_1$-$C_4$alkyl group, or a $C_3$-$C_6$cycloalkyl group;
$R^2$ is hydrogen, a $C_1$-$C_5$alkyl group, a fluoro$C_1$-$C_4$alkyl group, or a $C_3$-$C_6$cycloalkyl group;
$R^3$, $R^{3'}$ and $R^{3''}$ are independently of each other hydrogen; a $C_1$-$C_{18}$alkyl group, which can optionally be substituted by E and/or interrupted by D; a $C_3$-$C_{12}$cycloalkyl group, which can optionally be substituted by G; a $C_3$-$C_{10}$heterocycloalkyl radical which is interrupted by at least one of O, S and $NR^{65}$ and/or substituted by E; a $C_6$-$C_{14}$aryl group, which can optionally be substituted by G; a $C_2$-$C_{30}$heteroaryl group, which can optionally be substituted by G; a halogen atom; $CF_3$; CN; or $SiR^{80}R^{81}R^{82}$;

$R^3$ and $R^{3'}$, or $R^1$ and $R^{3'}$ together form a group of formula

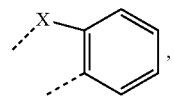

wherein X is O, S, $NR^{75}$ or $CR^{73}R^{74}$;
$R^4$, $R^{4'}$ and $R^5$ are independently of each other hydrogen; a $C_1$-$C_{18}$alkyl group, which can optionally be substituted by E and/or interrupted by D; a $C_3$-$C_{12}$cycloalkyl group, which can optionally be substituted by G; a $C_3$-$C_{10}$heterocycloalkyl radical which is interrupted by at least one of O, S and $NR^{65}$ and/or substituted by E; a $C_6$-$C_{14}$aryl group, which can optionally be substituted by G; a $C_2$-$C_{30}$heteroaryl group, which can optionally be substituted by G; a halogen atom; $CF_3$; CN; or $SiR^{80}R^{81}R^{82}$; or
$R^4$ and $R^{4'}$ together form a group of formula

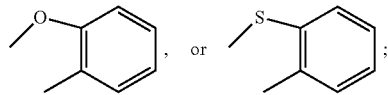

$R^6$ and $R^7$ are independently of each other hydrogen; a $C_1$-$C_8$alkyl group, optionally interrupted by at least one heteroatom selected from —O—, —S— and —$NR^{65}$—, optionally bearing at least one substituent, which is selected from the group consisting of $C_1$-$C_8$alkyl, $C_1$-$C_8$alkoxy, halogen, and $C_1$-$C_8$haloalkyl, a $C_3$-$C_6$cycloalkyl group, optionally bearing at least one substituent, which is selected from the group consisting of $C_1$-$C_8$alkyl, $C_1$-$C_8$alkoxy, halogen, and $C_1$-$C_8$haloalkyl; a hetero$C_3$-$C_6$cycloalkyl group, interrupted by at least one heteroatom selected from —O—, —S— and —$NR^{65}$—, optionally bearing at least one substituent, which is selected from the group consistiong of $C_1$-$C_8$alkyl, $C_1$-$C_8$alkoxy, halogen, and $C_1$-$C_8$haloalkyl; or a $C_6$-$C_{14}$aryl group, which can optionally be substituted by one, or two $C_1$-$C_8$alkyl groups; or
$R^6$ and $R^7$ form together a ring

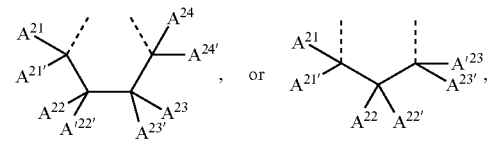

wherein $A^{21}$, $A^{21'}$; $A^{22}$, $A^{22'}$, $A^{23}$, $A^{23'}$, $A^{24'}$ and $A^{24}$ are independently of each other hydrogen, a $C_1$-$C_4$alkyl group, a $C_3$-$C_6$cycloalkyl group, a fluoro$C_1$-$C_4$alkyl group;
D is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$—, or —C≡C—;
E is —$OR^{69}$, —$SR^{69}$, —$NR^{65}R^{66}$, —$COR^{68}$, —$COOR^{67}$, —$CONR^{65}R^{66}$, —CN, or F;
G is E; or a $C_1$-$C_{18}$alkyl group; a $C_6$-$C_{14}$aryl group, which is optionally substituted by a substituent selected from the group consisting of F, $C_1$-$C_{18}$alkyl, which is optionally substituted by F and $C_1$-$C_{18}$alkyl, which is interrupted by O; a C₂-C₁₀heteroaryl group; or a C₂-C₁₀heteroaryl group, which is substituted by a substituent selected from the group consisting of F, $C_1$-$C_{18}$alkyl, which is optionally substituted by F, $SiR^{80}R^{81}R^{82}$, and $C_1$-$C_{18}$alkyl, which is interrupted by O;

$R^{63}$ and $R^{64}$ are independently of each other hydrogen; a $C_6$-$C_{18}$aryl group, which is optionally substituted by a substituent selected from the group consisting of $C_1$-$C_{18}$alkyl, and $C_1$-$C_{18}$alkoxy; or a $C_1$-$C_{18}$alkyl group, which is optionally interrupted by —O—;

$R^{65}$ and $R^{66}$ are independently of each other a $C_6$-$C_{18}$aryl group, which is optionally substituted by a substituent selected from the froup consisting of $C_1$-$C_{18}$alkyl and $C_1$-$C_{18}$alkoxy; or a $C_1$-$C_{18}$alkyl group, which is optionally interrupted by —O—; or $R^{65}$ and $R^{66}$ together form 5-membered ring or 6-membered ring;

$R^{67}$ is a $C_6$-$C_{18}$aryl group, which is optionally substituted by a substituent selected from the group consisting of $C_1$-$C_{18}$alkyl, and $C_1$-$C_{18}$alkoxy; or a $C_1$-$C_{18}$alkyl group, which is optionally interrupted by —O—, $R^{68}$ is hydrogen; a $C_6$-$C_{18}$aryl group, which is optionally substituted by a substituent selected from the group consisting of $C_1$-$C_{18}$alkyl and $C_1$-$C_{18}$alkoxy; or a $C_1$-$C_{18}$alkyl group, which is optionally interrupted by —O—;

$R^{69}$ is a $C_6$-$C_{18}$aryl group, which is optionally substituted by a substituent selected from the group consisting of $C_1$-$C_{18}$alkyl and $C_1$-$C_{18}$alkoxy; or a $C_1$-$C_{18}$alkyl group, which h is optionally interrupted by —O—;

$R^{70}$ and $R^{71}$ are independently of each other a $C_1$-$C_{18}$alkyl group; or a $C_6$-$C_{18}$aryl group, which is optionally substituted by $C_1$-$C_{18}$alkyl; and $R^{72}$ is a $C_1$-$C_{18}$alkyl group; or a $C_6$-$C_{18}$aryl group, which is optionally substituted by $C_1$-$C_{18}$alkyl;

$R^{73}$ and $R^{74}$ are independently of each other hydrogen; a $C_1$-$C_{25}$alkyl group, which is optionally interrupted by —O—; a $C_7$-$C_{25}$arylalkyl group; a $C_6$-$C_{24}$aryl group, which is optionally substituted by $C_1$-$C_{18}$alkyl; or a $C_2$-$C_{20}$heteroaryl group, which is optionally substituted by $C_1$-$C_{18}$alkyl; or $R^{73}$ and $R^{74}$ together form a 5-membered or 6-membered ring, which is optionally substituted by a $C_1$-$C_{18}$alkyl group, which is optionally interrupted by —O—, or $R^{73}$ and $R^{74}$ together form a group of formula $=CR^{76}R^{77}$, wherein $R^{76}$ and $R^{77}$ are independently of each other hydrogen; a $C_1$-$C_{18}$alkyl group, which is optionally interrupted by O; a $C_6$-$C_{24}$aryl group, which is optionally substituted by $C_1$-$C_{18}$alkyl; or a $C_2$-$C_{20}$heteroaryl group, which is optionally substituted by $C_1$-$C_{18}$alkyl; or $R^{75}$ is a $C_6$-$C_{18}$aryl group which is optionally substituted by a substituent selected from the group consisting of $C_1$-$C_{18}$alkyl and $C_1$-$C_{18}$alkoxy; or a $C_1$-$C_{18}$alkyl group, which is optionally interrupted by —O—; and $R^{80}$, $R^{81}$ and $R^{82}$ are independently of each other a $C_1$-$C_{25}$alkyl group, which is optionally interrupted by —O—; a $C_6$-$C_{14}$aryl group, which is optionally substituted by $C_1$-$C_{18}$alkyl; or a $C_2$-$C_{10}$heteroaryl group, which is optionally substituted by $C_1$-$C_{18}$alkyl.

2. The metal-carbene complex according to claim 1, which is a metal-carbene complex of formula (II):

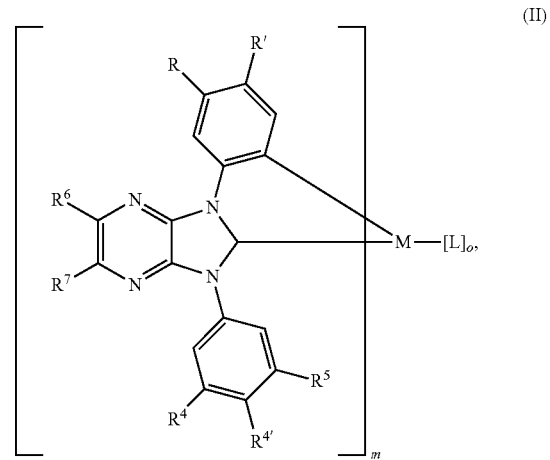

wherein
R is a group of formula

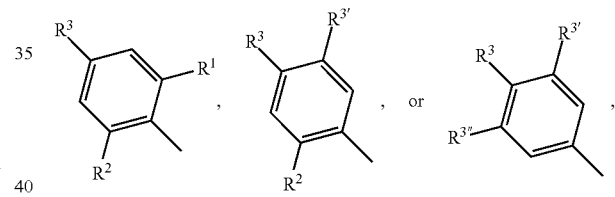

and
R' is hydrogen; or a $C_1$-$C_5$alkyl group.

3. The metal complex according to claim 1, which is a metal-carbene complex of formula (IIa), formula (IIb), or formula (IIc):

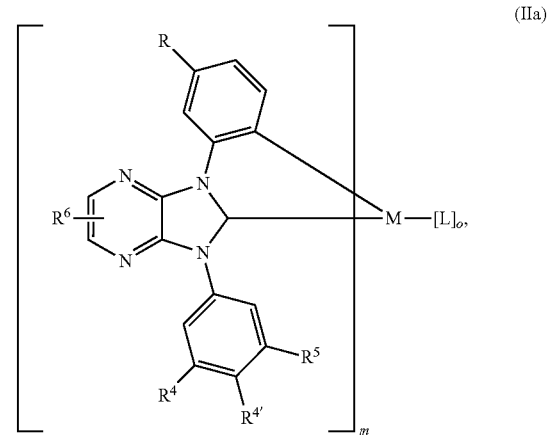

-continued

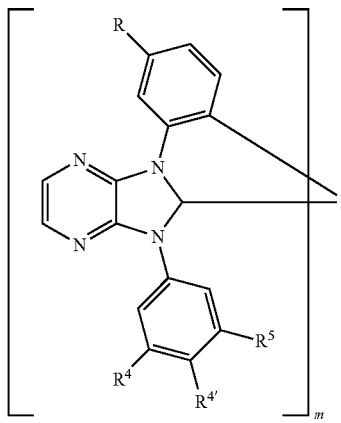
(IIb)

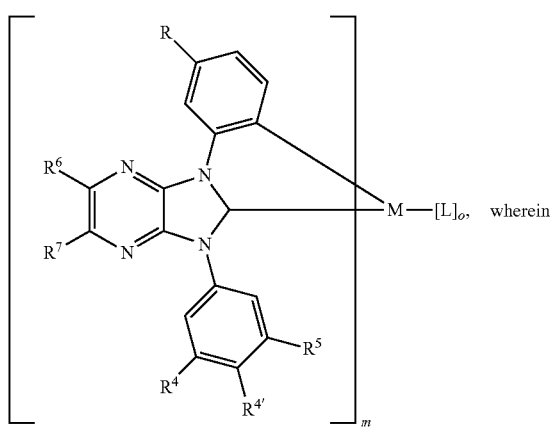
(IIc)

R is a group of formula

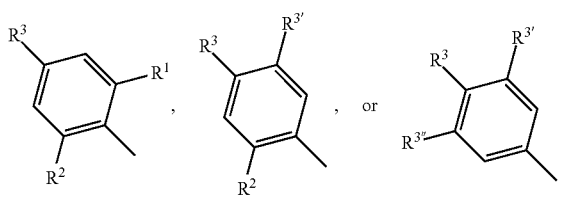

and $R^6$ in formula (IIa) is a $C_1$-$C_8$alkyl group, optionally interrupted by at least one heteroatom selected from —O—, —S— and —$NR^{65}$—, optionally bearing at least one substituent, which is selected from the group consisting of $C_1$-$C_8$alkyl, $C_1$-$C_8$alkoxy, halogen, and $C_1$-$C_8$haloalkyl; a $C_3$-$C_6$cycloalkyl group, optionally bearing at least one substituent, which is selected from the group consisting of $C_1$-$C_8$alkyl, $C_1$-$C_8$alkoxy, halogen, and $C_1$-$C_8$haloalkyl; a hetero$C_3$-$C_6$cycloalkyl group, interrupted by at least one heteroatom selected from —O—, —S— and —$NR^{65}$—, optionally bearing at least one substituent, which is selected from $C_1$-$C_8$alkyl, $C_1$-$C_8$alkoxy, $C_1$-$C_8$alkoxy, halogen, and $C_1$-$C_8$haloalkyl; or $R^6$ in formula (IIa) is a group of formula

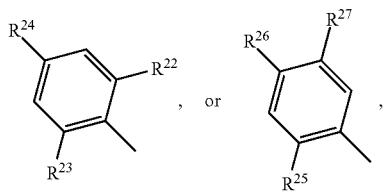

wherein:

(i) $R^{22}$, and $R^{23}$ and $R^{24}$ are independently of each other a hydrogen, or a $C_1$-$C_5$alkyl group, with the proviso that only one or two of $R^{22}$, $R^{23}$ and $R^{24}$ may be a $C_1$-$C_5$alkyl group; or (ii) $R^{25}$, $R^{26}$ and $R^{27}$ are independently of each other a hydrogen, or a $C_1$-$C_5$alkyl group, with the proviso that only one or two of $R^{25}$, $R^{26}$ and $R^{27}$ may be a $C_1$-$C_5$alkyl group; or $R^6$ and $R^7$ in formula (IIc) form together a ring

4. The metal-carbene complex according to claim 1, which is a metal-carbene complex of formula (IVa), formula (IVb), formula (IVc). or formula (IVd):

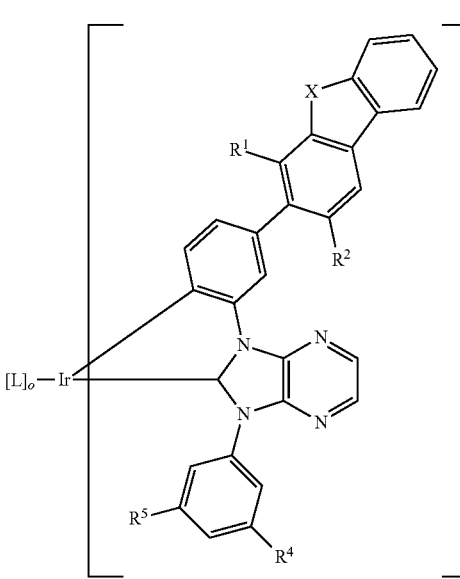
(IVa)

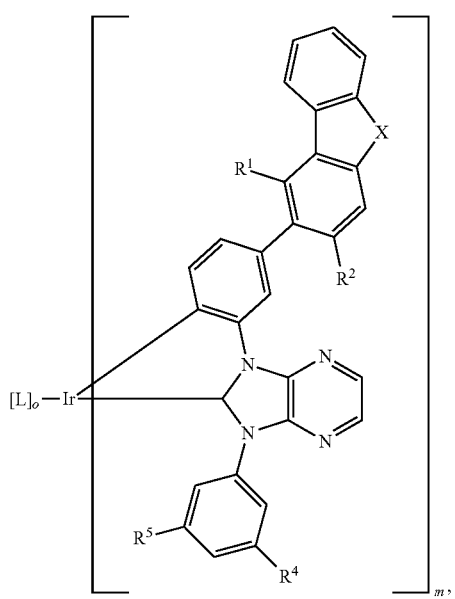

(IVb)

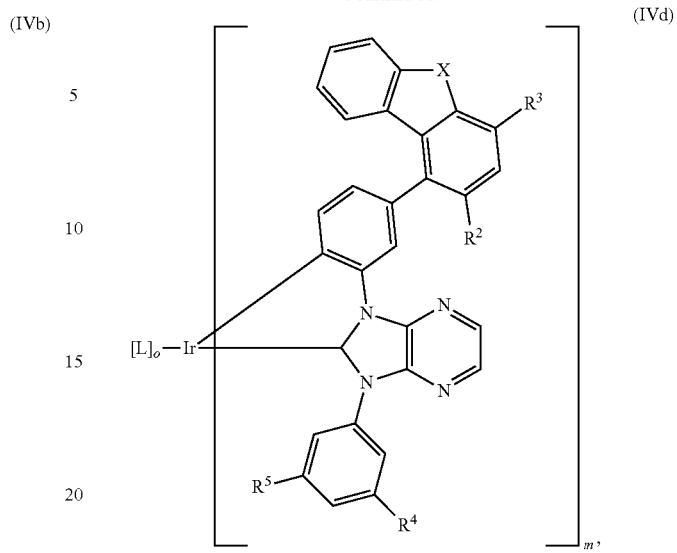

(IVd)

wherein
m is 1, 2, or 3,
o is 0, 1, or 2; and
the sum of m and o is 3;
X is O, or S;
$R^1$ is hydrogen, a $C_1$-$C_{5alkyl}$ group, a cyclopentyl group, or a cyclohexyl group;
$R^2$ is hydrogen, a $C_1$-$C_{5alkyl}$ group, a cyclopentyl group, or a cyclohexyl group;
$R^3$ is hydrogen, a $C_1$-$C_{5alkyl}$ group, a cyclopentyl group, or a cyclohexyl group;
$R^4$ and $R^5$ are independently hydrogen, a $C_1$-$C_{5alkyl}$ group, a cyclopentyl group, or a cyclohexyl group.

5. The metal-carbene complex according to claim 4, wherein $R^4$ and $R^5$ are hydrogen.

6. The metal-carbene complex according to claim 1 which is a metel-carbene complex of formula (IIIa), formula (IIIb), or formula (IIIc):

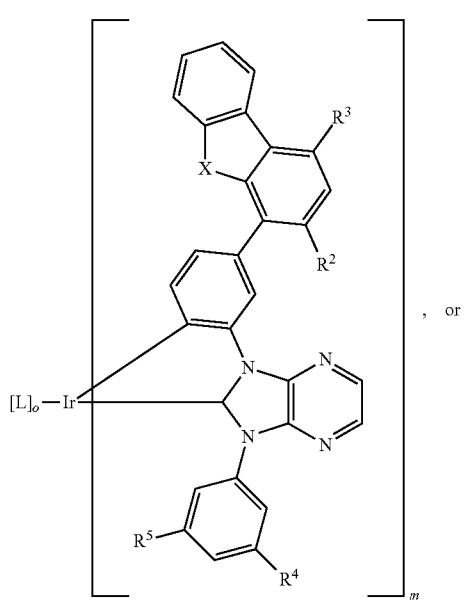

, or

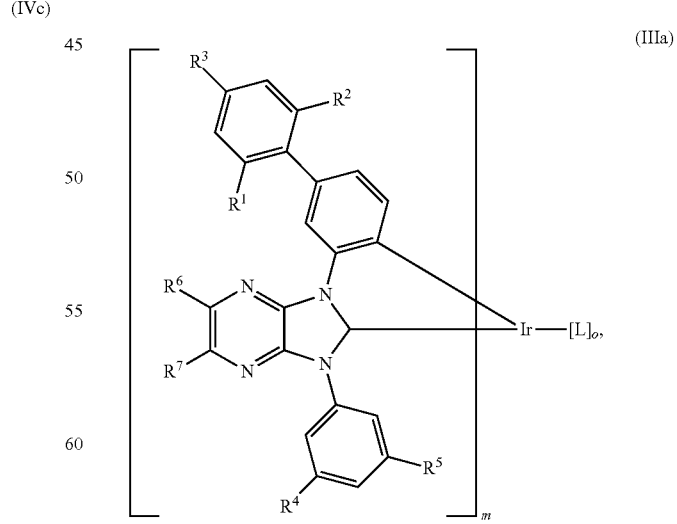

(IIIa)

wherein
$R^1$ and $R^2$ are independently of each other a $C_1$-$C_5$alkyl group, a cyclopentyl group or a cyclohexyl group; and $R^3$ is hydrogen, a $C_1$-$C_4$alkyl group, or a group of formula

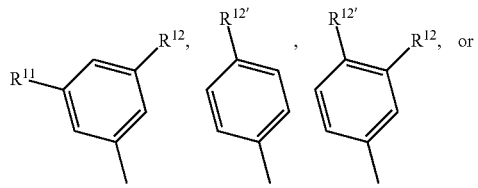

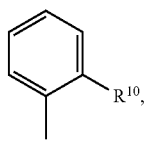

wherein
$R^{10}$ is hydrogen, or a $C_1$-$C_5$alkyl group;
$R^{11}$ is hydrogen, or a $C_1$-$C_5$alkyl group;
$R^{12}$ is a $C_1$-$C_5$alkyl group; and
$R^{12'}$ is a $C_1$-$C_5$alkyl group; or (IIIb)

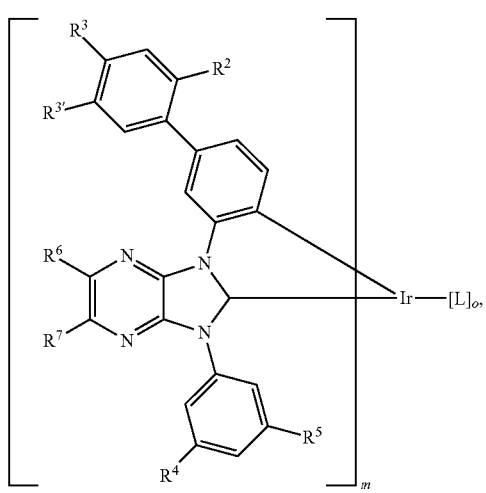

wherein
$R^2$ is $CF_3$, a $C_1$-$C_5$alkyl group, a cyclopentyl group or a cyclohexyl group;
$R^3$ is hydrogen, a $C_1$-$C_5$alkyl group, a cyclopentyl group or a cyclohexyl group; and
$R^{3'}$ is hydrogen, a $C_1$-$C_5$alkyl group, a cyclopentyl group or a cyclohexyl group;
with the proviso that if either of $R^3$ and $R^{3'}$ is a cyclopentyl group or a cyclohexyl group, then the other is hydrogen; or (IIIc)

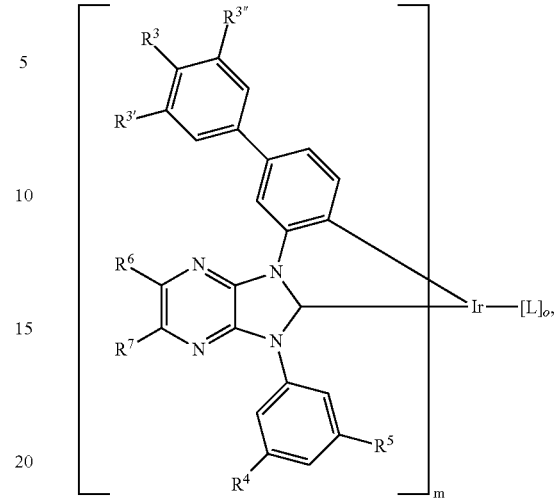

wherein
$R^3$ is hydrogen, a $C_1$-$C_5$alkyl group, a cyclopentyl group, or a cyclohexyl group;
$R^{3'}$ is hydrogen, especially a $C_1$-$C_5$alkyl group, a cyclopentyl group or a cyclohexyl group; and
$R^{3''}$ is hydrogen, a $C_1$-$C_5$alkyl group, a cyclopentyl group or a cyclohexyl group;
with the proviso that if either of $R^3$ and $R^{3'}$ is a cyclopentyl group or a cyclohexyl group, then the other is hydrogen;
and with the further proviso that if either of $R^{3''}$ and $R^3$ is a cyclopentyl group or a cyclohexyl group, then the other is hydrogen;

m is 1, or 2;
o is 1 or 2; and
the sum of m and o is 3;
L is a group of formula (X-1), (X-2), (X-3), (X-4), (X-5), (X-6), (X-7), (X-8), (X-9), (X-10), (X-11), (X-12), (X-13), (X-14), (X-15), (X-16), (X-17), (X-18), (X-19), (X-20), (X-21), (X-22), (X-23), (X-24), (X-25), (X-26), or (X-27)

(X-1)

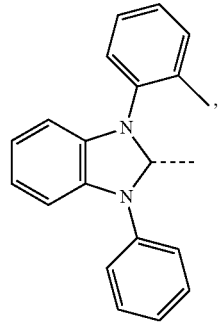

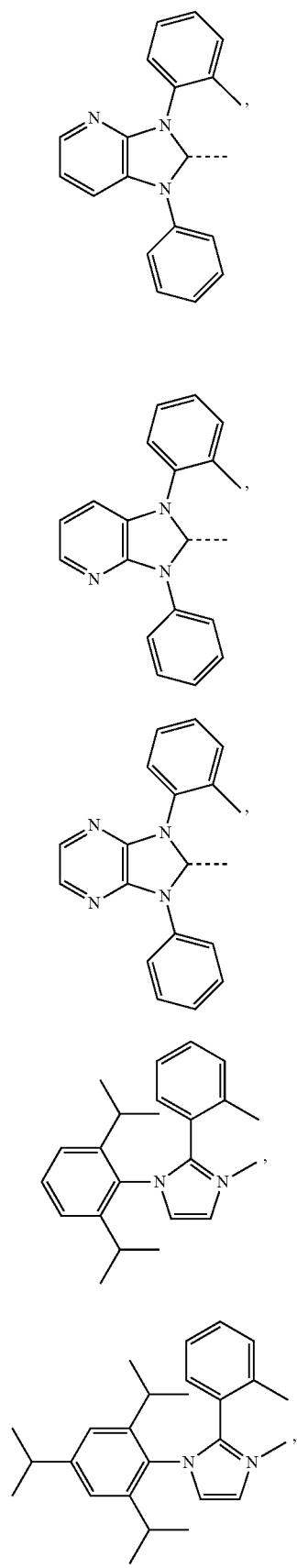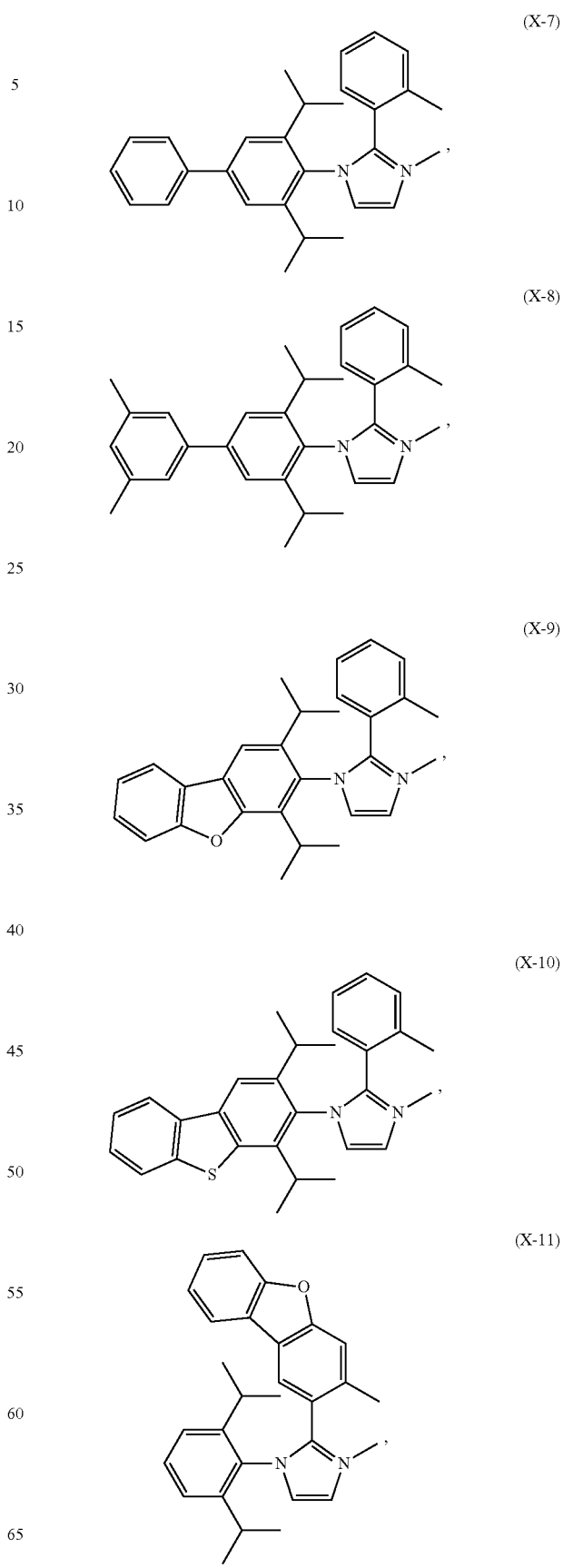

-continued
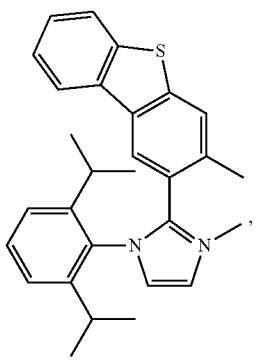 (X-12)
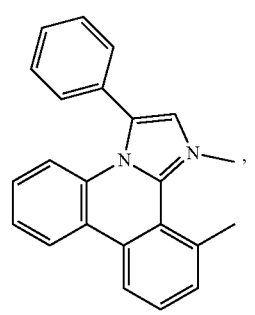 (X-13)
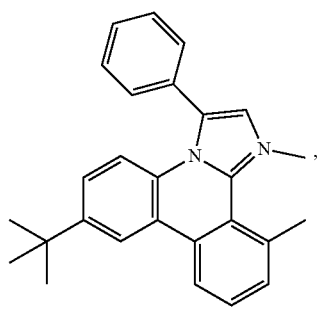 (X-14)
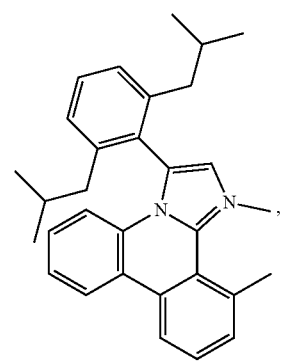 (X-15)
-continued
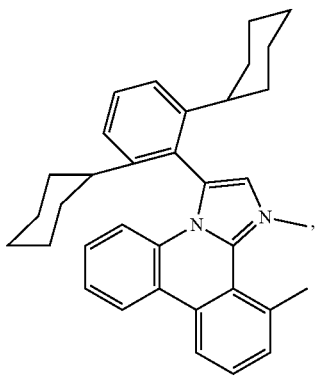 (X-16)
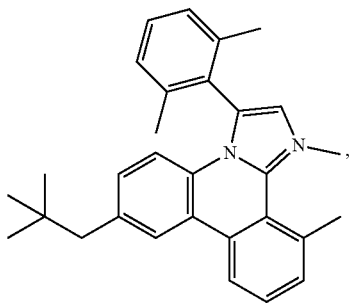 (X-17)
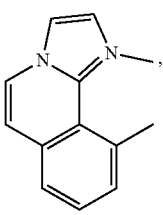 (X-18)
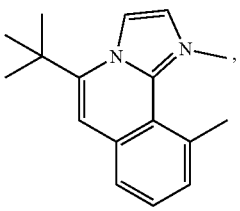 (X-19)
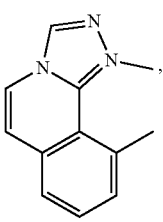 (X-20)
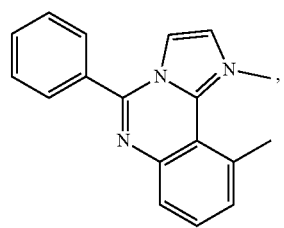 (X-21)

(X-22) 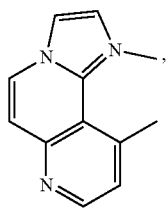

(X-23) 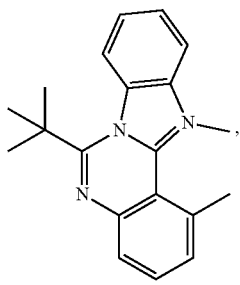

(X-24) 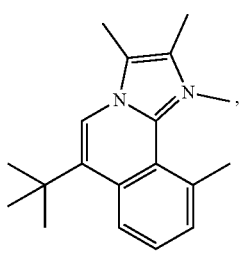

(X-25) 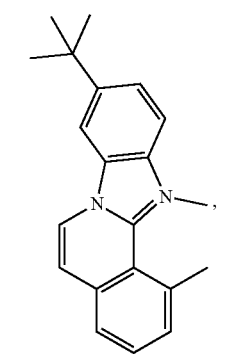

(X-26) 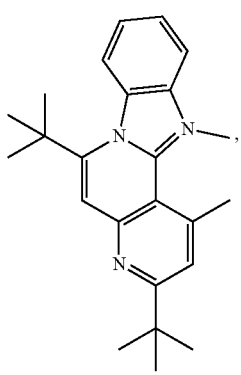 or (X-27) 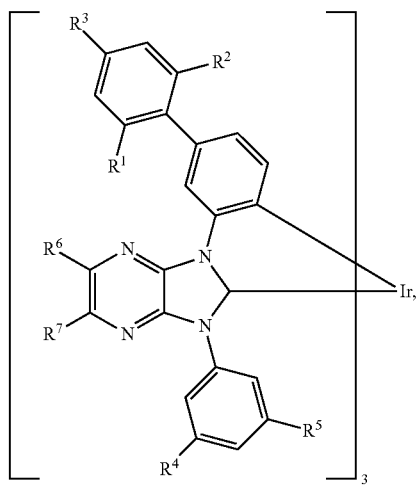

$R^4$ and $R^5$ are independently of each other hydrogen, or a $C_1$-$C_5$alkyl group, a cyclopentyl group or a cyclohexyl group; and $R^6$ and $R^7$ are independently of each other hydrogen, a $C_1$-$C_8$alkyl group, or a $C_3$-$C_6$cycloalkyl group; or $R^6$ and $R^7$ form together a ring with the proviso that if either of $R^6$ and $R^7$ is a $C_1$-$C_8$alkyl group, or a $C_3$-$C_6$cycloalkyl group, then the other is hydrogen.

7. The metal-carbene complex according to claim 1, which is a metal-carbene complex of formula (IIId), formula (IIIe), or formula (IIIf):

(IIId)

wherein $R^1$ and $R^2$ are independently of each other a $C_1$-$C_5$alkyl group; a cyclopentyl group or a or cyclohexyl group;

R³ is hydrogen, a C₁-C₄alkyl group, or a group of formula

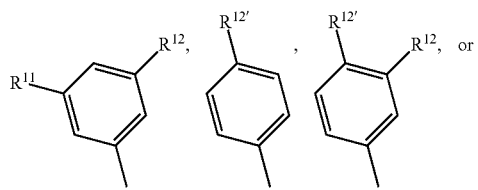

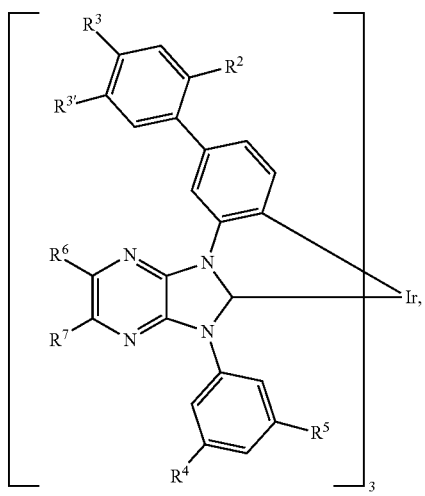

wherein
$R^{10}$ is hydrogen, or a $C_1$-$C_5$alkyl group;
$R^{11}$ is a $C_1$-$C_5$alkyl group;
$R^{12}$ is a $C_1$-$C_5$alkyl group; and
$R^{12'}$ a $C_1$-$C_5$alkyl group; or

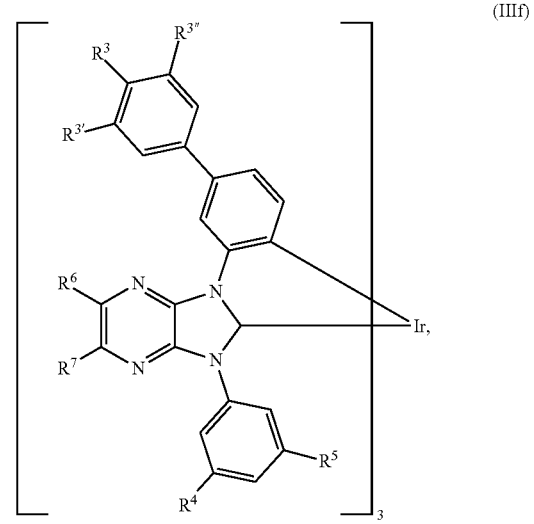

wherein
$R^2$ is hydrogen, $CF_3$, a $C_1$-$C_5$alkyl group, a cyclopentyl group or a cyclohexyl group;
$R^3$ is hydrogen, a $C_1$-$C_5$alkyl group, a cyclopentyl group or a cyclohexyl group; and
$R^{3'}$ is hydrogen, a $C_1$-$C_5$alkyl group, a cyclopentyl group or a cyclohexyl group;
with the proviso that if either of $R^3$ and $R^{3'}$ is a cyclopentyl group or a cyclohexyl group, then the other is hydrogen; or wherein
$R^3$ is hydrogen, or a $C_1$-$C_5$alkyl group; and
$R^{3'}$ is hydrogen, a $C_1$-$C_5$alkyl group; a cyclopentyl group or a cyclohexyl group; and
$R^{3''}$ is hydrogen, a $C_1$-$C_5$alkyl group, a cyclopentyl group or a cyclohexyl group;
with the proviso that if either of $R^3$ and $R^{3'}$ is a cyclopentyl group or a cyclohexyl group, then the other is hydrogen; and
with the further proviso that if either of $R^{3''}$ and $R^3$ is a cyclopentyl group or a cyclohexyl group, then the other is hydrogen.

8. The metal-carbene complex according to claim 1, which is a metal-carbene complex of formula (IIIa-1), formula (IIIb-1), formula (IIIc-1), formula (IIId-1), formula (IIIe-1), or formula (IIIf-1):

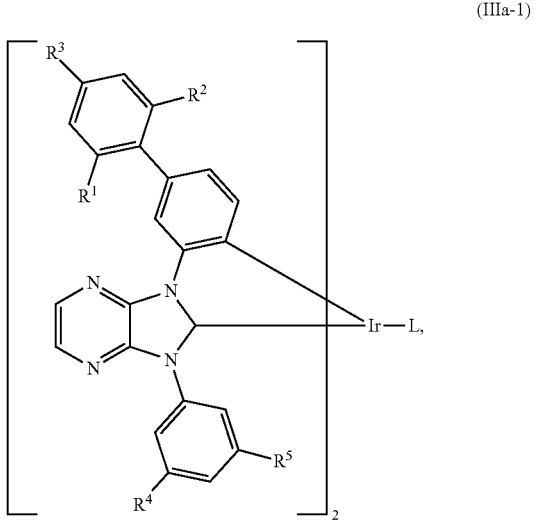

wherein

R¹ and R² are independently of each other a $C_1$-$C_5$alkyl group; and

R³ is hydrogen, or a $C_1$-$C_4$alkyl group; or

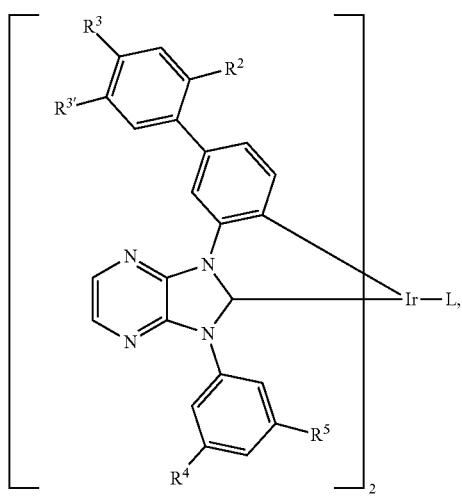

(IIIb-1)

wherein

R² is $CF_3$, a $C_1$-$C_5$alkyl group; a cyclopentyl group or a cyclohexyl group;

R³ is hydrogen, a $C_1$-$C_5$alkyl group; a cyclopentyl group or a cyclohexyl group; and R³' is hydrogen, a $C_1$-$C_5$alkyl group; a cyclopentyl group or a cyclohexyl group;

with the proviso that if either of R³ and R³' is a cyclopentyl group or a cyclohexyl group, then the other is hydrogen; or

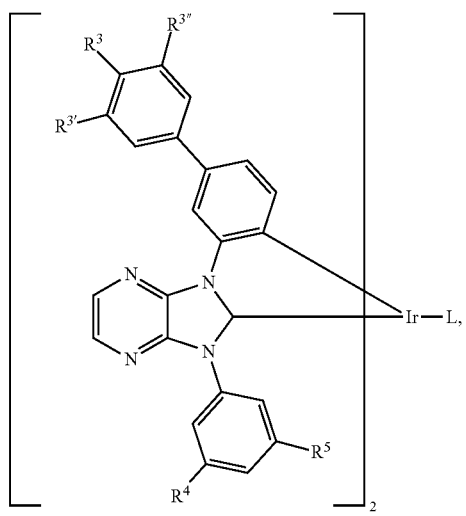

(IIIc-1)

wherein

R³ is hydrogen, a $C_1$-$C_5$alkyl group;

R³' is hydrogen, or a $C_1$-$C_5$alkyl group; and

R³'' is hydrogen, or a $C_1$-$C_5$alkyl group;

with the proviso that if both R³' and R³'' are independently a $C_1$-$C_5$alkyl group then R³ is hydrogen; or

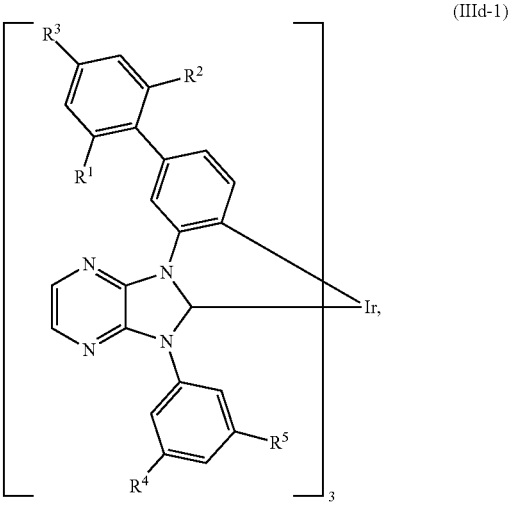

(IIId-1)

wherein

R¹ and R² are independently of each other a $C_1$-$C_5$alkyl group, a cyclopentyl group or a cyclohexyl group; and R³ is hydrogen, or a $C_1$-$C_4$alkyl group; or

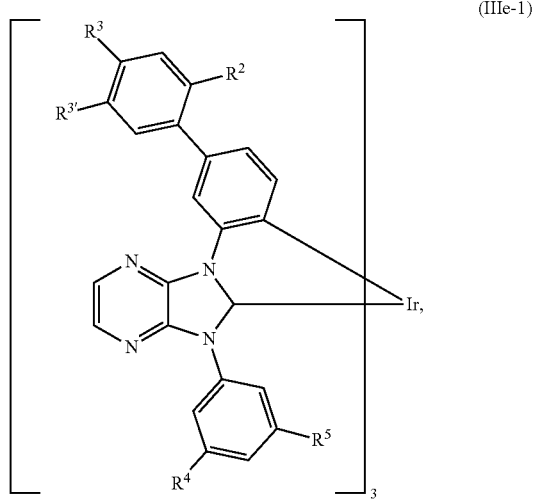

(IIIe-1)

wherein

R² is $CF_3$, a $C_1$-$C_5$alkyl group, a cyclopentyl group or a cyclohexyl group;

R³ is hydrogen, a $C_1$-$C_5$alkyl group, a cyclopentyl group or a cyclohexyl group; and R³' is hydrogen, a $C_1$-$C_5$alkyl group, a cyclopentyl group or a cyclohexyl group;

with the proviso that if either of R³ and R³' is a cyclopentyl group or a cyclohexyl group, then the other is hydrogen; or (IIIf-1)

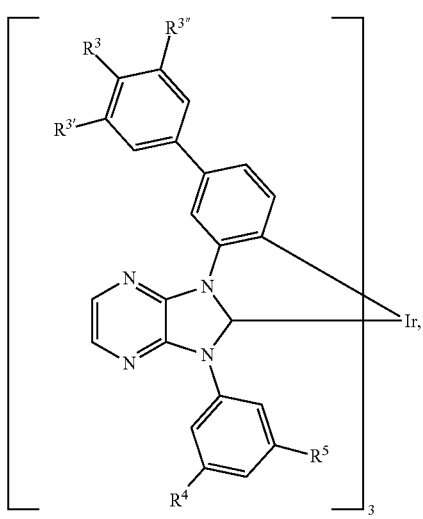

wherein $R^3$ is hydrogen, or a $C_1$-$C_5$alkyl group;

$R^{3'}$ is hydrogen, or a $C_1$-$C_5$alkyl group;

$R^{3''}$ is hydrogen, or a $C_1$-$C_5$alkyl group;

$R^4$ is hydrogen, or a $C_1$-$C_5$alkyl group;

$R^5$ is hydrogen, or a $C_1$-$C_5$alkyl group;

with the proviso that if both $R^{3'}$ and $R^{3''}$ are independently a $C_1$-$C_5$alkyl group, then $R^3$ is hydrogen.

9. The meta-carbene complex according to claim 1, wherein L is (X-1)

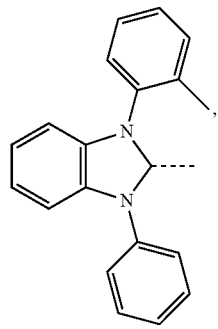

(X-2)

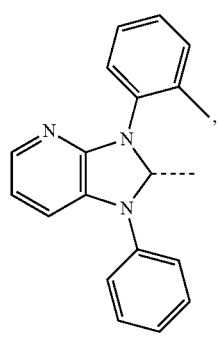

(X-3)

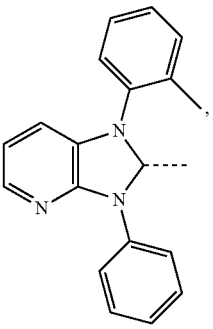

(X-4)

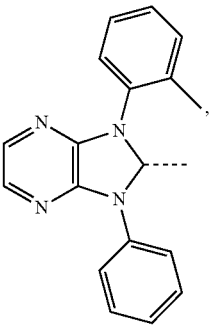

(X-5)

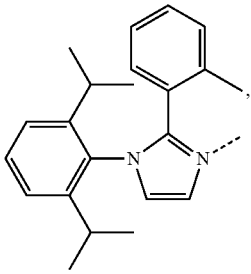

(X-6)

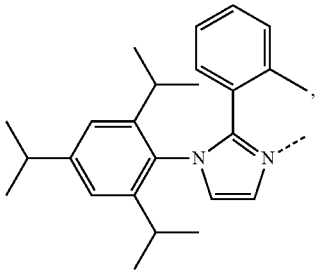

(X-7)

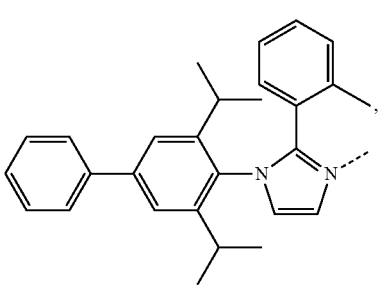

(X-8) 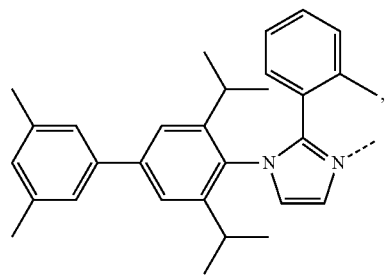
(X-9) 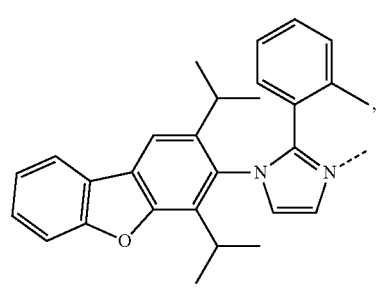
(X-10) 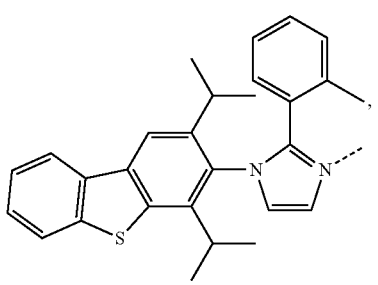
(X-11) 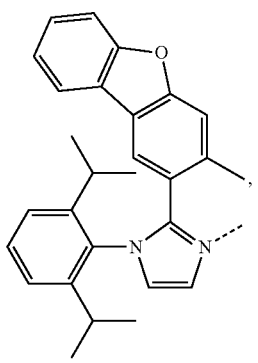
(X-12) 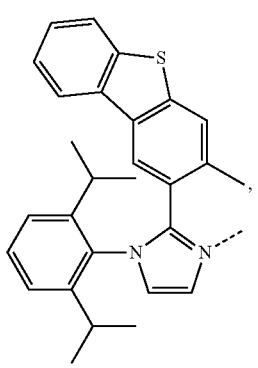
(X-13) 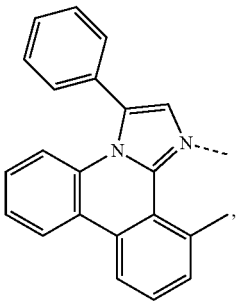
(X-14) 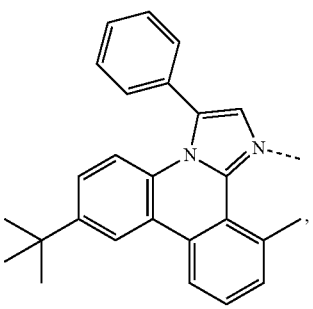
(X-15) 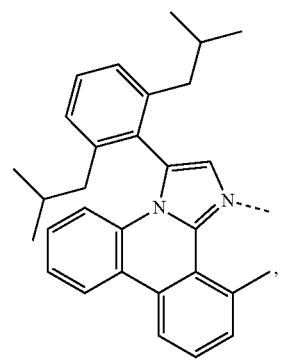
(X-16) 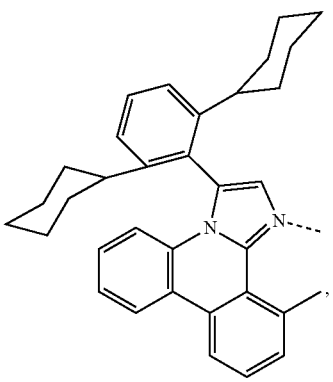

| 321 -continued | 322 -continued |
|---|---|
| 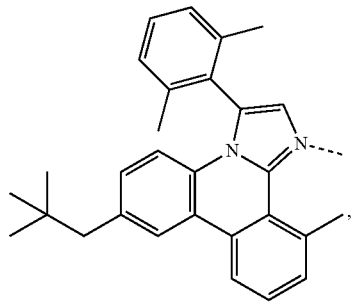 (X-17) | 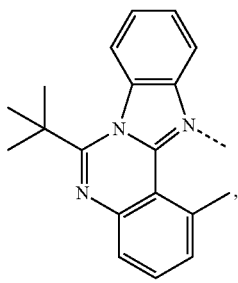 (X-23) |
| 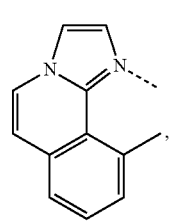 (X-18) | 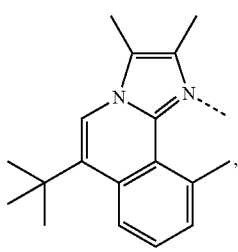 (X-24) |
| 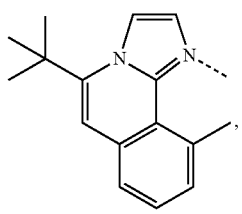 (X-19) | 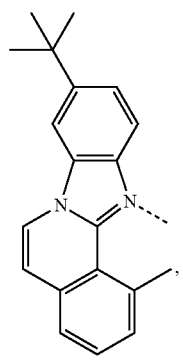 (X-25) |
| 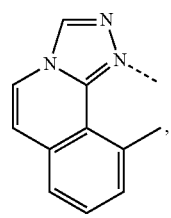 (X-20) | 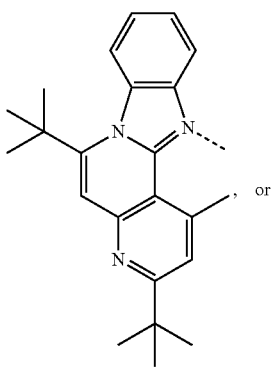 (X-26), or |
| 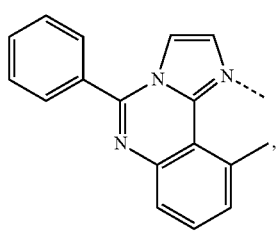 (X-21) | |
| 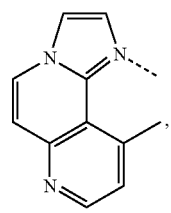 (X-22) | |

-continued

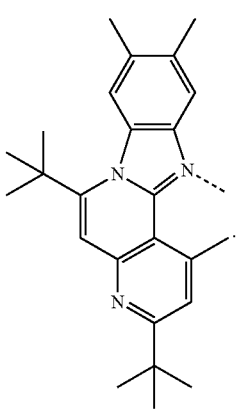

(X-27)

10. The metal-carbene complex according to claim 1, wherein L is formula (D'):

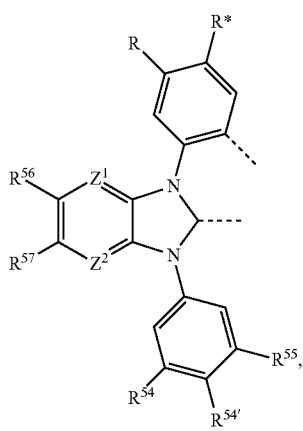

(D')

which is different from formula (D)

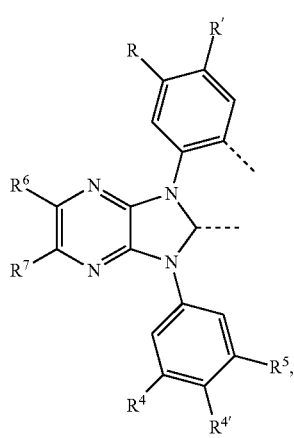

(D)

wherein
Z$^1$ and Z$^2$ are independently of each other N; or
Z$^1$ and Z$^2$ are independently of each other CH;
R* is R';
R$^{54}$ is R$^4$;
R$^{54'}$ is R$^{4'}$;
R$^{55}$ is R$^5$;
R$^{56}$ is $^6$; and
R$^{57}$ is R$^7$;
wherein each group R is the same within one metal-carbene complex.

11. The metal-carbene complex according to claim 1, wherein:
R is a group of formula

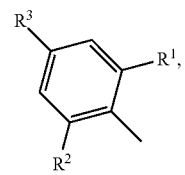

wherein
R$^1$ and R$^2$ are independently of each other a C$_1$-C$_5$alkyl group, a cyclopentyl group or a cyclohexyl group; and
R$^3$ is hydrogen, a C$_1$-C$_5$alkyl group, a group of formula

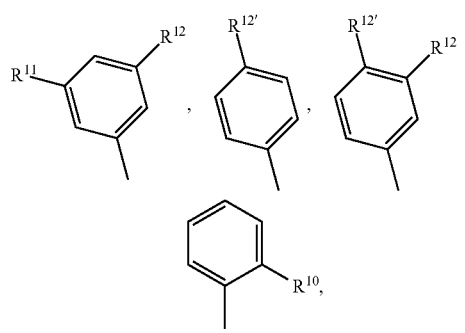

wherein
R$^{10}$ is hydrogen, or a C$_1$-C$_5$alkyl group;
R$^{11}$ is hydrogen H, or a C$_1$-C$_5$alkyl group;
R$^{12}$ is a C$_1$-C$_5$alkyl group; and
R$^{12'}$ is a C$_1$-C$_5$alkyl group.

12. The metal-carbene complex according to claim 1, wherein
R is a group of formula

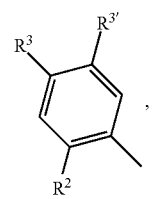

wherein
R$^2$ is a C$_1$-C$_5$alkyl group, a cyclopentyl group or a cyclohexyl group;
R$^3$ is hydrogen, a C$_1$-C$_5$alkyl group, a cyclopentyl group or a cyclohexyl group; and
R$^{3'}$ is hydrogen, a C$_1$-C$_5$alkyl group, a cyclopentyl group or a cyclohexyl group;
with the proviso that in case one of R$^3$ and R$^{3'}$ is a cyclopentyl or cyclohexyl group, the other is hydrogen.

13. The metal-carbene complex according to claim 1, wherein
R is a group of formula

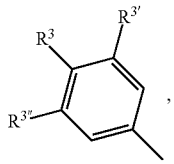

wherein
R³ is hydrogen, or a C₁-C₅alkyl group; and
R³' is hydrogen, a C₁-C₅alkyl group, a cyclopentyl group or a cyclohexyl group; and
R³" is hydrogen, a C₁-C₅alkyl group, a cyclopentyl group or a cyclohexyl group;
with the proviso that if both R³' and R³" are independently a ₁-C₅alkyl group, a cyclopentyl group or a cyclohexyl group, then R³ is hydrogen.

14. The metal-carbene complex according to claim 1, wherein
(i) R⁴ is hydrogen, or a C₁-C₅alkyl group;
R⁴' is hydrogen; and
R⁵ is hydrogen, or a C₁-C₅alkyl group; or
(ii) R⁴ is hydrogen, or a C₁-C₅alkyl group;
R⁴' is a group of

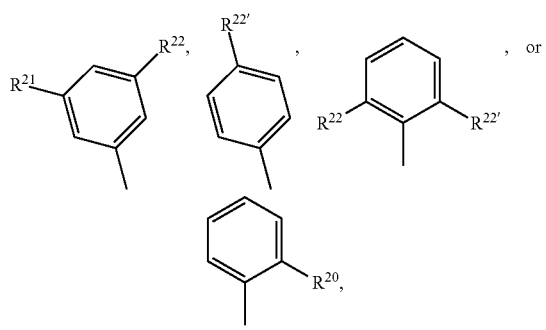

wherein
R²⁰ is hydrogen, or a C₁-C₅alkyl group;
R²¹ is hydrogen, or a C₁-C₅alkyl group;
R²² is a C₁-C₅alkyl group; and
R²²' is a C₁-C₅alkyl group; and
R⁵ is hydrogen, or a C₁-C₅alkyl group; or
(iii) R⁴ is hydrogen;
R⁴' is a group of formula

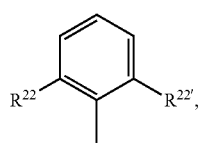

wherein
R²² and R²²' are independently a C₁-C₅alkyl group; and
R₅ is hydrogen.

15. The metal-carbene complex according to claim 1, wherein (i) R⁴ is hydrogen;
R⁴' is hydrogen, or a C₁-C₅alkyl group; and
R⁵ is hydrogen, or C₁-C₅alkyl group; or
(ii) R⁴ is hydrogen;
R⁴' is hydrogen; and
R⁵ is a group of formula

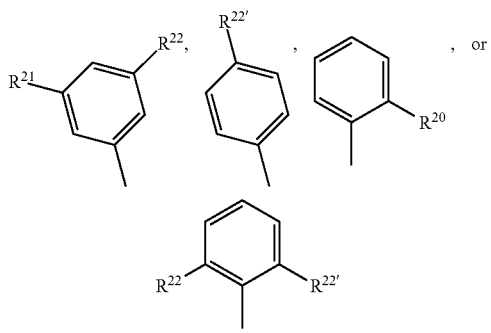

wherein
R²⁰ is hydrogen, or a C₁-C₅alkyl group;
R²¹ is hydrogen, or a C₁-C₅alkyl group;
R²² is a C₁-C₅alkyl group; and
R²²' is a C₁-C₅alkyl group.

16. The metal-corbene complex according to claim 1, wherein
R⁶ and R⁷ are independently of each other hydrogen, a C₁-C₅alkyl group,or a C₃-C₆cycloalkyl group; or
R⁶ and R⁷ form together a ring

with the proviso that if one of R⁶ and R⁷ is a C₃-C₆cycloalkyl group, the other is hydrogen.

17. An organic electronic device comprising at least one metal-carbene complex according to claim 1.

18. A light-emitting layer comprising at least one metal-carbene complex according to claim 1.

19. An apparatus selected from the group consisting of a stationary visual display unit, an illumination, information panel, a mobile visual display unit, an illumination unit, a keyboard, an item of clothing, a piece of furniture and a wallpaper comprising the organic electronic device according to claim 17, or the emitting layer according to claim 18.

20. An apparatus selected from the group consisting of an electrophotographic photoreceptor, a photoelectric converter, an organic solar cell a switching element, an organic light emitting field effect transistor, an image sensor, a dye laser and an electroluminescent device comprising the metal-complex according to claim 1.

21. A process for preparing a metal-carbene complex of the formula (I) according to claim 1

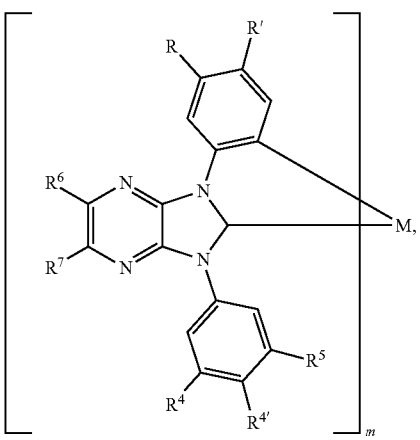

(I)

wherein:
  m is 3; and
  M, R, R', R⁴, R⁴', R⁵, R⁶ and R⁷ are as defined in claim 1;
which process comprises:
reacting a compound of formula (X):

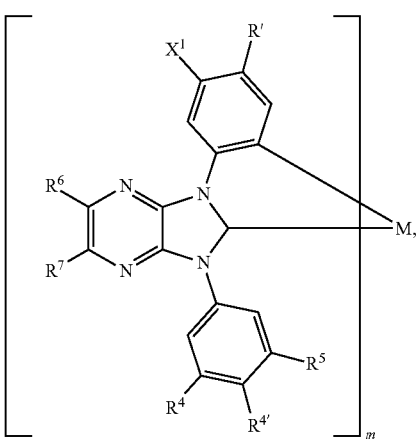

(X)

wherein:
  $X^1$ is Cl, Br or I; and
  m, M, R', R⁴, R⁴', R⁵, R⁶ and R⁷ are as defined in claim 1;
with a compound of the formula:

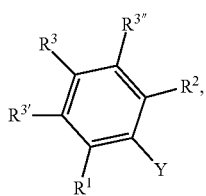

wherein
Y is:
(a) —B(OH)$_2$, —B(OY$^1$)$_2$,

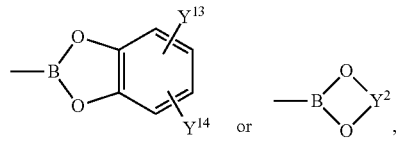

or wherein:
  each $Y^1$ is independently a $C_1$-$C_{10}$alkyl group;
  $Y^2$ is a $C_2$-$C_{10}$alkylene group;
  $Y^{13}$ is hydrogen or a $C_1$-$C_{10}$alkyl group; and
  $Y^{14}$ is hydrogen or a $C_1$-$C_{10}$alkyl group;
(b) —SnR$^{307}$R$^{308}$R$^{309}$, wherein:
  R$^{307}$, R$^{308}$ and R$^{309}$ are independently hydrogen or $C_1$-$C_6$alkyl, wherein two $C_1$-$C_6$alkyl radicals may optionally form a common ring;
(c) —ZnR$^{310}$R$^{311}$, wherein:
  R$^{310}$ is halogen; and
  R$^{311}$ is a $C_1$-$C_{10}$alkyl group, a $C_6$-$C_{12}$aryl group or a $C_2$-$C_{10}$alkenyl group; or
(d) —SiR$^{312}$R$^{313}$R$^{314}$, wherein:
  R$^{312}$, R$^{313}$ and R$^{314}$ are independently halogen or a $C_1$-$C_6$alkyl group; and
R$^1$, R$^2$, R$^3$, R$^{3'}$ and R$^{3''}$ are as defined in claim 1.

22. The process according to claim 21, which process comprises:
reacting a compound of formula (XI):

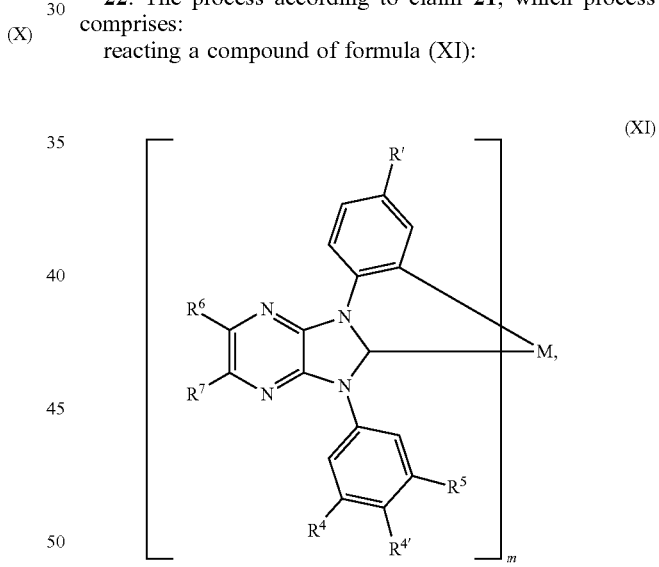

(XI)

wherein:
  m, M, R', R⁴, R⁴', R⁵, R⁶ and R⁷ are as defined in claim 21;
with a halogenating agent selected from the group consisting of chlorine, bromine, iodine, chlorine fluoride, bromine fluoride, iodine fluoride, bromine chloride, iodine chloride, iodine bromide, 1-(chloromethyl)-4-fluoro-1,4-diazoniabicyclo[2.2.2]octane bis(tetrafluoroborate), N-chloroacetamide, N-bromoacetamide, N-iodoacetamide, N-chloropropionamide, N-bromopropionamide, N-iodopropionamide, N-chlorobenzamide, N-bromobenzamide, N-iodobenzamide, N-chlorosuccinimide, N-bromosuccinimide, N-iodosuccinimide, N-chlorophthalimide, N-bromophthalimide, N-iodophthalimide, 1,3-dibromo-5,5-dimethylhydantoin, 1,3-dichloro-5,5-dimethylhydantoin, 1,3-diiodo-5,5-dimethylhydantoin, benzenesulfo-N-dibromamide, chloramine B and chloramine T;
to obtain a compound of formula (X):
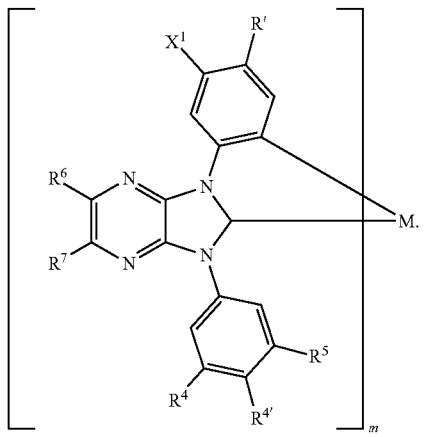
* * * * *